United States Patent
Philibert et al.

(10) Patent No.: US 6,566,061 B1
(45) Date of Patent: May 20, 2003

(54) IDENTIFICATION OF POLYMORPHISMS IN THE PCTG4 REGION OF XQ13

(75) Inventors: Robert A. Philibert, Iowa City, IA (US); Edward I. Ginns, Bethesda, MD (US); Lynn Delisi, Stony Brook, NY (US)

(73) Assignees: The University of Iowa, as represented by the University of Iowa Research Foundation, Iowa City, IA (US); The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/491,356

(22) Filed: Jan. 26, 2000

Related U.S. Application Data

(63) Continuation-in-part of application No. PCT/US99/09365, filed on Apr. 29, 1999.
(60) Provisional application No. 60/083,465, filed on Apr. 29, 1998.

(51) Int. Cl.$^7$ ............................. C07H 21/04; C12Q 1/68
(52) U.S. Cl. ........................ 435/6; 435/91.2; 536/23.1; 536/24.3; 536/24.33
(58) Field of Search ............................. 435/6; 536/23.1

(56) References Cited

FOREIGN PATENT DOCUMENTS

WO    WO 96/18730    6/1996

OTHER PUBLICATIONS

Philbert et al. "The segregation of HOPA mutations with hypothyroidism in a cohort of schizophrenic familes" Biological Psychiarty, vol. 47, No. 8, p. 687, Apr. 2000.*
Michaelis et al. "The HOPA gene dodecamer duplication is not a significant etiological factor in autism" J. of Autism and Devlopental Disorders, vol. 30, No. 4, Aug. 2000.*
Fiez et al. "Evidence that a dodecamer duplication in the gene HOPA in Xq13 is not associated with mental retardation" Hum. Genet. vol. 106, No. 1, pp. 36–39, Jan. 2000.*
Philbert et al. "Association of an X–chromosome dodecamer insertional variant allele with mental retardation" Molecular Psychiatry, vol. 4, No. 2, p. 197, 1999.*
"Diagnostic and Statistical Manual of Mental Disorders, Fourth Edition, DSM–IV™", *American Psychiatric Association*, pp. 78–85, 273–286, 320–359.
Aller, V. et al., "Familial Transmission Of A Duplication–Deficiency X Chromosome Associated With Partial Turner Syndrome", *Clinical Genetics*, vol. 48, pp. 317–320 (1995).
Goodwin, Frederick K., M.D. et al., "Manic–Depressive Illness", Oxford University Press, pp. 453–454 (1990).
Haggerty, Jr., MD, John J. et al., "Borderline Hypothyroidism And Depression", *Annual Review Med.*, vol. 46, pp. 37–46 (1995).

Ichtchenko, K. et al., "Structures, Alternative Splicing, And Neurexin Binding Of Multiple Neuroligins", *J. Biol. Chem.*, vol. 271 (1996).
Ichtchenko, K. et al., "Structures, Alternative Splicing, and Neurexin Binding of Multiple Neuroligins", *The American Society for Biochemistry and Molecular Biology, Inc.*, vol. 271, No. 5, (1996).
Ito, Mitsuhiro et al., "Identity between TRAP and SMCC Complexes Indicates Novel Pathways for the Function of Nuclear Receptors and Diverse Mammalian Activators", *Molecular Cell*, vol. 3 (Mar. 1999).
Näär, Anders M. et al., "Composite Co–Activator ARC Mediates Chromatin–Directed Transcriptional Activation", *Nature*, vol. 398, pp. 828–832 (Apr. 29, 1999).
Nagase, T. et al., "Prediction Of The Coding Sequences Of Unidentified Human Genes. V. The Coding Sequences Of 40 New Genes (KIAA0161—KIAA0200) Deduced By Analysis Of cDNA Clones From Human Cell Line KG–1.", *Kazusa DNA Research Institute*, 12 pgs. (Mar. 4, 1996).
NCI–CGAP, "National Cancer Institute, Cancer Genome Anatomy Project (CGAP), Tumor Gene Index", 1 pg. (1997).
Persad, E. MB, BS et al., "The Phenomenon of Rapid Cycling In Bipolar Mood Disorders: A Review", *Can J Psychiatry*, vol. 41, pp. 23–27 (Feb. 1996).
Philibert, RA et al., "Association Of An X–Chromosome Dodecamer Insertional Variant Allele With Mental Retardation", *Molecular Psychiatry*, pp. 303–309 (1998).
Rachez, Christophe et al., "Ligand–Dependent Transcription Activation By Nuclear Receptors Requires The DRIP Complex", *Nature*, vol. 398, pp. 824–828 (Apr. 29, 1999).
Shapira, Moshe et al., "Inherited Inverted Duplication of X Chromosome in a Male: Report of a Patient and Review of the Literature", *American Journal of Medical Genetics*, vol. 72, pp. 409–414 (1997).
Villard, Laurent et al., "Construction of a YAC Contig Spanning the Xq13.3 Subband", *Genomics*, vol. 26, No. 1, pp. 115–122 (Mar. 1, 1995).
Willems, Patrick et al., "Localization of a Gene Responsible for Nonspecific Mental Retardation (MRX9) to the Pericentromeric Region of the X Chromosome", *Genomics*, vol. 18, No. 2, pp. 290–294 (Nov. 1993).

(List continued on next page.)

*Primary Examiner*—W. Gary Jones
*Assistant Examiner*—Jeanine Goldberg
(74) *Attorney, Agent, or Firm*—Merchant & Gould P.C.

(57) ABSTRACT

Nucleic acid sequences within the q13 region of the X chromosome having polymorphisms associated with neuropsychiatric disorders and associated conditions are disclosed herein. One polymorphism occurs within the coding region of the HOPA gene and introduces a four amino acid insertion into a putative OPA domain, a domain which has been shown to be involved in tissue specific expression. Compositions including nucleic acids having these polymorphisms and antibodies to polymorphic regions within proteins encoded in the PCTG4 region are provided. Methods of using the information and nucleic acid sequences disclosed herein for the diagnosis and assessment of pathologies associated with neuropsychiatric disorders and associated conditions are also provided.

8 Claims, 12 Drawing Sheets

OTHER PUBLICATIONS

Philibert, R., et al., (2001) *"The Association of a HOPA polymorphism with Major Depression and Phobia"* Submitted, 22 pp.

Ito, M., et al. (2000) *"Involvement of the TRAP220 Component of the TRAP/SMCC Coactivator Complex in Embryonic Development and Thyroid Hormone Action"*, Mol Cell 5:683.

Zhang, H. and Emmons, S.E. (2000) *"A C. elegans mediator protein confers regulatory selectivity on lineage–specific expression of a transcription factor gene"*, Genes & Dev 14:2161.

Altshuler, D., et al. (2000) *"The common PPARγPro12Ala polymorphism is associated with decreased risk of type 2 diabetes"*, Nature Genetics 26:76.

DeLisi, L.E., et al. (2000) *"Investigation of a Candidate Gene for Schizophrenia on Xq13 Previously Associated With Mental Retardation and Hypothyroidism"*, Am J Med Gen, 96:398.

Philibert, R., et al. (2001) *"Populataion–Based Association Analyses of the HOPA$^{12bp}$ Polymorphism for Schizophrenia and Hypothyroidism"* Am J Med Gen, 105:130.

Beyer et al., "Association Studies of the *HOPA* Dodecamer Duplication Variant in Different Subtypes of Autism", *American Journal of Medical Genetics*, 114:110–115 (2002).

Ito et al., "Identity between TRAP and SMCC Complexes Indicates Novel Pathways for the Function of Nuclear Receptors and Diverse Mammalian Activators", *Molecular Cell*, vol. 3, pp. 361–370 (Mar. 1999).

Ito et al., "Involvement of the TRAP220 Component of the TRAP/SMCC Coactivator Complex in Embryonic Development and Thyroid Hormone Action", *Molecular Cell*, vol. 5, pp. 683–693 (Apr. 2000).

Ito et al., "The TRAP/SMCC/Mediator complex and thyroid hormone receptor function", *TRENDS in Endocrinology & Metabolism*, vol. 12, No. 3, pp. 127–134 (Apr. 2001).

Taatges et al., "Structure, Function, and Activator–Induced Conformations of the CRSP Coactivator", *Science*, vol. 295, pp. 1058–1062 (Feb. 2002).

Zhang et al., "A C. elegans mediator protein confers regulatory selectivity on lineage–specific expression of a transcription factor gene", *Genes & Development*, vol. 14, No. 7, pp. 2161–2172 (Sep. 1, 2000).

* cited by examiner

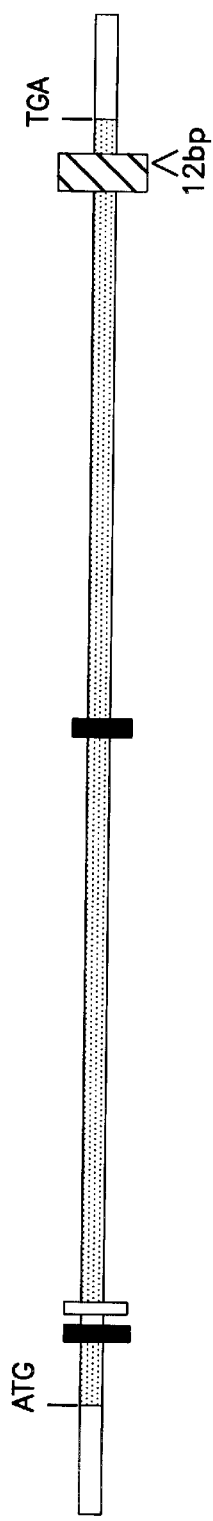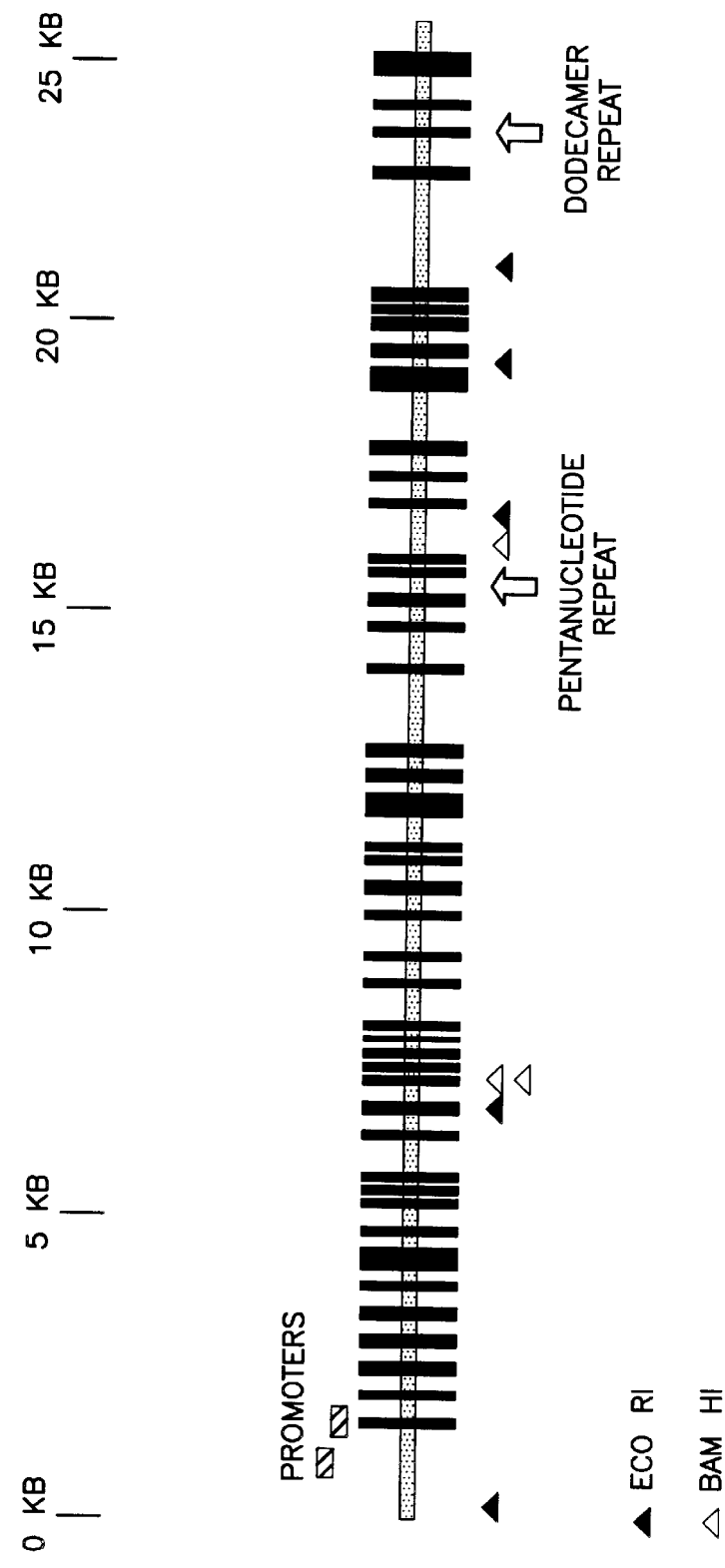
FIG.1A
FIG.1B

FIG. 5

CTGCTTCCTCATCCCTGCCCTTAGTTCAGAGGCTTAGCTCCCTCTG

CTCCTTCTGAAGTATCTTTGTGTTCTATAGCAGCAACAGCAA

CAGCAGCAGCAGCAACAGCAGCAACAGCAGCAACAGCAA
 Q   Q   Q   Q   Q   Q   Q   Q   Q   Q   Q

CACCAGCAGCAACAGCAACAGCAGCCTCCCAACCGGCTCCCAGCCCAGTCCCAGCCC
 H   Q   Q   Q   Q   Q   Q   A   A   P   P   P   Q   P   Q   S   Q   P

CAGGTAGCTGTTGGACTACAGCCC
 Q

FIG. 6

```
RNL1    MALPRCMWPNYVWRAMMACVVHRGSGAPLTLCLLGCLLQTFHVLSQKLDDVDPLVTTNFGKIRGIKKELNNEILG      75
RNL2                       MWLLALCLVGLAGAQRGGGPGGGAPGGPGLGLGSLGEERFPVVNTAYGRVRGVRRELNNEILG      64
RNL3                       MWLQLGLPSLSLSPTPTVGRSLCLILWFLSLVLRASTQAPAPTVNTHFGKLRGARVPLPSEILG      64
HNL3                       MWLRLGPPSLSLSPKPTVGRSLCLTLWFLSLALRASTQAPAPTVNTHFGKLRGARVPLPSEILG      64
HNL3s                      MWLRLGPPSLSLSPKPTVGRSLCLTLWFLSLALRASTQAPAPTVNTHFGKLRGARVPLPSEILG      64

RNL1    PVIQFLGVPYAAPPTGEHRFQPPEPPSPWSDIRNATQFAPVCPQNIIDGRLPEVMLPVWFTNNLDVVSSYVQDQS     150
RNL2    PVVQFLGVPYATPPLGARRFQPPEAPASWPGVRNATTLPPACPQNLH GALPAIMLPVWFTDNLEAAATYVQNQS     138
RNL3    PVDQYLGVPYAAPPIGEKRFLPPEPPPSWSGIRNATHFPPVCPQNIH TAVPEVMLPVWFTANLDIVATYIQEPN     138
HNL3    PVDQYLGVPYAAPPIGEKRFLPPEPPPSWSGIRNATHFPPVCPQNIH TAVPEVMLPVWFTANLDIVATYIQEPN     138
HNL3s   PVDQYLGVPYAAPPIGEKRFLPPEPPPSWSGIRNATHFPPVCPQNIH TAVPEVMLPVWFTANLDIVATYIQEPN     138

RNL1    EDCLYLNIYVPTEDVKRISKECARKPGKKICRKG                          DIRDSGGPKPVMVYIHGGSYM     205
RNL2    EDCLYLNLYVPTED                    GPLTKKRDEATL NPPDT   DIRDSG KKPVMLFLHGGSYM     189
RNL3    EDCLYLNVYVPTEDVKRISKECARKPNKKICRKGGSGAKKQGEDLADNDGDEDEDIRDSG AKPVMVYIHGGSYM     212
HNL3    EDCLYLNVYVPTED                    GSGAKKQGEDLADNDGDEDEDIRDSG AKPVMVYIHGGSYM     192
HNL3s   EDCLYLNVYVPTEDVKRISKECARKPNKKICRKGGSGAKKQGEDLADNDGDEDEDIRDSG AKPVMVYIHGGSYM     212

RNL1    EGTGNLYDGSVLASYGNVIVITVNYRLGVLGFLSTGDQAAKGNYGLLDLIQALRWTSENIGFFGGDPLRITVFGS     280
RNL2    EGTGNMFDGSVLAAYGNVIVATLNYRLGVLGFLSTGDQAAKGNYGLLDQIQALRWLSENIAHFGGDPERITIFGS     264
RNL3    EGTGNMIDGSVLASYGNVIVITLNYRVGVLGFLSTGDQAAKGNYGLLDQIQALRWVSENIAFFGGDPRRITVFGS     287
HNL3    EGTGNMIDGSIFASYGNVIVITLNYRVGVLGFLSTGDQAAKGNYGLLDQIQALRWVSENIAFFGGDPRRITVFGS     267
HNL3s   EGTGNMIDGSILASYGNVIVITLNYRVGVIGFLSTGDQAAKGNYGLLDQIQALRWVSENIAFFGGDPRRITVFGS     287

RNL1    GAGGSCVNLLTLSHYSEGNRWSNSTKGLFQRAIAQSGTALSSWAVSFQPAKYARILATKVGCNVSDTVELVECL     354
RNL2    GAGASCVNLLILSHHSE        GLFQKAIAQSGTAISSWSVNYQPLKYTRLLAAKVGCDREDSTEAVECLR     330
RNL3    GIGASCVSLLTLSHHSE        GLFQRAIIQSGSALSSWAVNYQPKYTSLLADKVGCNVLDTVDMVDCLR     353
HNL3    GIGASCVSLLTLSHHSE        GLFQRAIIQSGSALSSWAVNYQPVKYTSLLADKVGCNVLDTVDMVDCLR     333
HNL3s   GIGASCVSLLTLSHHSE        GLFQRAIIQSGSALSSWAVNYQPVKYTSLLADKVGCNVLDTVDMVDCLR     353

RNL1    QKKPYKELVDQDVQPARYHIAFGPVIDGDVIPDDPQILMEQGEFLNYDIMLGVNQGEGLKFVENIVDSDDGVSAS     429
RNL2    RKSS RELVDQDVQPARYHIAFGPVVDGDVVPDDPEILMQQGEFLNYDMLIGVNQGEGLKFVEDSAESEDGVSAS     404
RNL3    QKSA KELVEQDIQPARYHVAFGPVIDGDVIPDDPEILMEQGEFLNYDIMLGVNQGEGLKFVEGVVDPEDGVSGT     427
HNL3    QKSA KELVEQDIQPARYHVAFGPVIDGDVIPDDPEILMEQGEFLNYDIMLGVNQGEGLKFVEGVVDPEDGVSGT     407
HNL3s   QKSA KELVEQDIQPARYHVAFGPVIDGDVIPDDPEILMEQGEFLNYDIMLGVNQGEGLKFVEGVVDPEDGVSGT     427

RNL1    DFDFAVSNFVDNLYGYPEGKDVLRETIKFMYTDWADRHNPETRRKTLLALFTDHQWVAPAVATADLHSNFGSPTY     504
RNL2    AFDFTVSNFVDNLYGYPEGKDVLRETIKFMYTDWADRDNGEMRRKTLLALFTDHQWVAPAVATAKLHADYQSPVY     479
RNL3    DFDYSVSNFVDNLYGYPEGKDTLRETIKFMYTDWADRDNPETRRKTLVALFTDHQWVEPSVVTADLHARYGSPTY     502
HNL3    DFDYSVSNFVDNLYGYPEGKDTLRETIKFMYTDWADRDNPETRRKTLVALFTDHQWVEPSVVTADLHARYGSPTY     482
HNL3s   DFDYSVSNFVDNLYGYPEGKDTLRETIKFMYTDWADRDNPETRRKTLVALFTDHQWVEPSVVTADLHARYGSPTY     502

RNL1    FYAFYHHCQTDQVPAWADAAHGDEVPYVLGIPMIGPTELFPCNFSKNDVMLSAVVMTYWTNFAKTGDPNQPVPQD     579
RNL2    FYTFYHHCQAEGRPEWADAAHGDELPYVFGVPMVGATDLFPCNFSKNDVMLSAVVMTYWTNFAKTGDPNQPVPQD     554
RNL3    FYAFYHHCQSLMKPAWSDAAHGDEVPYVFGVPMVGPTDLFPCNFSKNDVMLSAVVMTYWTNFAKTGDPNKPVPQD     577
HNL3    FYAFYHHCQSLMKPAWSDAAHGDEVPYVFGVPMVGPTDLFPCNFSKNDVMLSAVVMTYWTNFAKTGDPNKPVPQD     557
HNL3s   FYAFYHHCQNLMKPAWSDAAHGDEVPYVFGVPMVGPTDLFPCNFSKNDVML*                              553

RNL1    TKFIHTKPNRFEEVAWTRYSQKDQLYLHIGLKPRVKEHYRANKVNLWLELVPHLHNLNDISQYTSTTTKVP          650
RNL2    TKFIHTKPNRFEEVVWSKFNSKEKQYLHIGLKPRVRDNYRANKVAFWLELVPHLHNLHT  ELFTTTTRLPPYAT    627
RNL3    TKFIHTKANRFEEVAWSKYNPRDQLYLHIGLKPRVRDHYRATKVAFWKHLVPHLYNLHDMFHYTSTTTKVPPPDT     652
HNL3    TKFIHTKANRFEEVAWSKYNPRDQLYLHIGLKPRVRDHYRATKVAFWKHLVPHLYNLHDMFHYTSTTTKVPPPDT     632

RNL1        STDITLRPTRKNSTPVTSAFPTAKQD          DPKQQPSPFSVDQ  RDYSTELSVTIAVGASLLFLNILAFA      715
RNL2    RWPPRTPGPGTSGTRRPPPPATLPPESDI          DLGPRAYDRFPGDSRDYSTELSVTAVGASLLFLNILAFA      696
RNL3    THSSHITRRPNGKTWSTKRPAISPAYSNENAPGSWNGDQDAGPLLVENPRDYSTELSVTIAVGASLLFLNVLAFA      727
HNL3    THSSHITRRPNGKTWSTKRPAISPAYSNENAQGSWNGDQDAGPLLVENPRDYSTELSVTIAVGASLLFLNVLAFA      707

RNL1    ALYYKKDKRRHDVH  RRCSPQR      TTTNDLTHA      PEEEIMSLQMKHTDLDHECESIHPHEVVLRTA     777
RNL2    ALYYKRD RRQELRCRRLSPPGGSGSGVPGGGPLLPTAGRELPPEEELVSLQLK    RGGGVADPAEA LRPA       765
RNL3    ALYYRKDKRRQEPL RQPSPQRG      TGAPELGTA      PEEELAALQLGPT HHECEAGPPHDT LRLT     787
HNL3    ALYYRKDKRRQEPL RQPSPQRG      AGAPELGAA      PEEELAALQLGPT HHECEAGPPHDT LRLT     767

RNL1    CPPDYTLAMRRSPDDVPLMTPNTITMIPNTIPGIQP     LHTFNTFTGGQ      NNTLPHPHPHPHSHSTTRV   843
RNL2    CPPDYTLALRRAPDDVPLLAPGALTLLPSGLGPPPPPPPPSLHPFGPFPPPPPTATSHNNTLPHPH     STTRV    836
RNL3    ALPDYTLTLRRSPDDIPLMTPNTITMIPNSLVGLQT     LHPYNTFAAGFNST   GLPNSH      STTRV    848
HNL3    ALPDYTLTLRRSPDDIPLMTPNTITMIPNSLVGLQT     LHPYNTFAAGFNST   GLPHSH                828
```

FIG. 8

IDENTIFICATION OF POLYMORPHISMS IN THE PCTG4 REGION OF XQ13

CROSS-REFERENCE TO RELATED APPLICATIONS

This application is a Continuation-In-Part of PCT international application Ser. No. PCT/US99/09365, filed Apr. 29, 1999, which claims benefit from provisional patent application Ser. No. 60/083,465, filed Apr. 29, 1998. The text of both of these applications is incorporated herein by reference.

The U.S. Government has a paid up license in this invention and the right in limited circumstances to require the patent owner to license others on reasonable terms as provided by Grant No. DK54759 awarded by the National Institute of Health.

FIELD OF THE INVENTION

The present invention relates generally to genetic polymorphisms that are associated with neuropsychiatric disorders and associated conditions including hypothyroidism.

BACKGROUND OF THE INVENTION

Over 2000 human pathological syndromes are known to result from DNA polymorphisms including insertions, deletions, multiplications and nucleotide substitutions. Finding genetic polymorphisms in individuals and following these variations in families provides a means to confirm clinical diagnoses and to diagnose both predispositions and disease states in carriers, preclinical and subclinical affected individuals. Counseling based upon accurate diagnoses allows patients to make informed decisions about potential parenting, ongoing pregnancy, and early intervention in affected individuals.

Polymorphisms associated with pathological syndromes are highly variable and, consequently, can be difficult to identify. Further, normal polymorphic nucleotide changes can complicate detection of abnormal alleles with changes at different nucleotides. Because multiple alleles within genes are common, one must distinguish disease syndrome-related alleles from neutral (non-disease-related) polymorphisms. Most alleles result from neutral polymorphisms that produce indistinguishable, normally active gene products or express normally variable characteristics like eye color. In contrast, some polymorphic alleles are associated with clinical diseases such as sickle cell anemia. Moreover, the structure of disease-related polymorphisms are highly variable and may result from a single point mutation such as occurs in sickle cell anemia, or from the expansion of nucleotide repeats as occurs in fragile X syndrome and Huntington's chorea.

Once a polymorphism or region of interest is identified, a wide variety of technologies exist which may be employed in the diagnosis of heritable syndromes. Traditionally, the diagnosis of such syndromes relied upon enzyme activity testing, statistical analysis, or invasive diagnostic procedures. Recent advances in DNA and related technologies including restriction fragment length polymorphism (RFLP) analysis, the polymerase chain reaction (PCR) and monoclonal or polyclonal antibody based assays provide additional rapid and highly accurate methods to screen for the presence of polymorphisms associated with heritable pathologies.

Among the different polymorphisms, the presence of unstable DNA sequences, such as the expansion of simple nucleotide sequence repeats in genomic DNA, has recently been implicated as a mechanism leading to a number of genetic disorders including pathologies associated with neuropsychiatric disorders such as mental retardation. Mental retardation (MR), which can be generally defined as a slowness or developmental impairment associated with adaptive behavior, is a prominent feature of many neurodevelopmental syndromes. MR is a lifelong disability that can place extreme demands on the families and on the health care system in general. Information obtained from the Incidence and Prevalence Database estimates that there are 6 million persons in the U.S. (3% of the population) with mental retardation. MR can be categorized as mild mental retardation (MMR, IQ 50–70) or as severe mental retardation (SMR, IQ less than 50). It is noted that SMR can be further subcategorized. An average SMR prevalence rate per 1000 people is thought to be as follows: ages 0–4, 1.7; ages 5–9, 2.8; ages 10–14, 3.6; ages 15–19, 4.0; ages 20–29, 3.8; ages 30–39, 3.3; 40–49, 2; ages 50–59, 1.2; ages over 60, 1.0. In 1977, nearly 150,000 adults with mental retardation were institutional residents; by 1992 their numbers had declined by 48% to just under 78,000.

The diagnosis of SMR does not usually occur in the first few years of life, rather it is usually identified later, typically at the school age years. The explanation why there is decreasing prevalence rates in the older age has been attributed to a higher than average mortality among the severely mentally retarded and possibly due to errors in the method used in gathering the data. Approximately one-half of the MR studies have shown rates of MR to be gender-specific. For SMR, the male-to-female ratio, there has been observed a 20% excess of males, which is thought to be due to sex-linked genetic factors.

Due to the prevalence of mental retardation (MR) and its pattern of heritability, the identification of chromosomal regions that are associated with MR pathologies has been the focus of significant research. Mental retardation affects approximately 1% of the U.S. population with mutations in the X-chromosome estimated to cause between 30–50% of these cases (Glass, I. A., (1991) X linked mental retardation. J Med Genet 28:361–371). The genetic mechanisms involved in a number of these X-linked syndromes have been identified and include repetitive DNA expansion in Fragile X (Verkerk, et al., "Identification of a gene (FMR-1) containing a CGG repeat coincident with a fragile X breakpoint cluster region exhibiting length variation in fragile X syndrome", Cell 65:905 (1991)) and FRAXE (Gecz, et al., "Identification of the gene FMR2, associated with FRAXE mental retardation", Nat Genet 13:105–108 (1996)), microdeletions (Billuart, et al., "Identification by STS PCR screening of a microdeletion in Xp21.3–22.1 associated with non-specific mental retardation", Hum Mol Genet 5:977–979 (1996)), and point mutations in the Mental retardation, Aphasia, Shuffling gait, and Adducted thumbs (MASA) syndrome (Schrander-Stumpel, et al., "Spectrum of X-linked hydrocephalus (HSAS), MASA syndrome, and complicated spastic paraplegia (SPG1): clinical review with six additional families", Am J Med Genet 57:107–116 (1995)) and Corpus callosum hypoplasia, Retardation, Adducted thumbs, Spastic paraplegia and Hydrocephalus syndrome (CRASH) (Fransen, et al., "CRASH syndrome: clinical spectrum of corpus callosum hypoplasia, retardation, adducted thumbs, spastic paraparesis and hydrocephalus due to mutations in one single gene", Eur J Hum Genet 3:273–284 (1995)). While this research has provided significant insight into these X-linked syndromes, the causes of the majority of MR remain idiopathic at the current time.

The identification and characterization of specific polymorphisms associated with heritable syndromes such as MR are crucial components in the design of informative diagnostic assays. By identifying specific regions in the human genome which contain disease related polymorphisms, statistical analysis of the prevalence and penetrance of the syndrome is possible. Further, as different formulas are utilized for the assessment of autosomal recessive, autosomal dominant, and X-linked genetic diseases, the identification of the chromosomal location of the polymorphism is a crucial factor in the assessment of pedigree related risk analysis. Such information allows accurate risk assessments to take into account 1) the number of different alleles at each gene locus, 2) the relative frequency of each allele in the population (the most informative have more than one common allele), and 3) whether alleles are distributed randomly throughout the population. As technologies for assessing the presence or absence of a specific polymorphism or polymorphic region are well developed, the primary limitation on diagnostic assays is the lack of information on polymorphisms associated with different pathologies.

What is needed in the art is the identification of novel regions in the human genome which contain polymorphisms that are associated with heritable syndromes. The identification of such regions is particularly useful in that it allows for the design of informative assays and diagnostic tests for susceptibility factors associated with the occurrence of such syndromes. The existence of informative assays which test for the presence of such heritable factors allows the accurate diagnosis of affected individuals and provides these individuals and health care professionals with the knowledge necessary to make informed decisions based on the presence or absence of a disease-associated polymorphism.

SUMMARY OF THE INVENTION

The present invention is directed to the discovery that polymorphisms in the q13 region of the X chromosome are associated with non-Fragile X mental retardation, hypothyroidism and a number of neuropsychiatric disorders including depression, bipolar affective disorder, attention-deficit/hyperactivity disorder (ADHD), and a psychotic disorder. Polymorphisms in this region, designated "PCTG4", were identified by genotyping a large sample of DNAs from a diverse population of mentally ill individuals with respect to a number of loci. These polymorphisms are found to have an increased prevalence in non-Fragile X males and females with mental retardation, autism, depression, hypothyroidism, attention-deficit/hyperactivity disorder (ADHD), and/or a psychotic disorder. The present invention relates to the utilization of the polymorphic regions disclosed herein in the diagnosis and assessment of mental retardation. Since such pathologies can now be detected earlier (i.e., before overt symptoms appear) and more definitively, better treatment options will be available in those individuals identified as having pathologies associated with the disclosed polymorphisms.

The PCTG4 region is shown by fluorescence in situ hybridization to be localized to Xq13 and to span more than 55 kb. A number of polymorphic regions exhibiting base pair insertions, base pair deletions, and repetitive nucleotide sequences associated with neuropsychiatric disorders in the PCTG4 region within Xq13 are identified herein. One of these polymorphisms consists of a 12 base pair insertion in the coding region of the HOPA gene. Another polymorphism consists of a 15 base pair deletion between 6 and 7 base pairs upstream from where the 12 base pair polymorphism occurs. An additional polymorphism consists of a pentanucleotide repeat approximately 7 kb upstream of the 12 base pair polymorphism. Another polymorphism consists of a dinucleotide repeat approximately 4.5 kb downstream of the 12 base pair polymorphism.

In one embodiment, the invention provides isolated nucleic acid molecules which encode PCTG4 region polymorphisms. Isolated nucleic acid can include PCTG4 region polymorphisms having the sequences identified in Table 1 or having sequences that are complementary to these nucleic acid sequences, preferentially hybridize to them and remain stably bound to them under at least moderate, and optionally, under high stringency conditions. In another embodiment, the invention provides a vector comprising polymorphic PCTG4 region sequences. A recombinant cell comprising such a vector inserted into a host cell is also provided. In another embodiment, the invention provides a polypeptide such as an antibody capable of specifically binding a polymorphic epitope on a polypeptide encoded by a gene in the PCTG4 region, for example a HOPA or neuroligin-3 polypeptide. Optionally, the antibody is a monoclonal antibody. In yet another embodiment, the invention provides animals having PCTG4 region transgenes.

In other embodiments, the invention provides methods for screening for PCTG4 region polymorphisms. In one embodiment, the invention provides a method for screening for a polymorphism associated with mental retardation in a subject by determining the presence of a polymorphism in the subject's PCTG4 nucleic acid sequence obtained from the subject, wherein the polymorphism associated with mental retardation is characterized by an insertion or repetitive nucleotide units. In a specific embodiment of this method the polymorphism is the PCTG4 12 base pair insert polymorphism, the 15 base pair deletion polymorphism, the PCTG4 dinucleotide repeat polymorphism, or the PCTG4 pentanucleotide repeat polymorphism disclosed herein. In a more specific embodiment of the invention, the presence of a polymorphism in the PCTG4 nucleic acid sequence is determined by a differential nucleic acid analysis technique such as restriction fragment length polymorphism analysis, direct sequence analysis or polymerase chain reaction analysis.

In another embodiment, the invention provides a method for identifying a patient's susceptibility to pathologies associated with mental retardation by determining the patient's PCTG4 polymorphism pattern, comparing it to the wild type PCTG4 pattern, and then looking for differences indicative of a susceptibility to pathologies associated with mental retardation. In a related embodiment, the invention provides a method of identifying a polymorphism associated with mental retardation by comparing a PCTG4 gene sequence isolated from a mentally retarded subject to a known wild-type PCTG4 gene sequence and identifying recurrent polymorphisms. Typically, a PCTG4 gene sequence used in such a comparison is the HOPA gene, the neuroligin-3 gene, or both the HOPA gene and the neuroligin-3 gene. In specific embodiments of these methods, the presence of a polymorphism in PCTG4 nucleic acid sequences is determined by a differential nucleic acid analysis technique such as restriction fragment length polymorphism analysis, direct sequence analysis, DNA chip analysis, or polymerase chain reaction analysis.

Other embodiments of the invention include kits and articles of manufacture for use in the methods disclosed herein as well as cell based assays for assessing the effects of candidate agents on the activity of genes from the PCTG4 region.

BRIEF DESCRIPTION OF THE DRAWINGS

FIG. 1A shows a schematic representation of the 7.3 kb HOPA cDNA. Transmembrane domains are indicated by filled boxes. The OPA box is indicated by a hatched box, while the topoisomerase domain is denoted by a clear box.

FIG. 1B shows a schematic of the organization of the genomic HOPA gene. Translated regions are indicated by filled boxes. Promoter sequences are denoted by hatched boxes above the main object. Filled triangles denote ECO R1 sites while open triangles denote BAM H1 sites. The sites of the pentanucleotide repeat and the insertion site of the dodecamer repeat are noted with open arrows.

FIG. 5 shows the sequence of a polymorphic region within the HOPA cDNA. The primers used to amplify the region appear in boldface type. Exonic regions of the sequence are underlined. The site of the 12 base pair insertion (CAGCAACACCAG) is denoted by an arrow (SEQ ID NO.: 10).

FIG. 6 shows a wild-type sequence of the HOPA cDNA (SEQ ID No.: 13). This sequence is compared to the sequence of a polymorphic region within the HOPA cDNA of each of 4 male hemizygotes who are schizophrenic or schizoaffective and of the father of 1 female heterozygote who is schizophrenic or schizoaffective (SEQ ID Nos.: 14–18). Exonic regions of the sequences are underlined, and the primers used to amplify the region appear in boldface type.

FIG. 8 shows an amino acid sequence comparison of rat neuroligin-1 (RNL-1) (SEQ ID NO.: 20), rat neuroligin-2 (RNL-2) (SEQ ID NO.: 21), rat neuroligin-3 (RNL-3) (SEQ ID NO.: 22), and two human neuroligin-3 amino acid sequences of cDNA representing the 4 kb (HNL-3) (SEQ ID NO.: 23) and 2.4 kb (HNL-3s) (SEQ ID NO.: 24) transcripts. The cDNA for the 4 kb transcript can be found in Table 3A (SEQ ID NO.: 3), and the cDNA for the 2.4 kb transcript can be found in Table 3B (SEQ ID NO.:4). In FIG. 8 putative signal peptide sequences are delineated by a double underline, and putative transmembrane sequences are denoted by a single underline. RNL-1, RNL-2, and RNL-3 sequences are from Ichtchenko et al., J. Biol. Chem., 271: 2676–682 (1995).

DETAILED DESCRIPTION OF THE INVENTION

Definitions

Figure 2A:
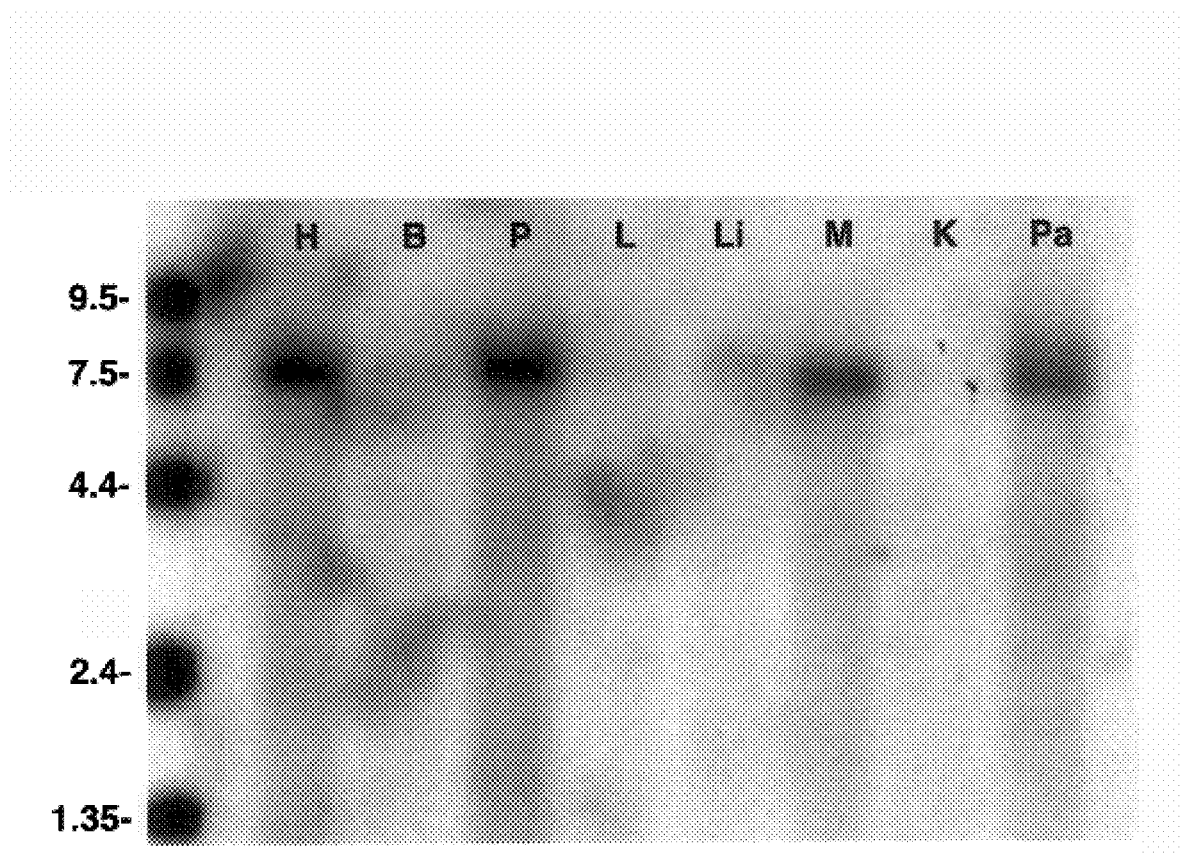
FIG. 2A shows a Northern blot analysis of HOPA mRNA expression in various tissues. The 7.3 kb transcript appears widely expressed as demonstrated by observed signals in human poly(A)+ RNA from heart (H), brain (B), placenta (P), lung (L), liver (Li), skeletal muscle (M), kidney (K) and pancreas (Pa). Hybridization with a beta-actin cDNA was conducted to ensure an even amount of mRNA in each of the lanes.

The term "mental retardation" when used herein is broadly defined as a significantly subaverage general intellectual functioning that is accompanied by significant limitations in adaptive functioning in at least two of the following skill areas: communication, self-care, home living, social/interpersonal skills, use of community resources, self-direction, functional academic skills, work, leisure, health, and safety.

The term "depression" when used herein is broadly defined as a depressed mood or loss of interest or pleasure in activities. The mood may be irritable rather than sad. Individuals suffering from depression typically experience additional symptoms including changes in appetite or weight, sleep and psychomotor activity; decreased energy; feelings of worthlessness or guilt; difficulty thinking, concentrating or making decisions; or recurrent thoughts of death or suicidal thoughts of death or suicidal ideation, plans or attempts.

The term "bipolar affective disorder" when used herein is broadly defined as a clinical course that is characterized by the occurrence of one or more manic episodes (manic episodes are characterized as a distinct period during which there is an abnormally and persistent elevated, expansive or irritable mood lasting for approximately 1 week) or mixed episodes (mixed episodes are characterized by a period of time (lasting approximately 1 week), in which both manic and depressive episodes occur).

The term "hypothyroidism" when used herein is broadly defined as a syndrome wherein the activity of an individual's thyroid system is insufficient for optimal physiological functioning. This syndrome can result from causes both within and outside of the thyroid gland, and is typically characterized by one or more of the following: fatigue, altered metabolic rate, altered thyroid function tests, menstrual disturbances, altered cognition including mental retardation, and sensitivity to cold.

The term "autism" when used herein is broadly defined as a type of pervasive developmental disorder that is defined by the presence of abnormal or impaired development that is manifested before the age of three years and by a characteristic type of abnormal functioning in social interaction, communication and repetitive behavior.

The term "attention-deficit/hyperactivity disorder" or "ADHD" when used herein is broadly defined as a disorder in which a person has a persistent pattern of inattention and/or hyperactivity-impulsivity that is more frequent or severe than is typically observed in individuals at a comparable level of development. Inattention may be manifested in academic, occupational, or social situations and may be characterized by, for example, failure to give close attention to details, careless mistakes, failure to complete tasks, etc. Hyperactivity may be characterized by fidgetiness, excessive talking, feelings of restlessness, difficulty engaging in sedentary activities, etc. Impulsivity may be characterized by, for example, impatience, difficulty in delaying response, frequent interruption of others, etc. This disorder may be characterized by association of one or more of the following, which vary depending on age and developmental stage: low frustration tolerance, temper outbursts, bossiness, stubbornness, mood lability, demoralization, dysphoria, poor self-esteem, rejection by peers, etc.

The term "psychotic disorder" when used herein is broadly defined as a mental disorder in which an individual loses contact with reality. Examples of psychotic disorders include, but are not limited to, schizophrenia, schizophreniform disorder, delusional disorder, schizoaffective disorder, and brief psychotic disorder. A psychotic disorder can be characterized by delusions, prominent hallucinations, disorganized speech, disorganized or catatonic behavior, etc.

The term "schizophrenia" when used herein is broadly defined as a mental disorder that is associated with psychosis and a decline in general functioning. This disorder is typically characterized by loss of contact with reality, hallucinations, delusions, abnormal thinking, disorganized speech, disorganized or catatonic behavior, and disrupted work and social functioning. The term "schizophrenia" includes all subtypes of schizophrenia including paranoid schizophrenia, disorganized schizophrenia, catatonic schizophrenia, undifferentiated schizophrenia, and residual schizophrenia.

The term "polymorphisms" is broadly defined to include all variations that are known to occur in nucleic and amino acid sequences including insertions, deletions, substitutions and repetitive sequences including multiplications.

The term "PCTG4 region" is defined as the area of the X chromosome which contains the nucleic acid sequences shown in Table 1.

The term "wild-type sequence" when used herein refers to a sequence in the PCTG4 region which does not contain pathogenic polymorphisms.

The terms "HOPA polypeptide" and "HOPA" when used herein encompass native sequence HOPA and HOPA polymorphic variants (which are further defined herein). HOPA polypeptides may be isolated from a variety of sources, such as from human tissue types or from another source, or prepared by recombinant or synthetic methods.

The terms "neuroligin polypeptide" and "neuroligin" when used herein encompass native sequence neuroligin-3 and neuroligin-3 polymorphic variants (which are further defined herein). Neuroligin-3 polypeptides may be isolated from a variety of sources, such as from human tissue types or from another source, or prepared by recombinant or synthetic methods.

A "native sequence" is a polypeptide having the same amino acid sequence as sequence derived from nature. Such native sequences can be isolated from nature or can be produced by recombinant or synthetic means. The terms "native sequence HOPA" or terms "native sequence neuroligin-3" specifically encompasses naturally-occurring variant forms (e.g., alternatively spliced forms) and naturally-occurring allelic variants of the PCTG4 gene embodiment of the invention. The native sequence HOPA, for example, is a mature or full-length native sequence human HOPA polypeptide comprising amino acids 1 to 2024 of Table 5.

"Variant" means a variant as defined below having at least about 80% amino acid sequence identity with HOPA or neuroligin-3, such as the HOPA polypeptide having the deduced amino acid sequence shown in Table 5 for a full-length native sequence HOPA. Such variants, include, for example, HOPA polypeptides wherein one or more amino acid residues are added, or deleted, at the N- or C-terminus of the sequence of Table 5. Ordinarily, a HOPA variant will have at least about 80% or 85% amino acid sequence identity with native HOPA sequences, more preferably at least about 90% amino acid sequence identity. Most preferably a HOPA variant will have at least about 95% amino acid sequence identity with native HOPA sequence of Table 5.

"Percent (%) amino acid sequence identity" with respect to the amino acid sequences identified herein is defined as the percentage of amino acid residues in a candidate sequence that are identical with the amino acid residues in the HOPA and neuroligin-3 sequences, after aligning the sequences in the same reading frame and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST software (see e.g. Altschul et al., J. Mol. Biol., 5; 215(3): 403–410 (1990)). Those skilled in the art can determine appropriate parameters for measuring alignment, including any algorithms needed to achieve maximal alignment over the full length of the sequences being compared.

"Percent (%) nucleic acid sequence identity" with respect to the PCTG4 sequences identified herein is defined as the percentage of nucleotides in a candidate sequence that are identical with the nucleotides in the PCTG4 sequences, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST software (see e.g. Altschul et al., J. Mol. Biol., 5; 215(3): 403–410 (1990)). Those skilled in the art can determine appropriate parameters for measuring alignment, including any algorithms needed to achieve maximal alignment over the full length of the sequences being compared.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified to a degree sufficient to obtain N-terminal or internal amino acid sequence by use of a spinning cup sequenator, or to homogeneity by SDS-PAGE under non-reducing or reducing conditions using Coomassie blue or silver stain. Isolated polypeptide includes polypeptide in situ within recombinant cells, since at least one component of the PCTG4 natural environment will not be present. Ordinarily, however, isolated polypeptide will be prepared by at least one purification step (referred to herein as an "isolated and purified polypeptide").

An "isolated" PCTG4 nucleic acid molecule is a nucleic acid molecule that is identified and separated from at least one contaminant nucleic acid molecule with which it is ordinarily associated in the natural source of the PCTG4 nucleic acid. An isolated PCTG4 nucleic acid molecule is other than in the form or setting in which it is found in nature. Isolated PCTG4 nucleic acid molecules therefore are distinguished from the PCTG4 nucleic acid molecule as it exists in natural cells. However, an isolated PCTG4 nucleic acid molecule includes PCTG4 nucleic acid molecules contained in cells that ordinarily express PCTG4 where, for example, the nucleic acid molecule is in a chromosomal location different from that of natural cells.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking may be accomplished by ligation at convenient restriction sites. If such sites do not exist, the synthetic oligonucleotide adaptors or linkers may be used in accordance with conventional practice.

"Polynucleotide" and "nucleic acid" refer to single or double-stranded molecules which may be DNA, comprised of the nucleotide bases A, T, C and G, or RNA, comprised of the bases A, U (substitutes for T), C, and G. The polynucleotide may represent a coding strand or its complement. Polynucleotide molecules may be identical in sequence to the sequence which is naturally occurring or may include alternative codons which encode the same amino acid as that which is found in the naturally occurring sequence (See, Lewin "Genes V" Oxford University Press Chapter 7, pp. 171–174 (1994)). Furthermore, polynucleotide molecules may include codons which represent conservative substitutions of amino acids as described. The polynucleotide may represent genomic DNA or cDNA.

"Polypeptide" refers to a molecule comprised of amino acids which correspond to those encoded by a polynucleotide sequence. The polypeptide may include conservative substitutions where the naturally occurring amino acid is replaced by one having similar properties, where such conservative substitutions do not alter the function of the polypeptide (See, Lewin "Genes V" Oxford University Press Chapter 1, pp.: 9–13 (1994)).

The term "antibody" is used in the broadest sense and specifically covers single anti-HOPA and anti-neuroligin-3 monoclonal antibodies (including agonist, antagonist, and neutralizing antibodies) and anti-HOPA and anti-neuroligin-3 antibody compositions with polyepitopic specificity. The term "monoclonal antibody" as used herein refers to an antibody obtained from a population of substantially homogeneous antibodies, i.e., the individual antibodies comprising the population are identical except for possible naturally-occurring mutations that may be present in minor amounts.

Identification of Neuropsychiatric and Hypothyroidism Associated Polymorphisms in the PCTG4 Region Polymorphisms were identified by isolating and sequencing a large number of human genomic cosmids containing large trinucleotide repeats. One of these cosmids, CTG-4, is shown to contain sequences of a region (designated "PCTG4") which maps to the q13 region of the X-chromosome and contains at least two genes. One of the genes localized to the PCTG4 region expresses a 7.3 kb mRNA which encodes a human OPA-containing gene (HOPA). A second gene localized to the PCTG4 region expresses four different transcripts of 2.4, 4.4, 7.0 and 7.5 kb mRNA which encodes a human orthologue of the rat neuroligin-3 gene (see e.g Ichtchenko et al. J. Biol. Chem. 271(5): 2676–2682).

As discussed in detail below, the gene encoding HOPA contains a rare polymorphism that is tightly associated with mental retardation, autism, depression, and hypothyroidism and that shows an increased prevalence for attention-deficit/hyperactivity disorder and a psychotic disorder. The genomic organization of the HOPA gene is illustrated in FIG. 1B. The gene consists of 44 exons ranging from 51 bp to 374 bp in size beginning at bp 1391 and ending at 20596 of the sequence shown in Table 1. All 44 exons obey the GT-AG splicing rule. The first in line ATG occurs in exon 4 (bp 2712) while the TGA stop codon occurs in exon 44 (bp 24,864) for the putative 2024 amino acid protein. A promoter analysis using Promoter Scan (Prestridge, J. Mol. Biol. 249(5): 923–932 (1995)) delineated two possible promoters for the gene stretching from bp 936 to 1186 (score 62.72, promoter cutoff score 53.00) and bp 1398 to 1648 (score 101.61, promoter cutoff score 53.00). Although the analysis predicts that the second promoter is the more likely one, neither site contains a TATA box. Since the first exon of the longest HOPA transcript sequenced begins at bp 1390 (which is in the middle of the second promoter site) and the apparent translation initiation (ATG) codon is at bp 2712 (exon 4), it is possible that both promoters may be used.

BLAST analysis (Alschul et al, 1990) of the HOPA cDNA sequence comparison analysis of this 26 kb genomic sequence fails to identify any significant matches outside the repetitive DNA regions except for the previously described cDNA/ESTs CAGH45 mRNA (U80742, Margolis et al., Hum. Genet. 100(1) 114–122 (1997)) and KLAA0192 (D83783, Nagase et al., DNA Res. 3(5):321–329, 341–354 (1996)) (Philibert et al., Mol. Psych. 3:303–309 (1998)). GRAIL analysis (Uberbacher and Mural, PNAS 88(24): 11261–11265 (1991)) of the 26 kb sequence fails to produce evidence of co-linear transcripts of other genes.

The HOPA gene sequence is rich with repetitive DNA elements. The dodecamer repeat, an insertion of the 12 bp CAGCAACACCAG (SEQ ID NO.: 10) associated with mental retardation, autism, attention-deficit/hyperactivity disorder, and schizophrenia occurs in exon 42 (at approximately bp 23950 in. Table 1) in affected individuals. The deletion of the 15 bp CAGCAGCAGCAACAG (SEQ. ID No.: 19) associated with schizophrenia occurs in exon 42 (between approximately bp 23929 and bp 23943 in Table 1) in affected individuals. A large pentanucleotide repeat $(CTCTT)_{15}$ occurs in the intron between exons 30 and 31. A small trinucleotide repeat $(ATT)_8$ is found between bp 629 and 652. Two large cryptic CAG repeats are found contained within exons 41 and 42. Finally, 14 distinct Alu repeats are interspersed through the 26 kb gene which is much higher than the normal occurrence rate for Alu repeats of 1 every ~6 kb (Novick et al., Electrophoresis 16: 1596–1601, (1995)). Many of these repetitive elements may be useful in the fine disequilibrium mapping of the region in the hope of demonstrating a clear relationship to the observed syndromes.

Figure 2B:
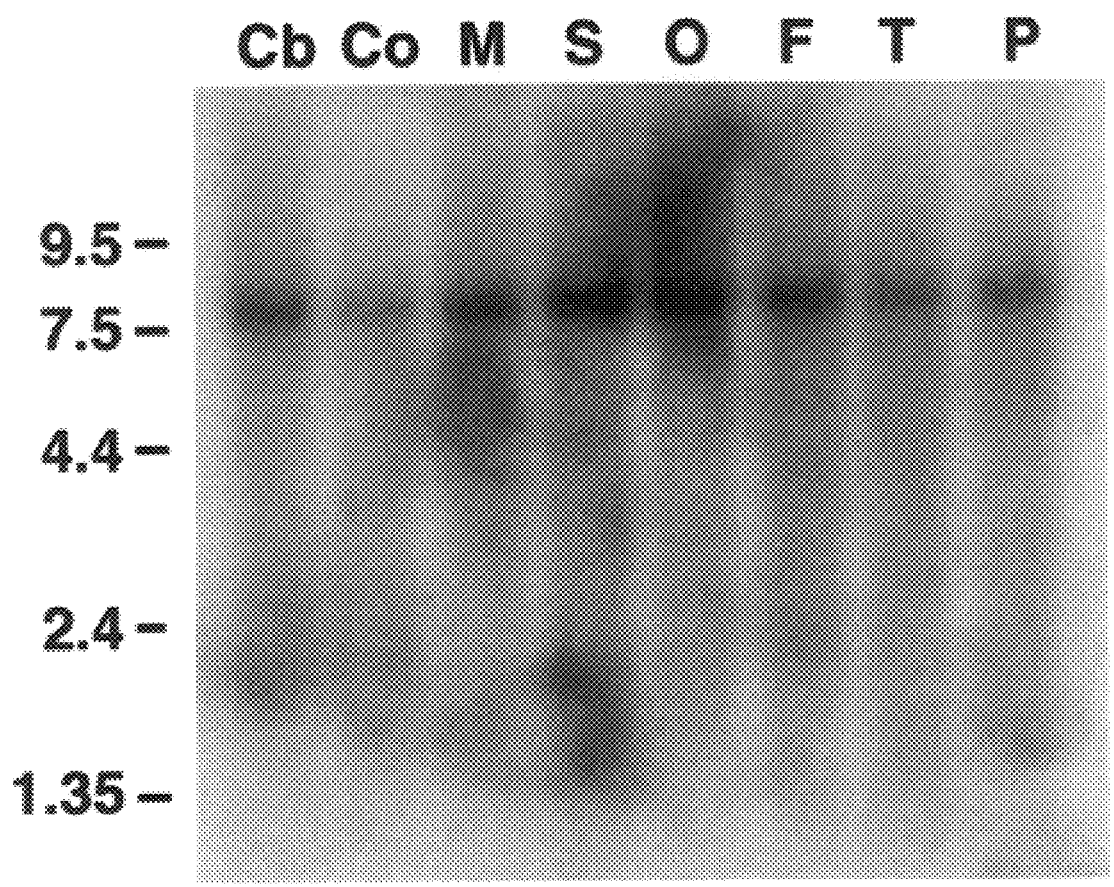
FIG. 2B shows a Northern blot analysis of HOPA mRNA expression in the adult brain. The 7.3 kb transcript appears widely expressed in adult human brain as demonstrated by observed signals in human poly(A)+ RNA from cerebellum (Cb), cortex (Co), medulla (M), spinal cord (S), occipital pole (O), frontal pole (F), thalamus (T), and putamen (P). Hybridization with a beta-actin cDNA was conducted to ensure an even amount of mRNA in each of the lanes.
Figure 2C:
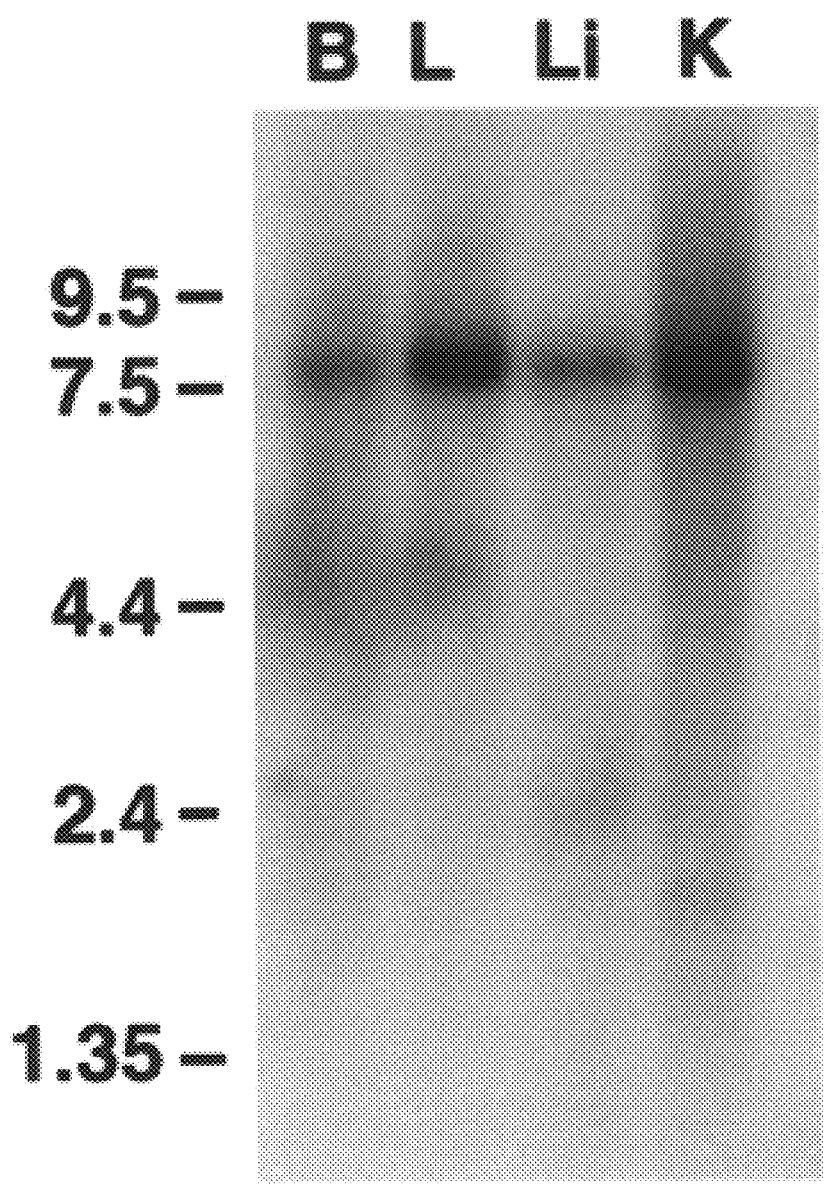
FIG. 2C shows a Northern blot analysis of HOPA mRNA expression in various human fetal tissues. The 7.3 kb transcript appears widely expressed as demonstrated by observed signals in human poly(A)+ RNA from fetal brain (B), lung (L), liver (Li) and kidney (K). Hybridization with a beta-actin cDNA was conducted to ensure an even amount of mRNA in each of the lanes.
Figure 3:
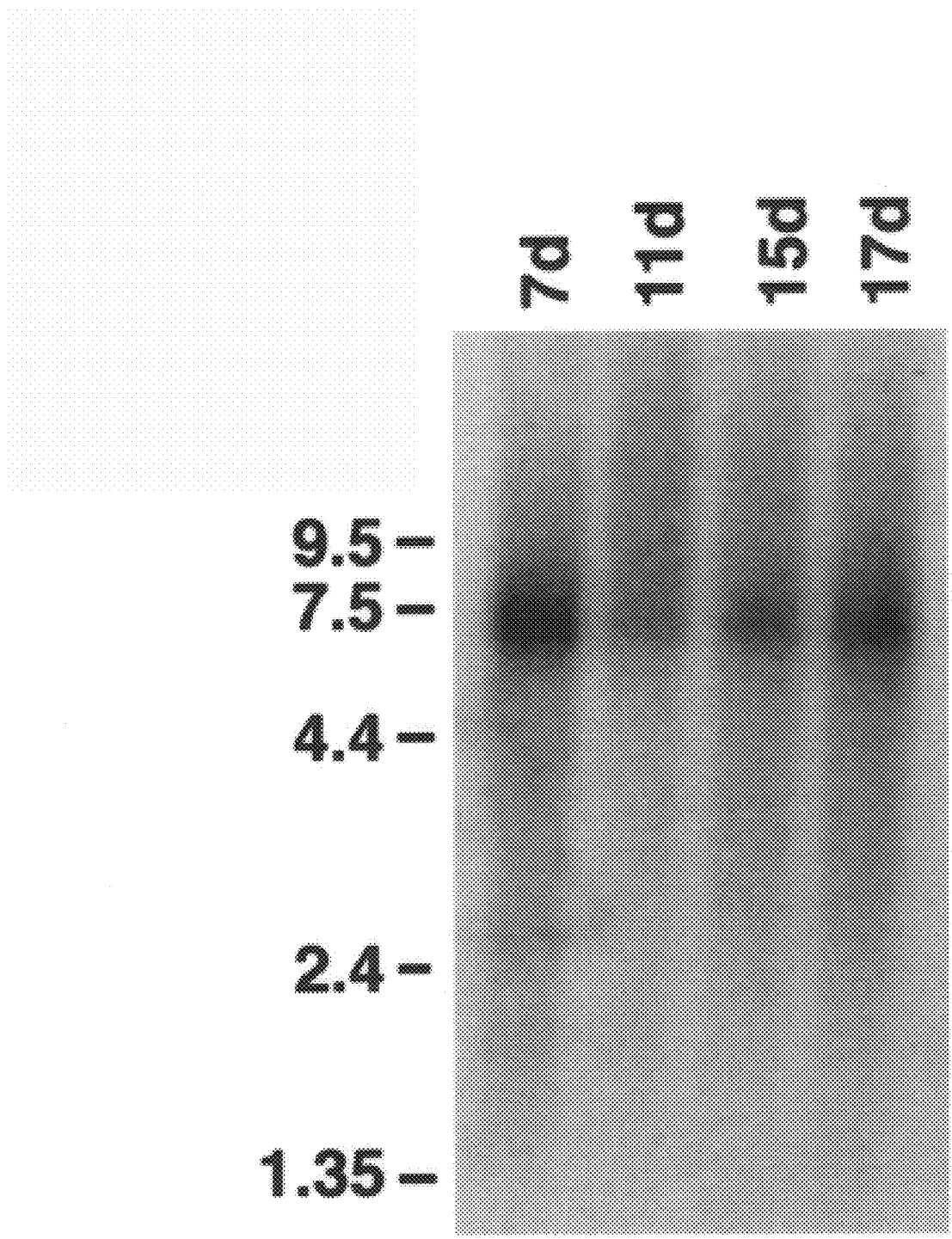
FIG. 3 demonstrates the expression of the murine HOPA orthologue, MOPA-1, in murine fetal development. As the blot demonstrates, expression is highest at embryonic day 7, declining rapidly to almost undetectable levels at day 11, and then recovering to easily visualized expression shortly before birth at day 17. Northern blotting analysis demonstrated that the ~7.5 kb transcript was expressed in all adult issues surveyed including heart, lung, pancreas, skeletal muscle and placenta, these results are consistent with the HOPA gene having an essential cellular function and with the need for this function being particularly significant early in gestation.

Northern blotting analysis demonstrates a widespread, yet chronologically regulated expression pattern. FIG. 2B demonstrates that a single ~7.5 kb transcript is expressed widely throughout the adult human brain tissues including those derived from the telencephalon (cerebral cortex, putamen, occipital lobe, frontal lobe and temporal lobe), metencephalon (cerebellum) and myencephalon (medulla). FIG. 2C illustrates the expression of the HOPA gene in human fetal tissues. Significant expression is seen in all four human fetal tissues examined including the brain and is particularly marked in fetal liver and kidney. FIG. 3 demonstrates the expression of the murine HOPA orthologue, MOPA-1, in murine fetal development. As the blot demonstrates, expression is highest at embryonic day 7, declining rapidly to almost undetectable levels at day 11, and then recovering to easily visualized expression shortly before birth at day 17. Northern blotting analysis demonstrated that the ~7.5 kb transcript was expressed in all adult issues surveyed including heart, lung, pancreas, skeletal muscle and placenta, these results are consistent with the HOPA gene having an essential cellular function and with the need for this function being particularly significant early in gestation.

The neuroligin-3 gene is one ligand for a family of neuronal cell surface receptors termed Neurexins. Together with the Neurexins, neuroregulins transmit signals between adjacent cells by functioning like a lock and key. These types of molecules control all aspects of a neuron's development including growth, replication, differentiation and cell death. These same molecules also govern the development and maintenance of individual neurons with respect to other neurons allowing the maturation of precisely wired neural networks. As many neuronal receptors play crucial roles in the development and homeostasis of the central nervous systems in metazoans, polymorphisms in the PCTG4 region which would effect the expression or function of neuroligin-3 in the brain are consistent with the association of such polymorphisms with neuropsychiatric disorders.

It is a discovery of the present invention that there is a genetic linkage between various neuropsychiatric disorders and hypothyroidism and polymorphisms in the PCTG4 region. DNA sequence analyses of PCTG4 region sequences revealed a number of distinct polymorphisms in affected individuals. Initial polymorphism analysis across a region of repetitive DNA in the HOPA gene revealed a rare 12 base pair exonic polymorphism (<<1% in non-ill males) having an increased prevalence in non-Fragile X males with mental retardation (4%, p<0.04, n=81). Subsequent polymorphism analysis has identified two additional polymorphisms consisting of a pentanucleotide repeat approximately 7 kb upstream and a dinucleotide repeat approximately 4.5 kb downstream of the 12 base pair polymorphism (see FIGS. 7 and 8).

The 12 base pair polymorphism is not present in the highly conserved mouse homologue that has 100% amino acid identity to the human sequence near the polymorphism. Subsequent screening of two additional independent cohorts of non-Fragile X mentally retarded patients and ethnically matched controls demonstrated an even higher prevalence of the 12 base pair polymorphism in males with mental retardation (8%, p<0.0003, n=125, and 14%, p<0.10, n=36) versus the controls. Multivariate analysis was conducted in an effort to identify other phenotypic components in affected individuals, and the findings suggested an increased incidence of histories of hypothyroidism (p<0.001) and treatment with antidepressants (p<0.001). Since many of the affected males also had autistic symptoms, segregation analysis was performed in a set of families containing autistic probands, and the results demonstrated that the polymorphism was present in 7% of these autistic male probands (3 of 44). These data establish that the presence of this 12 base pair polymorphism confers significant susceptibility for mental retardation, hypothyroidism, depression, and autism.

Schizophrenic or schizoaffective subjects from families in which at least 2 siblings were identified as schizophrenic or schizoaffective were screened for a variation in the HOPA gene and these findings were compared to the frequency of newborns that have a variation in the HOPA gene. This study revealed an increased frequency of allelic variants in schizophrenics (p<0.03) (see Example 6). These results establish that the presence of a 12 base pair insertion or a 15 base pair deletion confers an increased prevalence for a psychotic disorder, particularly schizophrenia.

A study of a small number of male cohorts with attention-deficit/hyperactivity disorder revealed the presence of a 12 base pair insertion in one cohort. Thus, a variation in the HOPA gene can confer an increased prevalence for attention-deficit/hyperactivity disorder. These results are consistent with findings that alterations in thyroid function, both in utero and during childhood development, are associated with alteration in concentration and attention, and in particular, attention-deficit/hyperactivity disorder. (Hauser et al., Toxicol. Ind. Health, 14: 85–101 (1998); Gorman, Thyroid, 9: 721–26 (1999); and Rovet et al., J. Child Psychol. Psychiatry, 37: 579–85 (1996)).

Observations from studies of individuals having duplications in segments of the long arm of the X chromosome are consistent with the disclosed association between polymorphisms in the PCTG4 region of Xq13 and mental retardation and hypothyroidism. In particular, individuals having an inverted duplication of a segment in the long arm of the X chromosome, 46, Y, dup, (X)(q21.2q13.3) are observed to have growth and mental retardation and hypothyroidism (see e.g. Shapira et al., Am. J. Med. 72:409–414 (1997)). In addition, a rearranged Xqter→q13::Xp11.4→qter has been described in a family exhibiting some of the traits of Turner syndrome including short stature, cubitis valgus and hypothyroidism (Aller et al., Clin. Genet. 48: 317–320 (1995)).

Studies in autistic individuals are consistent with the disclosed association between polymorphisms in the PCTG4 region of Xq13 and autism. In particular, some individuals with autism or autistic-like conditions also exhibit congenital hypothyroidism or have mothers who had probably been hypothyroid in pregnancy. Such studies suggest that hypothyroid hormone deficiency in early development might cause central nervous system damage such that autistic symptoms are likely to ensue. (see e.g. J Child Psychol Psychiatry, Mar, 33(3):531–42 (1992)).

Observations in individuals suffering from depression are consistent with the disclosed association between polymorphisms in the PCTG4 region of Xq13 and hypothyroidism and treatment with antidepressants. See generally Wartofsky, L "Diseases of the Thyroid" in Harrison's Principles of Internal Medicine, 14th edition, A S Fauci, E Braunwald, K J Isselbacher, J D Wilson, J B Martin, D L Kasper, S L Hauser, D L Longo, eds. pp 2012–2034, McGraw-Hill, New York, (1998). Hypothyroidism has long been known to cause depression (see e.g. Haggerty et al., Annu. rev. Med. 46: 37–46 (1995)) and almost 100% of patients with severe hypothyroidism are found to have serious concurrent depression (Whybrow et al., Arch. Gen. Psychiatry 20: 48–63 (1969)). Moreover, a thyrotropin-stimulating hormone driven increase of circulating thyroid hormone typically occurs in euthyroid individuals in the face of depression or other stress states: an increase in thyroid hormone favors recovery from depression (see e.g. Bauer et al., Integr. Psychiatry 6: 75–100 (1988); Chopra et al., Metabolism 39: 538–543 (1990)). Conversely, even subtle decrements in thyroid system resiliency impair recovery from depression (Prange et al., Neuropsychopharmacology ed. W E Bunney et al., 352–361 (1990)).

The disclosed association between polymorphisms in the PCTG4 region of Xq13 and hypothyroidism and depression is also linked to observations in individuals suffering from bipolar affective disorder (see e.g. Persad et al., Can. J. Psychiatry, 41: 23–27 (1996)). In particular, approximately 10% of individuals who develop clinical depression have a phenomenologically distinct form of mood disorder known as bipolar disorder, in which depressive episodes are interspersed with episodes of mania. Investigators find that subtypes of bipolar disorder in which depression and mania alternate very rapidly (rapid cycling bipolar disorder) or are intermixed (mixed episode) have particularly high rates of subclinical hypothyroidism (see e.g. Bauer et al., Arch. Gen. Psychiatry 47: 427–432 (1990)). Grade 2 or grade 3 hypothyroidism has been observed in as many as 40% of rapid cycling bipolar patients with overt hypothyroidism occurring in an additional 25–505 of patients. In addition, anti-thyroid antibodies have been reported in 33% of patients with mixed episodes, a rate much higher than that seen in other psychiatric disorders or in nonpsychiatric control subjects (Haggerty et al., Psychoneuroendocrinology 12(4): 359 (1990)).

Studies in schizophrenic or schizoaffective individuals are consistent with the disclosed association between polymorphisms in the PCTG4 region of Xq13 and hypothyroidism. In particular, some individuals with schizophrenia or schizoaffective disorder also have hypothyroidism or have a mother with hypothyroidism (see Example 6).

The 12 base pair insertion polymorphism is of interest as it occurs within a highly conserved region of the HOPA protein. Moreover, this polymorphism occurs in the middle of a putative OPA domain, a domain which is thought to play an important role in tissue specific development. While the mechanism(s) through which this 12 base pair polymorphism may contribute to the development of various neuropsychiatric disorders and hypothyroidism is not entirely clear, the data disclosed herein are consistent with models wherein polymorphisms in the PCTG4 protein are associated with a form of X-linked mental retardation, and suggest a cellular mechanism for this disorder. Like other genes associated with MR, such as FMR-1, the CTG-4 mRNA occurs ubiquitously in adult tissues. Verheij, et al., "Characterization of FMR1 proteins isolated from different tissues", Hum Mol Genet 4:895–901 (1995). The presence of both a DNA topoisomerase II domain in the 5' region and a OPA domain (Duboule, et al., "DNA sequences homologous to the Drosophila opa repeat are present in murine mRNAs that are differentially expressed in fetuses and adult tissues", Mol Cell Biol 7:2003–2006 (1987)), the mammalian counterpart of the drosophila OPA (odd paired) domain in the 3' region of HOPA suggests that a mutant HOPA gene product could alter brain development. (Grabowski, et al., "An adult male specific gene in Drosophila containing the repetitive element opa", Biochim Biophys Acta 1090:115–118 (1991); Wharton, et al., "Opa: a novel family of transcribed repeats shared by the Notch locus and other developmentally regulated loci in D. melanogaster", Cell 40:55–62 (1985).

Consistent with the above observations, the HOPA gene product is found to be a member of the thyroid receptor-associated protein (TRAP) complex (Ito et. al., Molecular Cell, 3: 361–370 (1999)). Specifically, the HOPA gene is shown to encode a protein also designated "TRAP 230", which is a member of a large multisubunit complex of thyroid hormone receptor associated proteins that, in a ligand dependent manner both interact with thyroid receptor and facilitate thyroid receptor function on naked DNA templates in conjunction with general initiation factors. As many nuclear receptors play crucial roles in the development and homeostasis of the central nervous systems in metazoans, polymorphisms in the PCTG4 region which would effect the expression or function of HOPA within the TRAP complex in the brain are consistent with the association of such polymorphisms with various neuropsychiatric disorders and hypothyroidism.

The present invention provides compositions of matter and diagnostic and prognostic methods related to the discovery that polymorphisms in the PCTG4 region are associated with mental retardation, autism, depression, hypothyroidism, attention-deficit/hyperactivity disorder, and a psychotic disorder. According to the methods of the present invention, alteration of wild-type PCTG4 sequences is detected. "Alteration of wild-type sequences" encompasses all forms of polymorphisms including deletions, insertions and point mutations in the coding and noncoding regions. Polymorphisms may occur anywhere in this region of the X chromosome including coding and noncoding regions.

A key component of this invention is the delineation of a specific chromosomal region having polymorphisms associated with neuropsychiatric disorders and hypothyroidism. While illustrative polymorphisms are provided, knowledge of a specific polymorphism is not require to practice the invention. Protocols well known in the art such as RFLP analysis (as discussed below) may be used to assess unidentified polymorphisms in nucleic acid samples. Further as multiple polymorphisms may be found in regions associated with heritable pathologies, it is anticipated that additional polymorphisms in this region will be identified. See e.g. Cuppens et al., J. Clin. Invest. 101(2): 487–496 (1998), discussing one of the over 120 polymorphisms associated with pathologies related to mutations in the cystic fibrosis transmembrane conductance regulator genes. The present invention therefore provides methods of identifying novel PCTG4 polymorphisms which are correlated with a predisposition for neuropsychiatric disorders and/or hypothyroidism by determining one or more sequences in the PCTG4 region from individuals known to have mental retardation and then comparing these sequences to that of known PCTG4 region wild type sequences.

The presence of PCTG4 polymorphisms associated with neuropsychiatric disorders and/or hypothyroidism may be ascertained by testing a biological sample from an individual. Biological samples are those samples of materials which have cells containing nucleic acid sequences. Biological samples may be obtained from a wide variety of sources including saliva, waste products and a variety of tissues. Most simply, blood can be drawn and DNA extracted from the cells of the blood. In addition, prenatal diagnosis can be accomplished by testing fetal cells, placental cells or amniotic cells. Alteration of wild-type PCTG4 sequences, whether, for example, by insertion or deletion, can be detected by any of a variety of means known in the art including the illustrative protocols discussed herein. Further, once a polymorphism is identified, its association with a pathology may be assessed by a variety of statistical and pedigree analyses that are well known in the art. See e.g. Handbook of Human Genetic Linkage (Joseph D. Terwilliger & Jurg Ott eds., 1st ed. 1994); Fundamentals of Biostatistics (Bernard Rosner ed., 1st ed., 1982). For example, evidence that polymorphisms in the PCTG4 region are associated with mental retardation can be obtained by finding sequences in DNA extracted from affected kindred members which may create abnormal PCTG4 gene products or abnormal levels of the gene products. Such mental retardation susceptibility alleles will co-segregate with the disease in large kindreds. They will also be present at a much higher frequency in non-kindred individuals with mental retardation than in individuals in the general population.

It is well known in the art that both genetic and environmental factors can play a role in the occurrence and severity of a large number of pathological conditions, including those conditions which are linked to polymorphisms in the PCTG4 region of Xq13. See e.g. Smits et al., Am. J. Med. Genet. 43(1–2): 365–372 (1992); Trottier et al., J. Psychiatry Neurosci, 24(2): 103–115 (1999); Agid et al., Mol. Psychiatry 4(2): 163–172 (1999) and De Braekeleer et al., Coll. Anthropol. 22(1) 9–15 (1998). Moreover, pathological conditions that are X-linked are likely to exhibit different characteristics depending upon the gender of the individual. In this context, the present invention provides a method for screening for the presence of a heritably linked form of mental retardation, autism, depression, bipolar affective disorder, hypothyroidism, attention-deficit/hyperactivity disorder, or a psychotic disorder in a subject, by determining the presence of a polymorphism associated with these disorders in a PCTG4 nucleic acid sequence obtained from the subject. As these syndromes are known to be of multifactorial origin, the determination of the presence of a heritably linked form of these pathologies may be assessed in individuals exhibiting a spectrum of characteristics (including no observable pathological phenotype).

Nucleic Acid Compositions of the Invention

The present invention provides isolated nucleotide sequences from the PCTG4 region having polymorphisms associated with various neuropsychiatric disorders and hypothyroidism. The invention further provides variations and modifications of these sequences and molecules that they encode using methods that are well known in the art such as site-directed PCR mutagenesis. Site-directed mutagenesis (Carter et al., Nucl. Acids Res., 13:4331 (1986); Zoller et al., Nucl. Acids Res., 10:6487 (1987)), cassette mutagenesis (Wells et al., Gene, 34:315 (1985)), restriction selection mutagenesis (Wells et al., Philos. Trans. R. Soc. London SerA, 317:415 (1986)) or other known techniques can be performed on the cloned DNA to produce the variant DNA. Covalent modifications of the sequences disclosed herein are included within the scope of this invention. See, e.g., Current Protocols In Molecular Biology, Volume 2, Units 10,11 and 14, Frederick M. Ausubul et al. eds., 1995: Molecular Cloning, A Laboratory Manual, § 12, Tom Maniatis et al. eds., 2d ed. 1989.

The description below relates primarily to production of the sequences of the invention by culturing cells transformed or transfected with a vector containing polymorphic sequences of the PCTG4 region. It is, of course, contemplated that alternative methods, which are well known in the art, may be employed to prepare these molecules. For instance, polymorphic sequences, or portions thereof, may be produced by direct oligomer or peptide synthesis using solid-phase techniques (see, e.g., Stewart et al., Solid-Phase Peptide Synthesis, W. H. Freeman Co., San Francisco, Calif. (1969); Merrifield, J. Am. Chem. Soc., 85:2149–2154 (1963)). In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PCTG4 sequences may be chemically synthesized separately and combined using chemical or enzymatic methods.

DNA having polymorphic sequences of the present invention may be obtained from genomic or cDNA libraries prepared from tissue from individuals having these sequences. Accordingly, human PCTG4 cDNA sequences (such as those encoding the HOPA and neuroligin-3 genes) can be conveniently obtained from a cDNA library prepared from human tissue. The polymorphic sequences may also be obtained from a genomic library or by oligonucleotide synthesis. Libraries can be screened with probes (such as oligonucleotides of at least about 20–80 bases) designed to identify the sequence of interest or the protein encoded by it. Illustrative libraries include λgt11 human heart cDNA library (Clonetech laboratories, Inc.) and λgt11 mouse heart cDNA library (Clonetech Laboratories, Inc.). Screening the cDNA or genomic library with the selected probe may be conducted using standard procedures, such as described in Sambrook et al., Molecular Cloning: A Laboratory Manual (New York: Cold Spring Harbor Laboratory Press, 1989). An alternative means to isolate a gene encoded by the PCTG4 region is to use PCR methodology [Sambrook et al., supra; Dieffenbach et al., PCR Primer: A Laboratory Manual (Cold Spring Harbor Laboratory Press, 1995)].

The Examples below describe techniques for screening DNA libraries. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs which employ various algorithms to measure homology.

Nucleic acid having protein coding sequences may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

Large amounts of the polynucleotides of the present invention may be produced by replication in a suitable host cell using any of a variety of techniques that are well known in the art. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian or plant or other eukaryotic cell lines. The purification of nucleic acids produced by the methods of the present invention are described, e.g., in Sambrook et al., 1989 or Ausubel et al., 1992.

Polynucleotide constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Such vectors may be prepared by means of standard recombinant techniques well known in the art and discussed, for example, in Sambrook et al., 1989 or Ausubel et al., 1992. An appropriate promoter and other necessary vector sequences will be selected so as to be functional in the host, and may include, when appropriate, those naturally associated with the PCTG4 region. Examples of workable combinations of cell lines and expression vectors are described in Sambrook et al., 1989 or Ausubel et al., 1992. Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 or promoters derived from murine Molony leukemia virus, mouse tumor virus, avian sarcoma viruses, adenovirus II, bovine papilloma virus or polyoma. In addition, the construct may be joined to an amplifiable gene (e.g., DHFR) so that multiple copies of the gene may be made. For appropriate enhancer and other expression control sequences, see also Enhancers and Eukaryotic Gene Expression, Cold Spring Harbor Press, Cold Spring Harbor, N.Y. (1983). While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g., ampicillin, neomycin, methotrexate, etc., b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection, or the vectors can be introduced directly into host cells by methods well known in the art, which vary depending on the type of cellular host, including electroporation; transfection employing calcium chloride, rubidium chloride calcium phosphate, DEAE-dextran, or other substances; microprojectile bombardment; lipofection; infection (where the vector is an infectious agent, such as a retroviral genome); and other methods. See generally, Sambrook et al., 1989 and Ausubel et al., 1992. The introduction of the polynucleotides into the host cell by any method known in the art, including, inter alia, those described above, will be referred to herein as "transformation." The cells into which have been introduced nucleic acids described above are meant to also include the progeny of such cells.

Large quantities of the nucleic acids and polypeptides of the present invention may be prepared by expressing PCTG4 nucleic acids or portions thereof in vectors or other expression vehicles in compatible prokaryotic or eukaryotic host cells. The most commonly used prokaryotic hosts are strains of *Escherichia coli*, although other prokaryotes, such as Bacillus subtilis or Pseudomonas may also be used. Mammalian or other eukaryotic host cells, such as those of yeast, filamentous fungi, plant, insect, or amphibian or avian species, may also be useful for production of the proteins of the present invention. Propagation of mammalian cells in culture is per se well known. Examples of commonly used mammalian host cell lines are VERO and HeLa cells, Chinese hamster ovary (CHO) cells, and WI38, BHK, and COS cell lines, although it will be appreciated by the skilled practitioner that other cell lines may be appropriate, e.g., to provide higher expression, desirable glycosylation patterns, or other features.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of PCTG4 polypeptides (such as the HOPA and neuroligin proteins). The probes and primers based on sequences disclosed herein can used to identify homologous sequences and proteins in other species such as the murine HOPA gene described in Example 3 below. These gene sequences and proteins are used in the diagnostic/prognostic, therapeutic and drug screening methods described herein for the species from which they have been isolated.

Nucleic acid sequences having polymorphisms associated with mental retardation, neuropsychiatric disorders and/or hypothyroidism can be detected by hybridization with a polynucleotide probe which forms a stable hybrid with that of the target sequence, under stringent to moderately stringent hybridization and wash conditions. The present invention allows for the design of probes which preferentially hybridize to polymorphic regions. The design of probes which preferentially target specific sequences and hybridization conditions for their use is well known in the art. See e.g. *Current Protocols In Molecular Biology*, Volumes I–III, Frederick M. Ausubel et al. eds., 1995. For example, if it is expected that the probes will be perfectly complementary to the target sequence, stringent conditions will be used. Hybridization stringency may be lessened if some mismatching is expected, for example, if variants are expected with the result that the probe will not be completely complementary. Conditions are chosen which rule out nonspecific/adventitious bindings, that is, which minimize noise.

Probes for polymorphisms in the PCTG4 region may be of any suitable length, which are proximal to or span all or a portion of the polymorphism, and which allow preferential hybridization to the region. If the target sequence contains a sequence identical to that of the probe, the probes may be short, e.g., in the range of about 8–30 base pairs, since the hybrid will be relatively stable under even stringent conditions. If some degree of mismatch is expected with the probe, i.e., if it is suspected that the probe will hybridize to a variant region, a longer probe may be employed which hybridizes to the target sequence with the requisite specificity.

The probes can include an isolated polynucleotide attached to a label or reporter molecule and may be used to isolate other polynucleotide sequences, having sequence similarity or being proximal to the sequences of interest by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. In expressed sequences, various codon substitutions may be introduced, e.g., by silent changes (thereby producing various restriction sites) or to optimize expression for a particular system. Polymorphisms may be introduced to modify the properties of the polypeptide, perhaps to change the polypeptide degradation or turnover rate. Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

The design of probes having a size and sequence organization which allows them to preferentially target specific sequences and hybridization conditions for their use is well known in the art. See, e.g., *Current Protocols In Molecular Biology*, Volumes I, units 2, 4, and 6, Frederick M. Ausubel et al. eds., 1995. Portions of polynucleotide sequences having at least about eight nucleotides, usually at least about 15 nucleotides, and fewer than about 6 kb, usually fewer than about 1.0 kb, from a polymorphic sequence are preferred as probes. Illustrative embodiments include probes encompassing a polymorphic region such as the 12 base pair insert in the HOPA gene. Also contemplated are probes having a specific portion of a polymorphic sequence. Moreover, probes which are proximal to a polymorphic region (such as the PCR primers described in Example 2 below) may also be used in evaluating nucleic acid samples. In addition to their use in evaluating genomic sequences, the probes may also be used to determine whether mRNA such as that encoding HOPA or neuroligin-3 is present in a cell or tissue.

Diagnostic Methods of the Invention

In order to detect the presence of a polymorphism associated with neuropsychiatric disorders and/or hypothyroidism, a biological sample such as blood is prepared and analyzed for the presence or absence of polymorphic sequences. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis.

The identification of the association between polymorphisms in the PCTG4 region and various neuropsychiatric disorders and/or hypothyroidism permits the early presymptomatic screening of individuals to identify those at risk for having pathologies associated with mental retardation. To identify such individuals, the PCTG4 region is screened for polymorphisms either directly or after cloning the sequences of interest. There are a number of different methods of the invention which may be employed both to evaluate individuals for potentially pathogenic polymorphisms and to specifically characterize those polymorphisms which are associated with neuropsychiatric disorders and/or hypothyroidism. For example, the invention provides a method for screening for a polymorphism associated with neuropsychiatric disorders and/or hypothyroidism in an individual by identifying one of the polymorphism identified herein in that individual's PCTG4 sequences. Moreover, the invention also provides method of identifying a polymorphism associated with neuropsychiatric disorders by comparing a PCTG4 sequence isolated from an affected subject to a known wild type PCTG4 sequence and identifying recurrent polymorphisms that are associated with neuropsychiatric disorders and/or hypothyroidism.

As discussed below, samples can be tested for the presence of nucleic acid sequences which are difference from normal sequences using any one of a wide variety of differential nucleic acid analysis techniques that are well known in the art. Differential nucleic acid analysis techniques include, but not limited to: fluorescent in situ hybridization (FISH), direct DNA sequencing, single stranded conformational analysis (SSCP), Southern blotting including restriction fragment length polymorphism analysis (RFLP), the polymerase chain reaction (PCR), polymorphism specific oligonucleotide hybridizations and PCR-SSCP analysis. As discussed below, for sequences coding for expressed molecules and polypeptides, additional techniques may also be utilized. For a review of techniques for evaluating and manipulating nucleic and amino acid sequences, see *Current Protocols In Molecular Biology*, Volumes I–III, Frederick M. Ausubel et al. eds., 1995.

Alteration of PCTG4 region mRNA expression (e.g. HOPA and Neuroligin-3 gene expression) can be detected by any techniques known in the art. These include Northern blot analysis, PCR amplification and RNase protection. Diminished mRNA expression indicates an alteration of the wild-type gene. Alteration of wild-type genes can also be detected by screening for alteration of wild-type PCTG4 protein (e.g. HOPA and Neuroligin-3 polypeptides). For example, monoclonal antibodies immunoreactive with specific HOPA or Neuroligin-3 epitopes can be used to screen a tissue. Lack of cognate antigen would indicate a polymorphism. Antibodies specific for products of mutant alleles could also be used to detect mutant gene product. Such immunological assays can be done in any convenient formats known in the art. These include Western blots, immunohistochemical assays and ELISA assays. Any means for detecting an altered protein can be used to detect alteration of wild-type PCTG4 region genes. Functional assays, such as protein binding determinations, can be used. In addition, assays can be used which detect the biochemical function of genes in the PCTG4 region. Typically, finding an alteration in the biochemical function of a polypeptide encoded by a gene in the PCTG4 region can indicate alteration of a wild-type gene in this region.

A number methods can be used to directly detect DNA sequence variation. Direct DNA sequencing, either manual sequencing or automated fluorescent sequencing can detect sequence variation. The allele(s) of genes in the PCTG4 region in an individual to be tested can be cloned using conventional techniques. For example, a blood sample is obtained from the individual, PCTG4 genomic DNA is isolated from the cells in this sample and ligated into an appropriate vector. The sequences of the clones can then be determined and compared to the normal PCTG4 region sequences. Techniques involving DNA cloning and sequencing are well known in the art, see e.g. *Current Protocols In Molecular Biology*, Volume I, unit 7, Frederick M. Ausubul et al. eds., 1995.

Another approach to detect variations in DNA sequences is the single-stranded conformation polymorphism assay (SSCP) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCP makes it an attractive, viable alternative to direct sequencing for polymorphism detection on a research basis. The fragments which have shifted mobility on SSCP gels are then sequenced to determine the exact nature of the DNA sequence variation. Other approaches based on the detection of mismatches between the two complementary DNA strands include clamped denaturing gel electrophoresis (CDGE) (Sheffield et al., Am. J. Hum. Genet., 49: 699–706 (1991)), heteroduplex analysis (HA) (White et al., Genomics 12: 301–306 (1992)) and chemical mismatch cleavage (CMC) (Grompe et al., P.N.A.S. 86: 5855–5892 (1989)). Other methods which might detect these classes of polymorphisms such as a protein truncation assay or the asymmetric assay, detect only specific types of polymorphisms and would not detect missense polymorphisms. A review of currently available methods of detecting DNA sequence variation can be found in a recent review by Grompe et al., Nature Genetics 5: 111–117, (1993).

A rapid preliminary analysis to detect polymorphisms in DNA sequences can be performed using RFLP, where DNA is cut with one or more restriction enzymes, preferably with a large number of restriction enzymes and analyzed with PCTG4 specific probes in a series of Southern blots. Each blot contains a series of normal individuals and a series of mental retardation cases. Southern blots displaying hybridizing fragments (differing in length from control DNA when probed with sequences near or including known polymorphic loci) indicate a possible polymorphism. Techniques involving RFLP are well known in the art, see, e.g., *Current Protocols In Molecular Biology*, Volume I, unit 2, Frederick M. Ausubul et al. eds., 1995.

Restriction fragment length polymorphism analysis is a preferred method of analysis due to its ability to identify uncharacterized polymorphisms. Specifically, by simply using sequences from various regions in PCTG4 as probes, the skilled practitioner may evaluate nucleic acid samples for a wide variety of polymorphisms including those which have yet to be identified. Probes in these analyses may include sequences having the illustrative polymorphisms (such as the 12 base pair insert) disclosed herein or alternatively, may include proximal sequences identified herein or isolated by chromosomal walking techniques that are well known in the art. See e.g. Ueghara et al., Mamm Genome 1(2): 92–99 (1991).

A particularly preferred method of nucleic acid analysis using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be analyzed by restriction endonuclease digestion, sequenced or used as a substrate for DNA probes. When the sequences encompassing a specific polymorphism are known, a variety of PCR primers targeting these sequences may be generated. For example, sequences flanking the polymorphism may be used to amplify those sequences as is shown in Example 2 below. For a variation of sequence-specific PCR, primers can be used which hybridize at their 3' ends to a particular PCTG4 polymorphism. If the particular polymorphism is not present, an amplification product is not observed. Amplification Refractory Polymorphism System (ARMS) can also be used, as disclosed in European Patent Application Publication No. 0332435 and in Newton et al., 1989. Alternatively, polymerase chain reactions (PCRs) can be performed with primer pairs for the 5' region or the exons of the HOPA or neuroligin-3 gene. PCRs can also be performed with primer pairs based on any sequence of the normal PCTG4 region. For example, primer pairs for one of the introns can be prepared and utilized. Finally, PCR can also be performed on the mRNA. The amplified products are then analyzed by single stranded conformation polymorphisms (SSCP) using conventional techniques to identify any differences and these are then sequenced and compared to the normal gene sequence.

Primer pairs of the present invention are useful for determination of the nucleotide sequence of a particular PCTG4 sequence using PCR. For example, the pairs of single-stranded DNA primers can be annealed to sequences within or surrounding PCTG4 sequences on the X chromosome in order to prime amplifying DNA synthesis of the gene itself. A complete set of these primers allows synthesis of all of the nucleotides of the gene coding sequences, i.e., the exons. The set of primers preferably allows synthesis of both intron and exon sequences. In addition, allele-specific primers can also be used. Such primers anneal only to particular PCTG4 mutant alleles, and thus will only amplify a product in the presence of the mutant allele as a template.

In order to facilitate subsequent cloning of amplified sequences, primers may have restriction enzyme site sequences appended to their 5' ends. For example, all nucleotides of the primers can be derived from sequences adjacent to one or more PCTG4 polymorphisms, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the level of skill in the art, the design of particular primers is well within the skill of the art. See, e.g., *Current Protocols In Molecular Biology*, Volume II, unit 15, Frederick M. Ausubel et al. eds., 1995.

DNA sequences of the PCTG4 region which have been amplified by use of PCR may also be screened using allele-specific probes. These probes are nucleic acid oligomers, each of which contains a region of the gene sequence harboring a known polymorphism. For example, one oligomer may be about 20 nucleotides in length, corresponding to a portion of the PCTG4 polymorphic sequence. By use of a battery of such allele-specific probes, PCR amplification products can be screened to identify the presence of a previously identified polymorphism in the gene. Hybridization of allele-specific probes with amplified PCTG4 sequences can be performed, for example, on a nylon filter. Hybridization to a particular probe under stringent hybridization conditions indicates the presence of the same polymorphism in the tissue as in the allele-specific probe. Individuals can be quickly screened for common PCTG4 variants by amplifying the individual's DNA using suitable primer pairs and analyzing the amplified product, e.g., by dot-blot hybridization using allele-specific oligonucleotide probes. Once a polymorphism has been characterized, an allele specific detection approach such as allele specific oligonucleotide (ASO) hybridization can be utilized to rapidly screen large numbers of other samples for that same polymorphism.

Another method employs RNase A to assist in the detection of differences between the wild type PCTG4 sequences and those containing polymorphisms. This comparison is performed in steps using small (approximately equal to 500 bp) restriction fragments of the PCTG4 region as a probe. First, the PCTG4 region is digested with a restriction enzyme(s) that cuts the gene sequence into fragments of approximately 500 bp. Suitable restriction enzymes can be chosen by one of ordinary skill in the art on the basis of their specific cleavage sites. These fragments are separated on an electrophoresis gel, purified from the gel and cloned individually, in both orientations, into an SP6 vector (e.g., pSP64 or pSP65). The SP6-based plasmids containing inserts of PCTG4 region fragments are transcribed in vitro using the SP6 transcription system, well known in the art, in the presence of $GTP^{32}$, generating radiolabeled RNA transcripts of both strands of the gene. Individually, these RNA transcripts are used to form heteroduplexes with the allelic DNA using conventional techniques. Mismatches that occur in the RNA:DNA heteroduplex, owing to sequence differences between the PCTG4 fragment and the polymorphic subclone from the individual, result in cleavage in the RNA strand when treated with RNase A. Such mismatches can be the result of point polymorphisms or small deletions in the individual's allele. Cleavage of the RNA strand yields two or more small RNA fragments, which run faster on the denaturing gel than the RNA probe itself.

The majority of the diagnostic assays described above incorporate nucleic acid probes as a crucial element. When the probes are used to detect the presence of the target sequences, the biological sample to be analyzed, such as blood or serum, may be treated to extract the nucleic acids. As discussed above, the sample nucleic acid may be prepared in various ways to facilitate detection of the target sequence, e.g., denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Target nucleic acids, probe and analyte can be incubated under conditions which promote stable hybrid formation of the target sequence in the probe with the putative targeted sequence in the analyte. The region of the probes which is used to bind to the analyte can be made completely complementary to the targeted region of human X chromosome. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., Molecular Cloning, A Laboratory Manual, Cold Springs Harbor Laboratory, 1982 and Sambrook et al., 1989. Under certain circumstances, the formation of higher order hybrids, such as triplexes, quadraplexes, etc., may be desired to provide the means of detecting target sequences.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. Probe sequences may also hybridize specifically to duplex DNA under certain conditions to form triplex or other higher order DNA complexes. The preparation of such probes and suitable hybridization conditions are well known in the art.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal front the labeled moiety. A number of these variations are reviewed in, e.g., Matthews & Kricka, Anal. Biochem., 169: 1, 1988; Landegren et al., Science, 242: 229, 1988; Mittlin, 1989; U.S. Pat. No. 4,868,105; and in EPO Publication No. 225,807.

As noted above, a number of non-PCR based screening assays are contemplated in this invention. One procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in an increase in sensitivity. For an example relating to the preparation of oligodeoxynucleotide-alkaline phosphatase conjugates and their use as hybridization probes, see Jablonski et al., N.A.R., 14: 6115–6128, 1986. Two-step label amplification methodologies are known in the art. These assays work on the principle that a small ligand (such as digoxigenin, biotin, or the like) is attached to a nucleic acid probe capable of specifically binding a PCTG4 region sequence. Allele specific probes are also contemplated within the scope of this example and exemplary allele specific probes include probes encompassing the predisposing polymorphisms of this patent application.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., BioTechniques 9: 762–768, 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Nguyen et al., BioTechniques 13: 116–123, 1992.

It is also contemplated within the scope of this invention that the nucleic acid probe assays of this invention will employ a combination of nucleic acid probes capable of detecting PCTG4 polymorphisms. Thus, in one example to detect the presence of polymorphisms in a cell sample, more than one probe complementary to the gene is employed and in particular the number of different probes is alternatively two, three, or five different nucleic acid probe sequences. In another example, to detect the presence of polymorphisms in the PCTG4 region sequence in a patient, more than one probe complementary to these genes is employed where the cocktail includes probes capable of binding to the allele-specific polymorphisms identified in populations of patients with alterations in this region. In this embodiment, any number of probes can be used, and will preferably include probes corresponding to the major polymorphisms identified as being associated with mental retardation.

Any sequence differences which are found by one of the techniques discussed above will identify an individual as having a molecular variant of the PCTG4 region and the consequent presence of a marker which may associate with a neuropsychiatric disorder and/or hypothyroidism. These variants can take a number of forms and can occur in both coding and non coding regions. Certain polymorphisms associated with an expressed gene could generate an abnormal protein (such as the 12 base pair insertion in HOPA) or significantly alter protein expression. Additional disruptive polymorphisms could include small in-frame deletions and nonconservative base pair substitutions which could have a significant effect on the protein produced, such as changes to or from a cysteine residue, from a basic to an acidic amino acid or vice versa, from a hydrophobic to hydrophilic amino acid or vice versa, or other polymorphisms which would affect secondary or tertiary protein structure. Silent polymorphisms or those resulting in conservative amino acid substitutions would not generally be expected to disrupt protein function.

The methods and PCTG4 sequences disclosed herein also provide for a variety of assays using DNA chip technology (see e.g. Wang et el., Science 15; 280: 1077–1082 (1998) and U.S. Pat. Nos. 5,858,661 and 5,837,832 which are incorporated herein by reference). In particular, the present invention provides arrays of PCTG4 specific oligonucleotide probes immobilized on a solid support (or "chip"). In this context, DNA chips containing arrays of oligonucleotide probes can be used to determine whether a target nucleic acid sample contains a nucleotide sequence identical to, or different from, a specific reference sequence. An exemplary array comprises probes exactly complementary to the reference sequence (such as the 12 base pair polymorphism in the HOPA cDNA), as well as probes that differ by one or more bases from the exactly complementary probes. In a typical embodiment, an array will comprise a set of oligonucleotide probes such that, for each base in a specific reference sequence, the set includes a probe that is exactly complementary to a section of the reference PCTG4 sequence and additional probes which are related to this reference sequence except that one or more nucleotides within this sequence been replaced by a predetermined set of nucleotides (typically encompassing a portion of a polymorphic region).

The detection of sequences binding to such arrays can be carried out by a variety of method that are known in the art (see e.g. U.S. Pat. No. 5,837,832). In an exemplary embodiment for detecting specific sequences in a target nucleic acid with a DNA chip, repeat sequences are detected as follows. The chip comprises probes of length sufficient to extend into the repeat region varying distances from each end. The sample, prior to hybridization, is treated with a labeled oligonucleotide that is complementary to a repeat region but shorter than the full length of the repeat. The target nucleic is labeled with a second, distinct label. After hybridization, the chip is scanned for probes that have bound both the labeled target and the labeled oligonucleotide probe; and the presence of such bound probes shows that a repeat sequence is present.

Antibodies of the Invention

The present invention further provides antibodies to polymorphic regions of proteins encoded by genes in the PCTG4 region, including HOPA and neuroligin-3. Exemplary antibodies include polyclonal, monoclonal, humanized, bispecific, and heteroconjugate antibodies well known in the art. In particular, the presence of mental retardation can also be detected on the basis of the alteration of wild-type HOPA or neuroligin-3 polypeptide. While such alterations can be determined by sequence analysis in accordance with conventional techniques, more preferably, antibodies (polyclonal or monoclonal) are used to detect differences in, or the absence of PCTG4 peptides. Techniques for generating and purifying antibodies are well known in the art and any such techniques may be chosen to achieve the preparations claimed in this invention. In a preferred embodiment of the invention, antibodies will immunoprecipitate polymorphic PCTG4 proteins from solution as well as react with these proteins on Western or immunoblots of polyacrylamide gels. In another preferred embodiment, antibodies will detect PCTG4 proteins in paraffin or frozen tissue sections, using immunocytochemical techniques.

Preferred embodiments relating to methods for detecting PCTG4 polypeptides or their polymorphisms include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486,530, hereby incorporated by reference.

Use of PCTG4 Nucleic Acids in the Generation of Transgenic Animals

Nucleic acids which encode genes in PCTG4 or their modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding HOPA can be used to clone genomic DNA encoding HOPA or neuroligin-3 (including polymorphic HOPA containing the 12 base pair insertion) in accordance with established techniques and the genomic sequences used to generate transgenic animals that contain cells which express DNA encoding HOPA or neuroligin-3 (for example a murine HOPA protein having the 12 base pair insertion seen in the human protein). Methods for generating transgenic animals, particularly animals such as mice or rats, have become conventional in the art and are described, for example, in U.S. Pat. Nos. 4,736,866 and 4,870,009. Typically, particular cells would be targeted for PCTG4 transgene incorporation with tissue-specific enhancers. Transgenic animals that include a copy of a transgene encoding various PCTG4 sequences introduced into the germ line of the animal at an embryonic stage can be used to examine the effect of increased expression of DNA encoding PCTG4 sequences. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of PCTG4 can be used to construct a PCTG4 "knock out" animal which has a defective or altered gene from the PCTG4 region as a result of homologous recombination between the endogenous gene encoding PCTG4 region sequences and altered genomic DNA encoding PCTG4 sequences introduced into an embryonic cell of the animal. For example, cDNA encoding HOPA or neuroligin-3 can be used to clone genomic DNA encoding HOPA or neuroligin-3 in accordance with established techniques. A portion of the genomic DNA encoding HOPA can be deleted or replaced with another gene such as a gene encoding a selectable marker which can be used to monitor integration. Typically, several kilobases of unaltered flanking DNA (both at the 5' and 3' ends) are included in the vector (see e.g., Thomas and Capecchi, Cell, 51:503 (1987) for a description of homologous recombination vectors). The vector is introduced into an embryonic stem cell line (e.g., by electroporation) and cells in which the introduced DNA has homologously recombined with the endogenous DNA are selected (see e.g., Li et al., Cell, 69:915 (1992)). The selected cells are then injected into a blastocyst of an animal (e.g., a mouse or rat) to form aggregation chimeras [see e.g., Bradley, in Teratocarcinomas and Embryonic Stem Cells: A Practical Approach, E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knock-out animals can be characterized for instance, for their ability to defend against certain pathological conditions and for their development of pathological conditions due to absence of the PCTG4 polypeptide.

PCTG4 Cell-Based Drug Screening Assays

The methods and PCTG4 sequences disclosed herein also provide for a variety of drug screening assays using cells containing PCTG4 sequences, typically PCTG4 sequences that having one or more polymorphisms that are associated with a pathological conditions. Such cells are particularly useful in the pharmacological characterization of novel modulators (i.e. inhibitors or activators) of the activity of proteins and protein complexes. Moreover, a variety of drug screening assays are known in the art, the methods of which are readily adapted for evaluating the PCTG4 sequences disclosed herein (see e.g. Vinggaard et al., Toxicol. Appl. Pharmacol. 155(2): 150–160 (1999); Fernandes et al., Curr. Opin, Chem. Biol., 2(5): 597–603 (1998); Gonzales et al., Curr. Opin. Biotechnol. 9(6): 624–31 (1998) and U.S. Pat. Nos. 5,877,007 and 5,780,258, the contents of which are incorporated herein by reference).

In an illustrative embodiment of such assays, cells can express a polymorphic protein encoded by the PCTG4 region, the presence of which affects a particular activity in the cell (typically the activity of a reporter gene) which changes in response to substances which modulate the activity of the protein encoded by the PCTG4 region. Such responsive changes in a particular activity or other cellular characteristic may be utilized in many useful ways, including the discovery, development or characterization of substances suitable for the treatment of diseases or other conditions in human beings or animals. Such cells may also be useful for studying diseases or other biological processes, for determining the effects of various drugs alone or in combination, as well as for identifying or characterizing substances which may be useful in reducing or preventing the occurrence of a disease or other condition.

A specific embodiment of the invention provides methods and compositions for screening for agents which regulate the activity of HOPA or the thyroid receptor-associated protein (TRAP) complex of which HOPA is a member (as discussed above, HOPA is the member of this complex designated TRAP 230). Such agents can find use in modulating a wide variety of physiological manifestations of thyroid expression including the pathologies which are associated with PCTG4 polymorphisms. An illustrative example of this embodiment is a mammalian cell comprising a polymorphic variant of HOPA (such as the 12 base pair insert disclosed herein) and, additionally, a reporter gene construct which is under the control of sequences modulated by the TRAP complex (see e.g. Fondell et al., PNAS USA 93, 8329–8333 (1996); Fondell et al., PNAS 96, 1959–1964 (1999) and Force et al., Biol Chem. 1994 Mar 25;269(12):8863–71. A cell-based assay to test the pharmacological activity of various agents can then be performed exposing such a cell to a candidate agent under conditions where the presence of the agent, causes the reporter gene to be expressed at level relative to a control level (for example, the level of background expression of the reporter gene construct, or alternatively, the level of expression observed in response to exposure to a specific factor). A difference between the expression level of the reporter gene relative to the control level indicates that the candidate agent modulates HOPA or TRAP activity. In a closely related embodiment, a comparison between the responses of cells containing the appropriate complement of (1) mutant and (2) wild type HOPA sequences and reporter gene constructs can be characterized.

While a cell-based assay utilizing HOPA construct is described above, a variety of additional embodiments utilizing other genes in the PCTG4 region are also contemplated. For example, alternative embodiments of the cell-based assays disclosed herein include constructs containing neuroligin-3 genes as means to assess the effects of various agents on the interaction of neuroligin-3 ligands and the neurexin family of neuronal cell surface receptors. An illustrative embodiment could entail, for example, the use of a reporter gene construct under the control of sequences modulated by a neurexin receptor complex in order to test the activities of various neuroligin-3 variants.

The cells of the assay described herein may generated from individuals having polymorphisms in the PCTG4 region or by a variety of protocols that are well known in the art including the transfection methods described above. Alternatively such cells can be generated by utilizing transgenic or genetic knock-out animals made by homologous recombination, e.g. recombination of a wild type PCTG4 sequence with a transgene comprising a polymorphic or modified PCTG4 sequence. In addition, a wide variety of reporter genes and assays that are known in the art can be adapted to the cell-based screening assays disclosed herein. For example, a reporter gene can encode an enzyme which produces calorimetric or fluorometric change in the host cell which is detectable by in situ analysis and which is a quantitative or semi-quantitative function of transcriptional activation. Exemplary enzymes include esterases, phosphatases, proteases (tissue plasminogen activator or urokinase) and other enzymes capable of being detected by activity which generates a chromophore or fluorophore as will be known to those skilled in the art. A preferred example is $E.$ $coli$ beta-galactosidase disclosed herein. This enzyme produces a color change upon cleavage of the indigogenic substrate indolyl-B-D-galactoside by cells bearing beta-galactosidase (see, e.g., Goring et al., Science, 235:456–458 (1987) and Price et al., Proc. Natl. Acad. Sci. U.S.A., 84:156–160 (1987)). This enzyme is preferred because the endogenous beta-galactosidase activity in mammalian cells ordinarily is quite low, the analytic screening system using β-galactosidase is not hampered by host cell background.

Kits and Articles of Manufacture

In a further embodiment of the invention, there are provided articles of manufacture and kits containing probes, oligonucleotides or antibodies which can be used, for instance, for the diagnostic applications described above. The article of manufacture comprises a container with a label. Suitable containers include, for example, bottles, vials, and test tubes. The containers may be formed from a variety of materials such as glass or plastic. The container holds a composition which includes an agent that is effective for diagnostic applications, such as described above. The label on the container indicates that the composition is used for a specific diagnostic application. The kit of the invention will typically comprise the container described above and one or more other containers comprising materials desirable from a commercial and user standpoint, including buffers, diluents, filters and package inserts with instructions for use.

The present invention is further detailed in the following Examples, which are offered by way of illustration and are not intended to limit the invention in any manner. Standard techniques well known in the art or the techniques specifically described below are utilized. All patent and literature references cited in the present specification are hereby incorporated by reference in their entirety.

EXAMPLES

Commercially available reagents referred to in the examples were used according to manufacturer's instructions unless otherwise indicated.

Example 1

Isolation of the CTG-4 Cosmid

The cosmid library of human genomic trinucleotide repeats was constructed as previously described (Philibert, et al., "The characterization and sequence analysis of thirty CTG-repeat containing genomic cosmid clones", Eur J Hum Genet 6:89–94 (1998)). Briefly, DNA was partially digested with Sau 3AI, ligated into a cosmid vector, packaged and then transfected into $E.$ $coli$. Colonies containing cosmids with CAG trinucleotide repeats were then identified by hybridization with an oligonucleotide probe [$(CTG)_{10}$] (Wallace et al., "Oligonucleotide probes for the screening of recombinant DNA libraries, In: Berger S L, Kimmel A R (eds) Guide to Molecular Cloning Techniques", Academic Press, New York, pp 432–442 (1987)). Cosmid DNA then was prepared and sequenced using either manual or automated fluorescent methods as described previously (Philibert, et al., "Direct sequencing of trinucleotide repeats from cosmid genomic DNA templates", Anal Biochem 225:372–375 (1995)). Primers for polymorphism analysis of the trinucleotide repeat containing regions were then prepared using this sequence.

Example 2

Polymorphism Analysis

Initial polymorphism analysis was conducted as described in Philibert, et al., "The characterization and sequence analysis of thirty CTG-repeat containing genomic cosmid clones", Eur J Hum Genet 6:89–94 (1998). PCR amplification of the trinucleotide repeat containing region was performed using standard PCR buffer [10 mM Tris-HCl (pH 8.3), 50 mM KCl, 0.001% gelatin, 2 mM $MgCl_2$, 200 $\mu$M of each deoxynucleotide], 0.8 $\mu$M primers (Forward: CTGCTTCCTCATCCCCTGCCCTCA, (SEQ ID NO.: 11), Reverse: GGGCTGTAGTCCAAACAGCTACCTG, (SEQ ID NO.: 12)) and 10% DMSO. Taq polymerase and genomic DNA concentration were 2.5U/100 $\mu$l and 50 ng/100 $\mu$l, respectively. The thermal cycling parameters for amplification were: initial denaturation of 95° C. for 5 min, then 45 cycles of 95° C.×1 min, 65° C.×30', and 72° C.×2 min, followed by an final extension at 72° C.×10 min. Approximately 3 μl of PCR product was loaded onto a standard 6% denaturing polyacrylamide gel and electrophoresed for approximately 3 hours. The separated products were electroblotted on to a N+ super charged nylon membrane and the membrane then hybridized overnight to a $^{32}$P-labeled (CTG)$_{10}$ probe and imaged using x-ray film (Kodak X-OMAT-AR). The size of the PCR product was determined by comparison to a sequencing ladder.

Example 3

Isolation of cDNA and DNA Sequence Analysis

Probable exons in the human genomic sequence in and around the CTG-4 trinucleotide repeat were originally identified using GRAIL (Oakridge National Laboratory) (Uberbacher, et al., "Locating protein-coding regions in human DNA sequences by a multiple sensor-neural network approach", Proc Nat Acad Sci USA 88:11261–11266 (1991). Probes from putative exons were then hybridized to multi-tissue northern blots to determine the size of RNA transcripts. Based on this information, corresponding cDNAs were isolated from a lambda gt11 human heart cDNA library (Clontech, La Jolla, Calif.). Phage DNA was prepared using a Wizard lambda prep kit (Promega, Madison, Wis., USA) and sequenced using automated fluorescent methods (Philibert, et al., "Direct sequencing of trinucleotide repeats from cosmid genomic DNA templates", Anal Biochem 225:372–375 (1995)). Sequence identity comparison of the resulting data was performed using BLAST (Altschul, et al., "Basic local alignment search tool", J Mol Biol 215:403–410 (1990)).

The mouse homologue of the human sequence was obtained by screening a lambda gt11 mouse heart library (Clontech, La Jolla, Calif.) with a portion of the human sequence. Lambda DNA was then prepared and sequenced as above. Sequence analysis was conducted using the PCGENE suite of programs (Intelligenetics, Geneva, Switzerland).

The sequence of the CTG-4 repeat that was initially isolated is shown in FIG. 5. The PCR primers used in this study flank a 254 bp region that is expanded to 266 bp by the addition of CAGCAACACCAG, (SEQ ID NO.: 10) corresponding to an insertion of QQHQ into the putative 2024 amino acid protein. Sequence analysis of the affected males in this study and a number of Caucasian controls failed to demonstrate any other polymorphisms in this 254 bp segment of DNA. The exons contained in this 254 bp segment of DNA are located in exon 42 of a 7.3 kb cDNA (FIG. 1B) that has also been partially described by Nagase and co-workers (Nagase, et al., "Prediction of the coding sequences of unidentified human genes. V. The coding sequences of 40 new genes (KIAA0161–KIAA0200) deduced by analysis of cDNA clones from human cell line KG-1", DNA Research 3:17–24 (1996)) (Genbank D83783, 1996; Ross and coworkers, Genbank 80742). Previous analysis of the cDNA sequence demonstrated the presence of a DNA topoisomerase II domain a OPA box (Duboule, et al., "DNA sequences homologous to the Drosophila opa repeat are present in murine mRNAs that are differentially expressed in fetuses and adult tissues", Mol Cell Biol 7:2003–2006 (1987)) (FIG. 3). Further analysis using PCGENE identified two putative transmembrane domains located from amino acid (AA) 204 to 224 and from AA 1061 to 1081. BLAST analysis did not identify any other sequence homologies at greater than $10^{-6}$ probability.

The corresponding mouse cDNA was also isolated. The mouse cDNA is 6580 bp in length and from the first in frame ATG encodes a protein of 2082 AA (accession # pending). Compared to the human sequence the mouse sequence is 97% identical at the amino acid level with almost half of the differences resulting from differential splicing in exon 39 (bp 5944–5976). Of particular significance is the fact that the DNA sequence flanking the 12 base pair repeat in the human is completely conserved in the mouse. BLAST analysis of this sequence reveals a previously reported 594 bp sequence (M16362) spanning the OPA domain. Duboule, et al., "DNA sequences homologous to the Drosophila opa repeat are present in murine mRNAs that are differentially expressed in fetuses and adult tissues", Mol Cell Biol 7:2003–2006 (1987). No other matches were present at over the $10^{-20}$ level of significance.

Example 4

Northern Blot Analysis and Chromosomal Localization

To establish the size of transcripts (Fransen, et al., "CRASH syndrome: clinical spectrum of corpus callosum hypoplasia, retardation, adducted thumbs, spastic paraparesis and hydrocephalus due to mutations in one single gene", Eur J Hum Genet 3:273–284 (1995)) and to ascertain possible alternative splicing, a $^{32}$P-labeled 540 bp DNA segment corresponding to region immediately 5' of the CAG repeat region of the cDNA was hybridized to multi-tissue northern blots (Clontech, La Jolla, Calif. USA) using Quick-Hyb™ (Stratagene, La Jolla, Calif. USA).

Fluorescence in situ Hybridization

The FISH procedure was carried out using 50% formamide, 10% dextran sulfate in 2×SSC as described previously. Tenhunen, et al., "Molecular cloning, chromosomal assignment, and expression of the mouse aspartylglucosaminidase gene", Genomics 30:244–250 (1995); Lichter, et al., "Rapid detection of human chromosome 21 aberrations by in situ hybridization", Proc Natl Acad Sci USA 85:9664–9668 (1998); Pinkel, et al., "Fluorescence in situ hybridization with human chromosome-specific libraries: detection of trisomy 21 and translocations of chromosome 4", Proc Natl Acad Sci USA 85:9138–9142 (1988); Rytkonen, et al., "The human gene for xanthine dehydrogenase (XDH) is localized on chromosome band 2q22", Cytogenet Cell Genet 68:61–63 (1995). Repetitive sequences were suppressed with 10–30 fold excess of COT-1 DNA (BRL, Gaithersburg, Md.). After overnight incubation, nonspecific hybridization signals were eliminated by washing the slides with 50% formamide/2×SSC, twice with 2×SSC, and once with 0.5×SSC at 45° C. Specific hybridization signals were visualized using FITC-conjugated Avidin (Vector Laboratories) and slides were counterstained with DAP I (4'-6'-diamino-2-phenlyindole) (0.025 μg/ml). Only double spot signals were considered to be specific acquisition. A multi-color image analysis was used for acquisition, display and quantification of hybridization signals of metaphase chromosomes.

The genomic sequence for this cDNA was localized to Xq13 by FISH and spans more than 40 kb. Northern blot analysis (FIG. 4) demonstrates a single 7.3 kb transcript in adult human tissues that is widely expressed, with the highest signals observed in heart, skeletal muscle, placenta and pancreas.

Example 5

Analysis of Polymorphisms in Individuals

All DNA samples used in this study were collected under protocols that were approved by the appropriate institutional review boards. The test statistics were generated by using either a 2×4 Chi-square for data using both male and female data or a 2×2 Chi-square when the male data was analyzed separately.

In the initial phase of these clinical studies, DNA from 206 non-retarded, unrelated European subjects recruited for psychiatric studies and DNA from retarded non-Fragile X probands of mixed European ancestry (81 males and 12 females) were screened for variation in this region of DNA. A 12 base pair insertion in the HOPA gene was found in samples from three males with MR while in the controls without retardation only one female heterozygote was found to have the expanded allele [Table A below; 4%, p<0.04 (0.04)] suggesting that the polymorphism might be enriched in males with MR.

In the second phase of this study, a second larger cohort of Caucasian non-Fragile X MR probands (115 males and 90 females) from California was compared to a cohort of Caucasian controls who were either blood bank donors (n=125) or participants in a metabolic disease study (n=26). The expanded allele was strongly associated with diminished cognition in males. It occurred in 8% of males in the MR cohort but not in any of the males in the control cohort [Table A, p<0.0003 (<0.002)]. Physical examination of the affected individuals did not reveal clear syndromal physical features. However, retrospective univariate analysis of components in the patients' histories from medical records demonstrated that the patients with the expanded allele had a much higher incidence of hypothyroidism [p<0.001; MR 3 of 9, non-MR 18 of 191] and a more frequent history of treatment with antidepressant medication [p<0.001; MR 3 of 9, non-MR 18 of 196].

In the third portion of the study, segregation analysis was performed in cohorts of non-Fragile X mentally retarded individuals and anonymous medically ill Finnish controls referred to a tertiary care center. The expanded allele was found in 14% of the males with MR.

Since several of the male individuals from the California sample of MR probands also had autistic features, a series of families containing male autistic probands was analyzed for the 12 base pair polymorphism. Forty-four triads of mother, father, and male proband were examined. The 12 base pair polymorphism was present in 3/44 (7%) male probands, 3/44 proband mothers, but not in any of the male probands' fathers (0/44)[p<0.08].

TABLE A

Association in Three MR Cohorts

| MR COHORT | male | female* | CONTROLS | male | female* | p-value |
|---|---|---|---|---|---|---|
| Mixed European | 81 | 12* | Mixed Psychiatric | 119 | 97 | <0.04 (<0.04) |
| 254 bp allele | 78 | 24 | | 119 | 193 | |
| 266 bp allele | 3 | 0 | | 0 | 1 | |
| California | 123 | 90* | Non-Psychiatric | 106 | 45 | <0.0003 (<0.002) |
| 254 bp allele | 114 | 177 | | 106 | 90 | |
| 266 bp allele | 9 | 3 | | 0 | 0 | |
| Finnish | 36 | 19* | Random Finnish | 42 | 52 | <0.10 (<0.15) |
| 254 bp allele | 31 | 37 | | 40 | 100 | |
| 266 bp allele | 5 | 1 | | 2 | 4 | |
| MR Total | 260 | 121* | Control Total | 269 | 194 | <0.0000012 (<0.000012) |
| | 243 | 238 | | 267 | 383 | |
| | 17 | 4 | | 2 | 5 | |

Demographics of the three cohorts used in the study. *Denotes the number of females in the study was multiplied by a factor of two to derive the number of female alleles. The p-values listed were generated by using a 2 × 4 Chi-test for analyses using both male and female data or a 2 × 2 Chi-test when the male data was analyzed separately (male only value given in parentheses).

A significant association between an X-chromosome exonic dodecamer expansion and MR in several male Caucasian samples is disclosed herein. The expansion may be causative or in strong disequilibrium with an etiologic mutation. If the 12 base pair expansion is directly involved, the range of phenotypic manifestations is not yet clearly defined. This is not unusual in X-linked MR syndromes (Neri, et al., "XLMR genes: update 1994", Am J Med Gen 15:542–549 (1994)). Indeed, the first Fragile X syndrome family (Martin and Bell 1943) was originally reported as possessing a non-specific phenotype (Scharwz, "Invited editorial: X-linked mental retardation: in the pursuit of a gene map", Am J Hum Gen 52:1025–1031 (1993)).

The syndromic phenotype identified by us has not been previously reported. Pathologies associated with the DNA expansion include MR and histories of hypothyroidism and treatment with antidepressants. This high rate of treatment of the severely affected individuals with anti-depressants and the presence of the allele in a subject recruited for psychiatric studies suggests a psychiatric forme fruste component of this syndrome including unipolar depression and bipolar affective disorder. Unblinded examinations of the non-retarded Caucasian male first degree relatives of the Chicago cohort of autistic males support this possibility.

If the polymorphism is causal for this MR syndrome then it is not fully penetrant with respect to the MR phenotype. In addition to the first degree male relatives of autistic probands noted in the Chicago cohort Autism study, there are several non-Caucasian males with the allele who may be psychiatrically ill, but do not have MR. Such incomplete penetrance is consistent with other X-Chromosome MR syndromes including Fragile X, where approximately 20% of males carrying the mutation are unaffected and in FRAXE, where 45 percent (5/11) of individuals in a series of cases were unaffected. Smeets, et al., Normal phenotype in two brothers with a full FRM1 mutation, Hum Mol Gen 4:2103–2108 (1995); Brown, et al., "Rapid fragile X carrier screening and prenatal diagnosis using a non-radioactive PCR test", JAMA 270:1569–1575 (1993); Gecz, et al., FMR2 expression in families with FRAXE mental retardation, Hum Mol Genet 6:435–441 1997).

In contrast to the frequencies found for control populations, the 12 base pair containing allele appears to be relatively common in the MR population. In three separate cohorts (366 patients: 232 males and 134 females) the allele was observed 19 times (17 occurring in males; 17/232 or 7%). If the 12 base pair allele is responsible, at least in part for illness, it may be a relatively significant genetic contribution to MR in the Caucasian population. Similarly, the finding that 3/44 (7%) of the male subjects with autistic disorder had the unusual polymorphism, suggests that it contributes to the development of autistic disorder.

Example 6

Analysis of Polymorphisms in Schizophrenic or Schizoaffective Individuals

All DNA samples used in this study were collected under protocols that were approved by the appropriate institutional review boards. The test statistics were generated by using either a 2×4 Chi-square analysis for data using both male and female data or a 2×2 Chi-square analysis when the male data was analyzed separately. The Chi-square analysis compared unrelated schizophrenic or schizoaffective subjects identified as having a variation in the HOPA gene with a newborn population having abnormalities in the HOPA gene.

In the initial phase of these clinical studies, DNA samples from 100 unrelated schizophrenic or schizoaffective subjects were screened for variation in the HOPA gene as described in Examples 1–4. The subjects were selected from families in which at least 2 siblings were identified with schizophrenia or schizoaffective disorder over about a 15-year period between 1985 and the present. (See DeLisi et al., Arch. Gen. Psychiatry, 44: 891–96 (1987); DeLisi et al., Neuropsych. Gen., 54: 113–21 (1994); Garner et al., Neuropsych. Gen., 67: 595–610 (1996); and Shaw et al., Neuropsych. Gen., 81: 364–76 (1998) for a description of clinical procedures for selecting families.) In summary, diagnoses were made using DSM-III-R criteria based on a combination of structured interviews, medical records from all hospitalizations or other relevant treatments, and structured information obtained from at least one reliable family member about each individual. Between 1985 and 1994 a modified Schedule for Affective Disorder and Schizophrenia (SADS) interview (see Spitzer & Endicott, New York State Psychiatric Institute (1978)) was used in combination with a Structured Interview for Personality Disorders (SIDP) (see Pfohl et al., University of Iowa (1990)). Between 1994 and the present these interviews were replaced by the comprehensive Diagnostic Interview for Genetic Studies (DIGS) (see Nurnberger et al., Arch. Gen. Psych., 51: 849–62 (1994)). Several of the ill individuals were reinterviewed using DIGS.

From 82 screened DNA samples, a 12 base pair insertion was found in 4 samples (3 male and 1 female) and a 15 base pair deletion was found in 1 sample (male).

In a second phase of this clinical study, DNA samples from 30 unrelated subjects that had no known history of thyroid disease were screened for variation in the HOPA gene as described in Examples 1–4. From 29 screened DNA samples, a 12 base pair insertion was found in 1 sample.

Overall, 111 DNA samples from unrelated subjects (82 males and 29 females) were examined between the first and second phases of the clinical study because 19 samples were either lost or provided ambiguous results. Fifty-three families from which subjects were drawn had a history of hypothyroidism. Specifically, 9 subjects, 32 mothers, 5 fathers, and 10 siblings were diagnosed with hypothyroidism.

Figure 6:
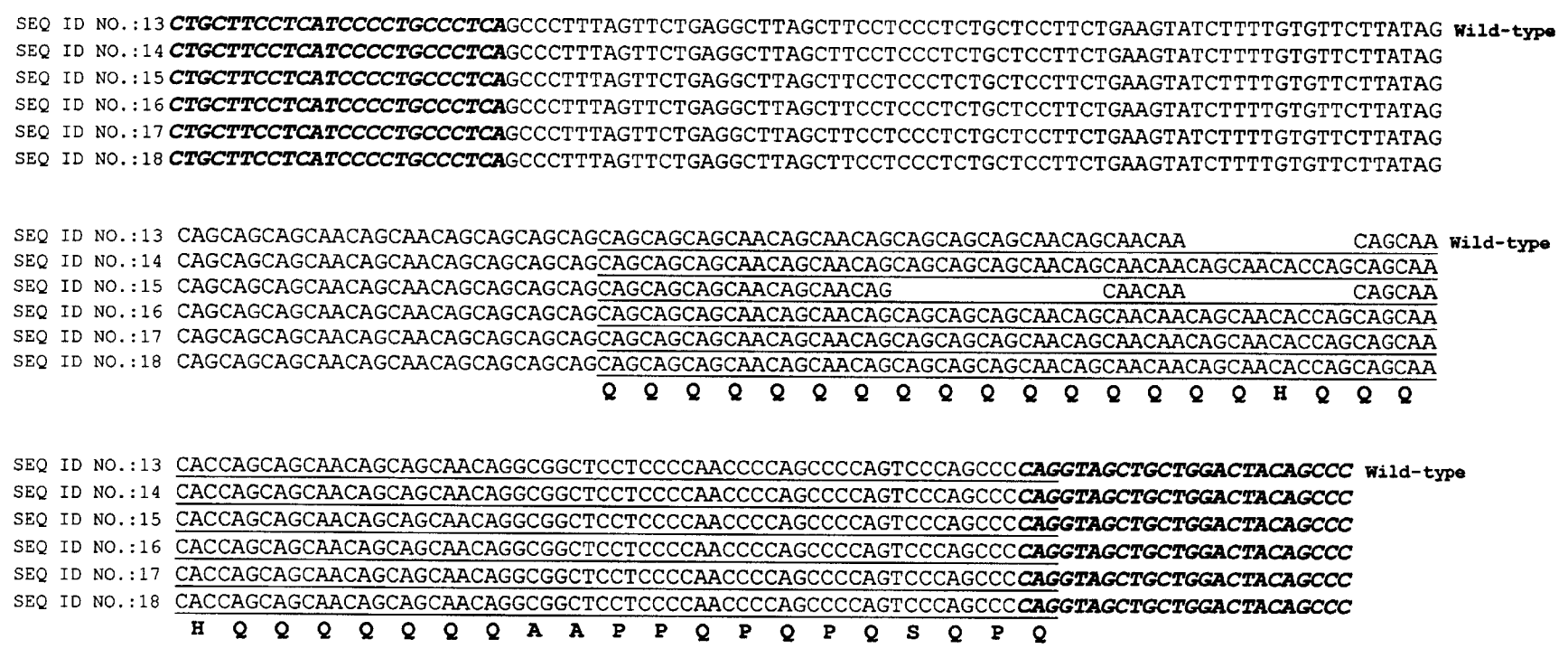

Allelic variations in the HOPA gene were found in 6 probands. All 6 of these subjects were identified as either having hypothyroidism (n=3) or having a mother with hypothyroidism (n=3). A Chi-square analysis demonstrated that the alternative allele segregated significantly with hypothyroidism. (p<0.009). DNA from all 4 male hemizygotes and DNA from the father of the 1 female heterozygote were sequenced. The results are shown in FIG. 6. These results from the 12 base pair insertion show the same 4 amino-acid polymorphism that is associated with the Xq13 increased prevalence for mental retardation, hypothyroidism, and depression. DNA from the single subject having the 15 base pair deletion in the HOPA gene also was sequenced, which showed the deletion of 5 glutamate residues in exon 42.

In a third phase of this clinical study, DNA samples from family members of subjects showing an allelic variation in the HOPA gene from the first and second phases were screened for variation in the HOPA gene as described in Examples 1–4. Although 6 subjects showed an allelic variation in the HOPA gene, only family members of 5 subjects were screened. A total of 19 relatives from the families of 5 subjects with a variation in the HOPA gene were screened. Screening the family members revealed a pattern of inheritance of either the 12 base pair insertion or the 15 base pair deletion that segregated with hypothyroidism in all 5 families. The only subject for which family members were not also screened for a variation in the HOPA gene also had a family history with hypothyroidism.

In a fourth phase of this clinical study, DNA samples from more than one thousand consecutive newborns from Iowa (484 males and 924 females) were also screened for variation in the HOPA gene as described in Examples 1–4. A 12 base pair insertion was found in 7 male samples and in 16 female samples. A 3 base pair deletion was found in 1 male sample, and a 3 base pair insertion was found in 1 female sample.

A Chi-square analysis that compared males and females with schizophrenia or schizoaffective disorder (from the first and second phases of the clinical study) with random Iowa newborns demonstrated an increased frequency of allelic variants found in schizophrenics (p<0.03).

These results show an increased prevalence for schizophrenia or schizoaffective disorder in individuals having a variation in the HOPA gene.

Example 7

Localization of the Neuroligin-3 to the PCTG4 Region

Following the cloning and sequencing protocols discussed above, the human orthologue of a rat gene, termed Neuroligin-3 (NL-3), known to mediate cell-to-cell contact communication, was identified. NL-3 is a member of a family of at least three distinct Neuroligin genes. These Neuroligin molecules serve as ligands for a family of cell surface receptors termed Neurexins. Together with the Neurexins, these molecules transmit signals between adjacent cells by functioning like a lock and key.

To briefly summarize the methods of the cloning and sequencing protocols, cosmids containing the neuroligin gene were first isolated from a Super Cos ™ library of genomic DNA partially digested with Sau3AI (Philibert et al., Anal. Biochem., 225: 372–75 (1995)). The first cosmid, CTG-4, contained the 3' portion of the gene. The second cosmid, C6, spanned the gene and was identified by screening the cosmid library with a portion of the CTG-4 genomic sequence using standard hybridization methods (Wallace and Miyada, Guide to Molecular Cloning Techniques, pp. 432–42 (Academic Press, New York, 1987)).

The sequence was derived by direct sequencing of the cosmids and plasmid subclones as well as by several sequencing reactions on PCR templates. Plasmid subclones of human neuroligin-3 were produced by excising the genomic insert from the C6 Super Cos ™ vector by Not I digestion, partial digestion of a gel-purified insert with Sau3 AI, and ligation into pGEM7zf(+). DNA for sequencing was produced from these plasmids using standard plasmid miniprep kits (5 Prime-3 Prime, Boulder, Colo. USA). PCR fragments were produced using standard PCR conditions (Philibert et al., Eur. J. Hum. Genetics, 6: 89–94 (1998)). The fragments were then separated by agarose gel electrophoresis and then purified by use of a Geneclean Kit (Bios101, Vista, Calif. USA) according to manufacturer's directions.

Sequence analysis was then performed by using an automated fluorescent sequencing method, and the finished sequence was assembled using Sequencher ™ (Genecodes Software, Ann Arbor, Mich. USA).

Surprisingly, from our sequencing of cDNAs produced from the human Neuroligin-3 gene, we found that the NL-3 gene is also differentially spliced and that the expression of these gene products is developmentally regulated (see FIG. 4). At least two different protein isoforms have been identified and more are expected to be identified pending the final sequencing of the longer transcripts although it is possible that these longer transcripts are genes that are only incidentally recognized from our probe (for instance by genes co-existing on the same stretch of DNA. What is more, sequencing of cDNAs of 4.4 kb in size isolated from various cDNA libraries demonstrates that the 4.4 kb transcript band on the northern blot in FIG. 1 represents at least two different mRNA splicing products (data not shown). These (at least two) 4.4 kb transcripts are not only strongly expressed in human fetal development but throughout the adult human CNS as well. These findings suggest that specificity of the communication between the cells using this mode of signaling is not only regulated by the Neurexin cell surface receptor (or lock) but by the Neuroligin ligand (or key) as well. Furthermore, it is suggested that the cell growth, differentiation and survival of certain groups of neurons may depend directly on the stable, precisely regulated production of certain protein products from the Neuroligin-3 locus.

In rat the three neuroligins contain an N-terminal hydrophobic sequence with the characteristics of a cleaved signal peptide followed by a large esterase homology domain, a highly conserved single transmembrane region, and a short cytoplasmic domain. The three neuroligins are alternatively spliced at the same position and are expressed at high levels only in brain. Binding studies demonstrate that all three neuroligins bind to beta-neurexins both as native brain proteins and as recombinant proteins. Tight binding of the three neuroligins to beta-neurexins is observed only for beta-neurexins lacking an insert in splice site 4. Thus, neuroligins constitute a multigene family of brain-specific proteins with distinct isoforms that may have overlapping functions in mediating recognition processes between neurons. See e.g. Ichtchenko et al., J. Biol. Chem. 271(5): 2676–2682 (1995).

Although only three different genes have been identified for the Neurexins, hundreds of different isoforms are known to be produced from these genes by differential splicing. Through this differential splicing, groups of neurons generate a combinatorial specificity in cell surface receptors that is thought to allow precise communication from using a limited number of intercellular messengers (Ullrich et al., Neuron. 1995 Mar; 14(3):497–507 (1995)).

Example 8

Further Characterization of Human Neuroligin-3 Gene and Protein

Figure 7:
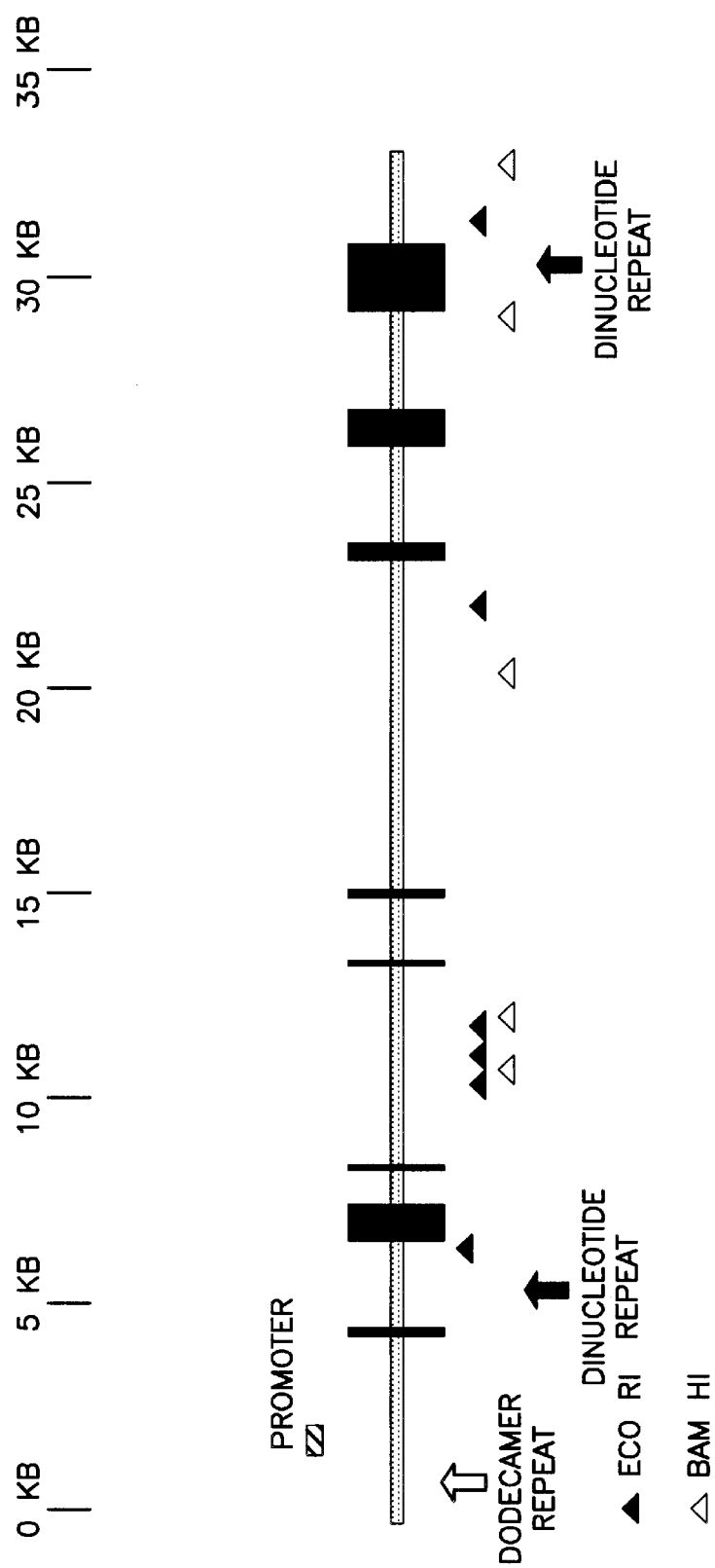
FIG. 7 shows a schematic of the organization of the genomic neuroligin-3 gene. Translated regions are indicated by filled boxes. Promoter sequences are denoted by hatched boxes above the main object. Filled triangles denote ECO R1 sites while open triangles denote BAM H1 sites. The sites of the dinucleotide repeats are noted with filled arrows, and the site of the dodecamer repeat is noted with an open arrow.

The genomic organization of human neuroligin-3 gene is illustrated in FIG. 7. Sequence comparison analysis was performed using BLAST-N (Altschul et al., J. Mol. Bio., 215: 403–10 (1990)) and GCG (Company, Madison, Wis. USA). Protein structural analysis was performed using PC Gene (Intelligenetics, Geneva, Switzerland) and GCG, and exon location analysis was performed using GRAIL suite programs (Uberbacher and Mural, Proc. Nat. Acad. Sci. USA, 88, 11261–266 (1991)). Sequence analysis of repetitive DNA elements was performed using the Virtual Genome Center (Scherer, URL (http://alces.med.umn.edu/VGC.html), unpublished), and promoter analysis scanning was performed using Promoter Scan II (URL (Http://biosci.umn.edu/software/proscan/promoterscan.htm); Prestridge, J. Mol. Biol., 249: 923–932 (1995)).

The gene sequence is 32,272 bp in length and contains 8 exons ranging from 60 to 1864 bp located between bp 4489 and bp 30749 of the sequence. All exons appear to follow the GT-AG consensus splicing rule. The first in-frame ATG is located in exon 2 at bp 7381. A putative promoter was identified as stretching from bp 1793 to bp 2041. A TATA box was identified within the putative promoter sequence at bp 2020, and a CAP site was identified within the putative promoter sequence at bp 2049. The putative promoter overlaps a portion of the neighboring HOPA gene on Xq13 and is less than 900 bp from the OPA element polymorphism that is associated with neuropsychiatric disorders.

GRAIL analysis of the 32 kb sequence did not identify any putative colinear transcripts oriented in the same direction as the neuroligin gene. But these results are not conclusive. For example, GRAIL analysis also did not identify three of the eight exons of the neuroligin gene. GRAIL analysis did predict four exons on the opposite strand. Three of these occur in repetitive DNA elements while the fourth occurs in the opposite strand of exon 4. But BLAST analysis of these putative exons does not reveal any significant matches to existing cDNAs.

Like the HOPA gene, the human neuroligin-3 gene was found to be rich in repetitive elements. For example, at least 17 Alu repeats are interspersed throughout the gene. This frequency exceeds the normal occurrence of 1 repeat every 6 kb (Novick et al., Electrophoresis, 16:1596–601(1995)). Other repeats that were identified include an intronic CA dinucleotide repeat at approximately 5,700 bp, an exonic CA dinucleotide repeat at approximately 29,700 bp, and two tetranucleotide repeats at approximately 28,400 bp $(GAA)_{10}$ and approximately 16,900 bp $(ATTT)_8$. The intronic CA repeat shows a heterozygosity of greater than 0.8 in a group of random Finnish males, and the exonic CA repeat shows a heterozygosity of less than 0.1 in a group of random Finnish males.

Figure 4A:
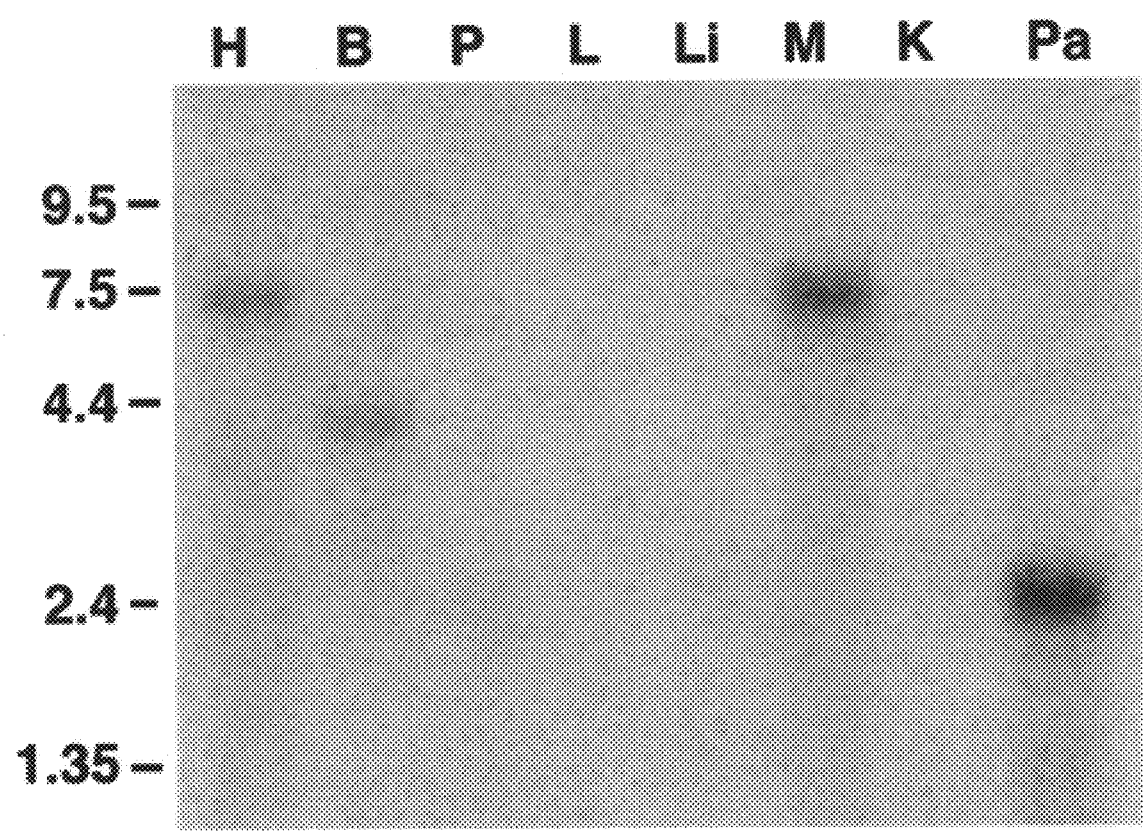
FIG. 4A provides Northern Blots showing neuroligin-3 expression in Adult tissues. (ADULT BLOT) Four different neuroligin-3 transcript of 2.4,4.4, 7.0 and 7.5 kb are expressed as demonstrated by observed signals in human poly(A)+ RNA from heart (H), brain (B), placenta (P), lung (L), liver (Li), skeletal muscle (M), kidney (K) and pancreas (Pa).
Figure 4B:
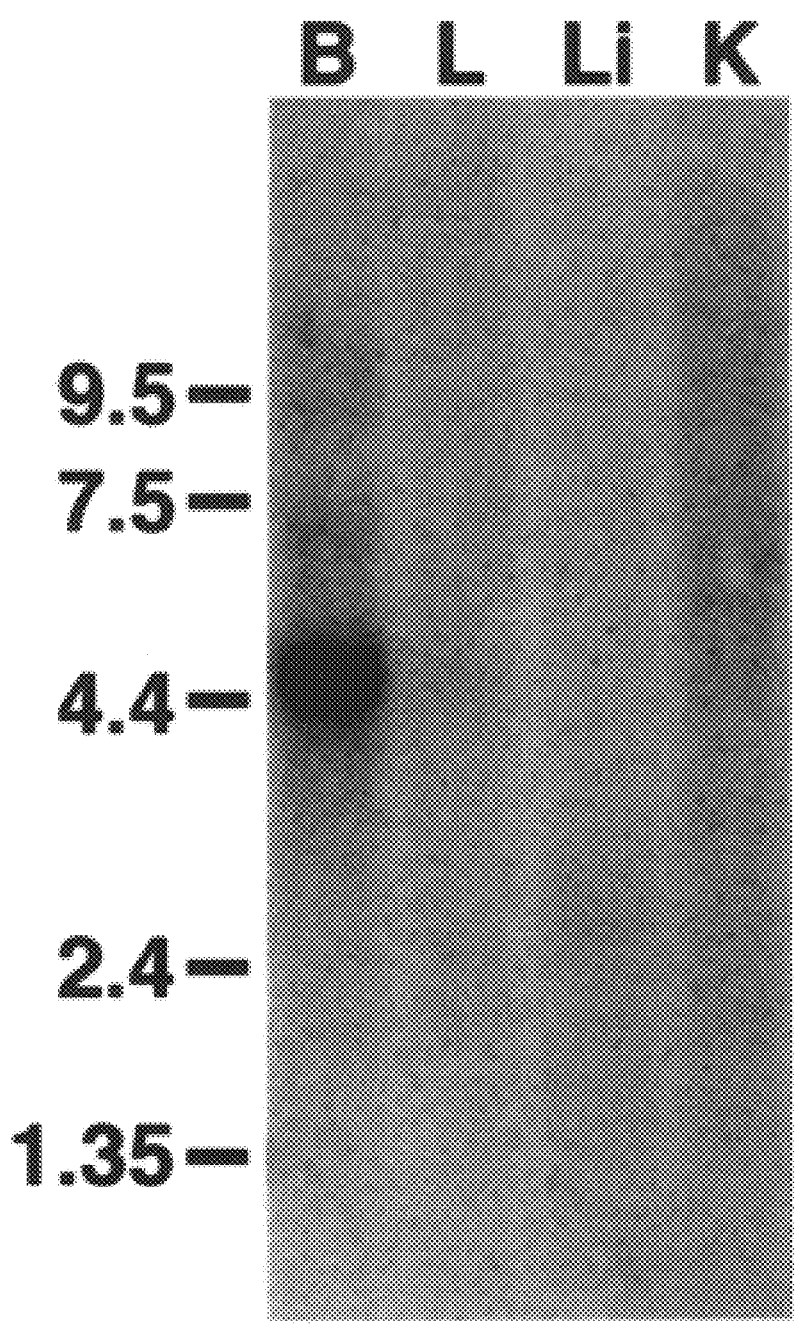
FIG. 4B provides Northern Blots showing neuroligin-3 expression in Fetal tissues as well as in adult brain. (FETAL BLOT) A blot of fetal tissues was performed using the same conditions. The 4.4 kb transcript appears to be heavily expressed in human fetal brain (B) but not in other tissues including lung (L), liver (Li) and kidney (K). Hybridization with a beta-actin cDNA was conducted to ensure an even amount of mRNA in each of the lanes.
Figure 4C:
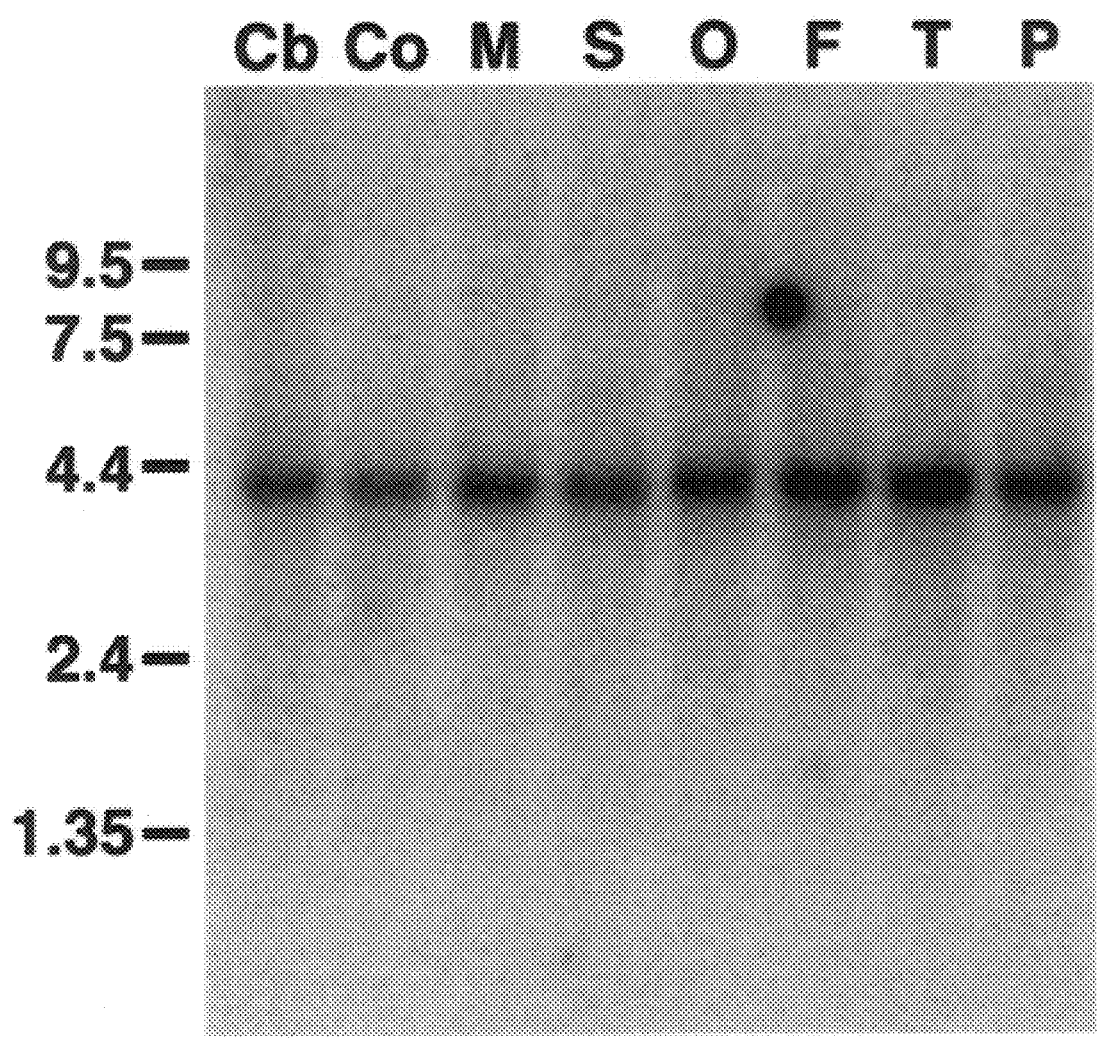
FIG. 4C shows a Northern blot analysis of neuroligin-3 mRNA expression the adult brain. The transcript appears widely expressed in adult human brain as demonstrated by observed signals in human poly(A)+ RNA from cerebellum (Cb), cortex (Co), medulla (M), spinal cord (S), occipital pole (O), frontal pole (F), thalamus (T), and putamen (P). Hybridization with a beta-actin cDNA was conducted to ensure an even amount of mRNA in each of the lanes.

As shown in FIGS. 4A–4C, a 4 kb transcript is expressed by neuroligin-3. The sequence of a cDNA representing this transcript demonstrates a high degree of sequence and amino acid identity to the previously isolated orthologous rat neuroligin-3 mRNA (Genbank U41663). Sequence comparison analysis using the GCG suite of programs demonstrates a 92% sequence identity of the longest human neuroligin-3 sequence compared to the orthologous rat transcript. Amino acid sequence conservation is even higher with the human sequence exhibiting 98.5% sequence identity and 98.7% sequence similarity over its 828 predicted amino acids to the predicted product of the rat neuroligin-3 gene. (FIG. 8). The human sequence contains 20 amino acids less than the predicted rat neuroligin-3 protein. This suggests that there may be another splicing variant that has not been found.

The GCG and PC Gene analyses of the human sequence confirms the structural predictions about the rat neuroligin-3 sequence that have been made (Ichtchenko et al., J. Biol. Chem., 271:2676–2682 (1996)). The analyses of the human sequence show a signal sequence from amino acids 1–36 and a transmembrane domain from amino acids 690–710. The analyses also show another putative transmembrane helix from amino acid 262 to 282. Because the rat and human sequences are identical over these two regions, any discrepancies in the analyses are likely to arise from differences in the PC Gene program parameters.

FIG. 4A also shows a 2.4 kb transcript. Sequence analysis of this transcript suggests that this transcript results from the alternative transcription of at least exons 2–7 and the use of an alternative polyadenylation signal. The truncation of transcription at this point results in the loss of the latter putative transmembrane segment.

FIGS. 4A and 4C also show a 7.5 kb transcript. This transcript appears to be a region in which the HOPA and neuroligin-3 genes overlap.

Example 9

GRAIL Analysis of the PCTG4 Region

GRAIL analysis (Uberbacher and Mural, PNAS 88(24): 11261–11265 (1991)) of the 58 kb sequence was performed to evaluate characteristics of this region. As the GRAIL analysis evaluates up to 25 kb at a time, the region was broken down into three segments for the analysis.

A. Analysis of nucleotides 1–25,000
[grail2exons -> Exons] PCTG4 55298 ANALYSIS OF FIRST 25000 BP IN FORWARD READING FRAME

| | St | Fr | Start | End | ORF-start | ORFend | Score | Quality |
|---|---|---|---|---|---|---|---|---|
| 1- | f | 0 | 1345 | 1488 | 1102 | 1554 | 92.000 | excellent |
| 2- | f | 0 | 2008 | 2112 | 1876 | 2205 | 100.000 | excellent |
| 3- | f | 1 | 2321 | 2512 | 2300 | 2587 | 100.000 | excellent |
| 4- | f | 2 | 2649 | 2805 | 2517 | 2813 | 100.000 | excellent |
| 5- | f | 2 | 3607 | 3686 | 3549 | 3710 | 100.000 | excellent |
| 6- | f | 1 | 3962 | 4096 | 3962 | 4366 | 75.000 | excellent |
| 7- | f | 2 | 4179 | 4281 | 4146 | 4484 | 46.000 | marginal |
| 8- | f | 2 | 5148 | 5247 | 5127 | 5597 | 93.000 | excellent |
| 9- | f | 2 | 5377 | 5513 | 5127 | 5597 | 96.000 | excellent |
| 10- | f | 0 | 5734 | 5865 | 5653 | 5883 | 96.000 | excellent |
| 11- | f | 1 | 6233 | 6382 | 6179 | 6397 | 80.000 | excellent |
| 12- | f | 1 | 6798 | 7027 | 6770 | 7066 | 100.000 | excellent |
| 13- | f | 1 | 7403 | 7483 | 7373 | 7690 | 50.000 | good |
| 14- | f | 2 | 7902 | 8133 | 7902 | 8153 | 92.000 | excellent |
| 15- | f | 2 | 8674 | 8792 | 8622 | 8804 | 100.000 | excellent |
| 16- | f | 2 | 9003 | 9122 | 8805 | 9143 | 100.000 | excellent |
| 17- | f | 2 | 9628 | 9769 | 9606 | 9773 | 98.000 | excellent |
| 18- | f | 1 | 9973 | 10104 | 9791 | 10108 | 100.000 | excellent |
| 19- | f | 0 | 10530 | 10757 | 10468 | 10773 | 98.000 | excellent |
| 20- | f | 1 | 10933 | 11077 | 10853 | 11104 | 94.000 | excellent |
| 21- | f | 2 | 11235 | 11355 | 11205 | 11381 | 77.000 | excellent |
| 22- | f | 1 | 11751 | 11852 | 11714 | 11860 | 89.000 | excellent |
| 23- | f | 2 | 11953 | 12066 | 11751 | 12107 | 98.000 | excellent |
| 24- | f | 0 | 12317 | 12492 | 12310 | 12537 | 100.000 | excellent |
| 25- | f | 2 | 12716 | 12851 | 12627 | 12947 | 93.000 | excellent |
| 26- | f | 2 | 14151 | 14258 | 14091 | 14342 | 82.000 | excellent |
| 27- | f | 0 | 14710 | 14858 | 14683 | 14901 | 90.000 | excellent |
| 28- | f | 2 | 15014 | 15120 | 14988 | 15179 | 72.000 | good |
| 29- | f | 1 | 15487 | 15621 | 15350 | 15691 | 63.000 | good |
| 30- | f | 2 | 15765 | 15938 | 15765 | 15974 | 97.000 | excellent |
| 31- | f | 0 | 17008 | 17109 | 16936 | 17187 | 62.000 | good |
| 32- | f | 2 | 17421 | 17492 | 17388 | 17675 | 81.000 | excellent |
| 33- | f | 2 | 17736 | 17919 | 17676 | 17975 | 100.000 | excellent |
| 34- | f | 2 | 19235 | 19301 | 18519 | 19349 | 86.000 | excellent |
| 35- | f | 0 | 19629 | 19675 | 19426 | 19740 | 53.000 | good |
| 36- | f | 1 | 19833 | 20038 | 19781 | 20083 | 94.000 | excellent |
| 37- | f | 0 | 23296 | 23505 | 23266 | 23616 | 100.000 | excellent |
| 38- | f | 1 | 23858 | 24018 | 23771 | 24022 | 85.000 | excellent |
| 39- | f | 2 | 24531 | 24612 | 24396 | 24653 | 68.000 | good |

[PolyA Sites]

| Str | Start | End | Score |
|---|---|---|---|
| f | 19414 | 19419 | 0.90 |

[CPG Islands]

| Start | End | CpGscore | GCscore |
|---|---|---|---|
| 1042 | 1661 | 0.81 | 65.89 |

[Repetitive]

| Type | Str | Start | End | Score |
|---|---|---|---|---|
| ALU | f | 1 | 292 | 142.67 |
| ALU | f | 16591 | 16850 | 225.33 |
| ALU | f | 20852 | 21130 | 136.34 |
| ALU | f | 22265 | 22521 | 221.00 |
| ALU | f | 24155 | 24376 | 174.33 |
| ALU | f | 21236 | 21343 | 62.00 |
| ALU | f | 21345 | 21376 | 24.00 |
| ALU | f | 21378 | 21409 | 24.00 |
| ALU | f | 15986 | 16265 | 212.00 |
| ALU | f | 3257 | 3426 | 130.00 |
| ALU | f | 22738 | 22899 | 122.00 |
| ALU | f | 13911 | 14032 | 96.00 |
| ALU | f | 13801 | 13909 | 85.00 |
| ALU | f | 22936 | 23029 | 76.00 |
| ALU | f | 3422 | 3479 | 52.00 |
| ALU | f | 3480 | 3543 | 52.00 |
| ALU | f | 21142 | 21199 | 46.00 |
| ALU | f | 22953 | 23044 | 40.00 |
| ALU | f | 3329 | 3410 | 38.00 |
| ALU | f | 3482 | 3542 | 37.00 |
| ALU | f | 16058 | 16139 | 36.00 |
| ALU | f | 22898 | 22936 | 33.00 |
| ALU | f | 13775 | 13800 | 26.00 |
| ALU | f | 22837 | 22891 | 25.00 |
| ALU | f | 21151 | 21190 | 24.00 |
| ALU | f | 13870 | 13909 | 20.00 |
| ALU | f | 13990 | 14026 | 19.00 |
| ALU | r | 53067 | 53327 | 214.67 |
| ALU | r | 51282 | 51573 | 178.67 |
| ALU | r | 46296 | 46574 | 231.33 |
| ALU | r | 44093 | 44373 | 206.67 |
| ALU | r | 33555 | 33841 | 247.00 |
| MIR | f | 13284 | 13358 | 45.00 |
| MIR | f | 13178 | 13256 | 36.00 |
| MIR | r | 13176 | 13418 | 139.67 |
| MIR2 | f | 13284 | 13358 | 45.00 |
| MIR2 | f | 13178 | 13256 | 36.00 |
| LTR11 | f | 10434 | 10469 | 22.00 |
| SVA | f | 22832 | 23007 | 58.00 |
| SVA | f | 16151 | 16253 | 51.00 |
| SVA | f | 3349 | 3430 | 44.00 |
| SVA | f | 16016 | 16067 | 40.00 |
| SVA | f | 13805 | 13859 | 39.00 |
| SVA | f | 3287 | 3339 | 39.00 |
| SVA | f | 22769 | 22822 | 38.00 |
| SVA | f | 21012 | 21068 | 37.00 |
| SVA | f | 3430 | 3480 | 33.00 |
| SVA | f | 3480 | 3521 | 32.00 |
| SVA | f | 16016 | 16061 | 30.00 |
| SVA | f | 13811 | 13850 | 26.00 |
| SVA | f | 3481 | 3538 | 24.00 |
| SVA | f | 3488 | 3521 | 24.00 |
| SVA | f | 16221 | 16253 | 23.00 |
| SVA | f | 22773 | 22813 | 23.00 |
| SVA | f | 22978 | 23007 | 22.00 |
| SVA | f | 3311 | 3332 | 18.00 |

A. Analysis of nucleotides 1–25,000
[grail2exons -> Exons] PCTG4 55298 ANALYSIS OF FIRST 25000 BP IN FORWARD READING FRAME

| | | Start | End | Score |
|---|---|---|---|---|
| SVA | f | 21013 | 21058 | 18.00 |
| SVA | f | 16872 | 16889 | 16.00 |
| SVA | f | 1317 | 1357 | 15.00 |
| SVA | f | 22747 | 22767 | 15.00 |
| SVA | f | 24174 | 24288 | 69.00 |
| SVA | f | 22470 | 22529 | 44.00 |
| SVA | f | 24374 | 24427 | 42.00 |
| SVA | f | 16799 | 16851 | 37.00 |
| SVA | f | 16654 | 16723 | 36.00 |
| SVA | f | 16732 | 16787 | 34.00 |
| SVA | f | 213 | 263 | 33.00 |
| SVA | f | 22479 | 22525 | 31.00 |
| SVA | f | 16613 | 16654 | 28.00 |
| SVA | f | 24177 | 24210 | 28.00 |
| SVA | f | 22287 | 22321 | 25.00 |
| SVA | f | 218 | 263 | 22.00 |
| SVA | f | 24383 | 24427 | 21.00 |
| SVA | f | 16613 | 16647 | 21.00 |
| SVA | f | 13767 | 13784 | 16.00 |
| SVA | f | 20064 | 20095 | 16.00 |
| SVA | f | 22730 | 22747 | 16.00 |
| SVA | f | 3218 | 3234 | 15.00 |
| SVA | f | 16852 | 16872 | 15.00 |
| (GGAAT) | f | 24720 | 24740 | 17.00 |
| (GGAAT) | f | 24720 | 24740 | 17.00 |
| (GGAAT) | f | 24720 | 24740 | 17.00 |
| (GGAAT) | f | 24720 | 24740 | 17.00 |
| (GGAAT) | f | 24720 | 24740 | 17.00 |
| (GGAAT) | f | 24720 | 24740 | 17.00 |
| (GGAAT) | f | 24720 | 24740 | 17.00 |
| (GGAAT) | f | 24720 | 24740 | 17.00 |
| (GGAAT) | f | 24720 | 24740 | 17.00 |
| (GGAAT) | f | 24720 | 24740 | 17.00 |
| (GGAAT) | r | 55018 | 55038 | 0.00 |

[Simple Repeats]

| Start | End | Score |
|---|---|---|
| 15377 | 15498 | 229 |
| 8475 | 8623 | 175 |
| 23389 | 23503 | 149 |
| 22705 | 22745 | 139 |
| 13761 | 13782 | 99 |
| 16874 | 16905 | 98 |
| 18352 | 18456 | 85 |
| 24272 | 24301 | 71 |
| 15979 | 15991 | 61 |
| 3251 | 3264 | 60 |
| 22892 | 22910 | 45 |
| 21681 | 21700 | 42 |
| 16706 | 16723 | 38 |
| 22547 | 22558 | 38 |
| 21218 | 21226 | 36 |
| 20968 | 20983 | 34 |

B. Analysis of Nucleotides 25,001–50,000
PCTG4 GENE REGION BP 25001–50000

| St | Fr | Start | End | ORFstart | ORFend | Score | Quality |
|---|---|---|---|---|---|---|---|
| 1- | f | 1 | 30171 | 30285 | 29787 | 30314 | 65 | good |
| 2- | f | 1 | 30732 | 30864 | 30315 | 31064 | 100 | excellent |
| 3- | f | 1 | 31504 | 31563 | 31485 | 31571 | 100 | excellent |
| 4- | f | 2 | 46805 | 46990 | 46732 | 46998 | 98 | excellent |
| 5- | f | 1 | 49718 | 49999 | 49401 | 49999 | 86 | excellent |
| 6- | r | 0 | 29024 | 29176 | 28975 | 29331 | 91 | excellent |
| 7- | r | 2 | 28732 | 28862 | 28530 | 28886 | 61 | good |
| 8- | r | 0 | 18913 | 19131 | 18826 | 19131 | 46 | marginal |
| 9- | r | 2 | 18055 | 18254 | 18009 | 18254 | 61 | good |
| 10- | r | 2 | 17293 | 17437 | 17277 | 17441 | 97 | excellent |
| 11- | r | 0 | 16516 | 16674 | 16495 | 16767 | 46 | marginal |
| 12- | r | 2 | 6095 | 16138 | 16047 | 16172 | 40 | marginal |
| 13- | r | 0 | 15247 | 15279 | 15241 | 15324 | 88 | excellent |
| 14- | r | 1 | 12944 | 13063 | 12875 | 13078 | 84 | excellent |

[PolyA Ss]

| Str | Start | End | Score |
|---|---|---|---|
| f | 44454 | 44459 | 0.9 |
| r | 14065 | 14070 | 1 |

[CPG Islands]

| Start | End | CpGscore | GCscore |
|---|---|---|---|

[Repetitive]

| Type | Str | Start | End | Score |
|---|---|---|---|---|
| ALU | f | 33079 | 33323 | 208.33 |
| ALU | f | 33697 | 33959 | 210.33 |
| ALU | f | 41707 | 41962 | 216.33 |
| ALU | f | 44127 | 44444 | 209.00 |
| ALU | f | 48836 | 49083 | 219.00 |
| ALU | f | 42889 | 43178 | 244.00 |
| ALU | f | 39997 | 39286 | 240.00 |
| ALU | f | 25730 | 25912 | 155.00 |
| ALU | f | 25237 | 25406 | 146.00 |
| ALU | f | 40882 | 41046 | 133.00 |
| ALU | f | 42398 | 42567 | 120.00 |
| ALU | f | 42944 | 43075 | 116.00 |
| ALU | f | 42812 | 42947 | 110.00 |
| ALU | f | 48371 | 48495 | 95.00 |
| ALU | f | 42588 | 42697 | 94.00 |
| ALU | f | 40754 | 40880 | 89.00 |
| ALU | f | 44975 | 45091 | 73.00 |
| ALU | f | 25646 | 25729 | 64.00 |
| ALU | f | 48237 | 48322 | 60.00 |
| ALU | f | 25405 | 25464 | 52.00 |
| ALU | f | 25465 | 25527 | 51.00 |
| ALU | f | 44797 | 44869 | 47.00 |
| ALU | f | 45024 | 45098 | 43.00 |
| ALU | f | 40971 | 41047 | 43.00 |
| ALU | f | 48419 | 49501 | 41.00 |
| ALU | f | 25472 | 25526 | 37.00 |
| ALU | f | 42999 | 43074 | 36.00 |
| ALU | f | 42874 | 42940 | 35.00 |
| ALU | f | 42622 | 42697 | 34.00 |
| ALU | f | 25846 | 26909 | 32.00 |
| ALU | f | 25315 | 25390 | 32.00 |
| ALU | f | 42485 | 42551 | 29.00 |
| ALU | f | 48321 | 48358 | 26.00 |
| ALU | f | 48190 | 48227 | 24.00 |
| ALU | f | 48372 | 48411 | 22.00 |
| ALU | f | 42786 | 43811 | 20.00 |
| ALU | r | 28530 | 28793 | 197.67 |
| ALU | r | 25109 | 25389 | 192.34 |
| ALU | r | 24125 | 24373 | 222.33 |
| ALU | r | 23256 | 23476 | 199.67 |
| ALU | r | 22694 | 22996 | 242.00 |
| ALU | r | 21129 | 21345 | 175.00 |
| ALU | r | 20318 | 20584 | 239.00 |
| ALU | r | 5935 | 6210 | 235.33 |
| ALU | r | 5535 | 5825 | 255.00 |
| MIR | f | 35086 | 35349 | 140.67 |
| MIR | f | 46315 | 46422 | 56.00 |
| MIR | f | 32303 | 32333 | 25.00 |
| MIR | r | 26528 | 26763 | 133.00 |
| MIR2 | f | 35140 | 35268 | 69.00 |
| MIR2 | f | 46315 | 46422 | 56.00 |
| MIR2 | f | 32303 | 32333 | 25.00 |
| L1 | f | 35067 | 35091 | 17.00 |
| L1 | f | 36084 | 36116 | 17.00 |

-continued

B. Analysis of Nucleotides 25,001–50,000
PCTG4 GENE REGION BP 25001–50000

| | | | | |
|---|---|---|---|---|
| L1 | r | 16328 | 16414 | 0.00 |
| L1PA2 | f | 35067 | 35091 | 17.00 |
| L1PA2 | f | 36084 | 35116 | 17.00 |
| L1PA2 | r | 11084 | 11116 | 0.00 |
| L1PA7 | f | 35067 | 35091 | 17.00 |
| L1PA7 | f | 36084 | 36116 | 17.00 |
| L1PA7 | r | 16382 | 16414 | 0.00 |
| L1PA11 | f | 35067 | 35091 | 17.00 |
| L1PA11 | f | 36084 | 36116 | 17.00 |
| L1PA11 | r | 16382 | 16414 | 0.00 |
| L1PA15 | f | 35067 | 35091 | 17.00 |
| L1PA15 | f | 36084 | 36116 | 17.00 |
| L1PA15 | r | 16382 | 16414 | 0.00 |
| L1PB1 | f | 35067 | 35091 | 17.00 |
| L1PB1 | f | 36084 | 36116 | 17.00 |
| L1PB1 | r | 16382 | 16414 | 0.00 |
| L1PB3 | f | 35067 | 35091 | 17.00 |
| L1PB3 | f | 36084 | 36116 | 17.00 |
| L1PB3 | r | 16382 | 16414 | 0.00 |
| L1MA2 | f | 35067 | 35091 | 17.00 |
| L1MA2 | f | 36084 | 36116 | 17.00 |
| L1MA2 | r | 16382 | 16414 | 0.00 |
| L1MA5 | f | 35067 | 35091 | 17.00 |
| L1MA5 | f | 36084 | 36116 | 17.00 |
| L1MA5 | r | 16382 | 16414 | 0.00 |
| L1MA9 | f | 35067 | 35091 | 17.00 |
| L1MA9 | f | 36084 | 36116 | 17.00 |
| L1MA9 | r | 16382 | 16414 | 0.00 |
| L1MA10 | f | 35067 | 35091 | 17.00 |
| L1MA10 | f | 36084 | 36116 | 17.00 |
| L1MA10 | r | 16382 | 16414 | 0.00 |
| L1MB3 | f | 35067 | 35091 | 17.00 |
| L1MB3 | f | 36084 | 36116 | 17.00 |
| L1MB3 | r | 16382 | 16414 | 0.00 |
| L1MB7 | f | 35067 | 35091 | 17.00 |
| L1MB7 | f | 36084 | 36116 | 17.00 |
| L1MB7 | r | 16382 | 16414 | 0.00 |
| L1MC2 | f | 35067 | 35091 | 17.00 |
| L1MC2 | f | 36084 | 36116 | 17.00 |
| L1MC2 | r | 16382 | 16414 | 0.00 |
| L1MD1 | f | 35067 | 35091 | 17.00 |
| L1MD1 | f | 36084 | 36116 | 17.00 |
| L1MD1 | r | 16382 | 16414 | 0.00 |
| L1MD2 | f | 35067 | 35091 | 17.00 |
| L1MD2 | f | 36084 | 36116 | 17.00 |
| L1MD2 | r | 16382 | 46414 | 0.00 |
| L1ME2 | f | 35067 | 35091 | 17.00 |
| L1ME2 | f | 36084 | 36116 | 17.00 |
| L1ME2 | r | 16382 | 16414 | 0.00 |
| L1ME3a | f | 35067 | 35091 | 17.00 |
| L1ME3a | f | 36084 | 36116 | 17.00 |
| L1ME3a | r | 16382 | 16414 | 0.00 |
| LTR13 | f | 35345 | 35389 | 21.00 |
| MER5 | f | 45963 | 45145 | 82.00 |
| MER5 | r | 26261 | 26443 | 106.67 |
| MER42a | f | 39942 | 39984 | 26.00 |
| MER42a | f | 39961 | 39999 | 25.00 |
| MER42a | f | 39969 | 40001 | 19.00 |
| SVA | f | 42054 | 18156 | 69.00 |
| SVA | f | 25788 | 890 | 67.00 |
| SVA | f | 40923 | 16028 | 62.00 |
| SVA | f | 40162 | 15264 | 61.00 |
| SVA | f | 42951 | 19053 | 61.00 |
| SVA | f | 48369 | 23476 | 60.00 |
| SVA | f | 42588 | 17676 | 53.00 |
| SVA | f | 42918 | 17971 | 44.00 |
| SVA | f | 44978 | 20069 | 44.00 |
| SVA | f | 25266 | 319 | 44.00 |
| SVA | f | 42812 | 18871 | 42.00 |
| SVA | f | 40088 | 15165 | 42.00 |
| SVA | f | 42983 | 18057 | 41.00 |
| SVA | f | 40026 | 15079 | 38.00 |
| SVA | f | 42879 | 18960 | 36.00 |
| SVA | f | 25650 | 702 | 35.00 |
| SVA | f | 40781 | 15835 | 33.00 |
| SVA | f | 44826 | 19873 | 30.00 |

-continued

B. Analysis of Nucleotides 25,001–50,000
PCTG4 GENE REGION BP 25001–50000

| | | | | |
|---|---|---|---|---|
| SVA | f | 25266 | 311 | 28.00 |
| SVA | f | 40224 | 15283 | 28.00 |
| SVA | f | 44019 | 19053 | 27.00 |
| SVA | f | 40026 | 15072 | 27.00 |
| SVA | f | 42428 | 17464 | 27.00 |
| SVA | f | 25856 | 890 | 27.00 |
| SVA | f | 42123 | 18156 | 26.00 |
| SVA | f | 40994 | 16025 | 26.00 |
| SVA | f | 48439 | 23473 | 25.00 |
| SVA | f | 40230 | 15264 | 25.00 |
| SVA | f | 42816 | 18862 | 25.00 |
| SVA | f | 25465 | 522 | 22.00 |
| SVA | f | 42924 | 17964 | 21.00 |
| SVA | f | 25472 | 504 | 21.00 |
| SVA | f | 25676 | 696 | 19.00 |
| SVA | f | 48289 | 23320 | 18.00 |
| SVA | f | 48244 | 23270 | 17.00 |
| SVA | f | 33361 | 8378 | 16.00 |
| SVA | f | 67 | 10091 | 17.00 |
| L1MC2 | f | 36084 | 11116 | 17.00 |
| L1MC2 | r | 16382 | 16414 | 0.00 |
| L1MD1 | f | 35067 | 10091 | 17.00 |
| L1MD1 | f | 36084 | 11116 | 17.00 |
| L1MD1 | r | 16382 | 16414 | 0.00 |
| L1MD2 | f | 35067 | 10091 | 17.00 |
| L1MD2 | f | 36084 | 11116 | 17.00 |
| L1MD2 | r | 16382 | 16414 | 0.00 |
| L1ME2 | f | 35067 | 10091 | 17.00 |
| L1ME2 | f | 36084 | 11116 | 17.00 |
| L1ME2 | r | 16382 | 16414 | 0.00 |
| L1ME3a | f | 35067 | 10091 | 17.00 |
| L1ME3a | f | 36084 | 11116 | 17.00 |
| L1ME3a | r | 16382 | 16414 | 0.00 |
| LTR13 | f | 35345 | 10389 | 21.00 |
| MER5 | f | 45963 | 21145 | 82.00 |
| MER5 | r | 26261 | 26443 | 106.67 |
| MER42a | f | 39942 | 14984 | 26.00 |
| MER42a | f | 39961 | 14999 | 25.00 |
| SVA | f | 33098 | 8276 | 91.00 |
| SVA | f | 48855 | 23987 | 57.00 |
| SVA | f | 44359 | 19414 | 46.00 |
| SVA | f | 41726 | 16804 | 43.00 |
| SVA | f | 49040 | 24099 | 42.00 |
| SVA | f | 41907 | 16966 | 40.00 |
| SVA | f | 33289 | 8341 | 39.00 |
| SVA | f | 33896 | 8952 | 39.00 |
| SVA | f | 41823 | 16897 | 33.00 |
| SVA | f | 33829 | 8884 | 28.00 |
| SVA | f | 33101 | 8134 | 26.00 |
| SVA | f | 49050 | 24095 | 26.00 |
| SVA | f | 33902 | 8948 | 25.00 |
| SVA | f | 33296 | 8341 | 24.00 |
| SVA | f | 44368 | 19414 | 23.00 |
| SVA | f | 48858 | 23891 | 22.00 |
| SVA | f | 42561 | 17595 | 17.00 |
| SVA | f | 42778 | 18795 | 16.00 |
| SVA | f | 42390 | 17407 | 16.00 |

[Simple Repeats]

| Start | End | Score |
|---|---|---|
| 28697 | 28893 | 368 |
| 28803 | 28877 | 207 |
| 33363 | 33418 | 164 |
| 43753 | 43798 | 137 |
| 39937 | 39996 | 136 |
| 35346 | 35456 | 129 |
| 42552 | 42575 | 118 |
| 42853 | 42896 | 112 |
| 40717 | 40758 | 92 |
| 44436 | 44462 | 79 |
| 41279 | 41400 | 76 |
| 49119 | 49140 | 70 |
| 33970 | 33993 | 70 |
| 42380 | 42404 | 69 |

B. Analysis of Nucleotides 25,001–50,000
PCTG4 GENE REGION BP 25001–50000

| | | |
|---|---|---|
| 25391 | 25409 | 44 |
| 48714 | 48726 | 43 |
| 41984 | 41996 | 43 |
| 48368 | 48378 | 32 |
| 26716 | 26728 | 27 |

C. Analysis of Nucleotides 50,001–55,251
[grail2exons -> Exons] Last 5298 bp of PCTG4 GENE REGION

| St | Fr | Start | End | ORF-start | ORFend | Score | Quality |
|---|---|---|---|---|---|---|---|
| 1- | f | 0 | 50368 | 50461 | 50001 | 50465 | 78.000 | excellent |
| 2- | f | 0 | 51911 | 52705 | 51885 | 52754 | 89.000 | excellent |

[PolyA Sites]

| Str | Start | End | Score |
|---|---|---|---|
| r | 3681 | 3686 | 0.90 |

[CPG Islands]

| Start | End | CpGscore | GCscore |
|---|---|---|---|

[Repetitive]

| Type | Str | Start | End | Score |
|---|---|---|---|---|
| ALU | f | 50724 | 50957 | 168.67 |
| ALU | f | 51110 | 51390 | 235.00 |
| L1MA10 | f | 53727 | 53747 | 17.00 |

C. Analysis of Nucleotides 50,001–55,251
[grail2exons -> Exons] Last 5298 bp of PCTG4 GENE REGION

| | | | | |
|---|---|---|---|---|
| L1MB3 | f | 53727 | 53747 | 17.00 |
| LTR5 | f | 51512 | 51553 | 20.00 |
| LTR11 | f | 54160 | 54180 | 17.00 |
| MER8 | f | 52252 | 52271 | 16.00 |
| MER8 | r | 52252 | 52271 | 0.00 |
| MER9 | f | 51001 | 51025 | 17.00 |
| MER21 | f | 52935 | 52955 | 17.00 |
| MER21B | f | 52935 | 52955 | 17.00 |
| MER30 | f | 53725 | 53753 | 17.00 |
| SVA | f | 51132 | 51230 | 57.00 |
| SVA | f | 50743 | 50850 | 48.00 |
| SVA | f | 51309 | 51361 | 33.00 |
| SVA | f | 50929 | 50980 | 30.00 |
| SVA | f | 50744 | 50780 | 29.00 |
| SVA | f | 51132 | 51165 | 28.00 |
| SVA | f | 51316 | 51355 | 22.00 |
| MER22 | f | 52542 | 52574 | 17.00 |

[Simple Repeats]

| Start | End | Score |
|---|---|---|
| 51383 | 51566 | 508 |
| 53716 | 53749 | 118 |
| 52809 | 52857 | 102 |
| 51003 | 51037 | 79 |
| 54003 | 54032 | 70 |
| 54796 | 54806 | 30 |

TABLE 1 shows the DNA sequences of the wild type human PCTG4 region of Xq13 (SEQ ID NO.: 1) as determined by DNA sequence analysis.

```
   1 CCCGCCTTGA ATTACTTCTT CTTTCCATTG TGATTCAATA GCATTTTGTT
  51 ATTTTTGTTA CTGGTGTTAT TTTTGTTTAT TGTTATTTGT TACTTTTGTT
 101 ACAGCACACT GGCTGTCTTT TCTCTAAAAG GCAATACAAG GCCGGCACAG
 151 TGGCGCACGC CTGTAGTCCA GGCTACTGGG AGGCTGAGGC GGGAGGATCG
 201 CTGGAGTCCA GAAGGTTGAT GCTGCAGTGA GCCGTGATAG CGCCACTGCA
 251 CTCCAGCCTA GGCGACAGAG GGAGAACCTG CCTCAAAATA AACAAATAGC
 301 AATACGACAA TAGGATATTG GCTCTGGAAT TCAGAATTTT AGTGCCAGCT ECO
 351 CTGTTACTCA GTAGCTGTAT AATATTGGAT AAGTGAATTT TCACACTTTG
 401 AAAACCAGCT TCCTCCATCC GCAAAATCGA GCCAATAATA ATCCCTAACT
 451 CATGAGGCTG TGAGCAGATT AAAGGAGATA GTGTNTGAAA AGCATCTGAC
 501 ACAATAGGTG CCTCTTTAGC TAGACCAAGG GTTCTTAACC TGGAGTTCAT
 551 GGACCCTTAG GGGATACATG GATGAACTTC AGGGGATCTA AGAATCTAAA
 601 GCAACATTTT GCATGTCAAT ATATGCATAT TATTATTATT ATTATTATTA TRIP
 651 TTTCTGGGAA GAAGGTCCAT AGCTTTCATC AGCACCTTTA AGGGTTGTG
 701 AATCAAAAAC GTTAGTATGC GGTACCCTTG GGCAGAAAAA CAAACAAGAA
 751 AAGGTTAGAC AACTCGATGG TAGACCTTGA GGGATTAGAG CCAGCCTTTC
 801 AGGGTTTAAT AGGTTCTTTC TCATGCATAC ATAGTTTNTA ATGTTCACAA
 851 TAGCCCCTTG AAGGAGGTGT TAGCGCACCT ATTTTTCAGA TGCCGGAACT
 901 AAGAAACGAA CTGATCTGTA ATAGACGGAG TTCCTAACCA ATGCAAATAT
 951 TATTGAAGAC TTTTCTAGGC CAAAACCGAG CTAGGCTATG GGAACCGAAG
1001 TCCAGTCAGA ACTCAGCACC ACAGAGGCCT CCTTCTTCCC TGGTTTGCAT
1051 CCCCAGCTCA TTCTGCGCCT CCGGAACGTT TCATAGATTT TTGCTGAGTG
1101 AAATCGACTT GCTGCCGCCA CCGCCGAAAA ACTCCCGGGG CACAGAGCTC
1151 CGCCCCCACC GGGCCAGGCC CCACCTCCTC TGCAGTCGGG ATTGTCCGAT
1201 GGTTCCCGGC GTACCTCGGC TTCCCTCGGT AGTTTCCGGC AATGGTCGAG
1251 AGTTTCTAAC GTGCCCCCTT GTTGTCTCTC GGCCGCCGTC CTCTCAACCA
1301 CCGCCCCCCT TTTCGGCTCC CTCTCCCCCT TCCCGTTCCC CCAGTCAGCC
1351 TGGCCCTGCT GGTGCCTCCG GCGCTACGGG CTGGGCAAGA T̲G̲G̲C̲G̲G̲C̲C̲T̲T̲
1401 C̲G̲G̲G̲A̲T̲C̲T̲T̲G̲ A̲G̲C̲T̲A̲C̲G̲A̲A̲C̲ A̲C̲C̲G̲G̲C̲C̲C̲C̲T̲ G̲A̲A̲G̲C̲G̲G̲C̲C̲G̲ C̲G̲G̲C̲T̲G̲G̲G̲G̲C̲
```

TABLE 1-continued

```
1451 CTCCCGATGT TTACCCTCAG GACCCCAAAC AGAAGGAGGT GCGTTCGAAA
1501 ATCGGGGCTC TGGAGGGGCC GGGGGCACGC GGTCAGCCTA GGAGGAGGCA
1551 CTGACGGCTG GGAATGAAGG GCGGGGCGGT TCGGTGAGAG CAAAAGTCCC
1601 GAAAGGGGGA AGAGTAAAGT GGGCTGGCGT GGGAGGGCAG GACGGGGGC
1651 GGTGGGGGGT TCCAAGGTAT GAATAGGGGG TGGTGTAGGG GCCGCACCAG
1701 AGGCGCCCTC CTCCACACAC ACCTCAGAAA GTTGTCTGAG ACAGCTTGGT
1751 GGGGTACGGC TGCTCGGCTG TTCGCAAGAG AAGAGTGATG TTTGAGGGC
1801 CGCTGGGTGG CTGGGAATCC TAGTGACCAT GGGAGTGAGG GTGGGGTCCA
1851 AGTGAACGTA AGGGCCCAGC TTTAAGTAAC GATCTGTTCT ACACGGAACC
1901 CTCCTCCTGC CCTTTCACCT TGTTCCTTCT TTTCTCCTGC CCTACTCTCC
1951 CACCCCTTCC CCCTTCCCCT AAGGAAAAAA CAACTAAACG CCGCTTTCCT
2001 GCCTCAGGAT GAACTGACGG CCTTGAATGT AAAACAAGGT TTCAATAACC
2051 AGCCTGCTGT CTCTGGGGAT GAGCATGGCA GTGCCAAGAA CGTCAGCTTC
2101 AATCCTGCCA AGGTGAGACA ACTCTGCCAG GCTGAAGGAA AAGGCTGGAA
2151 GAATCTAAGA AGGAGCAAAG GCCCTGGGTT GGGAAGACTT ATAGGGACAA
2201 CCTAAGTGGC TGAGTTTGCC TTCATGACCT AATACTATCT CATTGGCATT
2251 TGCCCAGCAA AAGGCAGGAC CACCTGTCTG CCCCTTCTTC CCACCCTGAG
2301 GTACACTTTT CTTCCCTCAG ATCAGTTCCA ACTTCAGCAG CATTATTGCA
2351 GAGAAATTAC GTTGTAATAC CCTTCCTGAC ACTGGTCGCA GGAAGCCCCA
2401 AGTGAACCAG AAGGATAACT TTTGGCTGGT GACTGCACGA TCCCAGAGTG
2451 CCATTAACAC TTGGTTCACT GACTTGGCTG GCACCAAGCC ACTCACGCAA
2501 CTAGCCAAAA AGGTAAGGTA CTGTTTCCTG TCCTTCAGGC CAAGGAGGGA
2551 GCATGGGGTA CCAAGTACCC TCCTATTCCC ATATTAAGCT ACATGGGTGT
2601 CAGCTCATGG GGATAATAGA GACCTCACTA TTTGCAATGT CCATCCAGGT
2651 CCCCATTTTC AGTAAGAAGG AAGAGGTGTT TGGGTACTTA GCCAAATACA
2701 CAGTGCCTGT GATGCGGGCT GCCTGGCTCA TTAAGATGAC CTGTGCCTAC
2751 TATGCAGCAA TCTCTGAGAC CAAGGTTAAG AAGAGACATG TTGACCCTTT
2801 CATGGGTGAG TAACTCCTAA CACCAGGTGT ACTGCTGATG GCTTCAAGGA
2851 GTGATAGAGA CACCCTTGGA ACCATCCTCC TTCTTAATCT AGATTCCTTG
2901 TTTCTGCTTG TTTCTTGCAT TTGTTTGATC AGTAAACACT GAGAAATTTG
2951 AGTGTCTACT GTGCGCATAT ACTGGGCTAC AAAGATGTCC GGTGCATAAT
3001 CTCTGCCCCT AGGATACTAG TAGTCTAACA GGGCTGCTAA GGTATATGTA
3051 CAAATAACAT AATTAAATAT AGAAAGTGGT GAATGTCAAG CTAGGAGCAG
3101 AAGGTTCTTT GAGTGGACAA AAGATTACTT TCTTATGGG GTACCCGGAA
3151 AGGCTTTAGG AAGGTGGGAT TTGACTAGAG ACTAAAAGGA TGAACTGAAT
3201 TTACAAATAT GGTGATTAGG GGTGGGGGTA AGGTATTCTA AGTAGAAGGA
3251 TTTTTTTTTT TTTTGAGACA GAGCAAGACT CTGTCACCCA GGCTAGAGTG
3301 CAGTGGCAGG ATCTTGGCTT ACTGCAACCT CCACCTCCCG GGTTAAAGTG
3351 ATTCTCCTGT CTCAGCCTCC CGAGTAGCTG GGATTACAGG CGCCCACCAC
3401 TGCGCCCGGC TAATTTTTGT ATTTTTCTAG AGACGGGGTT TCACCATCTT
3451 GGCCAGGCTG GTCTCGAACT CCTGACCTCG TGATCCACCT GCCTCAGCCT
3501 CCCAAAGTGC TGGGATTACA GGCATGAGCC ACCGCACCCA GCCAGTAGAA
3551 GGATATTCTA AGCAGAAGGA TAGTATCAAA TAGCCCTTTT TCCCTCTTTC
3601 CTCCAGAATG GACTCAGATC ATCACCAAGT ACTTATGGGA GCAGTTACAG
3651 AAGATGGCTG AATACTACCG CCAGGGCCTG CAGGAAGTGG GGGCTGTGGT
3701 TCCACGATAG GGCCCTTGCC CCATGATGTA GAGGTGGCAA TCCGGCAGTG
3751 GGATTACACC GAGAAGCTGG CCATGTTCAT GTTTCAGGTA GAGAGTAGGG
3801 CATGCTGTGT GGGGCATTGG GTTGAGCTTG AACTTGTACT GTGCCAGTAG
3851 AGAACAGAAT CTGCCTGCCA CCTTGCCCCA GTTGTGGTTC TCTTCATCTT
3901 TTCATTTACT TTATCTGCTT CATCTCTAAT AGTCCCCTCT TCCCTCCCCT
3951 GGTACCCATA GGATGGAATG CTGGACAGAC ATGAGTTCCT GACCTGGGTG
4001 CTTGAGTGTT TTGAGAAGAT CCGCCCTGGA GAGGATGAAT TGCTTAAACT
4051 GCTGCTGCCT CTGCTTCTCC GAGTAAGGCT TGGAATTTTG GTACTGGTGG
4101 GGCAGGGGGA GTCAAGAAG AATTTGAGGA AGAATAAAAT GTTAGAGCAG
4151 GGTCCCCTGG AGAGAACTAG GGGCTCTGAT GGTCGTGTCT TCACAGTACT
4201 CTGGGGAATT TGTTCAGTCT GCATACCTGT CCCGCCGGCT TGCCTACTTC
4251 TGTACACGGA GACTGGCCCT GCAGCTGGAT GGTGTGAGCA GTCACTCATC
4301 TCATGTTATA TCTGCTCAGT CAACAAGCAC GCTACCCACC ACCCCTGCTC
4351 CTCAGCCCCC AACTAGCAGC ACACCCTCGA CTCCCTTTAG TGACCTGCTT
4401 ATGTGCCCTC AGCACCGGCC CCTGGTTTTT GGCCTCAGCT GTATCCTACA
4451 GGTAGGTACT AGGCGGGCCC AAGGGAAGCA TTGAGAGATA GCCTGAGAAG
4501 AATCAGGTGC CCATCCCAGA GAATAGGGGT AATTCCAAAT TGGATGTGGG
4551 AGTAGGTGCT GAGTACTTGC TTGGAGGTTG TTGTTTCTTG GTAATGGGGT
4601 GTTAGTCCCC TTTGGGGGTT TTCACCAGCC TCTCTCTCCC TTCCAAGGCT
4651 AAATAGTGGG CCCAAAGCCT TTTAGGAAAG TGAGTGAAGG GAGGGGATCG
4701 GGGTGGAGTG ATGCCTGTCT TGGGGACCCA GTCAGAATAA CTTTGGATCT
4751 GGAATCTACG GGTTGGGTCT TAGAATGGGA TTCCAGGAGG GTAACCATG
4801 GTGAATGAGT TGGGACTTAG CTGTTTCCTA TCTGGTAGAC CATCCTCCTG
4851 TGCTGTCCTA GTGCCCTTGG TTTGGCACTA CTCACTGACT GATAGCAGAA
4901 TTAAGACCGG CTCACCACTT GACCACTTGC CTATTGCCCC GTCCAACCTG
4951 CCCATGCCAG AGGGTAACAG TGCCTTCACT CAGCAGGTAT GTCTGACCAC
5001 TAGCCTGGTA CTCTCAGATT GGGCTATGAG GCTAAATTAC TCTTTCAGAA
5051 GTAGTGATTT GGAGTCTAGT ACTATTCTTC TAGCCTGGGG CTCTGGCTT
5101 TTATATGCCT TGGTACATCC TTGTAGCCTT CCTTTTTAAG ATTGCAGGTC
5151 CGTGCAAAGT TGCGGGAGAT CGAGCAGCAG ATCAAGGAGC GGGGACAGGC
5201 AGTTGAAGTT CGCTGGTCTT TCGATAAATG CCAGGAAGCT ACTGCAGTA
5251 TGTGTCAGAG AACAGATAAT GGAAATATGT TTGAGGAAAG GATGGGGATA
5301 GTAAGGACAT GTAGATCTAA GAGCCAGAAT GCACCGGGCC TCTGGTTCAG
5351 TCCCCTTTAC CACTTTTCCT CCTTAGGCTT CACCATTGGA CGGGTACTTC
```

TABLE 1-continued

```
5401 ATACTTTGGA AGTGCTGGAC AGCCATAGTT TTGAACGCTC TGACTTCAGC
5451 AACTCTCTTG ACTCCCTTTG TAACCGAATC TTTGGATTGG GACCTAGCAA
5501 GGATGGGCAT GAGGTAAGCG AAAAGGGAA TAGAAGGAGC AAAAAACATT
5551 GCAAGAGCAA TAATATGTCT GAGAGGGAAG TCATGGTGAG GCATTGAAAG
5601 CAGAGCATAT CTGCAGAAAT GATCTTACTG GGCCCAGGAT GTTTTATGAT
5651 AGAGCCCAGT CTTTAGGAAA TTGAACTCA TTTCTTTGTC CCCACCCCTA
5701 CCTTACTCCT CCTTCTCTTC CTTTGTTCTC CAGATCTCCT CAGATGATGA
5751 TGCTGTGGTG TCATTGCTAT GTGAATGGGC TGTCAGCTGC AAGCGTTCTG
5801 GTCGGCATCG TGCTATGGTG GTAGCCAAGC TCCTGGAGAA GAGACAGGCG
5851 GAGATTGAGG CTGAGGTTAG AGGGCAGAGA TAAGAGAACA AGATTGGCCA
5901 ATGGGAAGGA ATTTACTGCG GTTGGGAGCC GAGAGATGGA GGTGGTGGAG
5951 GGACCAGAGT TGAAGGTGTG AGAACAGAGT AAAGAAGCAA AAGAGAACCT
6001 AAAGGCAAAG TTACGGACGT GAGGCGAAAG TAGAAGAAGAG TGGATTGTAG
6051 TAAGAGTTAG AGATAACATC AAGGCTTCAG TTGGGAGGTG GTAAAGAACA
6101 TGGAGGTCAG CAGGGGAATG AAAGTGAAAA GCATGGGGTA GAGGTCAAGC
6151 AGGTGGTAGT TTAAGGCTTA CACATTGAGG AGTGAAGAAG CAGGTAAAAG
6201 TCAGTTCTAC AATTTGTTCT GTCATCTTGC AGCGTTGTGG AGAATCAGAA
6251 GCCGCAGATG AGAAGGGTTC CATCGCCTCT GGCTCCCTTT CTGCTCCCAG
6301 TGCTCCCATT TTCCAGGATG TCCTCCTGCA GTTTCTGGAT ACACAGGCTC
6351 CCATGCTGAG TACGGACCCC TACCACTCTC TAGTTACCTC TGCCTAGACT
6401 CAGTTACCCA CCACTGTCAT CAGAAAGCAT AATTAACAGC CCTCTGGTCT
6451 ATATTTCTCT CTTGGGCTCT ATGCAGAATG ACTTTTAGAT GTAGTTCTAG
6501 TGATCCTCTT TAACTGGTCA TCTTACAGTT AAACAGAGTA GAGAAATACA
6551 GAGAAGGATA AAAACAAGAG CTTGTGATTG AAGCATTTTC ACTGCATAAA
6601 TCGCAACAAA GATGTTACAT TCCTTTCTGA GATGATGTGT GGGACAGCAT
6651 GTGGGGTAAC CAACCACACT TTGTCCCTCA ACAATTTCTG GGATTTCTAT
6701 TTGATCACTC TTATTATTGC CTTAGGTGTG TCCCTCTCTC TTTTGGCCCA
6751 CCTTTTTGTG TTCTCCTAAC TTATGTTTCC TCATTCCCTT CCTCCAGCGG
6801 ACCCTCGAAG TGAGAGTGAG CGGGTGGAAT TCTTTAACTT AGTACTGCTG    ECO
6851 TTCTGTGAAC TGATTCGACA TGATGTTTTC TCCCACAACA TGTATACTTG
6901 CACTCTCATC TCCCGAGGGG ACCTTGCCTT TGGAGCCCCT GGTCCCCGGC
6951 CTCCCTCTCC CTTTGATGAT CCTGCCGATG ACCCAGAGCA CAAGGAGGCT
7001 GAAGGCAGCA GCAGCAGCAA GCTGGAAGTG AGTGGGCTTT TCCTTGCACT
7051 AGATCGTTTC TTCTGACATT TCCATCTTCA TGGCTCCCAG GGGCCTCTAA
7101 GAGCCTCTTT TGCCTGGGGG AGGGGGGTAG TATTTTTTTT AGCACTTGGT
7151 GATTGACCAA GCACTCTCAC ATCAATTGTT TCATTGGTTC CTCCCATCAG
7201 CCTTGTGAGG TACTCTTATC CCCATTTTCA AACTGAAGAA AACAGAGGCC
7251 TATACTGGTT AAGTGATTGG ATGAGGCTTG ACTCCAGATC CTGTGCTTTC
7301 CCCAATCTGG TCTTCTCTCT CCACTTCCCC AATGAAGTTT TACAGATGGT
7351 GGGAGCCACT CCCTAGGGCT AAAGCAACTT CGCTTATGTT CTATGCCCTC
7401 AGGATCCAGG GCTCTCAGAA TCTATGGACA TTGACCCTAG TTCCAGTGTT    BAM
7451 CTCTTTGAGG ACATGGAGAA GCCTGATTTC TCAGTAAGTT CAATCCTGAG
7501 CGTGGCAGAA TCTGGATCCT TGGATCTTCC CATTATGCCT GCTTTTGGCA    BAM
7551 TGTTTTTTTG CCCCCTCATC CACTTTCCTT CTTCTCATGT TCTGCTTTCT
7601 CACCTTTCTC TCAGTTGTTC TCCCCTACTA TGCCCTGTGA GGGGAAGGGC
7651 AGTCCATCCC CTGAGAAGCC AGATGTCGAG AAGGAGGTGA AGCCCCCACC
7701 CAAGGAGAAG ATTGAAGGGA CCCTTGGGTT CTTTACGACC AGCCACGACA
7751 CGTGCAGTAC GCCACCCATT TTCCCATCCC CCAGGTACTA TTCCCCAGCA
7801 CCTTGTGATG ATCTGTTTTG AACCCAGATT GCTGTCAAAG GAATTTGCTG
7851 AGGGGTTGGA GCTGTTCTGA GGATGTGGGT TGGGAAAGGG AAGGGCTTTA
7901 GCATGTGGAT GCTGAGGGGT GTGGAGCATG CTTTCAAGAG GAGGGAAGGA
7951 GATCGGTGCT GGAGTCTGAT GGTGCTGCTG GGATGCAGGA GGAGTCATGC
8001 AGCCATGAGT GCAACCAGCG GTTGGTCGTA CTGTTTGGGG TGGGAAAGCA
8051 GCGAGATGAT GCCCGCCATG CCATCAAGAA AATCACCAAG GATATCTTGA
8101 AGGTTCTGAA CCGCAAAGGG ACAGCAGAAA CTGGTGGGTT TGAGGCTCCT
8151 TAAACAGATC TCCCCCAAAG AATGCCCTAG TCAGTCTTCC CTTCCCCAGT
8201 ATAGGGAACT CCCCAGTCAT GTCCCAATGT CCTGTCTCTT GGAGTCTCCT
8251 GAGAGCTCTA GTCCTTTTGA AACTTCCCCC CTCATTCCCC CCCTCTACAG
8301 ACCAGCTTGC TCCTATTGTG CCTCTGAATC CTGGAGACCT GACATTCTTA
8351 GGTACCTCAC AGTAAGCCCC ATACTGCCCT CCCTCCCTCT CCCTTCCCTC
8401 CCTGAACCTA GCACCTCCCT GTACATATTC CTTTAAGGTC CACATAGTCT
8451 GTGGTCCTCT AAACCTTTGC TTCACTGTCC CCTTCCCTTC ATTCCTCCCC
8501 CATCCCTTCC TTGACCCTCC CTTCCCTGTT TCCCTCTTCC TTCCTTCCCT
8551 CCCTCCCTCC TTCCATCTCT CCCTCCCTCC CTCCCATAGC CTTCTCTCCA
8601 TACCCCACTC CCCACCCCTA GTCAACTAGT TATCTTCCCT GTCTTGACTG
8651 GTCCCTTTCA ACTGTCCCCT CAGGTGGGA GGATGGGCAG AAGCGGCGAC
8701 GCAACCGGCC TGAAGCCTTC CCCACTGCTG AAGATATCTT TGCTAAGTTC
8751 CAGCACCTTT CACATTATGA CCAACACCAG GTCACGGCTC AGGTGTGGGC
8801 CTAAGCCCAG CCCCTTTCCC ACATTCTGGC CTCCTGTTCT GTTTTCCTTT
8851 TCTTCCCTAT CTTCTCCCTG CTAGGCAGGC TAAGCCTCCT GGTCTCATCC
8901 CCTTCCAGTG TCATCCTTTC CTCCTTCCCT GGTTCTTTCC TCTCTCCACT
8951 CCCATCTCAC TCCCACTGCC CTTATCAGGT CTCCCGGAAT GTTCTGGAGC
9001 AGATCACGAG CTTTGCCCTT GGCATGTCAT ACCACTTGCC TCTGGTGCAG
9051 CATGTGCAGT TCATCTTCGA CCTCATGGAA TATTCACTCA GCATCAGTTG
9101 CCTCATCGAC TTTGCCATTC AGGTGGGGAA GTTGGGAGA TGAGGGTGGA
9151 GGCAGGAGTT CATGCCATAT AGCGGCTACG GAGGTCATAA GGACAGGCGT
9201 AGAGGCTCCA GCCAGTTTCC CAAGCTATTT GAAGGGGCAG AAAGACTAGC
9251 ATGGGGGGAG TGGAACATGA GCTAAGACTG CAGGAATAGA GACTTAAGTG
9301 CTCCCTGGGG AGGCCAAGAG GCAGATTAGA GCATTGGGCA CAGACCATCC
```

TABLE 1-continued

```
 9351 TCCCACTGTG GAGTTCATAG AACTGTATCC TGGACACTGG TTAGAGGTGT
 9401 TGTTGATAGA ATAAACTATC AACAATAAAC TATCAATAGA GGTGTTGTTG
 9451 ATAGACTGTG GCATAGGGTA ACGAGCCCTT CTATCCTGTG GTGGCTCCAG
 9501 CAGGAAGGGG CTCAGGCCCA GCCTTGCCAG CGTCCCCACA GGAAGGTGGT
 9551 TTCTATGTAA CACAAGGGGC CTCTTTGCAT TTCTCACCCC CGTTTACTCT
 9601 GCTAGCTGCT GAATGAACTG AGTGTAGTTG AGGCTGAGCT GCTTCTCAAA
 9651 TCCTCGGATC TGGTGGGCAG CTACACTACT AGCCTGTGCC TGTGCATCGT
 9701 GGCTGTCCTG CGGCACTATC ATGCCTGCCT CATCCTCAAC CAGGACCAGA
 9751 TGGCACAGGT CTTTGAGGGG TAAGCAGAGC TTCGGAATAA CTGAAACAAA
 9801 GCTCTGGCGA ATGCCGGTGG AAGTGGCCTG GGAAGAGCAT GCACTTCCTC
 9851 ACACTCTGGG GAAGCACCTG CTGCTCAGGT GGGAAAAGAA TGGTATTTCC
 9901 CAGAGGCTTG AATCTGTTTG GAGGAGCCCG CATACCATCT GCTGACCCTC
 9951 CCAACCTTGC TTCTTCATGC AGGCTGTGTG GCGTCGTGAA GCATGGGATG
10001 AACCGGTCCG ATGGCTCCTC TGCAGAGCGC TGTATCCTTG CTTATCTCTA
10051 TGATCTGTAC ACCTCCTGTA GCCATTTAAA GAACAAATTT GGGGAGCTCT
10101 TCAGGTAAGA GAGGTGGAAG GTAAGGGGTA GCGAGTGGGA CCTACTCCCT
10151 TCTTCCCATG ACCACCCAAC TCAGGAGGAG AGGATGGCCC GGGACCCTGC
10201 TGCCTGTCTA GGGTCATTTG TGGACTGTGT CCTCCACATA CTGTTGTGTT
10251 ACCAAGAGTG GGCCCTCTTC CTCAGCAGGC TTGCTCCCCG CCTATATCTG
10301 TGGGGCCCAC CCTCTTCCCC CTTTTCCTCA CTGCCTTCAG AGGCCCCAGT
10351 TCCTTATTCC CATGTGGTTC CTTTCCTGCC CAGTCTGTTT TGTCCCATCT
10401 CCCTTTTCTT GTCTCAAGAT CCTTCATCCC TCACTTTCTC CTTTTTTTCT
10451 TTTCTCCCCT TTCCTGACCA TCCCTGACC TCAGCAGGCC TTCTTCAACA
10501 CTACTATCTA CTTTCCTCCA TCCCTGCAGC GACTTTTGCT CAAAGGTGAA
10551 GAACACCATC TACTGCAACG TGGAGCCATY GGAATCAAAT ATGCGCTGGG
10601 CACCTGAGTT CATGATCGAC ACTCTAGAGA ACCCTGCAGC TCACACCTTC
10651 ACCTACACGG GGCTAGGCAA GAGTCTTAGT GAGAACCCTG CTAACCGCTA
10701 CAGCTTTGTC TGCAATGCCC TTATGCACGT CTGTGTGGGG CACCATGATC
10751 CCGATAGGTA TGGGGTGTAC TGAGTGAGGA AGGGCACCAT GCCCCCATCT
10801 GAGATAGGGA GGGCTGAGGT ACCCGGGAGG TACTACAACC TTGATTATTT
10851 AGTGGGGCAG AGATGAGAAG TTAATGGGTC TGAGGTTTTG TGGAGCAAGG
10901 TTTTTCCTGA GGGCATTTGT ACTTTTCCCT AGGGTGAATG ACATCGCAAT
10951 CCTGTGTGCA GAGCTGACCG GCTATTGCAA GTCACTGAGT GCAGAATGGC
11001 TAGGAGTGCT TAAGGCCTTG TGCTGCTCCT CTAACAATGG CACTTGTGGT
11051 TTCAACGATC TCCTCTGCAA TGTTGATGTG AGACTTGGGG TGGGGTTTTG
11101 CTAGTGGGGC AGTGACCAGG GCAGGGGGCT GGTTGTGATC CTCTGACCAG
11151 GGACAGAGTT CCGTAGAGTG GAGGCACACC GCTTTGAGTG GGCCTCCACA
11201 CTGAGTCATG GTGTCTGTCT GTTTTTTCCT CCAGGTCAGT GACCTATCTT
11251 TTCATGACTC GCTGGCTACT TTTGTTGCCA TCCTCATCGC TCGGCAGTGT
11301 TTGCTCCTGG AAGATCTGAT TCGCTGTGCT GCCATCCCTT CACTCCTTAA
11351 TGCTGGTGAA CTACCAATCT GTAACCCCTA GCATTTCTAG ACCTCAAATT
11401 TCAATACACA CTGGACGGCC ATCCTCTCAT TGTTCACTGT GGGAGACCTT
11451 GCTGCGGCTC CCTGGCCTTC CTCAGAAGGC CAGTCCTTTG GTATGCTGAA
11501 GGCTAGAAGA AACCTGTTTT TTAGCCCTGG ATTTGCAGCC CTGACCTTTC
11551 CAATTTCTGA CCCTTCAACT GCGTAACAGT TCTCTGCTCT ACCTCGCTTT
11601 CAATATTATC TTGCTTTTTC TCCTTTCACT TTACCTCATC TTCTCTCCCA
11651 TGCCCCTGCC ATACACTTGC ATGCATGCAG GCACGCACAC ACATAAACCC
11701 ACATACAGTT TAACTTCATC CCTTCCAGAT CTGTTTTGTC TTCCTTTTAG
11751 CTTGTAGTGA ACAGGACTCT GTGCCAGGGG CCCGGCTTAC CTGCCGCATC
11801 CTCCTTCACC TTTTCAAGAC ACCGCAGCTC AATCCTTGCC AGTCTGATGG
11851 AAGTAAGTGA CCCTGATCTG AACCAGCCAA CAGTAGAAAG TGTGGTTCCC
11901 CTGCCTCCGT GGATTCTACT TTTGCTTCCC CTGACTTCAT CGCCTTCCCC
11951 AGACAAGCCT ACAGTAGGAA TCCGCTCCTC CTGCGACCGC CACCTGCTGG
12001 CTGCCTCCCA GAACCGCATC GTGGATGGAG CCGTGTTTGC TGTTCTCAAG
12051 GCTGTGTTTG TACTTGGTAC GGGGGTAGGA AGGGAGTGGT GCCAGAAGTG
12101 TGTATAGGGT GGAGTGCCAG CTAAACTACA AGGGACAGTC TTTCTCCCTT
12151 CTGAAGGTGG TCTCTCTGAC CTTTGGGGAG GAGGGGAGG AGAGAAGTAT
12201 ATTTCTGTCC CATAGGGCAG GATTTGGGGT GTTTCTACCT CTGTGGGCCC
12251 AGGGTGGGTC TCCACACGTG TTCCAATCTC ACTCTGCCCT CCCTATCTCC
12301 CACCCGTGAA CCACAGGGGA TGCGGAACTG AAAGGTTCAG GCTTCACTGT
12351 GACAGGAGGA ACAGAAGAAC TTCCAGAGGA GGAGGGAGGA GGTGGCAGTG
12401 GTGGTCGGAG GCAGGGTGGC CGCAACATCT CTGTGGAGAC AGCCAGTCTG
12451 GATGTCTATG CCAAGTACGT GCTGCGCAGC ATCTGCCAAC AGGTCAGTTT
12501 CACCTTCCTC CCACACCTCC TAAATGCCTC TGTGTAATAT AGTTCTGTTT
12551 CCAGCCCATG ATCACACCAG CTCCCTACTA TACATTGTGT TCCTTAACAA
12601 CTCCAGCCCA TCCCCCATAT TCCTAACCCC CTCACTGGTT GTTCCCAGTC
12651 CCTGATTGTC AGCTTCCTCA GGAATGGGTA GGAGAACGTT GCCTTAAGTC
12701 TCTGTGTGAG GACAGCAATG ACCTGCAAGA CCCAGTGTTG AGTAGTGCCC
12751 AGGCGCAGCG CCTCATGCAG CTCATTTGCT ATCCACATCG ACTGCTGAGA
12801 AATGAGGATG GGGAAAACCC CCAGCGGCAG CGCATAAAGC GCATTCTCCA
12851 GGTAGGCCAA GGCCGTGGGG CTGTGGAGG AAGCAGTGGG CCCAATCTGG
12901 GGAGAAACAA TAGGAACCTT GAGAAAAGGA GAGGGCAGT TAAGTAGAGA
12951 GGAAGACAAA CAAGGATATA GGGGAGGGGA GAGGTAGCGA GAGAAACAGC
13001 TCCASCATGG GCTGAGGAGT AAGTCCAGTA GGGTCTAGAC TCCAGTGTAA
13051 GAGTATTATG TGAGGGCATA GCTATCTGGA GTGAATCTAG CTTATCAATG
13101 GGAAGCATAG CATCTGGAG GCCTAGGTGT GGGCCGTGTA TATTTGGCAT
13151 TTTGGCCATG GCTCAGGAAC TGAATAGTAA TAGCTACTAC TTGCTGAGCA
13201 TGTGCTTTGT GCCAGGTACT GTGCTAGGCA CTCTGCACAC ATTTCCTCAT
13251 TTAATCTTTA TGACCCTATG AAGTAGGTGA GCCTCCCTGT TTGACCGATG
```

TABLE 1-continued

```
13301 AGGAAACTGA GGCTTGAAGA GGTTAAGTAA CTTGTCTAAC GTCACATAGC
13351 CCATAAGTTT AGAGTCAATA TGTGAACCCA GACATGTCTG TGCACTTTCC
13401 TCTTCACATT GCTTCACACC TTCAGATGAC CAGAGAGTGG AAAAATAAAG
13451 CCGTTGAGGA AAAGCTAAAG GAATAAGGTC TCTTCAGCCC AGAAGAGATA
13501 GTGTTGAAGA GAGATTAGCT AACAGTAGCC TTCTGGTCTC TACAGGACTT
13551 TGAGAGATTG TCTTATAAAG GTTCTGTCAG GGACTTTGAG CAGCTGGTCT
13601 AAAACAAGAG AAGCAGGCTT CAACTTTAAC ATCAAGGGTT TCAAGGTTAA
13651 GCATTAAGCA GAACTTCCTG ATACGAAGGG ATGGGAAAGA TGTGAAATCT
13701 TTCCTGAACT ATTTTAAAAA TTGGARAGAT TTTCAACTAR TTTGGACTAT
13751 TTAAAWGTAG TCTTTTTTTT TTTTTTTTTT TTGAGACGGA GTCTCGCTCT
13801 TGTCGCTCAG GCTGGAGTAC AGTGGTGCGA TCTCGGCTCA CTGCAACCTC
13851 TGCCTCCCAA GTTCAAACAA TTCTCSCGCC TCAGCCTCTT GAGTAACTGG
13901 GATTACAGGT CGCCCATCAC CACGCCCAGC TAATTTTTGT ATTTTTAGTA
13951 GAGATGGGGT TTTGCCATGT TGGCCAGGCT GGTCTTGAAC TCCTGACCTC
14001 AGGTGATCCG CCTGTCTCAG CCTCCCTAAA TGTAGTCTTT CTTAAAGATG
14051 GGGACATAGA GGTCCCTTTC AGACCTCCAG GAGTCTGTGA TTCAATGTTG
14101 CAGGAGATCA GGAATTGGCA TCAGATTGTT GGGTAGCTGG GGGTAACACG
14151 ATGATGACTA GCCTGGGTGT GGGGCCTCTA TCACAGAACT TGGACCAGTG
14201 GACCATGCGC CAGTCTTCCT TGGAGCTGCA GCTCATGATC AAGCAGACCC
14251 CTAACAATGT GAGTAGTGCC TGGACCCTCC CTTTCCTGTG CTCACGTTCA
14301 GCTCCATGTG TCAGGGAGGC GGTCCACCAC AGAAGAACCT AGATCCTACC
14351 CTTGGGCTCT TGAGCTGAAA GATAAGAGGG GATGGGAAAA TGGTGAACAA
14401 GTGGAGCTGA TGATAAGGGA AATGGGTTGA GAGTGTTGGA GCTCTGAGCT
14451 GTGGGGAAGC TTGGTGGTGG TGGTGGAGCC TGTTTCTCTG GCCATAGATG
14501 TAAGGAGGTA TGTAAAGGAG AAGACAGTGA GGAATTGGAG AAATATGGAG
14551 GTACTAGAGG GCATGATTCC CAACAGAGTT GCGTTCCTAT CTCCCCATCA
14601 ATCTCCGCCA GTGTTGTCCT TCTCCGTCAT CTCCGATCTC TCCTACCATC
14651 TGCTTTCCTT CACCCTTAGC TACCTATTTT AGCACTTCTG TGCCTTTCAT
14701 CCTCCCCAGG AGATGAACTC CCTCTTGGAG AACATCGCCA AGGCCACAAT
14751 CGAGGTTTTC CAACAGTCAG CAGAGACAGG GTCATCTTCT GGAAGTACTG
14801 CAAGCAACAT GCCCAGCAGC AGCAAGACCA AGCCTGTGCT CAGGTCGGAT
14851 AGAAACATGT TAGGACCCAT CCCCTTAGGA GTTTATCTGC TGGTAGCGTG
14901 AGTGATATCA GATGCGTGGA GATGCCAGCA TGTCCATCAG GGAAAGGAGA
14951 GGATAGATTG TTCCAGCCTT GCCTGGCTCC CCTGTGACCC TGTGTCCTCT
15001 GTCTGTTCTC CAGCTCTCTA GAGCGCTCTG GTGTATGGCT GGTGGCCCCC
15051 CTCATTGCTA AACTGCCCAC CTCAGTCCAG GGACATGTGT TAAAGGCTAC
15101 TGGGGAAGAA TTGGAGAAGG GTCAGCACCT GGGTTCCTCT TCACGCAAAG
15151 AACGTGATCG ACAAAAGCAG AAGAGGTAAA GGGGCTTAGG GAGTGGACCA
15201 AGATTGAGGG GTAGAAAGGA GAAGAGGCAG GCCCGGGGAA GAATAAAATG
15251 GGCCAAGGAG AAGCATCATA GGAAAGTGGA AAATCAGAGG ATAAGAGTGG
15301 GCATGGCTGA GCAAGAGGCT AGATCTTAAG AGAGTAGTCT GGAGAATGAG
15351 GTTGGAAGTT GACTCCCAAC CCACAGTCTC CCTTTTCTCC TCTCCTCTTC
15401 TCTCCTCTTC TCTTCTCTTC TCTTCTCTTC TCTTCTCTTC TCTTCTCTTC
15451 TCTTCTCTTC TCTTCTCTTC TTTCTCTTGT CTCTAGCATG TCCCTATTGA
15501 GCCAGCAGCC CTTCTTATCG CTGGTGCTAA CATGTCTGAA AGGGCAGGAT
15551 GAACAACGCG AGGGACTCCT TACCTCCCTC TACAGCCAGG TGCACCAGGT
15601 ACAGATCTCT GGGCCATGGA GGTGGGCAGG AGGTCAGGGA AGGATGCACC
15651 TAAGGGGTTA CTCTGTACTT GGAAACTTCA GTACTTTCTG ATAAACATAT
15701 TGGCTGCTGT GGGATGGAAA CACGAAGATC CCTGAGCTGC ATATTTTATT
15751 TGTTTCTATT CTAGATTGTG AATAATTGGC GAGATGACCA GTACTTAGAT
15801 GATTGCAAAC CAAAGCAGCT TATGCATGAG GCACTCAAAC TGCGGCTCAA
15851 CCTGGTGAGA AGGCCAGCTG GGGAGAAGAA GGAAGAGGGT AGGGCTGGAA
15901 ATGCGGAGTG CAAAAGCCTC AGGTTGGGGA GAATGGGGAT AAGGATAGAG
15951 GCCCCAGGTT ATTCTGAGTC TTGAAGGGTT TTTTTTTTTT TTGGAGTCAG
16001 AGTCTCACTC TGTCACCCAA GCTGGAGTGC AGTGGCGCCA TCTCAGCTCA
16051 CTGCAACCTC CACCTCCTGG GTTCAAGTGA TTCTCGTGCC TCAACCTCCT
16101 GAGTAGCTGG GATTACAGGT GTGTACCACC ACACCTGGCT AATTTTTGTA
16151 TTTTTCATAG AGATGGGGTT TGACCATGCT GGTCAGGCTG GTCTTGAACT
16201 CCTTACCTCA AATGATCCGT CTGTCTCGGC CTCCCAAAGT GCTGGGATTA
16251 CAGGCATGAG CCACCCGTGC CCAGCCTGAG TCTTGAAGTA TTAACCTTGT
16301 TCTCTGAAAG TATGCAGGGA CTGAAAGTGG TTAAGGGGGC TGGATCACTG
16351 TGGTCATGGT CCAATAGGTT ATGTACCCTG GATCCTTGCA GGGCCTCTGC    BAM
16401 CTCAGTATCC TAGATTCTGA CTGGGCCCTA GAAGCACTGG AAACCCACTG
16451 TGGAATGTTG AATGGAATCC TGGAAATCAT TCTGTCCAAT TCCCATCACT
16501 TTCTAAGTAT GGAAACAGAG GCCTAGAGAC GTCAAGAATT CCGTCATTGT    ECO
16551 CTTGAGATCA TGTAGCAAAT CATAGGCTCA ACTCAAGCAT GGCCGGGCGC
16601 GGTGGCTCAC TCCTGTAATC CCAACACTTT GGGAGGCCGA GGTGGGCGGA
16651 TCACGAGGTC AGGAGATCGA GACCATCCTG GTTAACACGA TGAAACCCCG
16701 TCTCTACTAA AAATACAAAA AAAATTANCT GGGCGTGGTG GCAGGCGCCT
16751 GTWRTCCCAG CTACTCGGGA GGCTGAGGCA GGAGAATGGC GTGAACCCGG
16801 GAGGCGGAGT TTGCAGTAAG CCGAGGTCGC GCCACTGCAC TCTAGCCTGG
16851 GTGACAGAGC GAGACTCCGT CTCAAAAAAA AAAAAAAAAA AAACTCAAGC
16901 ATGAACTCAG GCGTCCCAAC TCAGATTGGA ACTAAGCTTT CCTGAAACTC
16951 TGGCCTTTGT CCCTGAGCCA TCTGACTGAC TTGTTGTGGC CCTGGCAGGT
17001 GGGGGCATG TTTGACACGG TGCAGCGCAG CACCCAGCAG ACCACGGAGT
17051 GGGGCATGC TCCTCCTGGA GATCATCATC AGCGGCACTG TCGACATGCA    extra g?
17101 GTCCAACAAG TAAAGCATCC CCACCCGCTC CCTGCAGTTT CATACCCAAG
17151 AAGCTCCCCC TACTCCCATG CCAGGTGCAC CCACTGAGAT TGGTGTGGCT
17201 GTTACTGTGG ACTCCGTGGC CCTGGGCTCC CCATACAGTT TTGGTGCCCT
```

TABLE 1-continued

```
17251 TGGGATGACA TATTAAGCAC CTCTCCCTGC TTGTGTCCTC TGCTGAGGCC
17301 TTTTTCTATC TTCACCTCTT TCTTCTTTGG TTTTCTCTCT GGCTTCCTGT
17351 CTCAGTGAGC TCTTCACTAC TGTGTTGGAC ATGCTGAAGC GTGCTCATCA
17401 ATGGGACATT GGCTGCAGAC ATGTCTAGCA TCTCGCAAGG TAGCATGGAG
17451 GAAAACAAGC GTGCATACAT GAACCTGGCG AAGAAGTTGC AGGTAAGCAG
17501 AGGAAGCGGG GGCAAGGTTT GCGGTTACTG GAATCTGCTG TCCAGCCTCA
17551 GGAACTTGCT TCTGGCTGGA GCCCTCTACC TTTCCTTCTC ACGTCTGCCT
17601 TTTCTTTGTT ACTCATGCCG TGAGCATTTA CTGAGTGGGG GTCTTCTCTG
17651 TGCCAGGTTC TGTGCTGTCC CCTGAGACTT CCCATCCCTG TTTTCTGTAT
17701 CTCTGAACTC TTGTCCCATC TTCCTGTGCC TGCAGAAGGA GTTGGGGGAG
17751 CGCCAGTCAG ACAGTCTGGA AAAGGTTCGC CAGCTGCTGC CACTGCCCAA
17801 GCAGACCCGA GATGTCATCA CGTGTGAGCC ACAGGGCTCC CTTATCGATA
17851 CCAAGGGCAA CAAGATTGCT GGCTTCGATT CCATCTTCAA GAAGGAGGCA
17901 TGTTCCATTG TCTGCCCGTG TCCCTTGCCT TTTTTCCCCT TTGGGCAAGG
17951 AACTTTGCCT GCATCAGCTT TGTAGCTCCA ACAGACTCAT CAGGATTCAG
18001 GAGCCCATCA GTCTCTGCCG GTGAACACCA TCTCTGGGGT TTTGAGCAAA
18051 TCACTTAACT TTCCTTACAT TTCATCTCCA TCTTTGAAGT CCCACCCTCT
18101 TTCCTTCACC CTGCCCTCAC CTTTTAACAT ACCACCCATT TTTCAATACC
18151 CTACCCTCCT CTTTCCTCTG CTCCACCTGC CCCATGTCCT ACCCCACCCA
18201 TCTATCTGGC CGACAGCCTG TATCTCTTTT ATTTCTGTGT TTCCCTACAC
18251 CCACCCATCT CTGCACACTT TTATCTTTTC CCTCTCTGTC AGTTGCGGTA
18301 TTTGTTGAGT AACCATAATT ATTGTGTATA GTTTAAAACC CAAAGTCTAA
18351 CTCCTTCATA TATACATTCT CTTCATCTGT CTTCCTAGTC CATCTGTCTC
18401 TTTTCCTCCG TCTCTGTCTC TCTCCCTGTC TGACTCGTTT GCCTTTCTTT
18451 GTCTCTCCAC CTTTTTGTCT CTCTCTTCCT GTATCTTTCT CTCTCTGACT
18501 CTTTCTCGGC CTGCCTAAAG GCAGAGTCTC TCCCTGCCTT CCTCTCTCTC
18551 TTTCTCTGCC TTCCTTTTTC TGTCTTCCTC TGAATGTCAA TCCSTCTCCC
18601 TCCCCGCTCC CTCTCTGGCT TTCTCCCCAA CCCCTTTCTC TCCCGATCTT
18651 CTCTCCCMAC ACGCCCCCCG CCCCGTTAGT TCATCTCCTC TCCTGGTCTG
18701 GGCTGGCTTC ATCTTGTGCC TCCACACCTC TCCCTGTGCC CCACCCTTCA
18751 CTCTCTCCCC GCATAACTCT CTTCCGCATG TATATGTGTA TCCATGTCTG
18801 TCTGTCTGCT TCTTACCATC TCTCCTGAAT CTGCCTATGA CTTTCTTTCT
18851 ACCCATTCCT ACAAATGCTT GCAGTCTTCT GTTTTCTAAG TCCCAACAGC
18901 TTATTGTTTT TCATTTTCTG GAGCAGGGTC TACAGGTTTC CACCAAACAG
18951 AAGATCTCGC CCTGGGATCT TTTTGAGGGG TTGAAGCCGT CAGCACCACT
19001 CTCTTGGGGC TGGTTTGGAA CAGTCCGAGT GGACCGGCGA GTGGCTCGAG
19051 GAGAGGAGCA GCAGCGGTTG CTGCTCTACC ACACACACCT GAGGCCCCGG
19101 CCCCGCGCCT ATTACCTGGA GCCACTGCCA CTGCCCCCAG AAGATGAGGA
19151 GCCGCCTGCT CCTACCCTGC TAGAGCCTGA GAAAAAGGCT CCAGAGCCCC
19201 CCAAAACTGA CAAACCGGGG GCTGCTCCAC CCAGTACTGA GGAACGCAGG
19251 AAGAAGTCCA CCAAGGGCAA GAAACGCAGC CAGCCAGCTA CCAAGACAGA
19301 GGTGAGCGCC TCCCCCGTGA CAGTTCTCCC ACAGCCTCTC ACTTCATGAC
19351 GCTCCGGTTT CTGGTTTGTG GGAGGGGTGG GGGCGCATAA GGAAGGGGTG
19401 CCATTAGAAT CATAATAAAA ATTAACCATA TACGAATTCA GCTCCTCTTT ECO
19451 ACCTCATTCT CCCCCAGCTC CCCGACCCCA TTCAGCTACA ACCCACTCAC
19501 CCTCTTCCTC TGCCACTCAC ACAGGACTAT GGAATGGGCC CGGGTCGGAG
19551 CGGCCCTTAT GGTGTGACAG TGCCTCCGGA CCTCCTGCAC CACCCAAACC
19601 CTGGTTCTAT AACACACCTT AACTACAGGC AAGGCTCCAT AGGGCCTGTAC
19651 ACCCAGAACC AGCCACTACC TGCAGGTGAG TGCCAGCCAC TAGGAATGCT
19701 GGAGGGACCT ACCTGTACAC TCCCCCTGCC CAAAGGATGA TGCCATTCCC
19751 CTGAGGAGCT ATGGATGTCA AGGACACTGA GCAAGAGACA GAGGGATGAG
19801 GAGCCTAGAG GTCAGCCCAC TCTCCTTTTC AGGTGGCCCT CGTGTGGACC
19851 CATACCGTCC TGTGCGCTTA CCAATGCAGA AGCTGCCCAC CCGACCAACT
19901 TACCCTGGAG TGCTGCCCAC AACCATGACT GGCGTCATGG GTTTAGAACC
19951 CTCCTCTTAT AAGACCTCTG TGTACCGGCA GCAGCAACCT GCGGTGCCCC
20001 AAGGACAGCG CCTTCGCCAA CAGCTCCAGG CAAAGATAGT GAGAGGGGCA
20051 GTAGGGAGGG CTGTCAGGGA GAGGGGCTTT TGAGGGTCAC AGGACGGAGG
20101 AGACACTTGG GATCTTCACA AGGACACTCA GGGTGGGAGA CACAAGAGAT
20151 GAGATGGCAG CAAGCATTTC CTGAGTTTGA GTTGTTCTCT TTTCTCCCTT
20201 TAGCAGAGTC AGGGCATGTT GGGACAGTCA TCTGTCCATC AGATGACTCC
20251 CAGCTCTTCC TACGGTTTGC AGACTTCCCA GGTAAGAGCC TGGGATTGTG
20301 AGACTAGGGG GATGAGGCAA GCTGCTCTGC ATACTCTCGG CCCTGATTCC
20351 CTCTCTCCTT CTTCCCTCCA GGGCTATACT CCTTATGTTT CTCATGTGGG
20401 ATTGCAGCAA CACACAGGCC CTGCAGGTAC CATGGTGCCC CCCAGCTAC
20451 TCCAGCCAGC CTTACCAGAG CACCCACCCT TCTACCAATC CTACTCTTGT
20501 AGATCCTACC CGCCACCTGC AACAGCGGCC CAGTGGCTAT GTGCACCAGC
20551 AGGCCCCCAC CTATGGACAT GGACTGACCT CCACTCAAAG GTACCCAAAG
20601 TAGTGGTGAG CTAGGAAGAG ATGCAGAGGT ATAAGGGAGC ATTTGACTTG
20651 GGAAAGCCTG TGCCTGAAAG TGGTGGGACT GGTCAGAACT TTCGGAGACA
20701 TCAAGAATAC TTATCTGGCC ACATAGCCCA TAACCACAGA AGTCTCGAGC
20751 TGGAAGGGAC CCTGGAGACC AATAGTTTCA TGACTACTTC CTTAACAGTT
20801 CTTTGAGGCC CAGAGAGGGG AAATTGTTTA TCTGACTCAA GGAAAAATCT
20851 GGGCTGGGTG TGGTAGCTCA CACTGGTAGT CCCAGCACTT GGGGCCCAA
20901 GGTGGGAGAA TCAGTTGATT CCAGGAATTC GAGGCCAGCC TGGGCAACAT ECO
20951 AGGGAGATCC CATCTCTACA AAAAAAATAC ATATTTTTTT GAAACAGAGT
21001 CGCACTCCAT TTGCCCAGGC TGGAGTGTCG TGGCATGATC ATGGCTCACT
21051 GCAGCCTCGA CCTCYGAGGC TCAGGTGATC CTCCTACCTC AGCCTCCCAA
21101 GTAGCTAGAA CTACAGGCAC ACACCACCAC GCCCAGCTAA TTTTTTTGGAT
21151 TTTTAGTTGA GATGGGGTTT CGCCATGTTG CCCAGGCTGG TCTTGAACTG
```

TABLE 1-continued

```
21201 AGCCACCACA CCTGGCCAAA AAAAAATTTT TTTTTAATTA GACAGGCGTG
21251 TTGGTGCATG CCTGTAGTCC CAGCTACTCA GGAGGCTGAG GTGGGAAGAT
21301 TGCTTGAGCT TGGGAGTTTG AGGCTGCAGT GAGCTGTAAT YGCACAATGA
21351 GCCGAGATTG TGCCACAGCA CTCCAGTGGT GACAGAGTGA GACCCTGTYT
21401 CAAAAAAAAA AGAAGAAAGA AAAGAAAAAG AAAAAAATAT CTGGAGTTCA
21451 TAGATGAACT ACATGATAAG GAGTCGTAAA GCCAGTACCG GCTTTGAATA
21501 CCAGGTTAAA TACCAGGATG GACAAATGAA TGAATCCTCC CACCATGGTT
21551 AACGTTAGTC AAGCCTTAGT TGAGGCCTTG TAACCATGTA TAGAGACTCT
21601 GAAGCTTAGG ATTAAGAACA CTGGGGAGTG GGCTAACTGC CCATTGTGTG
21651 GCCAGCACTA TACCAGGACT GGGTGAGGTG AAGAAAGATA GCAAAAAAAA
21701 CCCCCACGAT ACATAGTTCC TCACTACAAA GAATCTTTAC TATAGCTGGG
21751 GAGATGAGAC TTATAGAAGA ATATTGAGAG AACACTCTGA GCAAAGATAT
21801 AATCAGGTAT GCAGTTGTAT GCTATGAGGT AAAATGTGGA TTGAGAAAAA
21851 GTACGTGGTA ATATCTGTGG GCCTGACTCM ATCAGAGAAT GTTTCATGAA
21901 GGAGGTCAGA CTTGAGTTGG CCTCTGAAGA ATAGCTGTGA TTGGGATTTG
21951 TGGAGAAGAG GAAAAGAAAG GGCATTCCAG GTAGAGGATG TAACGTGAAC
22001 AAAGACATGG GGACCAGAAT GAGGATGGTG CCTGGGGAGA AGGGCCTGGA
22051 TGGAGTGTAA AATCTGTGCT GGGGAAGTCA CTGGGGCTAG GCTAGGAGGG
22101 GGCAGGCTGA GAGATGGCCT TGAATGCTCA GCCGAAGAAT TGAGACGCAG
22151 TCCCAGAAAG GGCTCTTTTG ATCAGAAGAG TGATAGGAGG AGTTGGGTAT
22201 GTTGCAAGGT TCCTTGGAAT GAATGGATAG GATGTGTACT GGAAGGTGCA
22251 AGAAGAAGAC TTCAGGCCAG GCACGGTGGC TCATGCCTGT AATCCCAGTA
22301 CTTTGGGAGG CCCAGGCAGG CAGATCACCT AAGATCAGGA GTTCGAGACC
22351 AGCCTGGTCA ACATGGTGAA ATCCCGTCTC TACTAAAAAT ACAAAAATTA
22401 TCTGGGTGTG GTGGCATGTG CCTGTAATCC CAGCTACTTG GGGGGCTGAG
22451 GCAAGAGAAT CACTTGAACC TGAGAGGTGG AGGTTGCAGT GAGCCGAGAT
22501 CGCATCATTG CACTCCAGCC TGGGCAACAG AGTGAGACTC TGTCTCAAAA
22551 AAAAAAGAAR ACTTGAGACG GGGAGCCTGG CCAGTAGACT CTTGAAGTGA
22601 TATACACATG TGGTAGAACA ACTTGAAATG TTATTTGGGA ACAACAACAG
22651 CAACAGCAAA AAACCTCAAT GAGTGTTTAT AGAATGCCTA TCTTGTGCTA
22701 AGACTATTTT TTTCTTTTCT TTTCTTTCTT TTTTTTTTTT TTTTTGAGAN
22751 GGAGTNTCGC TCTGTCATCC AGGCTGGAGT GCAGTGGTGC AATTTTGCCT
22801 CACTGCAACT TCCACCTCCC AGGTTCAAGC AATTTTCCTG CCTCAGCCTC
22851 CTGAGTAGCT GGGATTACAG GCATCCACTA CCACGCTCAG CTATTTTTTT
22901 TTGTATTTTT GCTAGAGATG GGGTTTCACC ATGTTGCCAG GCTGGTCTAG
22951 AACTCCTGAC CTCAAGTGAT CCACCCACCT TAGCCTCCCA AAGTGCTGGG
23001 ATTACAGGTG TGAGCCACCG CACCCAGCCC TATTTTTCAT TTTTGTAACA
23051 GAAAAATAGC TAATGCAGAA TTGAAAAATT CCTAACCATT AAGGTTATGA
23101 GACACTAAAA TAGAGTATCA TYTTATGCAA CTTATTCCCC AGACTGGAAG
23151 TCTGGTTAGT GACACGAGGA ATGAATGAAA TAACCTCTCA ACGTTTYTTT
23201 CAGGTCAGGG ACCCAAGGTT TATACTGACC CCCTCTCCTC ACCTCCCTCA
23251 TGCCTTGACC TCTGACCCTC TTATCTTTGG AGGTTTTCAC ACCAGACACT
23301 GCAGCAGACA CCCATGATAA GTACCATGAC TCCAATGAGT GCCCAGGGCG
23351 TCCAGGCAGG CGTCCGTTCA ACAGCCATCC TACCTGAGCA GCAGCAGCAG
23401 CAGCAACAGC AGCAACAGCA ACAGCAGCAG CAGCAGCAAC AGCAACAGCA
23451 GCAGCAGCAG CAGCAGTACC ACATCCGGCA GCAGCAGCAG CAGCAGATCC
23501 TGCGGGTAAG GCACTGGGAT TTCATCTGGG ACCTGGGAGC CAGGGAGGA
23551 AGAGAGGCAC AAGTTCTTCC CACACAGTTA CCGAGACTAA ACAAGGCAGT
23601 GTACCAAAAC ACCTAGCAGA GCGGCTGGCC TCTAGTGGTG CTGGAGAAGT
23651 TTTCTACCCT CCCCCTTTTT GTTTTCTGGG GATCATAGTG GGAGAGAGTT
23701 GGACATTGTC TGCTGGGTAC CCTAGATTTG GTTTCTTTCT GTGCAGCTGT
23751 CTAAAAAGGG AAGGCAGTAG ACCCCGAGCT CCCACCCTGC TTCCTCATCC
23801 CCTGCCCTCA GCCCTTTAGT TCTGAGGCTT AGCTTCCTCC CTCTGCTCCT
23851 TCTGAAGTAT CTTTTGTGTT CTTATAGCAG CAGCAGCAAC AGCAACAGCA
23901 GCAGCAGCAG CAGCAGCAAC AGCAACAGCA GCAGCAGCAA CAGCAACAAC
23951 AGCAACACCA GCAGCAACAG CAGCAACAGG CGGCTCCTCC CCAACCCCAG
24001 CCCCAGTCCC AGCCCCAGGT AGCTGCTGGA CTACAGCCCA AGGCTCAGGA
24051 ACAGCTGCCC AGGTTGGGCA CGCAGCCAGT GAACTGGGTT GGGGACAGTA
24101 TGGAATAGGG TAGAGGTGGG AGGCAGGGCA TGGCACCCTA AAAATGGATT
24151 GGGGAGGCCAG GCGCAGTGGC TCACGCCTGT AATCCCAGCA CTTTGGGAGG
24201 CCAAGGCAGG TGGATCACTT GAGGTCAGGA GTTCAAGACC AGCCTGGCCA
24251 AGATGGTGAA ACCCCGTCTC TACTAAAAAT ACAAAAAATA ATAATAATAA
24301 ATAAGCCGGG CATGGTGGCA GGTGCCTGTT ATCTCAGCTA CTCAAGAGGC
24351 TGAGGCAGAG AATTGCTTGA ACTTGGGAGG CAGAGGTTGC AGTGAGCCAA
24401 GATCATGCCA CTGCACTCCA GCCTGGGGGA CAGAGCGAGA CTCCATCTCA
24451 AAAAAAAAAA CGGATTGGGA AAGGAGGTTG AAGAAGGAGA AAAGTTCGAC
24501 TTCAGTCTTC CACTTCCTAT TTCCACCCAG TTCCAGCGCC AGGGGCTTCA
24551 GCAGACCCAG CAGCAGCAAC AGACAGCAGC TTTGGTCCGG CAACTTCAAC
24601 AACAGCTCTC TAGTAAGCCT GCCTGCCTTC CCAAGGAGAA CCCCATGGAA
24651 TAAATTTAGG GGGCGGGGTG GGCCAAAGTA GCTGAAACGA TAGCTTCAGG
24701 CCCAGGTTAT GAGAGGAGGC ATTCCATTCC ATCCCCTTCC CTCGATACCT
24751 GAACAGCTTT CCTCGTGCAT ACCCACACCC CTGCCTGGTC TTCCATCCCT
24801 GATAATCTCT TGGTTTTCAC AGATACCCAG CCACAGCCCA GTACCAACAT
24851 ATTTGGACGC TACTGAGCCA CCTGGAGGAA CTGCTTGTGC ACTGGATGTG
24901 GCCCCACCCT TTCCTCTTAA TTCCCAATCC CATTCCTGGG CTAGCACCAG
24951 TAGTGGTTGG GGCCCTCCCC TCAGGCTCCA TTTTTAATAA GTTTTTAGTA
25001 TTTTTGTTAA TGTGAGGCAT TGAGCTGTTG GGTTTGTAT ATTATTTATA
25051 TAGAGACCCC AGAGCTGTTG CACCCAATAC ACAGAGCTTC TTTGCAAAGG
25101 GAGTGTGCGA GTTCTGCATG TCTGGGAAGG GTGGTCTCTT GGGAGAATGC
```

TABLE 1-continued

```
25151 AGGGGGTTGG ACCAACAAGT CAGAGTCTTC ATTCTATTCT GATCATCTCC
25201 CCTGTTTACC TTACACTCTA AAATTTCTTT TTTTCTTTTT TTTTGAGACG
25251 GAGTCTTGCT CTGTCGCCCA GGCTGGAGTG CAGTGGCGCG ATCTCGGCTC
25301 ACTGCAACCT CTGCCTCCCG GGTTCAGCG ATTCTCCTCC CTCAGCCTCC
25351 CGAGCAGCTG GGATTACAGT TATGTGCCAT CACGCCCGGC TAATTTTTGT
25401 GTTTTTTTTG GTAGAGACAG GGTTCCACCA TGTTGGCCAG GCTTGTCTCG
25451 AACTCCTGAC CTCATGATCT ACCTGCCTCA GCCTCCCAAA GTGCTGGGAC
25501 TACAAGCGTG AGCCACCGCG CCCGGCCTAA ATTTCTTAAT TCTAATTGGA
25551 TTGCTACCCT CTCTTCCTCT TCTTCAACAT GGCAACACAT TAAGGTATAG
25601 GCCCTTAGTC TCTTTTTATT TATTTTTGAG ATGGAGTTTT GCTCTTGTCG
25651 CCCAGGCTAG AGTTCAGTGG CACAGTCTCA GCTCACTGCA ACCTCCACCT
25701 CCTGGGTTCA AGTGATTATC CTGCCTCAGA GCCTCTCGAG TAGCTGGGAT
25751 TACAGGCATA TGCCACCAGG CCTGGCTAAT TTTTGTATTT TTAGTAGAGA
25801 CGGGGTTTCA CCATGTTGGC CAGGCTGGTC TCGAACTCCT GACCGCAGGT
25851 GATCTGCCCG CCTTGGCCTC CCAAAGTGCT GGGATTACAG GCATGAGCCA
25901 CCACACCCGT CCCCTTAGTC TTTTAAGAAG GGGCAATGAA CATTCTCAAC
25951 TAAATGTTGG AGCTTCTTTA CAGCTTTCCT CCATGGGGGA TATACCGCTG
26001 GGATTGAGGA GGGGCCATTA GGCCAGGGGA AACATCAATA GAACCTGATT
26051 CTTCTTCCAC AACACCCCAG ATGTTGGGCC TCAAACAAGC TGGGGAGGGT
26101 GGAGATGACA GACACTGCCT AC*CCTTCTTG TCATCTTGTG TGGTCCCCAT*
26151 *CATGCACCAA GTGGCATACC TTTCATAGGA CAGAGAACTT CCCTGAGAGT*
26201 *CACATTCCTG GATGAAAAAT TGCCCTCCAT TGGCATGTGC CATCATAGAA*
26251 *TAGGTCGTGG AAGGACCGTT TGGTT*CTAGG AGGAAGAGAG ACCAGTAAAA
26301 ATAAGCACCC TTTCTCTCTC TGCCCTACTG CCAGAACTGC CTGTTCTCAC
26351 GTGACCCACC TTGGCAGTTA CCCAGGATGA CTTGCTCGCT CCCATTTTAC
27151 GCTGAGAAAT AAGGGATGCT GATTGAGGTG GAGGTGTGTT TTTTGTGTAGT
27201 ATGACTGAGG GTTCCTGCAG GCAGTGCCTC AGTTTCTCCC TTTGGGACAA
27251 AGTCTCAAGC TTTGCGGGTA AAGTTTGGGC TAGCTGCCCT GGAAGATCAC
27301 CTGTCTGATA GCTTGCAATC TGAGGTGTGT GTGCGCGCCC GCGTGAGAGA
27351 GAGGGAGCGG AACGTGCCTG AGCATGGGGG GAATTGGGCC ATGCCCCAGG
27401 ACTTGAGCCA TCTCTGGCAC AAAAGGAGTT AATGGCAGGG ACCGCGCCCC
27451 CCCGTGTCCG GGAACGGCA GCGCGCCCCC TCGGTGCGCG GGCACAGCAG
27501 CCAGGCTGCC GGAGAGCTGA TCTCGGGGAT TCGGGTGCGG AGCCCTTGGC
27551 CTGGAGGCGA TATGGGTGGT CCGTGCCCG GTTCAGTCGC TTGCAGCAGC
27601 CCGGGGAACA GGTGAGGCCG CCTGCCCCGG TCTCTCATCC TCTAGCTGCC
27651 CATACCTTGC CCCCATCCTA ACCCCTCCCA ATCCCAGGCT CCTCCACTCT
27701 CCAGCCAGTG GCCCCCATCC CTCTCAACCC CATGTTCTCC ATCGGTACCC
27751 CTGACCCCCG ATCCTCCCCC GCTTCTGTTC TCCCTTCTAC CTCCTCCCTA
27801 AATCCCGCAT CCCTAACATC CTCCCGCCCA TGGTCCCTCT ATTTCCACAG
27851 CCCATCCCGC ATGCTCATCA AAATACCCCT ATTGAGGGCC CCCAGCCCCA
27901 TCCCGGGATT GCACATTGCC AGTCCCCCCT CCCCTGCAGT GCAGCCCCAT
27951 CCCCCTTCCA TCATAGCATC TCATAGCCAG GCTCCCTCCC CCACTATCTG
28001 CAGCCCCCCC ACCCAATGGA GGCTTTATC CTATCCTCCC CCATTCCAGT
28051 GCAACTCCAT CCCCCAATCC ATTCCAAGCC CTCGTAGCCC CCAATACTGC
28101 AGTTCTCAAT ATTGGTCCAT TCCTGCACAA TGCCCCGCGC CCAGCACCGC
28151 TGCAGCCCCA AAAGTACCCC GAGATGCCAT TCTCATCCCC GGCATTGCTG
28201 CCTCCCCTTG TCTTCTCCCA AATTGCAAGT TGGACCAGGA TGGAGATCTT
28251 GGCCTTGGGG ATTCACAGTG GGTCCTAGGG TACAGAGGGC GTTTGGGGGT
28301 CGGTCCGATT GTCTAGGTGT TCACGGGGGA GGGGCTGCAG GGAATTGACT
28351 CAAAGGAGAA TTTGGCATTT GGCGCCGAAG GGTTACTGGA GAGGAGGGCA
28401 TCCCGAAAGG GTTAATGGAA TTTGTGGGTT GGGGGCAGCA CCCAGGGGT
28451 TAATGTGGGG GGGTTGCTGG TGGGGAAGCT GTGTGAATGA GCGGTCTGTG
28501 CCCTGGAGTT GCCATGGANA CRGTGAATGG GGGGATTGTG TGAACTCAGC
28551 TGCGGACTAT GCCCCCCCA ATACACAACA CCCACCCACT CCCTCCTGCC
28601 CCACCTCCCT ACTCCTACCC CTTCCTTCCC CTTCCCCTCC TCCCCACACC
28651 CGGGTGCATT CTGGGCAGTG TCTGGGATCT TACCCCCCAT ACTTTGCTCC
28701 CCATTTCCTC ATTTCCTCTG AGCCCCCACC CCTTTAGCCA CTTTACCCGC
28751 CCTCCCTCCT CTTCCTTTTT CTTCTCTCTC TCTCTCTCTC TCTCTCTCTC
28801 TCACACACAC ACACACACAG ACACACACAC ACACACACAC ACACACACAC
28851 ACACACACAC ACACACACAC ACACACACAT TCTCATTCCC CTCTCGTGGT
28901 GGCTGATTGC CGGGCGTTCC CAATCTCCCT CCCCCACCCC TTCAGCCAGT
28951 TCTTAAAGGA GCAGGCCTGC AATCTGGGAA GGCGGGAGAA ATGAGGAAA
29001 ACTAAATGTG CATGTGCGCT GGGTGTGCGT GTGTGTGCGT GTGTGTGCGG
29051 GAGCATGCGG GAGTATCTGT GTGTGCCTGT GTCTATGTGT TGACTGTGTA
29101 ACTGTGTCAG AAGGCCTATG TGTCTGAGTG TGTTGCTATT TCTGTTTCTG
29151 TCTCCACCTA TGTGTCACCA TTATGCTGCA TGTGTCTGGA TATTTACCTA
29201 TGCGGGTATG TGTGATTATA TTTCAGTAAG TCTCTATGTG TGTCTCTGAA
29251 TGTATCATTC TGTGAGGCTC TGGCTGTGTG AGGTGCTCTG TCTCAGAATG
29301 TGGGACTATA TGAGGGGATC TCTGTGGGTT TGGAAATATAT GTCTCTGTGA
29351 GTGAATATCG CAGTGTCTGT GATCCTGGCT TGGTCTCTCT CATTCCCTCT
29401 TTGAGTCTTT GTGAGTTTAT TTCTATGAGT CTCTGAATAT GTGTTCCCCA
29451 TGCTCCGTTG TTTATTTTAT AATACACCGG AAGAGCATCC ACAATGCCTA
29501 GGGTGCTAGG CAGAACTCTT TCTGCCTCAC TTCTGGAATT CGGTGTGAAT
29551 TAAGAGAGAG CCAACCGAAA GGACCAAGGC TTAAGGATTT GGGAGCAGTG
29601 AGGGCTGAGG AGAAATGTAC AGGAGGGGCG CAGGAGGGTC CGAGGAGGAC
29651 TCCCGTGAAT GGCTGTCCCG CCCTCTGCCC TGCCTGAGGG TGAGGGAGTC
29701 TCTCTGTGGG ACTCTGCCGA TTTGCTGCTT TCTGTTCTTG TGTCTTAGTG
29751 TCCCGGAGTG AGGTTGACAA TCCCACCCTG TCCTGAAGTG GAGGTCCCTG
29801 TGTGGGCTTA CCAGGTCCCA AGGGCTACAC AGCTCTGTTC AAGCAGCATG
```

TABLE 1-continued

```
29851 CCCAGGGACC TGAGCTCCAT TTTTGTTTCT CCCCACCCCC TGGCTGTCAC
29901 ATGCTATTCT GGCTCCAGCC GACCCTGATG AACCCCTTTG GCTGTAGAAT
29951 TGAAGTTGGG CACCGGGAAC TTGCAGTGGC AACAACTGTC ACTGTCAAAC
30001 CCCTTGGATT TTCCAGCCAT GGCCAGGCAC ATAGAATGGT TCTGATTGGC
30051 AGTGGATCAT CTGTGGGATC ACAGTCCCTG GGCCCCTGGG CATGTGAAAC
30101 CTCTCCTAAC TATAAGAGAA TAGCCCAAGC CCAGCAGGGC CCCCAAAGAC
30151 CAACTCTGTT GCCCTCCCAG ACCATCTTGG ATGACGCATA CTTCCCTCTT
30201 TCCACAGGCC TGTCTGGCCC TGAGGGAGTC CCCTTTCTGA AGCTGTGGTG
30251 CTTGGACGAC CTGCTCTCTA CATTGCTGGG CACCTGTAGG TGTCCCTCGA
30301 GAGCTCAGTT TTGAGGTTCA AGTCAGTGTG GCCATGAAGG GGCTGCCTAT
30351 TGGGCTGATG CTGTGACCCT GGAGTCTGCC TCTCCTGCCA GTCCCCCTGC
30401 CCGGAACATG TGGCTGCGGC TTGGCCCGCC CTCGCTGTCC CTGAGCCCCA
30451 AGCCCACGGT TGGCAGGAGC CTGTGCCTCA CCCTGTGGTT CCTCAGTTTG
30501 GCGCTGAGGG CCAGTACCCA GGCCCCAGCA CCCACAGTCA ACACTCACTT
30551 TGGGAAGCTA AGGGGTGCCC GAGTACCACT GCCCAGTGAG ATCCTGGGGC
30601 CTGTGGACCA ATACCTGGGG GTGCCCTACG CAGCTCCCCC GATCGGCGAG
30651 AAACGTTTCC TGCCCCCTGA ACCACCCCCA TCCTGGTCGG GCATCCGGAA
30701 CGCCACACAC TTTCCCCCAG TGTGCCCCAC GAACATCCAC ACAGCTGTGC
30751 CCGAAGTCAT GCTGCCGGTC TGGTTCACTG CCAACTTGGA TATCGTCGCT
30801 ACTTACATCC AGGAGCCCAA CGAAGACTGT CTCTACCTGA ACGTCTATGT
30851 GCCGACGGAG GATGGTGAGT GCTGCGGCCA GGCACTGTGC CCTCCCTGCC
30901 TCCCGCCTGC CCTGCTGTGT TTGTGGCTTG CATGTGGTTG TGTGCCCTGC
30951 AGCATGCATC TGTCTGTCTG TGAAAATGCT TCTAACCATC ACTCTGCTTG
31001 GCCTCCCACC CCCCTCCCTG TTCTTCCCTC TCCCAGCATT GTCCGAGCTC
31051 CCATGTGTGA GTGACACTGT TGCCAGGAGG GGCCTGGCCC GGCCTGAGAG
31101 CTCTGACGGG TCTCGGTCCA GTGCTGGATG GGGTCCCCT GGGGGAGTAT
31151 GGGTCACGGC TGGCAGCTAC CCGCGGGAGG ATGCTGGCTC ACCAGGCCC
31201 CCCTGTTGCC ATTCCACCTG CTTCGAAAGG TGGTAGGTGT GTGTGGCCAA
31251 GGGCACTGGG TGTGTGGGGG GTGGGCAGC AAGCCTGGTG GGTGATGCTT
31301 AGGTGCCTCC TCTTTCACTA GCTGATGCCT CCTCCCGCGG GGTCACACT
31351 AAGGTAAGTG ACAGAAACAA GGAGATGGTG GGACAGGCTC TCTGCCATGT
31401 GCCGCCTGCA GAGCAGCTCA GCTCTTGGGG CCTGGGGGGT GGGGGGTGCA
31451 TGCCCCTGGG CAGAGGCCTC CTGTTATTTT TTAGTTTTTT ATTCATTTTA
31501 CAGTAAAGCG GATTTCCAAG GAATGCGCCC GAAAGCCCAA CAAGAAAATT
31551 TGTAGGAAAG GAGGTAGGTA GCGAGCCGGC GGGGAGGGAG AGAGAGAGAG
31601 AGGGAGGGCT GCCTGCCCAC CTGCCCTTGC CCCCAGGACC CAGCCTTCCT
31651 CCAAGTAGCC CAGGCTCAGG GGGCAGTAAG CAGGCATAAG CGCCACCTCA
31701 TCTGAGGGCC CTGGCTGCCT TGCAGGGAGG ATTTGGTGGC CTAAGGCAGG
31751 CTCAGAGCAG AAGCAGCAAC CCTATTTCTT CCAATCTTCC CAGCCCCAAA
31801 TTCCACCCTA AAGTGTGTGC CAAAGGCAGA GCCAGTGGCT CTCTCGGTGA
31851 CACCTCAGGA GAAACTCTAG GAAGCCAAGA TGGAGCCAGA GGCTCCACCC
31901 TTTTCCTAGT GGGTGGAGCC AGAAGACCAT CCCTTCTGTG TTCTTTCTCC
31951 TGGATTGAAA GTCTAGACTC AATTTTCCCA CCCTGAAGCT TAGACCAAAC
32001 GTGTACACAG GTTTAGTAAC TCCTGCCATA CACACCTCTG TCTCCCACCC
32051 CACTACCTCT GGCCAGAGTG TAGCTGATAG ACCCAGGCTG CTCTGGTGGC
32101 AGAACTTGGG GGTCTCTGGG AACTATGGAC TTTAAAGGAG GCAAAAGATC
32151 CTGAATTTTA AATTTACCCT CATGCTGAGA GGAGTTTCTC CCCCTGTATA
32201 ATAATTCTTC CTGTTGGAAT ATCACTTCAT GTTTTCTATA AAGTGCCTTG
32251 GCATTTACCT TAGAGAATCC TCCCTGTATC TCTGGAAGCG TCTAAGGCAG
32301 GAATCAGTAT CCCAATTTTA CAGATGAGGA AACAGGCCCA GGGGAGTGAC
32351 TTGCTGCTGC TCAAGGCCCC TGTCGCTGGT CTGTGGCAGA GCTGGGACCA
32401 AAACCTGGGT CTCTTGACCT TCAGGGCGTG TTCCTTTCCA CTGTAGCACA
32451 CAGAAGCAAC TCCCATCTGC TCATTCCCAT CTCCCCAACT CAAAAAAAAT
32501 GGTGAGATGT GGCTGGGCTG GGGAGAATTG GAACAGTAAC AGCCTAAGGA
32551 ACAGGTGGAA AAATCACAGC TTGATCCCTA CAACCCTCTG GCAAGCTGGG
32601 AGTTTGTTTT CCTTTGATGT CCTAGGGCAG AGTTTCTCAG AATGGGGTTG
32651 CCAGGATTTC TGGGATGGGG TGCTCCTTAC TGAATAAGAA TTTCTGGGAG
32701 CAGAGCCTGG AAATCTATAT GTTGAACATG AGCCCTGAGC GCTTCTAATG
32751 CACACCCGAG CATGGAATGA GACCCGCTGC TGTAGGGATA GTATTTCACC
32801 ACAGCCCCAT ACCCCACCCA GGACCTCACA CACCATAGGC AATTGATGTT
32851 TTTTGTGTAA TTCAGAAGCA TCATGGTGCT GCAGAAAGAG TACAGGTCTG
32901 GGAAGCACAA GGCCTGAGTC CCAGCTCTGC TGCCAACTCA CAGTGAGACC
32951 TTAGGCAAGT CTTGTCCTTC AAGAACCTCT GTTTCCACAT CTGAGGTTGG
33001 TAGGGTACAG TTCTGGCCTT AGCATTCCAT TAGCCTGTAA ATGAATTCAG
33051 GAGGAAGGTC TCTTAAACCT GCAGGAGAGG CCGGGCGTGG TGGCTCACGC
33101 CTGTAATCCC AGCACTTTGG GAGGCCGAGG CAGGTGGATC ACCTGAGGTC
33151 GGAAGTTCGA GACCATCCTG GCTAATACGG CAAAACCCCG TCTCTACTAA
33201 AAAATACAAA AAATTAGCTG GGCGTGGTGG CGGGTGCCTG TAGTTCCGGC
33251 TACTCGGGAG GTTGAGGCAG GAGAATGGCA TGAACCCAGG AGGCAGAGCT
33301 TGCAGTGAGC CGAGATCGTG CCACTGCACT CCAGCCTGGG CGACAGAGCG
33351 AGACTCCATC TCAAAAAAAA AAAAAAAAAA AAAGAAAGAA AAGAAAGAA
33401 AAAAACCTGA AGGAGAGATG GCATTCACAT TAACCATTTC TTAGGAAGAA
33451 TGATCGCCCA GTAAGAGCCT TGGGCTGTCC AGTCCAGCCA TGAGAGTGTG
33501 GCCAGAGAGC AGACTGGAAG CCCCGGCTCA AACATGCACA TTTACCAATC
33551 GTGATTGTTG ACTGTGGGCA AGGCCATGTG CTAGGTGTTG TTGGGATGTG
33601 GAGGGATGTG AGGTAGAGGA AAGATTTAGA AATGACTAAA GGCCTAATCA
33651 CTGCTCTGAA GAAGCTCTTA GCCTTGTATT AAAACTCAGC TGGTTTGGCC
33701 GGGCGCGGTG GCTTATGCCT ATAATTGCAG CACTTTGAGA GGCCAAGACG
33751 GGTGGGTCAC TTGAGTTCAG GAATTCGAGA CCAGCCTGGC CAATATGGTG
```

TABLE 1-continued

```
33801 AAACCCCATC CCTACTAAAA ATACAGGTGC ATGGTGGCAC ACACCTGTAG
33851 TCCCAGCTAC TTGGGAGGCT GGGGCAGGAG AATCGCTTGA ACCCAGGAGG
33901 TGGAGGTTGC AGTGAGCCGA GGTGGTGCCA TCGCACTCCA GCCTGGGCAA
33951 CAAGGCTGAA ACTCCATCTA AAAAAAGAAA AAAAAAAAAC TCAGCTGGTT
34001 TCCCTAAGTC CCATGGGCCA ATCAGGAAGT GGGTTCCAGA CAGTGCAAGG
34051 GAAGGCATTT GGTCATTTCA CTGTTCAAAT TAGTTCCCTA CCCAGGACCT
34101 GGTGGCCATT TGGAAGAGTG ACAAATCCCG CCTCTTGAGG GAGAGCCATC
34151 CTCGGAGGTC GTTAGGGTTG TGGTGTGCAG AGGTCTGGGG ACCAGCCTGG
34201 CTGGGATCCC TCAGCGGCGC AGGGTCTGGG AATGGTGGTC GGCAGTCAGG
34251 CTGGCCTGGG TGAGAGGCAT GGCGGCTAGG AGCTGCTCAG GAAGTGCCAG
34301 GCTGAAGGAG CAAAGGCATC TGTGTGAAGG AGGCTGAGAC AATGCAGCAA
34351 CCCAGGAACA CTTTCAGAGG GATTCACAAG GGACTTATCT TCTAAGTCAG
34401 GGATGATGGG AAATGAAGGG TTTCCTGGGG AAGACCTGCC CCATCTCCCC
34451 AACACCCCAC CCCATCAAGT TGGAAGGAAT TCGTGTCTGG GGATGAGCAA
34501 TTCCTTCCCG TTTGGTAGGC TGTCCGCAGT GTGAGGGATG ATGCCCATGT
34551 CCCATTAAGG TTTCTGAGGA CAGCACTGGC AGGTGTTGAG CTAATGTGTT
34601 AAGACGGTAG GTGCCACCGG AAGTTCAGGG AGCCAGAGGC AATTTCTCCC
34651 CTAGAGCTGT GCTCTTGTCC TGGTTGAAAA GCCATTTTGT AGGATGAGGG
34701 CAGTTCCTGT TTTGATGAAT GGCTGTAAGG AAATCTAGTC ATCAGAGTCC
34751 AGACCGGCTG GGAAAGAGGG CTCTTTACTC CCTCCAGGCT GAGGGTATCT
34801 GATGTCATAG ATGCCTGGGT TGGCAGCACA GCCCCCTCTG TTTCCACACA
34851 CTGACCAGCA TCCAGACAGC CGGTCCTCTC CCTCCACAGC CATCGCCAGG
34901 ATGCACTTCT AGCCTCCTTA GAACAGGAAG GAGAATCTGT GCCAGCTTAG
34951 CCCCAGATCC TAAATGTCTC CCTTCTCACC TCTAGTCTCT TCTTTTTTCT
35001 CTTCCCCTCC TTGCCCCTTC TCTCCCCCTA CATGCCCCAC TGCTTTTCTC
35051 ATCTATTTCT TCCCTTCCTT CCCCTTTCCC CCACCCCAGA AAGGTGGCAT
35101 GATGCAGTGG AAAGACCATG GGCTTTGGAG TCAAGCAGAC CTGGGTGTGA
35151 ATCGCACCTC TAGCACTTCC TAGCTGTGTG ATCTTGAGCA AGTCACTTTA
35201 CCCCTCTGAA CCTCAGTTTC CCCATCAGTG AAACAATAAT AAGGATAGGA
35251 CCTATCTCAC TGGGGTGTAA GGATCAAACA ATATGGCAGA AGCAGAGTGT
35301 CTGGCACATG GTGAATATTC AGTACATGGT TGGAGCTGTG ACCATTATTC
35351 CTATCTCTTT GTTTCTCTTC TATTTTTTTT CTCTCTCTCT CACCATCCCT
35401 CTCTCCTCTT CCCCTTTCTT CTGTCCCTCT CTCCCTCTCT GGCTCTCTCT
35451 ACATCTCAGA GCAATGCTTG CTGCTCTCAA CACTGGTTCC TGTGGGCAGG
35501 AACCCCATTT GCCATTAACC AGAGCAGGGG CTCCAACAAG GAAGACCAGA
35551 GGGAAAGCTT CATCTCCCAT TTTCTCCTGT GGGAATCAGG GTCAGCTGAG
35601 GCCCAGCTTG AGCCTGCCCA CTGGGCCCCA GGAGCTCAGG CCTGGGGTCC
35651 CTCTACACGT CTCTGCCCTA AGTTACCTCG TATCCACAAC CTCCACACTT
35701 GCTGGCAGTG TCACCCCTCA CCCTTGGTAC CTGACCCTGC TCTCCAGCTC
35751 GACCTGCCTG TGTTCACACA AGCAGCCCCT TCCACCCAGA ATGAATCCTT
35801 CCCCTGAGAG GGTCTCTGGC TCTGTGCCCT GGCCCACTTG CTGCTACCTC
35851 CTTCCTCACT GGAAAGGTAG TTGGTTGAGA TGGGCTGTTG GGGACAAGGA
35901 GGCGGGGCAA GGCGGTGCAG AAAGGCCAGC ACAGCAGGGG CCTGCAACAC
35951 CATCATCCTG ATGAAGGTCT GGGCCTCAGC CCACCCATTC CCTCAGTTCT
36001 TGCCATCCCT CCTGCCTGTC CTGGGCCCAG GCCCGGAGCT GGCTTGCTGG
36051 GCCACACTGC AGTCATGCTG TTTTTGAATT CTCTCTCTGT TTTGTTCTCT
36101 GTTCTGTGCT GTTGTGTCTC CCCGTGTCTG GTCCCCAGGA TCCGGCGCTA
36151 AGAAACAGGG CGAGGACTTA GCGATAATG ACGGGATGA AGATGAAGGT
36201 ATTTGGGGGC TGCAGGGCGC GGCGGCTGGT GCATGGCACA GAGCCCCTCC
36251 CCTTCTCGAT GGGGAGAAGC CCCGTCTGTC TGTCCGTCTG TCCGTTGGTG
36301 TGTTTCTGTT CCTGTACAAG GCCGTTGGGC TGTTCATCTG TCTTTGGCCC
36351 TGTTGGCCAC TGGGAGTTCC GGGGTGATGG ACATGGCTGG CAGGAGCAGG
36401 GGACCACAAG CAGAGCCATG GGGAGGACAT CCTCCTTGCC TGGGTCTCCC
36451 GCCCCTTCCC CATCTTCTGT GGTTCAGAGG CACCTGCCCC TACTGAGCAG
36501 CAGGGAGAGT GGAGAGAAAA CAGGACCACT GAGGGCGGGG AGAGGACAAA
36551 GACAACGGAA CGGCAAGGAG ATTACCTGTG TTTCAGTGAA GAGACCCCTG
36601 TGTCTCACAG GGAGCCTGGC TTCTGGGAGA GGGGCCCCGC AGGATGGTGA
36651 ACTGGGAAGT GAGGCAGTGA CAACCAAAGG GGCTGGAAAA GCAGCACCAG
36701 AACCTCCCCA GCCTTCTAGA AAAGAGAGAG ATGGTCTCGG GGCTAGGGGC
36751 TGCAGTAGGT ACAAGACAAG GCCAGAAAGA CTGGGCTAAA ATGCCAGGCT
36801 GAGGCCAGGA CACCACAGCC ATCAATAGAT GGCATAAGAT CCTTGGGCAA
36851 TGATCGGACC AGCCTTCCTC CTTGGAGAAA CAAGTTCTGT TTGCTCCGCA
36901 GCAGAGAGCA TTCCCTTCCT CCTCCATGCC CTGGCCCTGC CCCTCTGCCC
36951 CGAAGGGGCC AGGCAGCTCA GGGGGGCCCA GTGGTGATGG GTAGGGCTGT
37001 GCTGGCATGG CAGAGAGTAT TGGTCCAGTT CACGGACTGA CAGGCTACAG
37051 GCAGAGGTGA TCAGGCCTGG AGCCTTCTCT TGACTGCCCC AGCCCTGATG
37101 CCGTGCCGCC TGGGCTCGGG AGCAGCCGCT TGATGGTCCC TTGTTGAATG
37151 GCCTCTGGGG AGGCTCCATC TTCATCTTGG TGCTGACTGG AGCAGGCTC
37201 TGTCATTCTT AGTTCTTCCC CATCCCCAAT GCTTCTGGTT AAGTCTGCCC
37251 AGGGAGAATG GGGAAATGGG CACATGGCTA AGAAACCATG TCAACAAGGT
37301 TCCCCCCACC CTATCTCTGC CATTCACTCC CCTTTCCCAC ATCCTTCCTT
37351 GTTCTCTCCC TGTGCCACCC CTTATTCCCA CACCTCTTGT CTCTGTCTGC
37401 ACTGGGGGC CAGCTGCTGC CAATGCCGT TTTTCCATGT AACTGGTCTA
37451 GTCTTGGGGG TTTCAGGGCT CCCCAGCTCC TGCTCTCTAA AGCCATGTCA
37501 GGTCCCAGGA CTCCTGGGTG CCCAGGGCAG CGACTCACTT GATGTGGCTA
37551 AAGGACCAGC CCTTCCTCTT TCTGCTGCCC CCCGCCCCA GGGCCCAGCC
37601 ATGGCCCACT GAGGCCTGGC TGTATCACAT GCCTGGCTGC CTTCAGCTGG
37651 GAGGCACTTG AAACCAGAGC CTTTAAAAAT ATCACTGAAG CCCCACTGTC
37701 TCGGGCTGAT GCTTGAGCTC CAGGTTGAGC AACCCCATGA GTCCTGCCCT
```

TABLE 1-continued

```
37751 CAGGGATGGC GGTGGTGTCC TGGCACCTGG GATAGCTTTG CTGCCCGCAC
37801 CCACCCCCTG GGCTGGCAGG GGTGGGGGAA GCAAGGGCAT CCCACCCAGC
37851 CTGTGTCTCA CCCCTTCTCC TTGCAGACAT CCGGGACAGT GGTGCTAAAC
37901 CCGTCATGGT CTACATCCAC GGAGGTCTT ACATGGAAGG GACAGGCAAC
37951 ATGATTGATG GCAGCATCCT CGCCAGTTAT GGCAATGTCA TCGTCATCAC
38001 CCTCAACTAT CGGGTTGGAG TGCTAGGTAT GGTTCCCTGC CTGGTGCCTG
38051 GAAGGAAGAC TGGCTTCGCA AGGGGGGAGG AAAGAATGCT GGAGAATTTA
38101 AAAACAGATA GCCTTGCTTC TCTAGCTGGT GCTAATAACC ACAGTCAAAA
38151 TGGTGTTATC CTCTGGCCCC TACCCAAATG CTAGGGGCTT CCCCATATCC
38201 CCAGGCCCTT TCTTGGAAGG TTTAGATGCC ACCAGAAATT CAATTCAAAC
38251 TTCACACCTT CTCTCAGGTC CCAAGCCAGG TCTCTGCTTC CAGACTTTGA
38301 CTTGGCTGAG TTTTGTAGGA TGCTTCAATT TTCCACTGTC CTGTCTTCAC
38351 CTCTACCCAC CCGCCCCACA TCTCTAAACA CCCCACACAT GCACAGATAT
38401 TCCTTCCAGT CCACTCCATG GCCACACACC TATTTACCTT CATGTGTTTA
38451 CACATCCACC CCGCCATGCA CCTGCAGGAA GACGGTGATT TCTCACTCAC
38501 CCCCATAAAG TACACACACC TAGCCCCACA TTCACATCTC CAGGCCCCTC
38551 ACATGTAAAC ACATTCTCCT AGCACTCCAG GTAACTCCAT TCACATGGTC
38601 TCTCCAGAAC ACATATCCAC ATACCCACAC GGTCTGTGTA CTCCACGTCT
38651 GCACCCCGCA GATGGCTCTC ACCCTCCGCA TGTACACACA CACATGCTCA
38701 TATACTTCTC CCCATGTCTC TGTAGCCACA TCTAAACCGA TACCCACGAT
38751 GCATACACAC CCACACTCAC ACTTTACCCC CATATTTACA GCCCACACAA
38801 AAACCTACAC CCTGCACATC CATGTCCACA CCAAACTCCA CACATATACA
38851 CCTTAAATGT ACATAAATAT TCCTTCCACC CACCCCCAC AAATACCTAC
38901 ACACGCCCGT ATCCCCCTGC ACACCCTACT TCCACATCCA CTTTACACAT
38951 CCACCTACCA CACACACCTG TCCCTCACTA TCTCCTCAGA AACACAAACA
39001 AATATTCCCC TTCCCTACAC ACATATACTC TTACCTGTTT GTCCACACTG
39051 TCCCACCCCA CACATACACA GATACTACAC ACACACCATA TCCACATCTA
39101 TATACATCCC ACACACTGCC CTTATGTCAT TCCCCTACAC ATACATTCCC
39151 CCACACACAC ATCCACATAT GCATGCACGC GTATACATGC GCACACTCTT
39201 CCATATACAG CCTGTATATG TACACCCAGC ACACACCCAT GCACTTCTCC
39251 CCTCACCCCA CCCCACAAAT ATATACACAT CCGTGTACAT GGGGCTGCAT
39301 CTGTATCCAT ACATGCACAC ACACCTCTAC CCAGGCCCAA CCGCATCCCT
39351 CAAGTCTCCC CACACTTCCT TACCCCGTAT ATGCACACGT ACACACTCTT
39401 TGTACTCTAA GCATGTCCCC TGCACACTCC CACCCATCAC ACACATACTC
39451 CCATGCATAT GCACTCATTG CCGAAATGCC TCCTCATATG CACCCATACA
39501 CCTCCCCACC CCCGCATTCT CTGCTGTGCA CAAGCTTGTG TCAGTCATTT
39551 AGGCTGCCCT TGAACCCTGT ACCTTCCTTG GTGACCACCC ATGCCTATCT
39601 ATGGCCAAGG TCTTGAGGTA AACGAGTGCC TCAGAGAGGG TGACTAAGCA
39651 CACAGGGCCC TGCTCATGCT CCCCCAAGCC CCGCATCCCT GTAGTGGCAT
39701 GAAGAAGCCA ACTTCTTCCT GGAGGAAGAG TTTCAGCGGG AGTGTAGGCT
39751 CTTGGTCAGG TCTGTAGGCA TATGGGTGCT AAACCAGCAG TTAGGCGTGG
39801 CTTATTCCAT GGCTAACTAG GGGACACGAC CATATTTGAT TTTATTTTCA
39851 TTTAATTTTT GAGACAGGGT CTCACTCTTG CCCAGGCCAG TTTTGAACTC
39901 CTGAGCTCAA GTGATCATCC TCCCACCTCA AGGGCCTTAT TTTAATTTGA
39951 TTATTTATTT ATTTATTTAT TTATTTATTT ATTTATTATT TTTATTTTGT
40001 TTTTGAGGCA GAGTCTCACT CTGTCGCCCA GGCTGGAGTG CAATGGCACC
40051 ATCTTGGCTC ACTGCAACCT CCGCCTCCG GGTTCAACTG ATTCTCCTGC
40101 CTCAGCCTCC TGAGTAGCTG GGATTACAGG CACCTGCTAC CATGCCAGGC
40151 TAATTTTTGT ATTTTTAGTA GAGACAGGGT TTCACCATGT TGGCCAGGCT
40201 GGTCTCGAAC TCCTGACCTT AGGTGATCTG CCTGCCTCAG CCTCCCAAAG
40251 TGCTGGGATT ACAGGCATGA GCCACCACGC CTGGCCCTTA ATTTTCTCTT
40301 GACTATATTG CTTTGTCAGT TCCAATCTCA GAGGCTCCGG GGCTGCATTT
40351 CACTTCTGGG TGCAGTTGTA TGCCCAGAAC GGCAATCTTC TCTTGGTTTA
40401 CAATTAATAC TATGTGAGAT AGGAAGATAC TCTTTTGGGG TTCAAACTGC
40451 AGAAATGATG CTCCTTTAAA AAAGCAAAGT CGGTGTCCCC TTCATTGGCG
40501 CCCGGGAGAC TGAATATGGA GCATGCAGGC CATTCACGCT GGCCTCCCCA
40551 CGGTCTGGTA GGCTTGGGAT GTTGGGATGT CATGGTTCTG CTCCTGCCCC
40601 TCTGTCTTTC TGCATCACCT CAGACACCAT GGTGAGGCTC TTGTAAGCTG
40651 TTCTGTCCTG TTGAATCTCA TGGTACCATG AAGGTGGCTG GAAACCCACA
40701 CACTAGGGCT GCACACTTTC TTTTTTTAAT TAATTAATTA ATTAATTAAT
40751 TAATTTTTGA GACAGAGTCT CACTCTGTCA CCCAGGCTGG AGTGCAGTGG
40801 TGCAATCATG GCTCATCGCA GCCTCGACCT CCCAGGCTCA AGTGATCCTC
40851 CCACCTCAGC CTCCCGAGCA GCTGGGATTA TGGATTACAG GTGTGCACCA
40901 CCACACCCAG CTAATTTTTG TATTTTTAGT AGAGACAAGG TCTCACTATG
40951 TTGGCCAGGC TGGTCTGGAA CTCCTGATCT CAAGTGATCC ACTTGCCTTG
41001 GCCTCCCAAA GTGCTGGGAT TACAGGCGTG AGCCACCGCG CCCGGCTGGG
41051 CTGCACAGTT TCTAGAGAGG AATGAACGCG CAAATGTGAT CACAAACAGA
41101 TATGCAGACA CATGTACACG GTAGTTCAAA GCCAAAAGTA ATTTTGCTAC
41151 TTTCTTTTCT TAGAGTGACA GAAAACACTC AGCTCAGCTG CTTAAAAAAA
41201 TATAAACACA ATGCTCCATT CTATAAGGTT TATTGGAAAA TACAAAGAAT
41251 ACTAAAAATA TGCTTCAGAG CAGCTAGGAA TGAAGAAAGA GAGCATGGAA
41301 AAGAGGGAGA GAAAGAGGAG AAAGCAAGGA AGAGAAGAAA ATGAGAGGAT
41351 AATAGAGAGT CAGGGAGAGG AAGCAGAGAG GAGACAGAAG GAGAGACTTA
41401 GGATCTGGGG AGAGACTCGG CATTTCACGT AGGATGTGAA GTCTCCACAG
41451 TGTCAGTTGG GAACTGTGGG CCGCACAGAA GGCTGTCGCT GGTGAGCATT
41501 CCGTATGATA TCCTGATTTG CTGATTACTT CACAATCCTT CGGCTGCTCT
41551 AATCCTTAAG CTTCTACACC AGAAGTTCTT AACCTTTTGG GGCATCTTGG
41601 ACCCTTTTGA GATTCTGATG AAAGCTATGG ACTCTCCCCT GGAACAATGC
41651 ACACATGCGT GTGTGCACAC ACATGCATGT GCGCACACAC ACACTTAATT
```

TABLE 1-continued

```
41701 TTACAGGGCC GGGTGTGGTG GCTCACGCCT GTAATCCCAG CACTTTGGAA
41751 GGATGAGGTG GGTGGATCAC CTGAGGTCAG GAGTTCAAGA CCAGCCTGGG
41801 CAACTAAACC CTGTCTCTAC TAAAAATACA AAAGTGAGCT GGGCATGGTG
41851 GCATGCGCCC GTAGTCCCAG CTACTCAAGA GGCTGAGGCA GGAGAATTGC
41901 TTGAACCTGG GAGGCGGAAG TTGCAATGAG CCAAGATCGT GCCACTGCAC
41951 TCTAGCCTGG GCAACAGAGT GAGACTCCAT CTCAAAAAAA AAAGAAAAGG
42001 AAAAAGAAAA AGAAAAGAAA AGAAAGAAAG AAAAAACAAT TTTACAGATC
42051 CCCCTTAAGT TCATCCATGA AAGTCAGGTT AAGAACTCGC ACTTGACAGC
42101 CCCGTCATTT GGATAACCAG AACAGCACAT CTAGGGGGCA GGAACATTCT
42151 TCTTTGGGCT TAAGCAGTTG ATGATCAAAT ATCACCGAAA ACTCAGAAGG
42201 AGTCCTACAC TGAGATTTGC TCAGAAGTTC CTCACCACTT CCTGCACACC
42251 CTTCAGTTCC TGTTCTGGAA CACAAATATA ATCAATAAGC CCGTATTGGA
42301 TGCCGGGTAC ATATAAGATG TTTGTTTTTG TCTCTTGACA CCAGATGTAG
42351 AACATGGGTT TGTCCCTGAT GCTTGGGAAT TTTCTTTTCT TTTTTTTTTT
42401 TAATTGAGAC AGAGTCTTGC TCTGTCACCC AGGCTGGAGT GCAGTGGCAC
42451 AATCTCAGCT CACTGCCAAC CTCTGCCGCC GGGTTCAAGC GATTCTCGTG
42501 CCTCAGCCTC TGGAGTATCT GGGATTACAG GCGCGCACCA CCACGCCCAG
42551 CTATTTTTTT TTTTTTTTTT TTTTTTAAGD AGAGGCGGGG GTTTCGCCAT
42601 GTTGGCCAGG CTGGTCTCGA ACTCCTGATC TCAGGTGATC CGCCCTCCTC
42651 AGCCTTCCAA AGTGCTGGGA TTACAGGTGT GAGCCACTGC ACCCGGCGGG
42701 GAATTTTCCT GTGTAGTGGG GCCTTTGTTG TTTTGTTGCC CAAAGCATCC
42751 CAGAACAGGT GGTTTGTTTT GGACCCCAGT CACAGGCATT CATTCACTCT
42801 CCTTCCCATC AGCTTTCCTG AGCACTGAAC CCATCAGCGG TTCACTCTAA
42851 GGTGCTTATC TTTTTTCTTT CTTTCTTTTT TTTTTTTTTT CTTTTTGAGA
42901 CAGAGTCTCG CTCTGTCGCT CAGGCTGGAG TGCAATGGCA TGATCTCGGC
42951 TCACTACAAC CTCCGCCTCC CCGGTTAAAG CAATTCTCCT GCCTCAGCCT
43001 CCCAAGTAGC TGGGATTACA GGCGCCTGCC ACCACACCCG GCATATTTTT
43051 GTATTTTTAG TAGAGACGGG GTTTCACCAT GTTGGCCAGG CTGGTCTTGA
43101 ACTCCTGACC TCAGGTGATC CACCTGCCTC GGCCTCCCAA AGTGCTGGGA
43151 TTACAGGCAT GAGCCATCAC GCCCAGCCTC TAAGGTGCTT TTCTAGATAT
43201 CTTGGGTGAT TCATGAATGT TGAAATGTC ACAGGCTAAT CCATGGATCC
43251 TCTCCAAGGC AGAGGGGTAG CTATTATTTG AGAAGGCCCC ACTGGGCTTG
43301 AAGCCAACAA AGAAAGGGAC TCCAGCAGGA TATAGGATGT GGAAATCCCT
43351 GAGGCTGAGG AAGCAGGCAC TTGCCAAGTT TTACTCCAGG TTCCAGAATT
43401 GAATCCTACA TGCTTGCTCA GGTACCCTCC AGGCAAACCG AAAACCCAGT
43451 AAACATCAAG CCTTGAGTGA CACAAATATC TGGTTTTGTT ACAATCTGCC
43501 AGATTCCCCA TCTTCTGTTG ACGAGCAGTT TACCATGAAC TGCAGTATAA
43551 ACTTGGGCCC AGGGAGACTG GCTCCGATTT ATTCTGACAG TTTATGGAGT
43601 TTAGTATTTC AGCCTTCATT CTCACATGGT TTCTGTGGAT GGTTGAGTTA
43651 CTGGGGAACT AGCAGTGAGT GACCTCTCCC AGAATGCCAG ATATTGTGTG
43701 CTTGTGGTTG GTCAGGTTTG CTGTCATCTT CCTGAGCCTG TTGGAGATAG
43751 CATTTCTTTT TTCTTTTCTT TTCTTTCTTT TTTTTTTTTT TTTGAGATGG
43801 AGTTTCACTC TTGTTGCCCA GGCTGCAGTG CAATGGCGCT ATCTCGGCTC
43851 ACCGCAACCT CCGCCTCCCA GGTTCAAGTG ATTCTCCTGC CTCAGCCTCC
43901 CTAGTAGCTG GGATTACAGT CACATGCCAC CAAGCCCGGC TAATTTTGTA
43951 TTTTTAGTAG AGATGGGGTT TCTCCATGTT GGCCAGGCTG GTCTCGAACT
44001 CCAGACCTCA GGTGATCTGC CCGCCTTGGC CTCCCAAAGT GCTGGGATTA
44051 CAGGCATGAG CCACCACGCC TGGCCTGGAG ATAGCATTTC AAGCAGGACT
44101 CTTCATGGAG TAGGGATCAT TGACATGGCA TCATCCACAT GCTTCAGGGC
44151 CCCTTAACCA GAGACTCATA GGATCTGAGA GAGCAGAGAG TGATGGTCAA
44201 ATCCTCCATC CAATCACCTG AGGTCAGGAG TTCAAGACCA GCCTGGCCAA
44251 CATGGCGAAA CCCCATCTCT ATTAAAAATA TAAAAATTAG CCAGGCATGG
44301 TGGCAGGCAC CTGTAATCCC AGCTACTCGC AAGGCTGAGA CAGAAGAATC
44351 ACTTGAACCT GGGAGGCGGA GGTTGCAGCG AGCCGAGATC ATGCCATTGC
44401 ATTCCAGCCT GGGCGACAAG AGTGAAACTC CTTCTAAAAA AAAATAAATA
44451 AATAATAAAT AAATCCTCCA TCCAGCCCTT TCAGGCCTTT GTTCCTAACC
44501 CAGGAAATTG GTACATTGGA GAAATCTGCT CTACTACATC CAAATGCAGG
44551 CTTTGCCTGC TGATTAGGCC AGGCATGTTT GACACATTTC AGTAAATGAT
44601 GCCTTGGCAA AGGCTGAAGC CAAGACCACT ATTGCCTAAA TGAAAGAAAA
44651 GGAAAAGAGA ATACAGGGGA AGGAGAGAGG AGGGAGGACT AAAAGAAGGA
44701 CAGTGATTTC TGCCAGAGGG TCCCAAGGCT TGGGCAGCTG GGTTGGATCA
44751 TGGTCAACAG AGTTGGGGTT TTGAGGGATT TTTTTTTTTT GGTTGCTTTT
44801 TTANAGATGG AGTCTCATTC TGTCCCCCAG GCTGGAGTGC AGTGGGTAA
44851 TAACAGCTCA CTGCAGCCTT CACACCTAGG CTCAAGTGAT CCTCCAGCCC
44901 CAGCCTCCTG AGTGGCTGGG ACCACAGGCA TGCACCACCA CAACTGGCTA
44951 ATTTGTTTTG TTTTAAAAAC AAAAAGGGAC AGGGTCTTGC TACACTGGCC
45001 ANGTTGGTCT CAAACTTCTG ACCTCAAGTG ATCCTCCCAC CTCAGCCTCC
45051 TAAAGTGCTG GGATTACAGG TGTGAGCCAC CATGCCTGGC CAAGTTTTTA
45101 AGACTCAAAG GAGCAGCTTC AATTTCTGAA TGGGCCACGC AAAGGAAAAG
45151 CTGATTTCCT TGTCTGGAAG AGCAAGGGTT CCTTCTTCAT CCTCATGCAG
45201 GCTTTCTCTA ATTCATTCTC ATTTCCTCCT CTGGAACCTG GGGCTAAAGA
45251 GGACTTGTGA CTAGGGCCCG GGAGAAATAA CTAAGTACTT TACATACTTA
45301 ATTGTACCAG AGGTAAATTA ATAACACACT TGAAGAGGAT GAGATGAGCT
45351 CTTTTGCAGA AGCTAGGTAC AGAAGGACTT GAGAAAGACA GTGGTGAGGT
45401 CTTGTGACTG TTTGAGTCTA TTTGAATTCA GCCTCTGCCT ATGGACTGCA
45451 AGGACGCCAG AGAACTCCCC ATGAGCTCTG GGAGTCTTCT CCAACATGGC
45501 CTCTCACAAA GTTGATTCCA GGTGCTGTGA ATGAGCTTTT AACTGGGGAG
45551 TAAAAATAC TGATCCAAGT GTGGGTTTCC AATGTGTAGG AGCTTCACAA
45601 TTACCCACCT CCAAAGACTT CTTCCAAAAG CCTAGGGCAG GAGAAGACAG
```

TABLE 1-continued

```
45651 AGCCTTCCAA GGGACCCAAG GATTCAGGGA AGAGAGATGA AATAAGGCCG
45701 CAGGCTCAGT CTAAAATGGA AGCAGAGTAG GGGGGAATAT AGGACATCTC
45751 TGTGGGATAG CCAGCAGGTG GGCAGGAAGG TAGTCTCCAT GGCAACAAGT
45801 CTCCACAGCA GCAAATCCCA GCAGGTGGGT GGGAAGGTAG TCTCCATGGT
45851 GACATGTCTC CTCAGCAGCA AATTCCAGTG GGGGGCGGG AAGACCTGTT
45901 TCTGTGGTAA CGCACTGCGC TACTTCCCCA TTTCTCCACC AGATGAAAAA
45951 GATGGTCTGA CCCAGTGGTT TCTCAACTTT GGCAGGTATC AGCATCACCT
46001 GGAGAGCTTG TTAAAAACAC AGATTGCTGG GCCCCACCCC AGAGTTTCTG
46051 ATTCCTTAGG CCTCCAAGGG AGGGAAATGA GGACCTGCCC TGAAAATGAG
46101 GGGAAGGGGG CCATCAAGGC CCCGGAAGGA AGTGGAGAGG GACTGATTTG
46151 AACAGGAAGG GCAAGGAGAG CTTAGGGATT GTTGCCTCTT GGGATCATCT
46201 ACACTTCCTT TGGAGAGAGA AGAAAGGGGA AAGAGAAGTA ACTATAGAGC
46251 TGCAATGTGC CCAGCATGTT ATAGATGCTT ATGTTCATTT TATCCTTGTT
46301 ACAACCCTGT GAGGTATTTT TATCCCCATT TTACAGAAGA GGACACTATG
46351 GCCCAGAGAT TTTAAATTAA GTGCCCAAGG CTACATGCCT AAGATGTGAT
46401 AGAGCCAGGA TTCAAATCAA GGACCGTCTG ACTCCAGGGT TTCCATTCTA
46451 TCTTGCCAGA TGTTAGGGTA AGGTCCCCAA TAGTACATCA GGGCAGAGAA
46501 TGCTGAGTTC TGGACATTTG CAGTTTCTGC AGTTTGTCTC CCACCTGGAG
46551 GCATGCACTT CAAATGGTCT GCAGACCCCT CCTTCCAAGC TGGATAACAG
46601 GTGGGAGGCA GGGAGCTGAC CCCTCCTCTG TTGACGATGC TGGACATTGC
46651 AGAAAGGAGC ACTGCTTTAA GTTAACTATG TGGGAAGAAC TACACTGCGT
46701 GCTCATTCTC TATTCCCACC TCCCCTGTTG ACCCTGCCTG CCGTCATCAC
46751 CCAAATCCTC CATCCCTCTG CCTTCATTGT CTTCATGCCC TTTGTTGAAT
46801 CCAGGTTTCC TGAGTACTGG AGATCAGGCT GCCAAGGGCA ACTATGGGCT
46851 CCTTGACCAG ATCCAGGCCC TCCGCTGGGT GAGCGAGAAT ATTGCCTTCT
46901 TCGGGGGAGA CCCCCGCCGG ATCACTGTCT TTGGCTCGGG CATTGGTGCA
46951 TCCTGCGTCA GCCTCCTCAC GTTGTCACAT CACTCAGAGG GTGAGTAACT
47001 CGTGGGGCAA AACATGAACT AGCCAAGTGC CGGCTGTCCC AGCATGCCCC
47051 ATCCATGCCC CAGGGCATCC AAGGGAATCG GCCAGCTCTC TTCTACCAGC
47101 TTGGTATCCC TTTGGCAAGA AGTGGAAGAG AAATGTTTCT CTGGGAGAAG
47151 TACTTCTCCC AAAGCTGGAG AGGGAAGGAA GAGAATCCCA TTTATGTCCT
47201 GGGAAAGCAA GATTCTCCTT CTGATGTGGG AGTCTTATTT TGGGGAGTGG
47251 GAATAGAACA ATTGTCCCCT CAGAGGACAA TAGTTTGACA GGGGTTGGGG
47301 AGGATCTTTC AGTATGGGAA GGACATGTTA CTTCACAGTA GAGATATAGG
47351 GTGGAAATTG GTTTCTAGGT CTAAGAAACA TCCATTCTCT GCCTTTCTCT
47401 CTGAAGAACA AGTCTGTACA AGAGGGGAAA CATCCTAGAG GGGGAAGTGG
47451 GTCTGAAATG AGAGTCACTA ACCCACGAGG TGGGCTTCTT CCATAGGACG
47501 ATGGTCTATT ATCAGACTCC AGACCTCTCC CCGACTGTGC AAGCTGCCGG
47551 GGAGATTCTC ATTTTTGGCC TCTCTCCTTG TGGTGGGTCC CTTTGCCAGT
47601 GACCCTTCCA AGAGAGCAGA ATAGGTCCTT TTTGCTCGGC AGGAAATGTT
47651 TTCTCCACCT CTGGACTACT GGGAACATTC TATCTCTGAG AGGCAAAGCT
47701 GAGCTTCTCA TGAAGAAAAG ATCTTCCTGA AATAGGTGCC CTTTTCTGAA
47751 GTAAGGAAAT CTGTGAGCGA GGATGCTTTT TTTCTTTTTT AATTGAACAC
47801 TAACCCCCTG AGTTAGGGAC ATTCTCACAG GAAGACTTTC CATCTCTTGA
47851 AGAAGTTCTG TCTCTCTGAG AGAGAAGAAC CACCTTCTTT GACCTAGAAA
47901 TTCTGTCTTT GCCCCTCCAG GGACTACCCT GGTGAGGGAA GACTTAGGTG
47951 GGATCTGCCT CTCTAAAGAG AGAGACTGTG TTCCTAGGTG ACCATAGTGG
48001 GAACAGGAAT CTTCCCTTTT TCCCCAAAGG AGGGCGAAAT GACGGGCTGC
48051 AAGGGTGCCT TGGCCTGAAA AGACGTTCTG TGCCTCCTCT GACTGGGGAC
48101 TCCTCCCCTA GGAGAAGAAA GCCTTTCCTG GAGTGGTGCT ATGCTTTGTC
48151 TCATAGGGGG CCTGTGTCTC TGGAGGTTTG ACTTTTTTTT TTTCTTTGAG
48201 ACAAGATCTC GCTCTGTTCC CCAGGCTCTG TCCCCAGTG CAGTGGTGTG
48251 ATCACAGCTC ACTGCAACCT GTTCCTCCCA GGCTCAAGTG ATCCTCCTGC
48301 CTCAGCCCCC AGAGTAGCTG GGGACTACAG GTGCATGCTA CCATGCCCGG
48351 CTAATTTTGG GGATAAATTT TTTTTTGTAG AGACAGGTTT TCGCCATGTT
48401 GCCCAGGCTG GTCTCAAACT CCTGAGCTCA AGCGATCTGC CTACCTCGGC
48451 CTCCCAAAGT GCTGGGATTA CAGGCGTGAG CCACTGTGCC TGGCCGAGTT
48501 TGACTTCTTT AAAGATCTGT TCTCTCTGTT TTTCTGTAAT TGATGCATGG
48551 AGAATAATCT TTGGGAAAAT GAGGCTGTCT TTTAAGTAGT AATCTATCAT
48601 TTCTTTCCCT CTCTTTCCAC TCATGCAAAC TGGCTTTCTC TTAAAGGAAT
48651 GGAATTATGT GCCTGAGGGA CAAATTCTCC CTTGGGAATG TTGGGGCCAA
48701 GGAGAGAATG ATATCCTTTT TTTTTTTCTA GAGGGGAAAA TTATTTTCTT
48751 TTTGAGTTTG GGGGACTGGC TCCCTCTCTG CTAGGGGAAA ATCTGAATTT
48801 GAAGTATCGG TAGCTTCAGA TAAAAGGAAA GTCTCTGCCA GGCGCGGTGG
48851 CTCACGCCTG TAACCCCAGT ACTTTGGGAG GCCAAGGCGG GTGGATCACG
48901 TGAAGTCGGA AGTTCAAGAC CAGCCTGACC AACATGGTGA AACCCCGTCT
48951 CTACTAAAAA TACAAAATTA GCCGGGCGTG GTGGCGGGTG CCTGTAATCC
49001 CAGCTACTCG GGAGGCTGAG GCAAGAGAAA CGCTTGAACC TGGGAGGCAG
49051 AGGTTGCAGT TAGCCGAGAT CCCACCATTG CACTCCAGCC TGGGCAACAA
49101 GAGCAAAACT CCATCTCCAA AAAAAAAAAA AAACAAAGTA TCAGTGGAGA
49151 CCACAGACGG GGAGCACAGG TTCCCTGGAG ACTTTCGAC CCGAAGGCCT
49201 TTGCCCTTGG GCTCCTTCCC CAAGCCCTCA GAATGTGGGG CTCTTGCCTG
49251 CCTGCATTTC TCATCTCTCA TGAAAAAGAC TCCTTTGTGG TGCAAGTGCC
49301 AGCTCCCTGG TGGTGCGCTG GCACGGAGCT GGGCCCAGCT GGGCAGGAAG
49351 CAAGAGGGGA AGACAAGGAG AGATAAAGAG AGGCGGCATA AGGGGGCTGA
49401 TGTCTGGGAT TCAAGGGGTT AATTCTTCCT GACATTGCCT TAACCCCTAA
49451 GTTACCAGCC ATCGCACCAG GACAGGGAAG GGATGGTGGA AGCCATCAAG
49501 GAAGGGGTTC AGCAACCCCT CCTTTTGGCCC TACATCATCC CCTGCCAAAA
49551 GAGTTGTTCC CCCTTCCTAG CCCATTTAAA CCATGGGCA GCCTCAGTGA
```

TABLE 1-continued

```
49601 CAAAGGAATG AAGAGATTTA TGGCTATGTG TGACACGACA GATCTGACCT
49651 GGTGCTACCT GTCTTCTGTA GGACTTTTCC AGAGAGCCAT CATCCAAAGT
49701 GGCTCTGCTC TGTCCAGCTG GGCTGTGAAC TACCAACCAG TGAAGTACAC
49751 CAGCCTGCTG GCAGACAAAG TGGGCTGTAA TGTGCTGGAC ACCGTGGATA
49801 TGGTGGACTG TCTTCGGCAA AAGAGTGCCA AGGAGCTGGT AGAGCAGGAC
49851 ATCCAGCCAG CCCGCTACCA CGTGGCCTTT GGCCCTGTGA TTGATGGTGA
49901 TGTCATTCCT GATGACCCTG AGATCCTCAT GGAGCAGGGC GAGTTCCTCA
49951 ACTATGCAT CATGCTAGGT GTCAACCAGG GCGAGGGTCT CAAGTTTGTG
50001 GAAGGGGTGG TGGACCCTGA GGATGGTGTC TCTGGCACTG ACTTTGACTA
50051 TTCCGTCTCC AATTTTGTGG ACAATCTGTA TGGCTATCCT GAGGGTAAGG
50101 ACACCCTGCG AGAGACCATC AAGTTCATGT ATACAGACTG GGCAGACCGT
50151 GACAACCCTG AGACCCGCCG TAAAACACTG GTGGCACTCT TCACTGACCA
50201 CCAGTGGGTG GAGCCCTCAG TGGTGACAGC CGATCTGCAT GCCCGCTACG
50251 GCTCGCCTAC CTACTTCTAC GCCTTCTATC ATCACTGCCA GAGCCTCATG
50301 AAGCCTGCTT GGTCAGATGC AGCTCATGGG GATGAAGTAC CCTATGTTTT
50351 TGGGGTTCCT ATGGTAGGCC CCACTGACCT TTTCCCCTGC AACTTCTCCA
50401 AGAATGATGT TATGCTCAGT GCTGTCGTCA TGACCTATTG GACCAACTTT
50451 GCCAAGACTG GGTAAGGAGA AAATAGGGTT TTTTTCCTCT TTGAGACCCC
50501 AGCATGCCCT CCCCTCTGCT CCTCTAGCTA AACCTCTTCC ATCATATCCC
50551 TTCCTAAGAT ATTCCCAAAA TCTTGCTTGG TACCCCTTCA CTCATCTTCC
50601 TATCTCCCCT TCCTGAGTCT TTCATGCCAT TTTTCCTTCC TTCAAAAATG
50651 TTGTTGAGGC TTAGAACTCA GTTAGCATCG GGACTAGGAA GGAATGAGGG
50701 TTACTGGAAG AACTATGGGA TTTAGCCAGG CCCAGTGGCT CACGGCTGTA
50751 ATCCCAGCAC TTTGGGAGGC AAAGGCAGGC AGATCACTTG AGCCCAGGAG
50801 TTCAAGACCA GCCACGGCAA CATAGAAAGA CCCTGTCTCT AAAAGAAAAA
50851 GCATTAGCCA GGCATGGTAG TGCATGCCTG TAGTCCCAGG TATTTGGGAG
50901 GCTGAGGTGG GAGGATCGCT TGAGCCCCGG AGGGTGAGGC TACACTGAGC
50951 TGTGATCACG CCACTGTACT CTAGCCTGGG TGACAGAGCG AAACCTTATC
51001 TTAAACACAC ACACACACAC ACATATACAC ACACACACTA TGGGATTCAA
51051 GGTTAGCTGG TCACAGGCTA TGTGAAATAG GAATGCAGTG CTTCAGAAAG
51101 AGCCTTCAGG GCCAGGCGCG GAGGCTTATG CCTGTAATCC CAGCACTTTG
51151 GGAGGCCAAG GCAGGTGGAT TGCCTGAGCT CAGGAGTTCG AAACCAGCCT
51201 GGCCAACATG GTGAAACACC GTCTCTACTA TAATACAAAA AATTTGCCAG
51251 GCGTGGTGGC GGGTGCCTGT AGTCCCGGCT ACCTAGGCAG GAGAATTGCT
51301 TGAACCCAGG AGGCAGAGGT TGCAGTGAGC CGAGGTTGCC CCACCGCACT
51351 CCAGCCTGTG CGACAGAGCG AGACTCTGTC TCAAAAAAAA AAAAAGAAAA
51401 AAAAAGAGAG AAAGAAAGAG AGAGAGAGAA AGAAAAGGG AAGAAAGAAA
51451 GAAAGAGAGA GAAAGAAAGA AAGAGAAAAA AAAAAGAAAG AAAGAAAGAA
51501 AGAAAGAAAG AAAGAAAGAA AGAAAGAGAA AGAAAAGAAA GAGAAAGAAA
51551 GAAAGAAAGA AAAAGAGACT TCGGGTTCAG CAACTTCTGC TTGCTTAATA
51601 AAAGAAAGAG GCTTTATTAG GGGGCTCCTG GCAAAATTGG GCAGCTGAAA
51651 AGATTGATAA ATGCTCAGTA GCATGTGCAA AGAAAAAGCA TCTATAGCCT
51701 TAATCTTAAA GGATGAGCGC CGGGAAGGAG GATATAGGAG TTCAAGCCCT
51751 GGGGAAGAAG CAGGTGTGGG CAGAGCAGGG GACCCTGAAA AAGATGGAAA
51801 TGGTGGGAAG TTCTAAACTG GGAAAGAGGT TTGGCTGTCA GAGGAAAAAT
51851 GCTGGGCCTT TTCCTCATCC AGATAGAGTG GTGACCCCAG ATTTCCATGT
51901 GGTATTTCAG GGATCCCAAC AAGCCGGTCC CCCAGGACAC AAGTTCATT
51951 CACACCAAGG CCAACCGCTT TGAGGAAGTG GCCTGGTCCA AATACAATCC
52001 CCGAGACCAG CTCTACCTTC ACATCGGGCT GAAACCAAGG GTCCGAGATC
52051 ATTACCGGGC CACTAAGGTG GCCTTTTGGA AACATCTGGT GCCCCACCTA
52101 TACAACCTGC ATGACATGTT CCACTATACG TCCACCACCA CCAAAGTGCC
52151 GCCTCCGGAT ACCACCCACA GCTCCCACAT CACCCGCAGG CCCAATGGCA
52201 AGACCTGGAG CACCAAGCGG CCAGCCATCT CACCTGCCTA CAGCAACGAG
52251 AATGCCCAGG GGTCCTGGAA CGGGGACCAG GATGCAGGGC CACTCCTGGT
52301 GGAGAACCCT CGTGACTACT CCACTGAATT AAGTGTCACC ATCGCCGTGG
52351 GGGCCTCCCT CCTGTTCCTT AACGTTCTGG CCTTCGCTGC CCTCTACTAC
52401 CGTAAGGACA AACGGCGCCA GGAGCCCCTG CGGCAGCCTA GCCCTCAGCG
52451 GGGAGCCGGG GCCCCGGAGT TGGGAGCTGC TCCAGAGGAG GAGCTGGCAG
52501 CATTACAACT GGGCCCCACC CACCACGAGT GTGAGGCCGG TCCCCCCCAT
52551 GACACGCTGC GCCTCACTGC ATTGCCCGAC TACACCCTGA CCCTGCGGCG
52601 CTCCCCGGAT GACATCCCAC TCATGACCCC CAACACCATC ACTATGATCC
52651 CCAACTCCCT GGTAGGGCTG CAGACATTGC ACCCCTATAA CACCTTTGCC
52701 GCAGGGTTCA ACAGTACCGG GCTGCCCCAC TCACACTCCA CTACCCGGGT
52751 ATAGTCCAA CTCAGAGCAC AGCCAATCTC CAGGCTCCCT CCCTCCCAGA
52801 TCCAGGAACA CATGCACACA CACACACACA CACACGCACA CACACACACA
52851 CACACACATA TATGTATACG CACGCACCCA CACCCTACAG CAGATCCACC
52901 TGCACAAACA TAGACAGATG TGGACATGCA CCCGCATGTA CAAAAACACA
52951 AATACGGAAG TAAACCTGAA CAAACCCTTT AAATGGGGAC GCAGATGAGT
53001 CCTCGGTAAA CCGAGGACCC ATGAAACAGC AGCTGAAGCC AGCTCCCTGA
53051 ATCTGACCAC AGACACTCCT GGGGGCCTG AAAGCAACAG CTGGACACCC
53101 CCTTGGTGCT CGCCTTCGGC CTCTCTTGGA ACTGCACCAC CGACCAACTC
53151 CAGACTTGGG AGCTTTAAAG AGCAGGATAG CTCTTCCTCC CCAGGACTTG
53201 GTCTTTTTTC TGGGTCTTGT TTTGTTGATT TTTCTTTTTT AATTTTGGAA
53251 CAAATGCTTT TCCAACCCAT GAGTGCTAAG AGCCTCTGGA AGGGAGGGCT
53301 TCAGGCCCGA AGGTCTCTCT GGCTCTAGGA CCCCCAGTGC TCACACAATC
53351 AGACCAAGGA ACAAGACCCC CAGGAAGGAA ACAGATTTAA GCAAGACCAT
53401 GGGTGGAAG GAGAAAGGGG CTAGCACTGG ATGGAGCTGG AGGGTCGTAG
53451 GGGAGAGATC TCCAACTCTC TCTGTGTCCG TGTGGAGGGC TGCAGAGCCT
53501 GCAGGGTGAC CTGCTTCCCC AAAGGCCAAC AGCATTGGCC TGGCCAGACC
```

TABLE 1-continued

```
53551 AGGTGACCTT AGATTTGGTG AACAACGTAC TATGGAAGCC ACATCACTAT
53601 TGGGCCCCCA GGTCTGATCT GGGTTTTGCC TCTGCCCTTG GGGAAATGCT
53651 ATCAGAAATT CGCCCCATTT TCTTTACAGT CTTTTGTGTC TGTCATTTCT
53701 CTTTCAAAAA GGCGGTGTTT TTTGTTGTTG TTGGTTTTTT TTTTTTTTTA
53751 AAGAAAAGTT CTTAAAACAC TAACGAAAC CCATGGAGTT TGTCCTTTGT
53801 AAAAATTTTA AACACAGTGT CTTGATATAA AAATAAAAAA TCCAGTTAGC
53851 ACTCCCAACC TGCCTCCCTT GCACAGGCCT TGCCCCAACA GACCTCCGAA
53901 CAGGGTGCCT CTGCGGGCTG GGAATCAGGC AATCAGGCAG CCTCCCCCTG
53951 CCTCCTGTAT CTTTAAGCTG AGTCTGGGCT GCACTGTGCG GGGTTGGGGG
54001 TTGGGGGTTG GGGGGGTTGG GGGGTTTGGG GGCCCCCTGC ATGAAGGCNT
54051 CTCCAATCTT AATCAGGTTG CTCTTCCCAT CCCCCTGCCC CCAGCGCGCT
54101 GGGTTCCTGC AGCTGAAGCC TCCTCTCAGC ACTTCAGGCC TCCTAATGAA
54151 ATGGCAAAAA TACTTCCTTC CTTCTCTGCA CCGCTGCGGC CTCCTCCTCC
54201 TCTTACTTCT CCTCCTCCTC CTCTGNTGCA ACCACCCTGC CCTCACCTTG
54251 GACTGGGGGC TGGGAGGAGG TTTGACCTCT AACGTGCTGA AATTCTTTCT
54301 CCTATCTGAA TCCAGTGCAG CGTCAGACGT GGACTCCCTG GCCTTGAGTG
54351 ACTGACAGAG CAGAGGCCCT CTCCTTCCCC AGGGATACTT GTTTGCTGCT
54401 CTGTGAATTA GAACTGGAGA AGTCCTTGGG GCCCTGGGAG CGATTTTTCT
54451 ACAGGATTGT GATCAGTGAC TCCCTATCAA CCCTGGGGCA TGGATTCAGT
54501 GGGGCCTCAC AGGGTTAGCA TTATGGGATT TCATATTATT CTCAGTGACT
54551 TGAAAGACTG AACTGGGAGT GTGCTCGGCA AGTATGATAG TTGGGTGGGG
54601 TTGCTGATAC CTCAGAAAGC AGGAATAGAA TTCTTCAAAT GACCCTGATA
54651 AAATGAGGGA GATGAACCAT CACAAGGAGG ACCATGTTCA GAGAGGACGA
54701 ACACAGGTAG TGTGTACAAA GACCAAAACC TAGAACTAAT ACACTAATAT
54751 GGTACACTGG AGATGGGCAG TGATTGACTT GACACAAGTA TAGTTAAAAA
54801 GAAGAAGAAC TGGGGAGATG GTGTAAGGGT ACATCACAAG TGAGTCCATG
54851 GTGTAAAACT GGTTTTTCCC CCTCCTTTCC TCACACCCTT CTTTCCTTTC
54901 TTTTTTCCAA AACTAATGTG GATCCTGCAT ATAGTAACAA AAACACAGCA
54951 TGGAGGATCT GAGAAGTCAT CCAAGTGTGA GTTTTAGAAC CAGAAGTCAC
55001 CCGAGAGTCA TCTAGTCCAA CCCATTTATT TTATAGTTGA GGAAATGGGC
55051 CCAGAAAAGC CCGTCACAGT TAGTATTAGA AACAGACCTA GAATGCCACC
55101 CAGCACTACA CGACCCTTGC CATAGTCCCA CTCAACTCGT TCCACTCTAC
55151 CTGCCATTGG TCATACCTTT CAAAGCATGA TGGGTCTACC CTTGGCCAAC
55201 ACATTTTTAG CAAAAGTGGA AAGCTAGAGA GGGTCTGGAG AAGAGCATAA
55251 ATAATGCCAC GGGACTAGGT GCTGTGTGTG TGTGCATGCG TGTGTGTG
```

LEGEND
UNDERLINE     HOPA EXONS IN FORWARD READING FRAME
DOUBLE UNDERLINE     NEUROLIGIN 3 CLONE 4 EXONS
DOUBLE UNDERLINE AND ITALIC     ONE OF SEVERAL GRAIL2 PREDICTION IN REVERSE FRAME
CLEAR PROMOTERS IN THE FORWARD FRAME 1398 TO 1648 HOPA 24410 TO 24660 PROBABLE NL-3 PROMOTER UNKNOWN PROMOTER AT 1815 TO 1565 ON REVERSE STRAND

TABLE 2 shows the cDNA and amino acid sequences of human OPA (HOPA) as determined by double strand DNA sequence analysis (SEQ ID NO.: 2).

```
GAATTCGCGGCCGCGTCGACGGCGGCCTTCGGGATCTTGAGCTACGAACA
CCGGCCCCTGAAGCGGCCGCGGCTGGGGCCTCCCGATGTTTACCCTCAGG        100
ACCCCAAACAGAAGGAGGATGAACTGACGGCCTTGAATGTAAAACAAGGT
TTCAATAACCAGCCTGCTGTCTCTGGGGATGAGCATGGCAGTGCCAAGAA        200
CGTCAGCTTCAATCCTGCCAAGATCAGTTCCAACTTCAGCAGCATTATTG
CAGAGAAATTACGTTGTAATACCCTTCCTGACACTGGTCGCAGGAAGCCC        300
CAAGTGAACCAGAAGGATAACTTCTGGCTGGTGACTGCACGATCCCAGAG
TGCCATTAACACTTGGTTCACTGACTTGGCTGGCACCAAGCCACTCACGC        400
AACTAGCCAAAAAGGTCCCCATTTTCAGTAAGAAGGAAGAGGTGTTTGGG
TACTTAGCCAAATACACAGTGCCTGTGATGCGGGCTGCCTGGCTCATTAA        500
GATGACCTGTGCCTACTATGCAGCAATCTCTGAGACCAAGGTTAAGAAGA
GACATGTTGACCCTTTCATGGAATGGACTCAGATCATCACCAAGTACTTA        600
TGGGAGCAGTTACAGAAGATGGCTGAATACTACCGGCCAGGGCCTGCAGG
AAGTGGGGCTGTGGTTCCACGATAGGGCCCTTGCCCCATGATGTAGAGG        700
TGGCAATCCGGCAGTGGGATTACACCGAGAAGCTGGCCATGTTCATGTTT
CAGGATGGAATGCTGGACAGACATGAGTTCCTGACCTGGGTGCTTGAGTG        800
TTTTGAGAAGATCCGCCCTGGAGAGGATGAATTGCTTAAACTGCTGCTGC
CTCTGCTTCTCCGATACTCTGGGGAATTTGTTCAGTCTGCATACCTGTCC        900
CGCCGGCTTGCCTACTTCTGTACACGGAGACTGGCCCTGCAGCTGGATGG
TGTGAGCAGTCACTCATCTCATGTTATATCTGCTCAGTCAACAAGCACGC      1000
TACCCACCACCCCTGCTCCTCAGCCCCCAACTAGCAGCACACCCTCGACT
CCCTTTAGTGACCTGCTTATGTGCCCTCAGCACCGGCCCCTGGTTTTTGG      1100
CCTCAGCTGTATCCTACAGACCATCCTCCTGTGCTGTCCTAGTGCCTTGG
TTTGGCACTACTCACTGACTGATAGCAGAATTAAGACCGGCTCACCACTT      1200
```

TABLE 2-continued shows the cDNA and amino acid sequences of human OPA (HOPA) as determined by double strand DNA sequence analysis (SEQ ID NO.: 2).

```
GACCACTTGCCTATTGCCCCGTCCAACCTGCCCATGCCAGAGGGTAACAG
TGCCTTCACTCAGCAGGTCCGTGCAAAGTTGCGGGAGATCGAGCAGCAGA      1300
TCAAGGAGCGGGGACAGGCAGTTGAAGTTCGCTGGTCTTTCGATAAATGC
CAGGAAGCTACTGCAGGCTTCACCATTGGACGGGTACTTCATACTTTGGA      1400
AGTGCTGGACAGCCATAGTTTTGAACGCTCTGACTTCAGCAACTCTCTTG
ACTCCCTTTGTAACCGAATCTTTGGATTGGGACCTAGCAAGGATGGGCAT      1500
GAGATCTCCTCAGATGATGATGCTGTGGTGTCATTGCTATGTGAATGGGC
TGTCAGCTGCAAGCGTTCTGGTCGGCATCGTGCTATGGTGGTAGCCAAGC      1600
TCCTGGAGAAGAGACAGGCGGAGATTGAGGCTGAGCGTTGTGGAGAATCA
GAAGCCGCAGATGAGAAGGGTTCCATCGCCTCTGGCTCCCTTTCTGCTCC      1700
CAGTGCTCCCATTTTCCAGGATGTCCTCCTGCAGTTTCTGGATACACAGG
CTCCCATGCTGACGGACCCTCGAAGTGAGAGTGAGCGGGTGGAATTCTTT      1800
AACTTAGTACTGCTGTTCTGTGAACTGATTCGACATGATGTTTTCTCCCA
CAACATGTATACTTGCACTCTCATCTCCCGAGGGGACCTTGCCTTTGGAG      1900
CCCCTGGTCCCCGGCCTCCCTCTCCCTTTGATGATCCTGCCGATGACCCA
GAGCACAAGGAGGCTGAAGGCAGCAGCAGCAGCAAGCTGGAAGATCCAGG      2000
GCTCTCAGAATCTATGGACATTGACCCTAGTTCCAGTGTTCTCTTTGAGG
ACATGGAGAAGCCTGATTTCTCATTGTTCTCCCCTACTATGCCCTGTGAG      2100
GGGAAGGGCAGTCCATCCCCTGAGAAGCCAGATGTCGAGAAGGAGGTGAA
GCCCCCACCCAAGGAGAAGATTGAAGGGACCCTTGGGGTTCTTTACGACC      2200
AGCCACGACACGTGCAGTACGCCACCCATTTTCCCATCCCCCAGGAGGAG
TCATGCAGCCATGAGTGCAACCAGCGGTTGGTCGTACTGTTTGGGGTGGG      2300
AAAGCAGCGAGATGATGCCCGCCATGCCATCAAGAAAATCACCAAGGATA
TCTTGAAGGTTCTGAACCGCAAAGGGACAGCAGAAACTGACCAGCTTGCT      2400
CCTATTGTGCCTCTGAATCCTGGAGACCTGACATTCTTAGGTGGGGAGGA
TGGGCAGAAGCGGCGACGCAACCGGCCTGAAGCCTTCCCCACTGCTGAAG      2500
ATATCTTTGCTAAGTTCCAGCACCTTTCACATTATGACCAACACCAGGTC
ACGGCTCAGGTCTCCCGGAATGTTCTGGAGCAGATCACGAGCTTTGCCCT      2600
TGGCATGTCATACCACTTGCCTCTGGTGCAGCATGTGCAGTTCATCTTCG
ACCTCATGGAATATTCACTCAGCATCAGTGGCCTCATCGACTTTGCCATT      2700
CAGCTGCTGAATGAACTGAGTGTAGTTGAGGCTGAGCTGCTTCTCAAATC
CTCGGATCTGGTGGGCAGCTACACTACTAGCCTGTGCCTGTGCATCGTGG      2800
CTGTCCTGCGGCACTATCATGCCTGCCTCATCCTCAACCAGGACCAGATG
GCACAGGTCTTTGAGGGGCTGTGTGGCGTCGTGAAGCATGGGATGAACCG      2900
GTCCGATGGCTCCTCTGCAGAGCGCTGTATCCTTGCTTATCTCTATGATC
TGTACACCTCCTGTAGCCATTTAAAGAACAAATTTGGGGAGCTCTTCAGC      3000
GACTTTTGCTCAAAGGTGAAGAACACCATCTACTGCAACGTGGAGCCATC
GGAATCAAATATGCGCTGGCACCTGAGTTCATGATCGACACTCTAGAGA       3100
ACCCTGCAGCTCACACCTTCACCTACACGGGGCTAGGCAAGAGTCTTAGT
GAGAACCCTGCTAACCGCTACAGCTTTGTCTGCAATGCCCTTATGCACGT      3200
CTGTGTGGGGCACCATGATCCCGATAGGGTGAATGACATCGCAATCCTGT
GTGCAGAGCTGACCGGCTATTGCAAGTCACTGAGTGCAGAATGGCTAGGA      3300
GTGCTTAAGGCCTTGTGCTGCTCCTCTAACAATGGCACTTGTGGTTTCAA
CGATCTCCTCTGCAATGTTGATGTCAGTGACCTATCTTTTCATGACTCGC      3400
TGGCTACTTTTGTTGCCATCCTCATCGCTCGGCAGTGTTTGCTCCTGGAA
GATCTGATTCGCTGTGCTGCCATCCCTTCACTCCTTAATGCTGCTTGTAG      3500
TGAACAGGACTCTGAGCCAGGGGCCCGGCTTACCTGCCGCATCCTCCTTC
ACCTTTTCAAGACACCGCAGCTCAATCCTTGCCAGTCTGATGGAAACAAG      3600
CCTACAGTAGGAATCCGCTCCTCCTGCGACCGCCACCTGCTGGCTGCCTC
CCAGAACCGCATCGTGGATGGAGCCGTGTTTGCTGTTCTCAAGGCTGTGT      3700
TTGTACTTGGGGATGCGGAACTGAAAGGTTCAGGCTTCACTGTGACAGGA
GGAACAGAAGAACTTCCAGAGGAGGAGGGAGGAGGTGGCAGTGGTGGTCG      3800
GAGGCAGGGTGGCCGCAACATCTCTGTGGAGACAGCCAGTCTGGATGTCT
ATGCCAAGTACGTGCTGCGCAGCATCTGCCAACAGGAATGGGTAGGAGAA      3900
CGTTGCCTTAAGTCTCTGTGTGAGGACAGCAATGACCTGCAAGACCCAGT
GTTGAGTAGTGCCCAGGCGCAGCGCCTCATGCAGCTCATTTGCTATCCAC      4000
ATCGACTGCTGGACAATGAGGATGGGAAAACCCCCAGCGGCAGCGCATA
AAGCGCATTCTCCAGAACTTGGACCAGTGGACCATGCGCCAGTCTTCCTT      4100
GGAGCTGCAGCTCATGATCAAGCAGACCCCTAACAATGAGATGAACTCCC
TCTTGGAGAACATCGCCAAGGCCACAATCGAGGTTTTCCAACAGTCAGCA      4200
GAGACAGGGTCATCTTCTGGAAGTACTGCAAGCAACATGCCCAGCAGCAG
CAAGACCAAGCCTGTGCTCAGCTCTCTAGAGCGCTCTGGTGTATGGCTGG      4300
TGGCCCCCTCATTGCTAAACTGCCCACCTCAGTCCAGGGACATGTGTTA
AAGGCTGCTGGGGAAGAATTGGAGAAGGGTCAGCACCTGGGTTCCTCTTC      4400
ACGCAAAGAACGTGATCGACAAAAGCAGAAGAGCATGTCCCTATTGAGCC
AGCAGCCCTTCTTATCGCTGGTGCTAACATGTCTGAAAGGGCAGGATGAA      4500
CAACGCGAGGGACTCCTTACCTCCCTCTACAGCCAGGTGCACCAGATTGT
GAATAATTGGCGAGATGACCAGTACTTAGATGATTGCAAACCAAAGCAGC      4600
TTATGCATGAGGCACTCAAACTGCGGCTCAACCTGGTGGGGGGCATGTTT
GACACGGTGCAGCGCAGCACCCAGCAGACCACGGAGTGGGCCATGCTCCT      4700
CCTGGAGATCATCATCAGCGGCACTGTCGACATGCAGTCCAACAATGAGC
TCTTCACTACTGTGTTGGACATGCTGAGCGTGCTCATCAATGGGACATTG      4800
GCTGCAGACATGTCTAGCATCTCGCAAGGTAGCATGGAGGAAAACAAGCG
TGCATACATGAACCTGGCGAAGAAGTTGCAGAAGGAGTTGGGGGAGCGCC      4900
AGTCAGACAGTCTGGAAAAGGTTCGCCAGCTGCTGCCACTGCCCAAGCAG
```

TABLE 2-continued shows the cDNA and amino acid sequences of human
OPA (HOPA) as determined by double strand DNA
sequence analysis (SEQ ID NO.: 2).

| | |
|---|---|
| ACCCGAGATGTCATCACGTGTGAGCCACAGGGCTCCCTTATCGATACCAA | 5000 |
| GGGCAACAAGATTGCTGGCTTCGATTCCATCTTCAAGAAGGAGGGTCTAC | |
| AGGTTTTCCACCAAACAGAAGATCTCGCCCTGGGATCTTTTTGAGGGGTTG | 5100 |
| AAGCCGTCAGCACCACTCTCTTGGGGCTGGTTTGGAACAGTCCGAGTGGA | |
| CCGGCGAGTGGCTCGAGGAGAGGAGCAGCAGCGGTTGCTGCTCTACCACA | 5200 |
| CACACCTGAGGCCCCGGCCCCGCGCCTATTACCTGGAGCCACTGCCACTG | |
| CCCCCAGAAGATGAGGAGCCGCCTGCTCCTACCCTGCTAGAGCCTGAGAA | 5300 |
| AAAGGCTCCAGAGCCCCCCAAAACTGACAAACCGGGGGCTGCTCCACCCA | |
| GTACTGAGGAACGCAAGAAGAAGTCCACCAAGGGCAAGAAACGCAGCCAG | 5400 |
| CCAGCTACCAAGACAGAGGACTATGGAATGGGCCCGGGTCGGAGCGGCCC | |
| TTATGGTGTGACAGTGCCTCCGGACCTCCTGCACCACCCAAACCCTGGTT | 5500 |
| CTATAACACACCTTAACTACAGGCAAGGCTCCATAGGCCTGTACACCCAG | |
| AACCAGCCACTACCTGCAGGTGGCCCTCGTGTGGACCCATACCGTCCTGT | 5600 |
| GCGCTTACCAATGCAGAAGCTGCCCACCCGACCAACTTACCCTGGAGTGC | |
| TGCCCACAACCATGACTGGCGTCATGGGTTTAGAACCCTCCTCTTATAAG | 5700 |
| ACCTCTGTGTACCGGCAGCAGCAACCTGCGGTGCCCCAAGGACAGCGCCT | |
| TCGCCAACAGCTCCAGAGTCAGGGCATGTTGGGACAGTCATCTGTCCATC | 5800 |
| AGATGACTCCCAGCTCTTCCTACGGTTTGCAGACTTCCCAGGGCTATACT | |
| CCTTATGTTTCTCATGTGGGATTGCAGCAACACACAGGCCCTGCAGGTAC | 5900 |
| CATGGTGCCCCCAGCTACTCCAGCCAGCCTTACCAGAGCACCCACCCTT | |
| CTACCAATCCTACTCTTGTAGATCCTACCCGCCACCTGCAACAGCGGCCC | 6000 |
| AGTGGCTATGTGCACCAGCAGGCCCCCACCTATGGACATGGACTGACCTC | |
| CACTCAAAGGTTTTCACACCAGACACTGCAGCAGACACCCATGATAAGTA | 6100 |
| CCATGACTCCAATGAGTGCCCAGGGCGTCCAGGCAGGCGTCCGTTCAACA | |
| GCCATCCTACCTGAGCAGCAGCAGCAGCAGCAACAGCAGCAACAGCAACA | 6200 |
| GCAGCAGCAGCAGCAACAGCAACAGCAGCAGCAGCAGCAGTACCACA | |
| TCCGGCAGCAGCAGCAGCAGCAGATCCTGCGGCAGCAGCAGCAACAGCAA | 6300 |
| CAGCAGCAGCAGCAGCAGCAACAGCAACAGCAGCAGCAGCAACAGCA | |
| ACAACAGCAACACCAGCAGCAACAGCAGCAACAGGCGGCTCCTCCCCAAC | 6400 |
| CCCAGCCCCAGTCCCAGCCCCAGTTCCAGCGCCAGGGGCTTCAGCAGACC | |
| CAGCAGCAGCAACAGACAGCAGCTTTGGTCCGGCAACTTCAACAACAGCT | 6500 |
| CTCTAATACCCAGCCACAGCCCAGTACCAACATATTTGGACGCTACTGAG | |
| CCACCTGGAGGAACTGCTTGTGCACTGGATGTGGCCCCACCCTTTCCTCT | 6600 |
| TAATTCCCAATCCCATTCCTGGGCTAGCACCAGTAGTGGTTGGGGCCCTC | |
| CCCTCAGGCTCCATTTTTAATAAGTTTTTAGTATTTTTGTTAATGTGAGG | 6700 |
| CATTGAGCTGTTGGGTTTTGTATATTATTTATATAGAGACCCCAGAGCTG | |
| TTGCACCCAATACACAGAGCTTCTTTGCAAAAAAAAAAAAAAAAA | 6794 |

TABLE 3 shows the cDNA and amino acid sequences of various
human neuroligin-3 clones as determined by double strand
DNA sequence analysis.

A. Clone NL-3, cDNA #2,
isolated from brain (SEQ ID NO.: 3).

| | |
|---|---|
| GAATTCCCGGGTCGACCCACGCGTCCGTGTGACCCTGGAGTCTGCCTCTC | |
| CTGCCAGTCCCCCTGCCCGGAACATGTGGCTGCGGCTTGGCCCGCCCTCG | 100 |
| CTGTCCCTGAGCCCCAAGCCCACGGTTGGCAGGAGCCTGTCGCTCACCCT | |
| GTGGTTCCTCAGTTTGGCGCTGAGGGCCAGTACCCAGGCCCCAGCACCCA | 200 |
| CAGTCAACACTCACTTTGGGAAGCTAAGGGGTGCCCGAGTACCACTGCCC | |
| AGTGAGATCCTGGGGCCTGTGGACCAATACCTGGGGGTGCCCTACGCAGC | 300 |
| TCCCCCGATCGGCGAGAAACGTTTCCTGCCCCCTGAACCACCCCCCATCCT | |
| GGTCGGGCATCCGGAACGCCACACACTTTCCCCCAGTGTGCCCCCAGAAC | 400 |
| ATCCACACAGCTGTGCCCGAAGTCATGCTGCCGGTCTGGTTCACTGCCAA | |
| CTTGGATATCGTCGCTACTTACATCCAGGAGCCCAACGAAGACTGTCTCT | 500 |
| ACCTGAACGTCTATGTGCCGACGGAGGATGTAAAGCGGATTTCCAAGGAA | |
| TGCGCCCGAAAGCCCAACAAGAAAATTTGTAGGAAAGGAAGATCCGGCGC | 600 |
| TAAGAAACAGGGCGAGGACTTAGCGGATAATGACGGGGATGAAGATGAAG | |
| ACATCCGGGACAGTGGTGCTAAACCCGTCATGGTCTACATCCACGGAGGC | 700 |
| TCTTACATGGAAGGGACAGGCAACATGATTGATGGCAGCATCCTCGCCAG | |
| TTATGGCAATGTCATCGTCATCACCCTCAACTATCGGGTTGGAGTGCTAG | 800 |
| GTTTCCTGAGTACTGGAGATCAGGCTGCCAAGGGCAACTATGGGCTCCTT | |
| GACCAGATCCAGGCCCTCCGCTGGGTGAGCGAGAATATTGCCTTCTTCGG | 900 |
| GGAGACCCCCGCCGGATCACTGTCTTTGGCTCGGGCATTGGTGCATCCT | |
| GCGTCAGCCTCCTCACGTTGTCACATCACTCAGAGGGACTTTTCCAGAGA | 1000 |
| GCCATCATCCAAAGTGGCTCTGCTCTGTCCAGCTGGGCTGTGAACTACCA | |
| ACCAGTGAAGTACACCAGCCTGCTGGCAGACAAAGTGGGCTGTAATGTGC | 1100 |
| TGGACACCGTGGATATGGTGGACTGTCTTCGGCAAAAAGAGTGCCAAGGAG | |
| CTGGTAGAGCAGGACATCCAGCCAGCCCGCTACCACGTGGCCTTTGGCCC | 1200 |
| TGTGATTGATGGTGATGTCATTCCTGATGACCCTGAGATCCTCATGGAGC | |

TABLE 3-continued shows the cDNA and amino acid sequences of various human neuroligin-3 clones as determined by double strand DNA sequence analysis.

```
AGGGCGAGTTCCTCAACTATGACATCATGCTAGGTGTCAACCAGGGCGAG
GGTCTCAAGTTTGTGGAAGGGGTGGTGGACCCTGAGGATGGTGTCTCTGG       1300
CACTGACTTTGACTATTCCGTCTCCAATTTTGTGGACAATCTGTATGGCT       1400
ATCCTGAGGGTAAGGACACCCTGCGAGAGACCATCAAGTTCATGTATACA
GACTGGGCAGACCGTGACAACCCTGAGACCCGCCGTAAAACACTGGTGGC       1500
ACTCTTCACTGACCACCAGTGGGTGGAGCCCTCAGTGGTGACAGCCGATC
TGCATGCCCGCTACGGCTCGCCTACCTACTTCTACGCCTTCTATCATCAC       1600
TGCCAGAACCTCATGAAGCCTGCTTGGTCAGATGCAGCTCATGGGGATGA
AGTACCCTATGTTTTTGGGGTTCCTATGGTAGGCCCCACTGACCTTTTCC       1700
CCTGCAACTTCTCCAAGAATGATGTTATGCTCAAAAAAAAAAAAAAGGG
CGGCCGCTCTAAAG                                           1764
```

B. Clone NL-3. cDNA #3,
isolated from brain (SEQ ID NO.: 4).

```
CTCGGGCATTGGTGCATCCTGCGTCAGCCTCCTCACGTTGTCACATCACT
CAGAGGGACTTTTCCAGAGAGCCATCATCCAAAGTGGCTCTGCTCTGTCC        100
AGCTGGGCTGTGAACTACCAACCAGTGAAGTACACCAGCCTGCTGGCAGA
CAAAGTGGGCTGTAATGTGCTGGACACCGTGGATATGGTGGACTGTCTTC        200
GGCAAAAGAGTGCCAAGGAGCTGGTAGAGCAGGACATCCAGCCAGCCCGC
TACCACGTGGCCTTTGGCCCTGTGATTGATGGTGATGTCATTCCTGATGA        300
CCCTGAGATCCTCATGGAGCAGGGCGAGTTCCTCAACTATGACATCATGC
TAGGTGTCAACCAGGGCGAGGGTCTCAAGTTTGTGGAAGGGGTGGTGGAC        400
CCTGAGGATGGTGTCTCTGGCACTGACTTTGACTATTCCGTCTCCAATTT
TGTGGACAATCTGTATGGCTATCCTGAGGGTAAGGACACCCTGCGAGAGA        500
CCATCAAGTTCATGTATACAGACTGGGCAGACCGTGACAACCCTGAGACC
CGCCGTAAAACACTGGTGGCACTCTTCACTGACCACCAGTGGGTGGAGCC        600
CTCAGTGGTGACAGCCGATCTGCATGCCCGCTACGGCTCGCCTACCTACT
TCTACGCCTTCTATCATCACTGCCAGAGCCTCATGAAGCCTGCTTGGTCA        700
GATGCAGCTCATGGGGATGAAGTACCCTATGTTTTTGGGGTTCCTATGGT
AGGCCCCACTGACCTTTTCCCCTGCAACTTCTCCAAGAATGATGTTATGC        800
TCAGTGCTGTCGTCATGACCTATTGGACCAACTTTGCCAAGACTGGGGAT
CCCAACAAGCCGGTCCCCCAGGACACCAAGTTCATTCACACCAAGGCCAA        900
CCGCTTTGAGGAAGTGGCCTGGTCCAAATACAATCCCCGACAGCTCT
ACCTTCACATCGGGCTGAAACCAAGGGTCCGAGATCATTACCGGGCCACT       1000
AAGGTGGCCTTTTGGAAACATCTGGTGCCCCACCTATACAACCTGCATGA
CATGTTCCACTATACGTCCACCACCACCAAAGTGCCGCCTCCGGATACCA       1100
CCCACAGCTCCCACATCACCCGCAGGCCCAATGGCAAGACCTGGAGCACC
AAGCGGCCAGCCATCTCACCTGCCTACAGCAACGAGAATGCCCAGGGGTC       1200
CTGGAACGGGGACCAGGATGCAGGGCACTCCTGGTGGAGAACCCTCGTG
ACTACTCCACTGAATTAAGTGTCACCATCGCCGTGGGGGCCTCCCTCCTG       1300
TTCCTTAACGTTCTGGCCTTCGCTGCCCTCTACTACCGTAAGGACAAACG
GCGCCAGGAGCCCCTGCGGCAGCCTAGCCCTCAGCGGGGAGCCGGGGCCC       1400
CGGAGTTGGGAGCTGCTCCAGAGGAGGAGCTGGCAGCATTACAACTGGGC
CCCACCCACCACGAGTGTGAGGCCGGTCCCCCCCATGACACGCTGCGCCT       1500
CACTGCATTGCCCGACTACACCCTGACCCTGCGGCGCTCCCCGGATGACA
TCCCACTCATGACCCCCAACACCATCACTATGATCCCCAACTCCCTGGTA       1600
GGGCTGCAGACATTGCACCCCTATAACACCTTTGCCGCAGGGTTCAACAG
TACCGGGCTGCCCCACTCACACTCCACTACCCGGGTATAGCTCCAACTCA       1700
GAGCACAGCCAATCTCCAGGCTCCCTCCCTCCCAGATCCAGGAACACATG
CACACACACACACACACACACGCAGACACACACACACACACATATATG       1800
TATACGCACGCACCCACACCCTACAGCAGATCCACCTGCACAAACATAGA
CAGATGTGGACATGCACCCGCATGTACAAAAACACAAATACGGAAGTAAA       1900
CCTGAACAAACCCTTTAAATGGGGACGCAGATGAGTCCTCGGTAAACCGA
GGACCCATGAAACAGCAGCTGAAGCCAGCTCCCTGAATCTGACCACAGAC       2000
ACTCCTGGGGGCCTGAAAGCAACAGCTGGACACCCCCTTGGTGCTCGCC
TTCGGCCTCTCTTGGAACTGCACCACCGACCAACTCCAGACTTGGGAGCT       2100
TTAAAGAGCAGGATAGCTCTTCCTCCCCAGGACTTGGTCTTTTTTCTGGG
TCTTGTTTTGTTGATTTTTCTTTTTTAATTTTGGAACAAATGCTTTTCCA       2200
ACCCATGAGTGCTAAGAGCCTCTGGAAGGGAGGGCTTCAGGCCCGAAGGT
CTCTCTGGCTCTAGGACCCCCAGTGCTCACACAATCAGACCAAGGAACAA       2300
GACCCCCAGGAAGGAAACAGATTTAAGCAAGACCATGGGGTGGAAGGAGA
AAGGGGCTAGCACTGGATGGAGCTGGAGGGTCGTAGGGGAGAGATCTCCA       2400
ACTCTCTCTGTGTCCGTGTGGAGGGCTGCAGAGCCTGCAGGGTGACCTGC
TTCCCCAAAGGCCAACAGCATTGGCCTGGCCAGACCAGGTGACCTTAGAT       2500
TTGGTGAACAACGTACTATGGAAGCCACATCACTATTGGGCCCCAGGTC
TGATCTGGGTTTTGCCTCTGCCCTTGGGAAATGCTATCAGAAATTCGCC       2600
CCATTTTCTTTACAGTCTTTTGTGTCTGTCATTTCTCTTTCAAAAAGGCG
GTGTTTTTTGTTGTTGTGGTTTTTTTTTTTTAAAGAAAAGTTCTTA         2700
AAACACTAACGAAACCCATGGAGTTTGTCCTTTGTAAAAATTTTAAACA
CAGTGTCTTGATATAAAAATAAAAAATCCAGTTAGCACTCCCAAAAAAAA       2800
AAAAAAAAAAAAAAAA
```

TABLE 3-continued shows the cDNA and amino acid sequences of various human neuroligin-3 clones as determined by double strand DNA sequence analysis.

C. Clone NL-3, cDNA #4,
isolated from heart (SEQ ID NO.: 5).

| Sequence | Position |
|---|---:|
| TCNGCACGCGGAAAGAAGCACATGGCTGAATATCGACGGTTTCCATATGG | |
| GGATTGGTGGCGACGACTCCTGGAGCCCGTCAGTATCGGCGGAATTCGCG | 100 |
| GCCGCGTCGACCTGATCTCGGGGATTCGGGTGCGGAGCCCTTGGCCTGGA | |
| GGCGATATGGGTGGTCCGTGGCCCGGTTCAGTCGCTTGCAGCAGCCCGGG | 200 |
| GAACAGGCCTGTCTGGCCCTGAGGGAGTCCCCTTTCTGAAGCTGTGGTGC | |
| TTGGACGACCTGCTCTCTACATTGCTGGGCACCTGTAGGTGTCCCTCGAG | 300 |
| AGCTCAGTTTTGAGGTTCAAGTCAGTGTGGCCATGAAGGGGCTGCCTATT | |
| GGGCTGATGCTGTGACCCTGGAGTCTGCCTCTCCTGCCAGTCCCCCTGCC | 400 |
| CGGAACATGTGGCTGCGGCTTGGCCCGCCCTCGCTGTCCCTGAGCCCCAA | |
| GCCCACGGTTGGCAGGAGCCTGTGCCTCACCCTGTGGTTCCTCAGTTTGG | 500 |
| CGCTGAGGGCCAGTACCCAGGCCCCAGCACCCACAGTCAACACTCACTTT | |
| GGGAAGCTAAGGGGTGCCCGAGTACCACTGCCCAGTGAGATCCTGGGGCC | 600 |
| TGTGGACCAATACCTGGGGGTGCCCTACGCAGCTCCCCCGATCGGCGAGA | |
| AACGTTTCCTGCCCCCTGAACCACCCCCATCCTGGTCGGGCATCCGGAAC | 700 |
| GCCACACACTTTCCCCCAGTGTGCCCCCAGAACATCCACACAGCTGTGCC | |
| CGAAGTCATGCTGCCGGTCTGGTTCACTGCCAACTTGGATATCGTCGCTA | 800 |
| CTTACATCCAGGAGCCCAACGAAGACTGTCTCTACCTGAACGTCTATGTG | |
| CCGACGGAGGATGGATCCGGCGCTAAGAAACAGGGCGAGGACTTAGCGGA | 900 |
| TAATGACGGGGATGAAGATGAAGCATCCGGGACAGTGGTGCTAAACCCG | |
| TCATGGTCTACATCCACGGAGGCTCTTACATGGAAGGGACAGGCAACATG | 1000 |
| ATTGATGGCAGCATCTTCGCCAGTTATGGCAATGTCATAGTCATCACCCT | |
| CAACTATCGGGTTGGAGTGATAGGTTTCCTGAGTACTGGAGATCAGGCTG | 1100 |
| CCAAGGGCAACTATGGGCTCCTTGACCAGATCCAGGCCCTCCGCTGGGTG | |
| AGCGAGAATATTGCCTTCTTCGGGGGAGACCCCCGCCGGATCACTGTCTT | 1200 |
| TGGCTCGGGCATTGGTGCATCCTGCGTCAGCCTCCTCACGTTGTCACATC | |
| ACTCAGAGGGACTTTTCCAGAGAGCCATCATCCAAAGTGGCTCTGCTCTG | 1300 |
| TCCAGCTGGGCTGTGAACTACCAACCAGTGAAGTACACCAGCCTGCTGGC | |
| AGACAAAGTGGGCTGTAATGTGCTGGACACCGTGGATATGGTGGACTGTC | 1400 |
| TTCGGCAAAAGAGTGCCAAGGAGCTGGTAGAGCAGGACATCCAGCCAGCC | |
| CGCTACCACGTGGCCTTTGGCCCTGTGATTGATGGTGATGTCATTCCTGA | 1500 |
| TGACCCTGAGATCCTCATGGAGCAGGGCGAGTTCCTCAACTATGACATCA | |
| TGCTAGGTGTCAACCAGGGCGAGGGTCTCAAGTTTGTGGAAGGGGTGGTG | 1600 |
| GACCCTGAGGATGGTGTCTCTGGCACTGACTTTGACTATTCCGTCTCCAA | |
| TTTTGTGGACAATCTGTATGGCTATCCTGAGGGTAAGGACACCCTGCGAG | 1700 |
| AGACCATCAAGTTCATGTATACAGACTGGGCAGACCGTGACAACCCTGAG | |
| ACCCGCCGTAAAACACTGGTGGCACTCTTCACTGACCACCAGTGGGTGGA | 1800 |
| GCCCTCAGTGGTGACAGCCGATCTGCATGCCCGCTACGGCTCGCCTACCT | |
| ACTTCTACGCCTTCTATCATCACTGCCAGAGCCTCATGAAGCCTGCTTGG | 1900 |
| TCAGATGCAGCTCATGGGATGAAGTACCCTATGTTTTGGGGTTCCTAT | |
| GGTAGGCCCCACTGACCTTTTCCCCTGCAACTTCTCCAAGAATGATGTTA | 2000 |
| TGCTCAGTGCTGTCGTCATGACCTATTGGACCAACTTTGCCAAGACTGGG | |
| GATCCCAACAAGCCGGTCCCCCAGGACACCAAGTTCATTCACACCAAGGC | 2100 |
| CAACCGCTTTGAGGAAGTGGCCTGGTCCAAATACAATCCCCGAGACCAGC | |
| TCTACCTTCACATCGGGCTGAAACCAAGGGTCCGAGATCATTACCGGGCC | 2200 |
| ACTAAGGTGGCCTTTTGGAAACATCTGGTGCCCCACCTATACAACCTGCA | |
| TGACATGTTCCACTATACGTCCACCACCACCAAAGTGCCGCCTCCGGATA | 2300 |
| CCACCCACAGCTCCCACATCACCCGCAGGCCCAATGGCAAGACCTGGAGC | |
| ACCAAGCGGCCAGCCATCTCACCTGCCTACAGCAACGAGAATGCCCAGGG | 2400 |
| GTCCTGGAACGGGGACCAGGATGCCAGGGCCACTCCTGGTGGAGAACCCT | |
| CGTGACTACTCCACTGAATTAAGTGTCACCATCGCCGTGGGGGCCTCCCT | 2500 |
| CCTGTTCCTTAACGTTCTGGCCTTCGCTGCCCTCTACTACCGTAAGGACA | |
| AACGGCGCCAGGAGCCCCTGCGGCAGCCTAGCCCTCAGCGGGGAGCGGG | 2600 |
| GCCCCGGAGTTGGGAGCTGCTCCAGAGGAGGAGCTGGCAGCATTACAACT | |
| GGGCCCCACCCACCACGAGTGTGAGGCCGGTCCCCCCCATGACACGCTGC | 2700 |
| GCCTCACTGCATTGCCCGACTACACCCTGACCCTGCGGCGCTCCCCGGAT | |
| GACATCCCACTCATGACCCCCAACACCATCACTATGATCCCCAACTCCCT | 2800 |
| GGTAGGGCTGCAGACATTGCACCCCTATAACACCTTTGCCGCAGGGTTCA | |
| ACAGTACCGGGCTGCCCCACTCACACTCCACTACCCGGGTATAGCTCCAA | 2900 |
| CTCAGAGCACAGCCAATCTCCAGGCTCCCTCCCTCCCAGATCCAGGAACA | |
| CATGCACACACACACACACACACGCAGACACACACACACACACATA | 3000 |
| TATGTATACGCACGCACCCACACCCTACAGCAGATCCACCTGCACAAACA | |
| TAGACAGATGTGGACATGCACCCGCATGTACAAAAACACAAATACGGAAG | 3100 |
| TAAACCTGAACAAACCCTTTAAATGGGGACGCAGATGAGTCCTCGGTAAA | |
| CCGAGGACCCATGAAACAGCAGCTGAAGCAGCTCCCTGAATCTGACCAC | 3200 |
| AGACACTCCTGGGGGCCTGAAAGCAACAGCTGGACACCCCTTGGTGCT | |
| CGCCTTCGGCCTCTCTTGGAACTGCACCACCGACCAACTCCAGACTTGGG | 3300 |
| AGCTTTAAAGAGCAGGATAGCTCTTCCTCCCCAGGACTTGGTCTTTTTTC | |
| TGGGTCTTGTTTTGTTGATTTTCTTTTTTAATTTTGGAACAAATGCTTT | |
| TCCAACCCATGAGTGCTAAGAGCCTCTGGAAGGGAGGGCTTCAGGCCCGA | 3400 |
| AGGTCTCTCTGGCTCTAGGACCCCAGTGCTCACACAATCAGACCAAGGA | 3500 |
| ACAAGACCCCCAGGAAGGAAACAGATTTAAGCAAGACCATGGGTGGAAG | |
| GAGAAAGGGGCTAGCACTGGATGGAGCTGGAGGGTCGTAGGGGAGAGATC | 3600 |

TABLE 3-continued shows the cDNA and amino acid sequences of various human neuroligin-3 clones as determined by double strand DNA sequence analysis.

```
TCCAACTCTCTCTGTGTCCGTGTGGAGGGCTGCAGAGCCTGCAGGGTGAC
CTGCTTCCCCAAAGGCCAACAGCATTGGCCTGGCCAGACCAGGTGACCTT      3700
AGATTTGGTGAACAACGTACTATGGAAGCCACATCACTATTGGGCCCCCA
GGTCTGATCTGGGTTTTGCCTCTGCCCTTGGGGAAATGCTATCAGAAATT      3800
CGCCCCATTTTCTTTACAGTCTTTTGTGTCTGTCATTTCTCTTTCAAAAA
GGCGGTGTTTTTGTTGTTGTTGGTTTTTTTTTTTTTAAAGAAAAGTT          3900
CTTAAAACACTAACGAAAAAAAAAGTCGACGCGGCCGCGAATTCCAGCT
GAGCGCCGGTCGCTACCATTACCAGTTGGTCTGGTGTCAAAAATAATAAT      4000
AACCGGGCAGGCCATGTCTGCCCGTATTTCGCGTAAGGAAATCCATTGTA
CTGCCGGACCACCGACTGTGAGCCACTCCGGCCATGGCGTACGCACTGAC      4100
CTGCTTACTGATTTGTAAAACCGGTCCGGCCATCACGCTCACATAACGTC
CACGCAGGCTCTCATAGTGANACGTATCNTNCCCCGGTCATCACTGNGCT      4200
GCTCTTTTTCGACGCGGCGAACCCCCCNGGCAG                       4233
D. Clone NL-3 cDNA #5,
isolated from heart (SEQ ID NO.: 6).

GNNRWTACGCTAGCTTGGGTGGTCATATGGCCATGGAGGCCCCGGGGATC
CGAATTCGCGGCCGCGTCGACGGAACATGTGGCTGCGGCTTGGCCCGCCC      100
TCGCTGTCCCTGAGCCCCAAGCCCACGGTTGGCAGGAGCCTGTGCCTCAC
CCTGTGGTTCCTCAGTTTGGCGCTGAGGGCCAGTACCCAGGCCCCAGCAC      200
CCACAGTCAACACTCACTTTGGGAAGCTAAGGGGTGCCCGAGTACCACTG
CCCAGTGAGATCCTGGGGCCTGTGGACCAATACCTGGGGGTGCCCTACGC      300
AGCTCCCCCGATCGGCGAGAAACGTTTCCTGCCCCCTGAACCACCCCCAT
CCTGGTCGGGCATCCGGAACGCCACACTTTCCCCCAGTGTGCCCCCAG       400
AACATCCACACAGCTGTGCCCCAAGTCATGCTGCCGGTCTGGTTCACTGC
CAACTCGGATATCGTCGCTACTTACATCCAGGAGCCCAACGAAGACTGTC      500
TCTACCTGAACGTCTATGTGCCGACGGAGGATGGTGAGTGCTGCGGCCAG
GCACTGTGCCCTCCCTGCCTCCCGCCTGCCCTGCTGTGTTTGTGGCTTGC      600
ATGTGGTTGTGTGCCCTGCAGCATGCATCTGTCTGTCTGTGAAAATGCTT
CTAACCATCACTCTGCTTGGCCTCCCACCCCCCTCCCTGTTCTTCCCTCT      700
CCCAGCATTGTCCGAGCTCCCATGTGTGAGTGACACTGTTGCCAGGAGGG
GCCTGGCCCGGCCTGAGAGCTCTGACGGGTCTCGGTCCAGTGCTGGATGG      800
GGGTCCCCTGGGGGAGTATGGGTCACGGCTGGCAGCTACCCGCGGGAGGA
TGCTGGCTCCACCAGGCCCCCCTGTTGCCATTCCACCTGCTTCGAAAGGT      900
GGTAGGTGTGTGTGGCCAAGGGCACTGGGTGTGTGGGGGGTGGGGCAGCA
AGCCTGGTGGGTGATGCTTAGGTGCCTCCTCTTTCACTAGCTGATGCCTC      1000
CTCCCGCGGGGGTCACACTAAGGTAAGTGACAGAAACAAGGAGATGGTGG
GACAGGCTCTCTGCCATGTGCCGCCTGCAGAGCAGCTCAGCTCTTGGGGC      1100
CTGGGGGGTGGGGGGTGCATGCCCCTGGGCAGAGGCCTCCTGTTATTTTT
TAGTTTTTTTATTCATTTTACAGTAAAGCGGATTTCCAAGGAATGCGCCCG    1200
AAAGCCCAACAAGAAAATTTGTAGGAAAGGAGGATCCGGCGCTAAGAAAC
AGGGCGAGGACTTAGCGGATAATGACGGGGATGAAGATGAAGACATCCGG     1300
GACAGTGGTGCTAAACCCGTCATGGTCTACATCCACGGAGGCTCTTACAT
GGAAGGGACAGGCAACATGATTGATGGCAGCATCCTCGCCAGTTATGGCA     1400
ATGTCATCGTCATCACCCTCAACTATCGGGTTGGAGTGCTAGGGTTTCCTG
AGTACTGGAGATCAGGCTGCCAAGGGCAACTATGGGCTCCTTGACCAGAT     1500
CCAGGCCCTCCGCTGGGTGAGCGAGAATATTGCCTTCTTCGGGGGAGACC
CCCGCCGGATCACTGTCTTTGGCTCGGGCATTGGTGCATCCTGCGTCAGC     1600
CTCCTCACGTTGTCACATCACTCAGAGGGACTTTTCAGAGAGCCATCAT
CCAAAGTGGCTCTGCTCTGTCCAGCTGGGCTGTGAACTACCAACCAGTGA     1700
AGTACACCAGCCTGCTGGCAGACAAAGTGGGCTGTAATGTGCTGGACACC
GTGGATATGGTGGACTGTCTTCGGCAAAAGAGTGCCAAGGAGCTGGTAGA     1800
GCAGGACATCCAGCCAGCCCGCTACCACGTGGCCTTTGGCCCTGTGATTG
ATGGTGATGTCATTCCTGATGACCCTGAGATCCTCATGGAGCAGGGCGAG     1900
TTCCTCAACTATGACATCATGCTAGGTGTCAACCAGGGCGAGGGTCTCAA
GTTTGTGGAAGGGGTGGTGGACCCTGAGGATGGTGTCTCTGGCACTGACT     2000
TTGACTATTCCGTCTCCAATTTTGTGGACAATCTGTATGGCTATCCTGAG
GGTAAGGACACCCTGCGAGAGACCATCAAGTTCATGTATACAGACTGGGC     2100
AGACCGTGACAACCCTGAGACCCGCCGTAAAACACTGGTGGCACTCTTCA
CTGACCACCAGTGGGTGGAGCCCTCAGTGGTGACAGCCGATCTGCATGCC     2200
CGCTACGGCTCGCTACCTACTTCTACGCCTTCTATCATCACTGCCAGAG
CCTCATGAAGCTGCTTGGTCAGATGCAGCTCATGGGGATGAAGTACCCT     2300
ATGTTTTTGGGGTTCCTATGGTAGGCCCCACTGACCTTTTCCCCTGCAAC
TTCTCCAAGAATGATGTTATGCTCAGTGCTGTCGTCATGACCTATTGGAC     2400
CAACTTTGCCAAGACTGGGGATCCCAACAAGCCGGTCCCCCAGGACACCA
AGTTCATTCACACCAAGGCCAACCGCTTTGAGGAAGTGGCCTGGTCCAAA     2500
TACAATCCCCGAGACCAGCTCTACCTTCACATCGGGCTGAAACCAAGGGT
CCGAGATCATTACCGGGCCACTAAGGTGGCCTTTTGGAAACATCTGGTGC     2600
CCCACCTATACAACCTGCATGACATGTTCCACTATACGTCCACCACCACC
AAAGTGCCGCCTCCGGATACCACCCACAGCTCCCACATCACCCAGGGCC     2700
CAATGGCAAGACCTGGAGCACCAAGCGGCCAGCCATCTCACCTGCCTACA
GCAACGAGAATGCCCAGGGGTCCTGGAACGGGGACCAGGATGCAGGGCCA     2800
CTCCTGGTGGAGAACCCTCGTGACTACTCCACTGAATTAAGTGTCACCAT
CGCCGTGGGGGCCTCCTCCTGTTCCTTAACGTTCTGGCCTTCGCTGCCC     2900
TCTACTACCGTAAGGACAAACGGCGCCAGGAGCCCCTGCGGCAGCCTAGC
```

TABLE 3-continued shows the cDNA and amino acid sequences of various human neuroligin-3 clones as determined by double strand DNA sequence analysis.

| | |
|---|---|
| CCTCAGCGGGGAGCCGGGGCCCCGGAGTTGGGAGCTGCTCCAGAGGAGGA | 3000 |
| GCTGGCAGCATTACAACTGGGCCCCACCCACCACGAGTGTGAGGCCGGTC | |
| CCCCCCATGACACGCTGCGCCTCACTGCATTGCCCGACTACACCCTGACC | 3100 |
| CTGCGGCGCTCCCCGGATGACATCCCACTCATGACCCCCAACACCATCAC | |
| TATGATCCCCAACTCCCTGGTAGGGCTGCAGACATTGCACCCCTATAACA | 3200 |
| CCTTTGCCGCAGGGTTCAACAGTACCGGGCTGCCCCACTCACACTCCACT | |
| ACCCGGGTATAGCTCCAACTCAGAGCACAGCCAATCTCCAGGCTCCCTCC | 3300 |
| CTCCCAGATCCAGGAACACATGCACACACACACACACACACACGCAGACA | |
| CACACACACACACACATATATGTATACGCACGCACCCACACCCTACAGCA | 3400 |
| GATCCACCTGCACAAACATAGACAGATGTGGACATGCACCCGCATGTACA | |
| AAAACACAAATACGGAAGTAAACCTGAACAAACCCTTTAAATGGGGACGC | 3500 |
| AGATGAGTCCTCGGTAAACCGAGGACCCATGAAACAGCAGCTGAAGCCAG | |
| CTCCCTGAATCTGACCACAGACACTCCTGGGGGGCCTGAAAGCAACAGCT | 3600 |
| GGACACCCCCTTGGTGCTCGCCTTCGGCCTCTCTTGGAACTGCACCACCG | |
| ACCAACTCCAGACTTGGGAGCTTTAAAGAGCAGGATAGCTCTTCCTCCCC | 3700 |
| AGGACTTGGTCTTTTTTCTGGGTCTTGTTTTGTTGATTTTTCTTTTTTAA | |
| TTTTGGAACAAATGCTTTTCCAACCCATGAGTGCTAAGAGCCTCTGGAAG | 3800 |
| GGAGGGCTTCAGGCCCGAAGGTCTCTCTGGCTCTAGGACCCCCAGTGCTC | |
| ACACAATCAGACCAAGGAACAAGACCCCCAGGAAGGAAACAGATTTAAGC | 3900 |
| AAGACCATGGGTGGAAGGAGAAAGGGGCTAGCACTGGATGGAGCTGGAG | |
| GGTCGTAGGGGAGAGATCTCCAACTCTCTCTGTGTCCGTGTGGAGGGCTG | 4000 |
| CAGAGCCTGCAGGGTGACCTGCTTCCCCAAAGGCCAACAGCATTGGCCTG | |
| GCCAGACCAGGTGACCTTAGATTTGGTGAACAACGTACTATGGAAGCCAC | 4100 |
| ATCACTATTGGGCCCCCAGGTCTGATCTGGGTTTTGCCTCTGCCCTTGGG | |
| GAAATGCTATCAGAAATTCGCCCCATTTTCTTTACAGTCTTTTGTGTCTG | 4200 |
| TCATTTCTCTTTCAAAAAGGCGGTGTTTTTTGTTGTTGTTGGTTTTTTTT | |
| TTTTTTTTTAAAGAAAAGTTCTTAAAACACTAACGGAAACCCATGGAGTT | 4300 |
| TGTCCTTTGTAAAAATTTTAAACACAGTGTCTTGATATAAAAATAAAAAA | |
| TCCAGTTAGCCCTCCCAAAAAAAAAAAAAAAAAAAAAAAARCTCGAGAGA | 4400 |
| TCTATGAATCGTAGATACTGAAAAACCCCGCAACCC | 4436 |

TABLE 4 shows the cDNA sequence of murine MOPA as determined by double strand sequence analysis (SEQ ID NO.: 7).

| | |
|---|---|
| GCACATGGCTGAATATCGACGGTTTCCATATGGGGATTGGTGGCGACGAC | |
| TCCTGGAGCCCGTCAGTATCGGCGGAATTCGCGGCCGCGTCGACAGGAGG | 100 |
| ATGAACTGACGGCTTTGAATGTAAAACAAGGTTTCAATAACCAGCCTGCT | |
| GTCTCTGGGGACGAACATGGCAGTGCCAAGAACGTCAACTTCAATCCTGC | 200 |
| CAAGATCAGTTCCAACTTCAGCAGCATCATCGCAGAGAAGTTAAGGTGTA | |
| ATACTCTCTCTGACACTGGTCGCAGGAAGTCCCTAATGAACCAGAAGGAC | 300 |
| AACTTCTGGCTGGTGACTGCAAGATCTCAGAGTGCTATTAACACCTGGTT | |
| CACTGACCTGGCTGGCACCAAACCACTCACACACCTAGCCAAAAAGGTCC | 400 |
| CCATTTTCAGTAAAAAGGAAGAAGTATTTGGGTATTTGGCCAAATACACG | |
| GTGCCTGTGATGCGGGCGTGCCTGGCTCATTAAGATGACTTGTGCCTACTA | 500 |
| TGCAGCAATGTCTGAGACTAAGGTTAAGAAGAAAAATACTGCTGACCCCT | |
| TCACTGAATGGACTCAAATCATCACAAAGTACTTGTGGGAGCAGCTACAG | 600 |
| AAGATGGCTGAGTACTATCGGCCAGGGCCTGCAGGAAGTGGAGGCTGTGG | |
| TTCTACTATAGGGCCTTTGCCCCATGATGTAGAGATGGCCATCGTGCAGT | 700 |
| GGGATTACAATGAGAAGCTCGCCTTGTTCATGTTTCAGGATGGAATGCTG | |
| GACAGACATGAGTTCCTGACTTGGGTGCTTGAGTGTTTTGAGAAAATACG | 800 |
| CCCTGGAGAAGATGAATTGCTTAAATTGCTGCTTCCCCTACTGCTGCGAT | |
| ACTCAGGGGAGTTTGTTCAGTCTGCCTATCTGTCCCGCCGCCTTGCCTAC | 900 |
| TTCTGTACCCGGAGATTGGCTCTCCAGCTGGATGGTGTGAGCAGCCACTC | |
| ATCTCATGTCATAGCTGCTCAGTCAACAAGTTCTCTGCCCACTACCCCAG | 1000 |
| CACCTCAGCCCCAACTAGCAGTACACCCTCGACTCCCTTTAGTGACCTG | |
| CTTATGTGCCCTCAGCATCGTCCCCTGGTTTTGGCCTCAGCTGTATCCT | 1100 |
| TCAGACCATCCTTCTGTGTTGCCCTAGTGCCCTAGTTTGGCACTACTCAT | |
| TGACTGATAGCCGAATTAAGACCGGCTCACCACTTGACCACCTGCCTATT | 1200 |
| GCTCCTTCCAACTTGCCCATGCCAGAGGGTAACAGTGCCTTTACTCAGCA | |
| GGTCCGTGCAAAATTACGAGAGATCGAACAACAGATCAAGGAGCGTGGAC | 1300 |
| AAGCAGTTGAGGTTCGCTGGTCTTTTGATAAGTGCCAGGAAGCTACTGCA | |
| GGTTTCACCATTGGACGGGTGCTCCATACTTTAGAAGTGCTGGATAGCCA | 1400 |
| TAGTTTCGAGCGCTCTGACTTTAGTAACTCTCTTGACTCCCTTTGTAATC | |
| GAATCTTTGGATTGGGGCCTAGTAAGGATGGTCATGAGATTTCCTCTGAT | 1500 |
| GATGATGCTGTGTGGTATCATTATTGTGTGAATGGGCTGTAAGCTGCAAACG | |
| CTCAGGTCGGCATCGTGCTATGGTAGTAGCCAAACTCCTAGAGAAGAGAC | 1600 |
| AAGCAGAAATTGAGGCTGAGCGCTGCCGGAGAATCTGAAGCAGCTGATGAG | |
| AAGGGCTCCGTCGCCTCTGGTTCCCTTTCCGCTCCTAGTGCACCCATTTT | 1700 |
| CCAGGATGTCCTCCTGCAGTTTCTGGATACACAGGCTCCCATGCTGACTG | |
| ATCCCCGAAGTGAAAGTGAGCGAGTAGAATTCTTTAACTTGGTACTGCTC | 1800 |

TABLE 4-continued shows the cDNA sequence of murine MOPA as determined by double strand sequence analysis (SEQ ID NO.: 7).

| | |
|---|---|
| TTCTGTGAACTGATCCGACATGATGTCTTCTCCCATAATATGTACACCTG | |
| CACTCTCATCTCTCGGGGGATCTTGCATTTGGAGCCCCTGGTCCTCGGC | 1900 |
| CTCCCTCTCCCTTTGATGATCCTACAGATGATCCAGAGCGCAAGGAGGCT | |
| GAAGGCAGCAGCAGCAAGCTAGAGGACCCAGGGCTCTCTGAATCTAT | |
| GGACATCGACCCTAGTTCCACTGTGCTTTTTGAGGACATGGAAAAGCCTG | 2000 |
| ATTTCTCATTGTTCTCCCCTACTATGCCTTGTGAGGGGAAGGGAAGCCCA | 2100 |
| TCCCCTGAGAAACCAGATGTCGAAAAGGAAGTAAAACCCCCAGCCAAAGA | |
| GAAGATCGAGGGGACACTTGGGATTCTGTATGACCAGCCACGACATGTGC | 2200 |
| AGTATGCCACACACTTTCCAATCCCACAGGAGGAGTCATGCAGCCATGAG | |
| TGCAACCAGCGGTTGGTCGTACTGTTTGGGGTGGGGAAGCAGCGAGATGA | 2300 |
| TGCCCGCCATGCCATCAAGAAGATTACCAAGGATATCCTGAAGGTTCTGA | |
| ATCGCAAGGGGACAGCAGAAACTGACCAGCTTGCTCCTATTGTGCCTCTG | 2400 |
| AATCCTGGAGACCTGACATTCTTAGGTGGGGAAGATGGGCAGAAGCGACG | |
| ACGCAACCGGCCCGAAGCCTTCCCCACTGCTGAAGATATTTTTGCTAAGT | 2500 |
| TCCAGCACCTTTCCCATTATGACCAACACCAGGTCACGGCTCAGGTCTCC | |
| CGGAACGTTCTGGAGCAGATCACGAGCTTCGCCCTTGGCATGTCGTACCA | 2600 |
| CTTGCCTCTGGTGCAGCATGTGCAGTTCATCTTCGACCTCATGGAATATT | |
| CACTGAGCATCAGTGGCCTCATCGACTTTGCCATCCAGTTACTGAATGAG | 2700 |
| CTGAGTGTGGTTGAGGCGGAGCTCCTTCTCAAATCGTCGGATCTGGTGGG | |
| CAGCTACACTACCAGCCTGTGCTTATGTATCGTGGCTGTCCTTCGACACT | 2800 |
| ATCATGCCTGCCTCATCCTCAATCAGGACCAGATGGCGCAAGTGTTTGAG | |
| GGGCTCTGTGGCGTGGTGAAACATGGAATGAACCGTTCAGATGGCTCCTC | 2900 |
| TGCAGAGCGCTGTATCCTTGCTTATCTCTATGATCTGTATACCTCCTGTA | |
| GCCATTTAAAGAGCAAATTTGGGGAGCTCTTCAGTGACTTTTGCTCAAAA | 3000 |
| GTGAAGAACACCATCTACTGTAACGTGGAGCCATCGGAATCCAATATGCG | |
| CTGGGCACCGGAGTTCATGATTGACACTCTGGAGAACCCTGCCGCTCACA | 3100 |
| CTTTCACCTACACGGGGCTCGGCAAGAGTCTTAGTGAGAACCCTGCTAAC | |
| CGCTATAGCTTTGTGTGCAATGCTCTTATGCACGTCTGCGTGGGCCACCA | 3200 |
| TGATCCTGATAGGGTAAATGACATCGCCATCCTTTGTGCAGGCTGACCG | |
| GCTATTGCAAGTCCTTGAGTGCTGAGTGGCTAGGAGTACTTAAGGCCTTG | 3300 |
| TGCTGCTCCTCGAACAATGGCACTTGTGGTTTCAATGATCTCCTGTGCAA | |
| CGTAGACGTCAGTGATTTGTCTTTTCATGATTCCTTGGCTACTTTTGTTG | 3400 |
| CTATCCTCATCGCCCGTCAATGTTTGCTCCTAGAAGACCTGATTCGCTGT | |
| GCAGCCATCCCTTCACTCCTCAATGCTGCTTGTAGTGAGCAGGATTCTGA | 3500 |
| GCCAGGAGCCAGGCTTACTTGCCGAATCCTCCTCCACCTGTTCAAGACGC | |
| CACAACTCAATCCTTGCCAGTCTGATGGAAACAAACCTACTGTTGGAATC | 3600 |
| CGGTCCTCCTGTGACCGCCACCTGCTGGCTGCCTCCCAGAACCGCATCGT | |
| GGATGGGGCTGTGTTTGCTGTTCTCAAGGCTGTGTTTGTACTCGGAGATG | 3700 |
| CGGAGCTAAAAGGTTCAGGCTTTACTGTGCCGGGAGGAACAGAAGAACTT | |
| CCAGAAGAGGAGGGAGGAGGTGGTAGTAGCGGTCGGAGACAGGGTGGCCG | 3800 |
| CAACATCTCTGTGGAGACAGCAAGTCTGGATGTCTATGCCAAGTACGTGC | |
| TGCGAAGCATCTGCCAACAGGAATGGGTAGGAGAACGTTGCCTTAAGTCA | 3900 |
| CTGTGTGAGGATAGCAATGATCTACAAGACCCAGTGTTGAGTAGTGCCCA | |
| GGCCCAGCGCCTCATGCAACTTATCTGCTACCCACATCGACTGCTGGACA | 4000 |
| ATGAGGATGGAGAAAACCCCCAGCGGCAGCGCATTAAACGTATTCTCAAG | |
| AATTTAGACCAATGGACCATGCGCCAGTCCTCTTTGGAGCTACAGTTGAT | 4100 |
| GATCAAGCAGACCCCCAACACTGAGATGAACTCTCTCTTGGAGAACATTG | |
| CCAAGGCCACAATCGAGGTTTTCCAACAGTCAGCAGAGCGGGGTCATCT | 4200 |
| TCTGGAAGTACAGCAAGCAACATGCCCAGCAGCAGCAAGACCAAACCTGT | |
| GCTCAGCTCTCTAGAGCGATCTGGTGTATGGTTGGTGGCTCCTCTCATTG | 4300 |
| CCAAACTGCCCACTTCAGTCCAGGGCCATGTATTAAAAGCTGCTGGGGAG | |
| GAACTGGAAAAGGGTCAGCACCTGGGCTCTTCTTCCCGTAAAGAACGAGA | 4400 |
| TCGACAGAAACAGAAGAGCATGTCCCTGTTGAGCCAACAGCCTTTCTTAT | |
| CACTGGTGCTAACATGTCTGAAAGGACAGGATGAGCAGCGCGAGGGACTC | 4500 |
| CTGGCCTCCCTCCACAGCCAGGTGCACCAGATTGTGATTAATTGGCGAGA | |
| AAACCAGTACTTAGATGATTGCAAACCAAAGCAGCTAATGCATGAGGCAC | 4600 |
| TCAAACTGCGGCTCAACCTGGTGGGGGCATGTTTGACACTGTGCAGCGT | |
| AGTACCCAGCAGACTACAGAGTGGGCCCAGCTTCCTTGAGATCATCAT | 4700 |
| CAGCGGCACTGTGGACATGCAGTCTAACAATGAGCTCTTCACTACTGTGT | |
| TGGACATGCTGAGCGTGCTTATCAACGGAACGTTGGCTGCAGACATGTCC | 4800 |
| AGTATCTCGCAAGGCAGCATGGAGGAAAACAAGCGTGCATATATGAACCT | |
| GGTGAAGAAGCTTCAGAAGGACTTGGGGGAGCGCCAATCAGACAGTCTGG | 4900 |
| AGAAGGTTCACCAACTGTTGCCACTACCCAAGCAGAACCGAGATGTCATA | |
| ACCTGTGAGCCACAGGGCTCCCTTATTGACACCAAGGGCAACAAGATTGC | 5000 |
| TGGCTTCGATTCCATCTTCAAGAAGGAGGGTCTACAAGTTTCTACCAAAC | |
| AAAAGATCTCTCCCTGGGAGCTTTTTGAGGGCCTGAAGCCATCAACAGCA | 5100 |
| CCACTGTCATGGGCCTGGTTTGGCACAGTCCGAGTGGACCGCAGAGTGGC | |
| ACGAGGGGAGGAGCAGCAGCGGCTGTTGCTCTATCATACCCACCTGAGGC | 5200 |
| CTCGACCCAGAGCCTATTACCTGGAACCACTACCTCTGCCCCCAGAAGAT | |
| GAGGAGCCACCAGCCCTGCCCTACTAGAGCCTGAGAAAAAGGCTCCTGA | 5300 |
| GCCCCCCAAGACTGACAAACCAGGGGCTGCTCCTCCGAGCACTGAGGAGC | |
| GCAAAAAGAAGTCTACCAAGGGCAAAAAACGCAGCCAGCCAGCCACCAAG | 5400 |
| AACGAGGACTATGGCATGGGGCAGGTCGGAGTGGCCCCTATGGTGTGAC | |
| AGTGCCTCCAGACCTTCTACACCATGCAAATCCTGGTTCTATATCCCACC | 5500 |
| TTAGCTACAGGCAAAGCTCCATGGGCCTGTATACCCAAAACCAGCCACTA | |
| CCTGCTGGTGGCCCTCGTGTGGATCCATACCGCCCCGTGCGATTACCAAT | 5600 |

TABLE 4-continued shows the cDNA sequence of murine MOPA as determined by double strand sequence analysis (SEQ ID NO.: 7).

```
GCAAAAGCTGCCAACTCGACCAACTTATCCCGGTGTGCTGCCTACAACTA
TGTCTACTGTCATGGGCCTAGAACCCTCTTCTTATAAGACATCTGTATAC      5700
CGGCAGCAGCAACCCACAGTGCCCCAGGGACAGCGCCTTCGCCAACAGCT
CCAGCAGAGTCAGGGGATGTTGGGACAGTCATCTGTCCATCAGATGACCC      5800
CTAGTTCTTCCTATGGTTTGCAGACTTCCCAGCTCTCTTCTCCTTCTCTC
CAGGGCTATACATCCTATGTTTCTCATGTGGGATTGCAGCAACACACAGG      5900
CCCTGCAGATCCTACCCGCCACCTGCAACAGCGGCCCAGTGGCTATGTGC
ATCAGCAGGCCCCAACCTATGGGCATGGACTGACTTCCACTCAAAGGTTT      6000
TCACACCAGACACTGCAGCAGACACCCATGATGGGTACCATGACTCCGTT
GAGTGCCCAGGGTGTCCAGGCAGGCGTCCGTTCAACTTCCATCCTGCCTG      6100
AGCAGCAGCAACAACAACAGCAGCAACAACAACAGCAGCAGCAGCAACAG
CAGCAGCAGCAACAACAACAGCAGCAGCAGCAGCAACAACAACAGCA         6200
GTACCATATCCGACAGCAACAGCAGCAGCAGCAGATGCTACGGCAACAGC
AGCAACAACAGCAACAGCAGCAGCAGCAACAGCAGCAGCAGCAACAA         6300
CAACAGCAACAGCAGCAGCAGCAGCCACACCAGCAGCAGCAGCAGGCAGC
TCCTCCCCAACCCCAGCCCCAGTCCCAGCCCCAGTTCCAGCGCCAGGGCC      6400
TGCAGCAGACCCAGCAGCAGCAACAGACAGCAGCTTTGGTCCGGCAAATT
CAACAACAGCTCTCTAATACCCAGCCACAGCCCAGCACCAACATATTTGG      6500
ACGCTACTGAGTCACCTGGAGGAACTGCTTGTCCACTGGATGTGGCCCAG
CAGGCMTC                                                6558
```

TABLE 5 shows a comparison of the amino acid sequence homology between the human (SEQ ID NO.:8) and murine (SEQ ID NO.:9) PCTG4 proteins. The character to show that two aligned residues are identical is '|' The character to show that two aligned residues are similar is '.'Amino acids said to be 'similar' are: A,S,T; D,E; N,Q; R,K; I,L,M,V; F,Y,W

```
MOUSE  - MNQKDNFWLVTARSQSAINTWFTDLAGTKPLTHLAKKVPIFSKKEEVFGY  -50
HUMAN  - --------------------------------------------------  -1
MOUSE  - LAKYTVPVMRAAWLIKMTCAYYAAMSETKVKKKNTADPFTEWTQIITKYL  -100
           ||||||||||||||||||.||||||. ||| ||||||||||
HUMAN  - --------MRAAWLIKMTCAYYAAISETKVKKRH-VDPFMEWTQIITKYL  -41
MOUSE  - WEQLQKMAEYYRPGPAGSGGCGSTIGPLPHDVEMAIRQWDYNEKLALFMF  -150
         |||||||||||||||||||||||||||||||||.||||||  ||||.|||
HUMAN  - WEQLQKMAEYYRPGPAGSGGCGSTIGPLPHDVEVAIRQWDYTEKLAMFMF  -91
MOUSE  - QDGMLDRHEFLTWVLECFEKIRPGEDELLKLLLPLLLRYSGEFVQSAYLS  -200
         ||||||||||||||||||||||||||||||||||||||||||||||||||
HUMAN  - QDGMLDRHEFLTWVLECFEKIRPGEDELLKLLLPLLLRYSGEFVQSAYLS  -141
MOUSE  - RRLAYFCTRRLALQLDGVSSHSSHVIAAQSTSSLPTTPAPQPPTSSTPST  -250
         ||||||||||||||||||||||||||.|||| .|||||||||||||||||
HUMAN  - RRLAYFCTRRLALQLDGVSSHSSHVISAQSTSTLPTTPAPQPPTSSTPST  -191
MOUSE  - PFSDLLMCPQHRPLVFGLSCILQTILLCCPSALVWHYSLTDSRIKTGSPL  -300
         ||||||||||||||||||||||||||||||||||||||||||||||||||
HUMAN  - PFSDLLMCPQHRPLVFGLSCILQTILLCCPSALVWHYSLTDSRIKTGSPL  -241
MOUSE  - DHLPIAPSNLPMPEGNSAFTQQVRAKLREIEQQIKERGQAVEVRWSFDKC  -350
         ||||||||||||||||||||||||||||||||||||||||||||||||||
HUMAN  - DHLPIAPSNLPMPEGNSAFTQQVRAKLREIEQQIKERGQAVEVRWSFDKC  -291
MOUSE  - QEATAGFTIGRVLHTLEVLDSHSFERSDFSNSLDSLCNRIFGLGPSKDGH  -400
         ||||||||||||||||||||||||||||||||||||||||||||||||||
HUMAN  - QEATAGFTIGRVLHTLEVLDSHSFERSDFSNSLDSLCNRIFGLGPSKDGH  -341
MOUSE  - EISSDDDAVVSLLCEWAVSCKRSGRHRAMVVAKLLEKRQAEIEAERCGES  -450
         ||||||||||||||||||||||||||||||||||||||||||||||||||
HUMAN  - EISSDDDAVVSLLCEWAVSCKRSGRHRAMVVAKLLEKRQAEIEAERCGES  -391
MOUSE  - EAADEKGSVASGSLSAPSAPIFQDVLLQFLDTQAPMLTDPRSESERVEFF  -500
         ||||||||.|||||||||||||||||||||||||||||||||||||||||
HUMAN  - EAADEKGSIASGSLSAPSAPIFQDVLLQFLDTQAPMLTDPRSESERVEFF  -441
MOUSE  - NLVLLFCELIRHDVFSHNMYTCTLISRGDLAFGAPGPRPPSPFDDPTDDP  -550
         |||||||||||||||||||||||||||||||||||||||||||||||.||
HUMAN  - NLVLLFCELIRHDVFSHNMYTCTLISRGDLAFGAPGPRPPSPFDDPADDP  -491
MOUSE  - ERKEAEGSSSSKLEDPGLSESMDIDPSSTVLFEDMEKPDFSLFSPTMPCE  -600
         | |||||||||||||||||||||||||.||||||||||||||||||||||
HUMAN  - EHKEAEGSSSSKLEDPGLSESMDIDPSSSVLFEDMEKPDFSLFSPTMPCE  -541
MOUSE  - GKGSPSPEKPDVEKEVKPPAKEKIEGTLGILYDQPRHVQYATHFPIPQEE  -650
         |||||||||||||||||||||.||||||||.|||||||||||||||||||
HUMAN  - GKGSPSPEKPDVEKEVKPPPKEKIEGTLGVLYDQPRHVQYATHFPIPQEE  -591
MOUSE  - SCSHECNQRLVVLFGVGKQRDDARHAIKKITKDILKVLNRKGTAETDQLA  -700
         ||||||||||||||||||||||||||||||||||||||||||||||||||
HUMAN  - SCSHECNQRLVVLFGVGKQRDDARHAIKKITKDILKVLNRKGTAETDQLA  -641
MOUSE  - PIVPLNPGDLTFLGGEDGQKRRRNRPEAFPTAEDIFAKFQHLSHYDQHQV  -750
         ||||||||||||||||||||||||||||||||||||||||||||||||||
```

TABLE 5-continued shows a comparison of the amino acid sequence homology between the human (SEQ ID NO.:8) and murine (SEQ ID NO.:9) PCTG4 proteins. The character to show that two aligned residues are identical is '|' The character to show that two aligned residues are similar is '.'Amino acids said to be 'similar' are: A,S,T; D,E; N,Q; R,K; I,L,M,V; F,Y,W

```
HUMAN - PIVPLNPGDLTFLGGEDGQKRRRNRPEAFPTAEDIFAKFQHLSHYDQHQV  -691
MOUSE - TAQVSRNVLEQITSFALGMSYHLPLVQHVQFIFDLMEYSLSISGLIDFAI  -800
        ||||||||||||||||||||||||||||||||||||||||||||||||||
HUMAN - TAQVSRNVLEQITSFALGMSYHLPLVQHVQFIFDLMEYSLSISGLIDFAI  -741
MOUSE - QLLNELSVVEAELLLKSSDLVGSYTTSLCLCIVAVLRHYHACLILNQDQM  -850
        ||||||||||||||||||||||||||||||||||||||||||||||||||
HUMAN - QLLNELSVVEAELLLKSSDLVGSYTTSLCLCIVAVLRHYHACLILNQDQM  -791
MOUSE - AQVFEGLCGVVKHGMNRSDGSSAERCILAYLYDLYTSCSHLKSKFGELFS  -900
        |||||||||||||||||||||||||||||||||||||| |||||||||
HUMAN - AQVFEGLCGVVKHGMNRSDGSSAERCILAYLYDLYTSCSHLKNKFGELFS  -841
MOUSE - DFCSKVKNTIYCNVEPSESNMRWAPEFMIDTLENPAAHTFTYTGLGKSLS  -950
        ||||||||||||||||||||||||||||||||||||||||||||||||||
HUMAN - DFCSKVKNTIYCNVEPSESNMRWAPEFMIDTLENPAAHTFTYTGLGKSLS  -891
MOUSE - ENPANRYSFVCNALMHVCVGHHDPDRVNDIAILCAELTGYCKSLSAEWLG  -1000
        ||||||||||||||||||||||||||||||||||||||||||||||||||
HUMAN - ENPANRYSFVCNALMHVCVGHHDPDRVNDIAILCAELTGYCKSLSAEWLG  -941
MOUSE - VLKALCCSSNNGTCGFNDLLCNVDVSDLSFHDSLATFVAILIARQCLLLE  -1050
        ||||||||||||||||||||||||||||||||||||||||||||||||||
HUMAN - VLKALCCSSNNGTCGFNDLLCNVDVSDLSFHDSLATFVAILIARQCLLLE  -991
MOUSE - DLIRCAAIPSLLNAACSEQDSEPGARLTCRILLHLFKTPQLNPCQSDGNK  -1100
        ||||||||||||||||||||||||||||||||||||||||||||||||||
HUMAN - DLIRCAAIPSLLNAACSEQDSEPGARLTCRILLHLFKTPQLNPCQSDGNK  -1041
MOUSE - PTVGIRSSCDRHLLAASQNRIVDGAVFAVLKAVFVLGDAELKGSGFTVPG  -1150
        |||||||||||||||||||||||||||||||||||||||||||||||| |
HUMAN - PTVGIRSSCDRHLLAASQNRIVDGAVFAVLKAVFVLGDAELKGSGFTVTG  -1091
MOUSE - GTEELPEEEGGGGSSGRRQGGRNISVETASLDVYAKYVLRSICQQEWVGE  -1200
        |||||||||||||  |||||||||||||||||||||||||||||||||||
HUMAN - GTEELPEEEGGGGSGGRRQGGRNISVETASLDVYAKYVLRSICQQEWVGE  -1141
MOUSE - RCLKSLCEDSNDLQDPVLSSAQAQRLMQLICYPHRLLDNEDGENPQRQRI  -1250
        ||||||||||||||||||||||||||||||||||||||||||||||||||
HUMAN - RCLKSLCEDSNDLQDPVLSSAQAQRLMQLICYPHRLLDNEDGENPQRQRI  -1191
MOUSE - KRILKNLDQWTMRQSSLELQLMIKQTPNTEMNSLLENIAKATIEVFQQSA  -1300
        |||| |||||||||||||||||||||| ||||||||||||||||||||||
HUMAN - KRILQNLDQWTMRQSSLELQLMIKQTPNNEMNSLLENIAKATIEVFQQSA  -1241
MOUSE - ETGSSSGSTASNMPSSSKTKPVLSSLERSGVWLVAPLIAKLPTSVQGHVL  -1350
        ||||||||||||||||||||||||||||||||||||||||||||||||||
HUMAN - ETGSSSGSTASNMPSSSKTKPVLSSLERSGVWLVAPLIAKLPTSVQGHVL  -1291
MOUSE - KAAGEELEKGQHLGSSSRKERDRQKQKSMSLLSQQPFLSLVLTCLKGQDE  -1400
        ||||||||||||||||||||||||||||||||||||||||||||||||||
HUMAN - KAAGEELEKGQHLGSSSRKERDRQKQKSMSLLSQQPFLSLVLTCLKGQDE  -1341
MOUSE - QREGLLASLHSQVHQIVINWRENQYLDDCKPKQLMHEALKRLNLVGGMF   -1450
        |||||.|| |||||| |||.||||||||||||||||||||||||||||
HUMAN - QREGLLTSLYSQVHQIVNNWRDDQYLDDCKPKQLMHEALKRLNLVGGMF   -1391
MOUSE - DTVQRSTQQTTEWAQLLLEIIISGTVDMQSNNELFTTVLDMLSVLINGTL  -1500
        ||||||||||||||| ||||||||||||||||||||||||||||||||||
HUMAN - DTVQRSTQQTTEWAMLLLEIIISGTVDMQSNNELFTTVLDMLSVLINGTL  -1441
MOUSE - AADMSSISQGSMEENKRAYMNLVKKLQKDLGERQSDSLEKVHQLLPLPKQ  -1550
        ||||||||||||||||||||| ||||| ||||||||||| ||||||||||
HUMAN - AADMSSISQGSMEENKRAYMNLAKKLQKELGERQSDSLEKVRQLLPLPKQ  -1491
MOUSE - NRDVITCEPQGSLIDTKGNKIAGFDSIFKKEGLQVSTKQKISPWELFEGL  -1600
        ||||||||||||||||||||||||||||||||||||||||||||.||||
HUMAN - TRDVITCEPQGSLIDTKGNKIAGFDSIFKKEGLQVSTKQKISPWDLFEGL  -1541
MOUSE - KPSTAPLSWAWFGTVRVDRRVARGEEQQRLLLYHTHLRPRPRAYYLEPLP  -1650
        ||| ||||| |||||||||||||||||||||||||||||||||||||||
HUMAN - KPS-APLSWGWFGTVRVDRRVARGEEQQRLLLYHTHLRPRPRAYYLEPLP  -1590
MOUSE - LPPEDEEPPAPALLEPEKKAPEPPKTDKPGAAPPSTEERKKKSTKGKKRS  -1700
        |||||||||.||||||||||||||||||||||||||||||||||||||||
HUMAN - LPPEDEEPPAPTLLEPEKKAPEPPKTDKPGAAPPSTEERKKKSTKGKKRS  -1640
MOUSE - QPATKNEDYGMGPGRSGPYGVTVPPDLLHHANPGSISHLSYRQSSMGLYT  -1750
        ||||| ||||||||||||||||||||||||.||| || .||. ||
HUMAN - QPATKTEDYGMGPGRSGPYGVTVPPDLLHHPNPGSITHLNYRQGSIGLYT  -1690
MOUSE - QNQPLPAGGPRVDPYRPVRLPMQKLPTRPTYPGVLPTTMSTVMGLEPSSY  -1800
        ||||||||||||||||||||||||||||||||||||||. ||||||||||
HUMAN - QNQPLPAGGPRVDPYRPVRLPMQKLPTRPTYPGVLPTTMTGVMGLEPSSY  -1740
MOUSE - KTSVYRQQQPTVPQGQRLRQQLQQSQGMLGQSSVHQMTPSSSYGLQTSQ-  -1849
        ||||||||||.|||||||||||||||||||||||||||||||||||||
HUMAN - KTSVYRQQQPAVPQGQRLRQQLQQSQGMLGQSSVHQMTPSSSYGLQTSQG  -1790
MOUSE - LSSPSLQGYTSYVSHVGLQQHTGPA         DPTRHLQQ         -1882
         .|  || |  .   .                  |||||||||
HUMAN - YTPYVSHVGLQQHTGPAGTMVPPSYSSQPYQSTHPSTNPTLVDPTRHLQQ  -1840
MOUSE - RPSGVYHQQAPTYGHGLTSTQRFSHQTLQQTPMMGTMTPLSAQGVQAGVR  -1932
        |||||||||||||||||||||||||||||||||.  ||||.|||||||||
```

TABLE 5-continued shows a comparison of the amino acid sequence homology between the human (SEQ ID NO.:8) and murine (SEQ ID NO.:9) PCTG4 proteins. The character to show that two aligned residues are identical is '|' The character to show that two aligned residues are similar is '.'Amino acids said to be 'similar' are: A,S,T; D,E; N,Q; R,K; I,L,M,V; F,Y,W

```
HUMAN - RPSGYVHQQAPTYGHGLTSTQRFSHQTLQQTPMISTMTPMSAQGVQAGVR    -1890
MOUSE - STSILPEQQQQQQQQQQQQQQQQQQQQQQQQQQQQQQQQQYHIRQQQQQQ    -1982
         ||·||||        ||||||||||||||||||||||||||||||||||
HUMAN - STAILPE-------QQQQQQQQQQQQQQQQQQQQQQQQQQYHIRQQQQQQ    -1933
MOUSE - QMLRQQQQQQQQQQQQQQQQQQQQQQQQQQQQQQPHQQQQQAAPPQPQPQSQP  -2032
         ·||||||||||||||||||||||||||           ||||||||||||
HUMAN - -ILRQQQQQQQQQQQQQQQQQQQQQQQQQQHQQQQQQQAAPPQPQPQSQP    -1982
MOUSE - QFQRQGLQQTQQQQQTAALVRQIQQQLSNTQPQPSTNIFGRY           -2074
         |||||||||||||||||||||||·||||||||||||||||
HUMAN - QFQRQGLQQTQQQQQTAALVRQLQQQLSNTQPQPSTNIFGR            -2023
```

---

What is claimed is:

1. A method of determining increased susceptibility to hypothyroidism in a subject comprising:
   a) obtaining a sample from a subject;
   b) determining the presence of an insert polymorphism consisting of a nucleic acid sequence CAGCAACAC-CAG (SEQ ID NO.: 10) of a HOPA nucleic acid sequence in the sample; and
   c) associating the presence of the insert polymorphism with an increased susceptibility to hypothyroidism in the subject.

2. A method of determining increased susceptibility to schizophrenia in a subject comprising:
   a) obtaining a sample from a subject;
   b) determining the presence of an insert polymorphism consisting of a nucleic acid sequence CAGCAACAC-CAG (SEQ ID NO.: 10) of a HOPA nucleic acid sequence in the sample; and
   c) associating the presence of the insert polymorphism with an increased susceptibility to schizophrenia disorder in the subject.

3. The method according to claim 1, wherein the presence of the insert polymorphism in the HOPA nucleic acid sequence is determined by an assay selected from the group consisting of direct sequence analysis, differential nucleic acid analysis, restriction fragment length polymorphism analysis, DNA chip analysis and polymerase chain reaction analysis.

4. The method according to claim 1, wherein the insert polymorphism is determined by polymerase chain reaction utilizing a forward primer having the sequence CTGCTTC-CTCATCCCCTGCCCTCA (SEQ ID NO: 11) and a reverse primer having the sequence GGGCTGTAGTCCAAA-CAGCTACCTG (SEQ ID NO: 12).

5. The method according to claim 1, wherein the insert polymorphism is determined by polymerase chain reaction utilizing primers that are complementary to portions of the HOPA gene.

6. The method according to claim 2, wherein the presence of the insert polymorphism in the HOPA nucleic acid sequence is determined by an assay selected from the group consisting of direct sequence analysis, differential nucleic acid analysis, restriction fragment length polymorphism analysis, DNA chip analysis and polymerase chain reaction analysis.

7. The method according to claim 2, wherein the insert polymorphism is determined by polymerase chain reaction utilizing a forward primer having the sequence CTGCTTC-CTCATCCCCTGCCCTCA (SEQ ID NO: 11) and a reverse primer having the sequence GGGCTGTAGTCCAAA-CAGCTACCTG (SEQ ID NO: 12).

8. The method according to claim 2, wherein the insert polymorphism is determined by polymerase chain reaction utilizing primers that are complementary to portions of the HOPA gene.

* * * * *

SEQUENCE LISTING

<160> NUMBER OF SEQ ID NOS: 24

<210> SEQ ID NO 1
<211> LENGTH: 55298
<212> TYPE: DNA
<213> ORGANISM: Homo sapiens
<220> FEATURE:
<221> NAME/KEY: misc_feature
<222> LOCATION: (485)..(485)
<223> OTHER INFORMATION: n is not determined
<221> NAME/KEY: misc_feature
<222> LOCATION: (838)..(838)
<223> OTHER INFORMATION: n is not determined
<221> NAME/KEY: misc_feature
<222> LOCATION: (16728)..(16728)
<223> OTHER INFORMATION: n is not determined
<221> NAME/KEY: misc_feature
<222> LOCATION: (22750)..(22750)
<223> OTHER INFORMATION: n is not determined
<221> NAME/KEY: misc_feature
<222> LOCATION: (22756)..(22756)
<223> OTHER INFORMATION: n is not determined
<221> NAME/KEY: misc_feature
<222> LOCATION: (28519)..(28519)
<223> OTHER INFORMATION: n is not determined
<221> NAME/KEY: misc_feature
<222> LOCATION: (44804)..(44804)
<223> OTHER INFORMATION: n is not determined
<221> NAME/KEY: misc_feature
<222> LOCATION: (45002)..(45002)
<223> OTHER INFORMATION: n is not determined
<221> NAME/KEY: misc_feature
<222> LOCATION: (54049)..(54049)
<223> OTHER INFORMATION: n is not determined
<221> NAME/KEY: misc_feature
<222> LOCATION: (54226)..(54226)
<223> OTHER INFORMATION: n is not determined

<400> SEQUENCE: 1

```
cccgccttga attacttctt ctttccattg tgattcaata gcattttgtt attttgtta        60 ctggtgttat ttttgtttat tgttatttgt tactttgtt acagcacact ggctgtcttt      120
tctctaaaag gcaatacaag gccggcacag tggcgcacgc ctgtagtcca ggctactggg      180
aggctgaggc gggaggatcg ctggagtcca gaaggttgat gctgcagtga gccgtgatag      240
cgccactgca ctccagccta ggcgacagag ggagaacctg cctcaaaata aacaaatagc      300
aatacgacaa taggatattg gctctggaat tcagaatttt agtgccagct ctgttactca      360
gtagctgtat aatattggat aagtgaattt tcacactttg aaaaccagct tcctccatcc      420
```

```
gcaaaatcga gccaataata atccctaact catgaggctg tgagcagatt aaaggagata    480
gtgtntgaaa agcatctgac acaataggtg cctctttagc tagaccaagg gttcttaacc    540
tggagttcat ggacccttag gggatacatg gatgaacttc aggggatcta agaatctaaa    600
gcaacatttt gcatgtcaat atatgcatat tattattatt attattatta tttctgggaa    660
gaaggtccat agctttcatc agcacctttaa agggtttgtg aatcaaaaac gttagtatgc    720 ggtaccctg gcagaaaaa caaacaagaa aaggttagac aactcgatgg tagaccttga    780
gggattagag ccagcctttc agggtttaat aggttctttc tcatgcatac atagtttnta    840
atgttcacaa tagccccttg aaggaggtgt tagcgcacct atttttcaga tgccggaact    900
aagaaacgaa ctgatctgta atagacggag ttcctaacca atgcaaatat tattgaagac    960
ttttctaggc caaaaccgag ctaggctatg ggaaccgaag tccagtcaga actcagcacc    1020
acagaggcct ccttcttccc tggtttgcat ccccagctca ttctgcgcct ccggaacgtt    1080
tcatagattt ttgctgagtg aaatcgactt gctgccgcca ccgccgaaaa actcccgggg    1140
cacagagctc cgcccccacc gggccaggcc ccacctcctc tgcagtcggt attgtccgat    1200
ggttcccggc gtacctcggc ttccctcggt agtttccggc aatggtcgag agtttctaac    1260
gtgccccctt gttgtctctc ggccgccgtc ctctcaacca ccgccccct tttcggctcc    1320 ctctccccct tcccgttccc ccagtcagcc tggccctgct ggtgcctccg gcgctacggg    1380
ctgggcaaga tggcggcctt cgggatcttg agctacgaac accggcccct gaagcggccg    1440
cggctggggc ctcccgatgt ttaccctcag gaccccaaac agaaggaggt gcgttcgaaa    1500
atcggggctc tggaggggcc ggggcacgc ggtcagccta ggaggaggca ctgacggctg    1560
ggaatggggg gcgggcggt tcggtgagag caaaagtccc gaaaggggga agagtaaagt    1620
gggctggcgt gggagggcag gacggggggc ggtgggggt tccaaggtat gaataggggg    1680
tggtgtaggg gccgcaccag aggcgccctc ctccacacac acctcagaaa gttgtctgag    1740
acagcttggt ggggtacggc tgctcggctg ttcgcaagag aagagtgatg tttgagggcg    1800 cgctggtgg ctgggaatcc tagtgaccat gggagtgagg gtggggtcca agtgaacgta    1860
agggcccagc tttaagtaac gatctgttct acacggaacc ctcctcctgc cctttcacct    1920
tgttccttct tttctcctgc cctactctcc caccccttcc cccttcccct aaggaaaaaa    1980
caactaaacg ccgctttcct gcctcaggat gaactgacgg ccttgaatgt aaaacaaggt    2040
ttcaataacc agcctgctgt ctctggggat gagcatggca gtgccaagaa cgtcagcttc    2100
aatcctgcca aggtgagaca actctgccag gctgaaggaa aaggctggaa gaatctaaga    2160
aggagcaaag gccctgggtt gggaagactt atagggacaa cctaagtggc tgagtttgcc    2220
ttcatgacct aatactatct cattggcatt tgcccagcaa aaggcaggac cacctgtctg    2280
ccccttcttc ccaccctgag gtacactttt cttccctcag atcagttcca acttcagcag    2340
cattattgca gagaaattac gttgtaatac ccttcctgac actggtcgca ggaagcccca    2400
agtgaaccag aaggataact tttggctggt gactgcacga tcccagagtg ccattaacac    2460
ttggttcact gacttggctg gcaccaagcc actcacgcaa ctagccaaaa aggtaaggta    2520 ctgttcctg tccttcaggc caaggaggga gcatgggta ccaagtaccc tcctattccc    2580
atattaagct acatgggtgt cagctcatgg ggataataga gacctcacta tttgcaatgt    2640
ccatccaggt ccccattttc agtaagaagg aagaggtgtt tgggtactta gccaaataca    2700
cagtgcctgt gatgcgggct gcctggctca ttaagatgac ctgtgcctac tatgcagcaa    2760
```

```
tctctgagac caaggttaag aagagacatg ttgacccttt catgggtgag taactcctaa    2820
caccaggtgt actgctgatg gcttcaagga gtgatagaga caccttggga accatcctcc    2880
ttcttaatct agattccttg tttctgcttg tttcttgcat ttgtttgatc agtaaacact    2940
gagaaatttg agtgtctact gtgcgcatat actgggctac aaagatgtcc ggtgcataat    3000
ctctgcccct aggatactag tagtctaaca gggctgctaa ggtatatgta caaataacat    3060
aattaaatat agaaagtggt gaatgtcaag ctaggagcag aaggttcttt gagtggacaa    3120
aagattactt tcttatgggg gtacccggaa aggctttagg aaggtgggat ttgactagag    3180
actaaaagga tgaactgaat ttacaaatat ggtgattagg ggtgggggta aggtattcta    3240
agtagaagga tttttttttt ttttgagaca gagcaagact ctgtcaccca ggctagagtg    3300
cagtggcagg atcttggctt actgcaacct ccacctcccg ggttaaagtg attctcctgt    3360
ctcagcctcc cgagtagctg ggattacagg cgcccaccac tgcgcccggc taattttgt     3420 attttttctag acggggtt tcaccatctt ggccaggctg gtctcgaact cctgacctcg     3480
tgatccacct gcctcagcct cccaaagtgc tgggattaca ggcatgagcc accgcaccca    3540
gccagtagaa ggatattcta agcagaagga tagtatcaaa tagcccttt tccctctttc    3600 ctccagaatg gactcagatc atcaccaagt acttatggga gcagttacag aagatggctg    3660
aatactaccg ccagggcctg caggaagtgg gggctgtggt tccacgatag ggcccttgcc    3720
ccatgatgta gaggtggcaa tccggcagtg ggattacacc gagaagctgg ccatgttcat    3780
gtttcaggta gagagtaggg catgctgtgt ggggcattgg gttgagcttg aacttgtact    3840
gtgccagtag agaacagaat ctgcctgcca ccttgcccca gttgtggttc tcttcatctt    3900
ttcatttact ttatctgctt catctctaat agtcccctct tccctcccct ggtacccata    3960
ggatggaatg ctggacagac atgagttcct gacctgggtg cttgagtgtt ttgagaagat    4020
ccgccctgga gaggatgaat tgcttaaact gctgctgcct ctgcttctcc gagtaaggct    4080
tggaattttg gtactggtgg ggcaggggga gtctaagaag aatttgagga agaataaaat    4140
gttagagcag ggtcccctgg agagaactag gggctctgat ggtcgtgtct tcacagtact    4200
ctggggaatt tgttcagtct gcatacctgt cccgccggct tgcctacttc tgtacacgga    4260
gactggccct gcagctggat ggtgtgagca gtcactcatc tcatgttata tctgctcagt    4320
caacaagcac gctacccacc accctgctc ctcagccccc aactagcagc acaccctcga    4380 ctcccttag tgacctgctt atgtgccctc agcaccggcc cctggttttt ggcctcagct     4440
gtatcctaca ggtaggtact aggcgggccc aagggaagca ttgagagata gcctgagaag    4500
aatcaggtgc ccatcccaga gaataggggt aattccaaat tggatgtggg agtaggtgct    4560
gagtacttgc ttggaggttg ttgtttcttg gtaatggggt gttagtcccc tttgggggtt    4620
ttcaccagcc tctctctccc ttccaaggct aaatagtggg cccaaagcct tttaggaaag    4680
tgagtgaagg gaggggatcg gggtggagtg atgcctgtct tggggaccca gtcagaataa    4740
ctttggatct ggaatctacg ggttgggtct tagaatggga ttccaggagg ggtaaccatg    4800
gtgaatgagt tgggacttag ctgtttccta tctggtagac catcctcctg tgctgtccta    4860
gtgcccttgg tttggcacta ctcactgact gatagcagaa ttaagaccgg ctcaccactt    4920
gaccacttgc ctattgcccc gtccaacctg cccatgccag agggtaacag tgccttcact    4980
cagcaggtat gtctgaccac tagcctggta ctctcagatt gggctatgag ctaaattac     5040 tctttcagaa gtagtgattt ggagtctagt actattcttc tagcctgggg ctctggcctt    5100
ttatatgcct tggtacatcc ttgtagcctt ccttttaac attgcaggtc cgtgcaaagt     5160
```

```
tgcgggagat cgagcagcag atcaaggagc ggggacaggc agttgaagtt cgctggtctt    5220
tcgataaatg ccaggaagct actgcaggta tgtgtcagag aacagataat ggaaatatgt    5280
ttgaggaaag gatggggata gtaaggacat gtagatctaa gagccagaat gcaccgggcc    5340
tctggttcag tcccctttac cacttttcct ccttaggctt caccattgga cgggtacttc    5400
atactttgga agtgctggac agccatagtt ttgaacgctc tgacttcagc aactctcttg    5460 actcccttttg taaccgaatc tttggattgg gacctagcaa ggatgggcat gaggtaagcg    5520 aaaggggaa tagaaggagc aaaaaacatt gcaagagcaa taatatgtct gagagggaag    5580
tcatggtgag gcattgaaag cagagcatat ctgcagaaat gatcttactg ggcccaggat    5640
gttttatgat agagcccagt ctttaggaaa ttggaactca tttctttgtc cccacccta    5700 ccttactcct ccttctcttc ctttgttctc cagatctcct cagatgatga tgctgtggtg    5760
tcattgctat gtgaatgggc tgtcagctgc aagcgttctg gtcggcatcg tgctatggtg    5820
gtagccaagc tcctggagaa gagacaggcg gagattgagg ctgaggttag agggcagaga    5880
taagagaaca agattggcca atgggaagga atttactgcg gttggagacc gagagatgga    5940
ggtggtggag ggaccagagt tgaaggtgtg agaacagagt aaagaagcaa agagaaccct    6000
aaaggcaaag ttacggacgt gaggcgaaag tagagaagag tggattgtag taagagttag    6060
agataacatc aaggcttcag ttgggaggtg gtaaagaaca tggaggtcag caggggaatg    6120
aaagtgaaaa gcatgggta gaggtcaagc aggtggtagt ttaaggctta cacattgagg    6180
agtgaagaag caggtaaaag tcagttctac aatttgttct gtcatcttgc agcgttgtgg    6240
agaatcagaa gccgcagatg agaagggttc catcgcctct ggctcccttt ctgctcccag    6300
tgctcccatt ttccaggatg tcctcctgca gtttctggat acacaggctc ccatgctgag    6360 tacgacccc taccactctc tagttacctc tgcctagact cagttaccca ccactgtcat    6420
cagaaagcat aattaacagc cctctggtct atatttctct cttgggctct atgcagaatg    6480
acttttagat gtagttctag tgatcctctt taactggtca tcttacagtt aaacagagta    6540
gagaaataca gagaaggata aaaacaagag cttgtgattg aagcattttc actgcataaa    6600
tcgcaacaaa gatgttacat tccttttctga gatgatgtgt gggacagcat gtggggtaac    6660
caaccacact ttgtccctca acaatttctg ggatttctat ttgatcactc ttattattgc    6720
cttaggtgtg tccctctctc ttttggccca cctttttgtg ttctcctaac ttatgtttcc    6780 tcattcccctt cctccagcgg accctcgaag tgagagtgag cgggtggaat tctttaactt    6840
agtactgctg ttctgtgaac tgattcgaca tgatgttttc tcccacaaca tgtatacttg    6900
cactctcatc tcccgagggg accttgcctt tggagcccct ggtccccggc ctccctctcc    6960
ctttgatgat cctgccgatg acccagagca caaggaggct gaaggcagca gcagcagcaa    7020
gctggaagtg agtgggcttt tccttgcact agatcgtttc ttctgacatt tccatcttca    7080
tggctcccag gggcctctaa gagcctcttt tgcctggggg agggggtag tatttttttt    7140 agcacttggt gattgaccaa gcactctcac atcaattgtt tcattggttc ctcccatcag    7200
ccttgtgagg tactcttatc cccatttca aactgaagaa aacagaggcc tatactggtt    7260
aagtgattgg atgaggcttg actccagatc ctgtgctttc cccaatctgg tcttctctct    7320
ccacttcccc aatgaagttt tacagatggt gggagccact ccctagggct aaagcaactt    7380
cgcttatgtt ctatgccctc aggatccagg gctctcagaa tctatggaca ttgacccctag    7440 ttccagtgtt ctctttgagg acatggagaa gcctgatttc tcagtaagtt caatcctgag    7500
```

-continued

```
cgtggcagaa tctggatcct tggatcttcc cattatgcct gcttttggca tgttttttg     7560 cccctcatc cactttcctt cttctcatgt tctgctttct caccttctc tcagttgttc     7620 tcccctacta tgccctgtga ggggaagggc agtccatccc ctgagaagcc agatgtcgag     7680
aaggaggtga agcccccacc caaggagaag attgaaggga cccttgggtt ctttacgacc     7740
agccacgaca cgtgcagtac gccacccatt ttcccatccc ccaggtacta ttccccagca     7800
ccttgtgatg atctgttttg aacccagatt gctgtcaaag gaatttgctg aggggttgga     7860
gctgttctga ggatgtgggt tgggaaaggg aagggcttta gcatgtggat gctgaggggt     7920
gtggagcatg ctttcaagag gagggaagga gatcggtgct ggagtctgat ggtgctgctg     7980
ggatgcagga ggagtcatgc agccatgagt gcaaccagcg gttggtcgta ctgtttgggg     8040
tgggaaagca gcgagatgat gcccgccatg ccatcaagaa aatcaccaag gatatcttga     8100
aggttctgaa ccgcaaaggg acagcagaaa ctggtgggtt tgaggctcct taaacagatc     8160
tcccccaaag aatgccctag tcagtcttcc cttccccagt atagggaact ccccagtcat     8220
gtcccaatgt cctgtctctt ggagtctcct gagagctcta gtccttttga aacttccccc     8280
ctcattcccc ccctctacag accagcttgc tcctattgtg cctctgaatc ctggagacct     8340
gacattctta ggtacctcac agtaagcccc atactgccct ccctcctct cccttccctc     8400 cctgaaccta gcacctccct gtacatattc ctttaaggtc cacatagtct gtggtcctct     8460
aaacctttgc ttcactgtcc ccttcccttc attcctcccc catccttcc ttgaccctcc     8520 cttccctgtt tccctcttcc ttccttccct ccctcccctcc ttccatctct ccctccctcc     8580
ctcccatagc cttctctcca taccccactc cccaccccta gtcaactagt tatcttccct     8640
gtcttgactg gtccctttca actgtccct caggtgggga ggatgggcag aagcggcgac     8700
gcaaccggcc tgaagccttc cccactgctg aagatatctt tgctaagttc cagcaccttt     8760
cacattatga ccaacaccag gtcacggctc aggtgtgggc ctaagcccag ccctttccc     8820 acattctggc ctcctgttct gttttccttt tcttccctat cttctccctg ctaggcaggc     8880
taagcctcct ggtctcatcc ccttccagtg tcatccttc ctccttccct ggttctttcc     8940
tctctccact cccatctcac tcccactgcc cttatcaggt ctcccggaat gttctggagc     9000
agatcacgag ctttgccctt ggcatgtcat accacttgcc tctggtgcag catgtgcagt     9060
tcatcttcga cctcatggaa tattcactca gcatcagtgg cctcatcgac tttgccattc     9120
aggtggggaa gttgggggaga tgagggtgga ggcaggagtt catgccatat agcggctacg     9180
gaggtcataa ggacaggcgt agaggctcca gccagtttcc caagctattt gaaggggcag     9240
aaagactagc atgggggag tggaacatga gctaagactg caggaataga gacttaagtg     9300
ctccctgggg aggccaagag gcagattaga gcattgggca cagaccatcc tcccactgtg     9360
gagttcatag aactgtatcc tggacactgg ttagaggtgt tgttgataga ataaactatc     9420
aacaataaac tatcaataga ggtgttgttg atagactgtg catagggta acgagcccttt     9480 ctatcctgtg gtggctccag caggaagggg ctcaggccca gccttgccag cgtcccaca     9540 ggaaggtggt ttctatgtaa cacaagggc ctctttgcat ttctcacccc cgtttactct     9600
gctagctgct gaatgaactg agtgtagtta aggctgagct gcttctcaaa tcctcggatc     9660
tggtgggcag ctacactact agcctgtgcc tgtgcatcgt ggctgtcctg cggcactatc     9720
atgcctgcct catcctcaac caggaccaga tggcacaggt ctttgagggg taagcagagc     9780
ttcggaataa ctgaaacaaa gctctggcga atgccggtgg aagtggcctg ggaagagcat     9840
gcacttcctc acactctggg gaagcacctg ctgctcaggt gggaaaagaa tggtatttcc     9900
```

```
cagaggcttg aatctgtttg gaggagcccg cataccatct gctgaccctc ccaaccttgc   9960
ttcttcatgc aggctgtgtg gcgtcgtgaa gcatgggatg aaccggtccg atggctcctc  10020
tgcagagcgc tgtatccttg cttatctcta tgatctgtac acctcctgta gccatttaaa  10080
gaacaaattt ggggagctct tcaggtaaga gaggtggaag gtaagggggta gcgagtggga  10140
cctactccct tcttcccatg accacccaac tcaggaggag aggatggccc gggaccctgc  10200
tgcctgtcta gggtcatttg tggactgtgt cctccacata ctgttgtgtt accaagagtg  10260
ggccctcttc ctcagcaggc ttgctccccg cctatatctg tggggcccac cctcttcccc  10320
cttttcctca ctgccttcag aggccccagt tccttattcc catgtggttc ctttcctgcc  10380
cagtctgttt tgtcccatct ccctttctt gtctcaagat ccttcatccc tcactttctc   10440
ctttttttct ttctccccct ttcctgacca tccctcgacc tcagcaggcc ttcttcaaca  10500
ctactatctc ctttcctcca tccctgcagc gacttttgct caaaggtgaa gaacaccatc  10560
tactgcaacg tggagccaty ggaatcaaat atgcgctggg cacctgagtt catgatcgac  10620
actctagaga accctgcagc tcacaccttc acctacacgg ggctaggcaa gagtcttagt  10680
gagaaccctg ctaaccgcta cagctttgtc tgcaatgccc ttatgcacgt ctgtgtgggg  10740
caccatgatc ccgataggta tggggtgtac tgagtgagga agggcaccat gcccccatct  10800
gagatagggga gggctgaggt acccgggagg tactacaacc ttgattattt agtggggcag  10860
agatgagaag ttaatgggtc tgaggttttg tggagcaagg ttttttcctga gggcatttgt  10920
acttttcccct agggtgaatg acatcgcaat cctgtgtgca gagctgaccg gctattgcaa  10980
gtcactgagt gcagaatggc taggagtgct taaggccttg tgctgctcct ctaacaatgg  11040
cacttgtggt ttcaacgatc tcctctgcaa tgttgatgtg agacttgggg tggggttttg  11100
ctagtggggc agtgaccagg gcaggggggct ggttgtgatc ctctgaccag ggacagagtt  11160
ccgtagagtg gaggcacacc gctttgagtg ggcctccaca ctgagtcatg gtgtctgtct  11220
gttttttcct ccaggtcagt gacctatctt ttcatgactc gctggctact tttgttgcca  11280
tcctcatcgc tcggcagtgt ttgctcctgg aagatctgat tcgctgtgct gccatccctt  11340
cactccttaa tgctggtgaa ctaccaatct gtaaccccta gcatttctag acctcaaatt  11400
tcaatacaca ctggacggcc atcctctcat tgttcactgt gggagacctt gctgcggctc  11460
cctggccttc ctcagaaggc cagtccttttg gtatgctgaa ggctagaaga aacctgttttt 11520
ttagccctgg atttgcagcc ctgacctttc caatttctga cccttcaact gcgtaacagt  11580
tctctgctct acctcgcttt caatattatc ttgctttttc tcctttcact ttacctcatc  11640
ttctctccca tgccctgcc atacacttgc atgcatgcag gcacgcacac acataaaccc   11700
acatacagtt taacttcatc ccttccagat ctgttttgtc ttccttttag cttgtagtga  11760
acaggactct gtgccagggg cccggcttac ctgccgcatc ctccttcacc tttttcaagac 11820
accgcagctc aatccttgcc agtctgatgg aagtaagtga ccctgatctg aaccagccaa  11880
cagtagaaag tgtggttccc ctgcctccgt ggattctact tttgcttccc ctgacttcat  11940
cgccttcccc agacaagcct acagtaggaa tccgctcctc ctgcgaccgc cacctgctgg  12000
ctgcctccca gaaccgcatc gtggatggag ccgtgtttgc tgttctcaag gctgtgtttg  12060
tacttggtac gggggtagga agggagtggt gccagaagtg tgtatagggt ggagtgccag  12120
ctaaactaca agggacagtc tttctccctt ctgaaggtgg tctctctgac ctttggggag  12180
gaggggaggg agagaagtat atttctgtcc cataggggcag gatttggggt gtttctacct  12240
```

```
ctgtgggccc agggtgggtc tccacacgtg ttccaatctc actctgccct ccctatctcc   12300
cacccgtgaa ccacagggga tgcggaactg aaaggttcag gcttcactgt gacaggagga   12360
acagaagaac ttccagagga ggagggagga ggtggcagtg gtggtcggag cagggtggc    12420
cgcaacatct ctgtggagac agccagtctg gatgtctatg ccaagtacgt gctgcgcagc   12480
atctgccaac aggtcagttt caccttcctc ccacacctcc taaatgcctc tgtgtaatat   12540
agttctgttt ccagcccatg atcacaccag ctccctacta tacattgtgt tccttaacaa   12600
ctccagccca tcccccatat tcctaacccc tcactggtt gttcccagtc cctgattgtc    12660
agcttcctca ggaatgggta ggagaacgtt gccttaagtc tctgtgtgag acagcaatg    12720
acctgcaaga cccagtgttg agtagtgccc aggcgcagcg cctcatgcag ctcatttgct   12780
atccacatcg actgctggac aatgaggatg gggaaaaccc ccagcggcag cgcataaagc   12840
gcattctcca gtaggccaa ggccgtgggg gctgtggagg aagcagtggg cccaatctgg    12900
ggagaaacaa taggaacctt gagaaaagga gaggggcagt taagtagaga ggaagacaaa   12960
caaggatata ggggagggga gaggtagcga gagaaacagc tccascatgg gctgaggagt   13020
aagtccagta gggtctagac tccagtgtaa gagtattatg tgagggcata gctatctgga   13080
gtgaatctag cttatcaatg ggaagcatag catctgggag gcctaggtgt gggccgtgta   13140
tatttggcat tttgccatg gctcaggaac tgaatagtaa tagctactac ttgctgagca    13200
tgtgctttgt gccaggtact gtgctaggca ctctgcacac atttcctcat ttaatcttta   13260
tgaccctatg aagtaggtga gcctcccgt ttgaccgatg aggaaactga ggcttgaaga    13320
ggttaagtaa cttgtctaac gtcacatagc ccataagttt agagtcaata tgtgaaccca   13380
gacatgtctg tgcactttcc tcttcacatt gcttcacacc ttcagatgac cagagagtgg   13440
aaaaataaag ccgttgagga aaagctaaag gaataaggtc tcttcagccc agaagagata   13500
gtgttgaaga gagattagct aacagtagcc ttctggtctc tacaggactt tgagagattg   13560
tcttataaag gttctgtcag ggactttgag cagctggtct aaaacaagag aagcaggctt   13620
caactttaac atcaagggtt tcaaggttaa gcattaagca gaacttcctg atacgaaggg   13680
atgggaaaga tgtgaaatct ttcctgaact attttaaaaa ttggaragat tttcaactar   13740
tttggactat ttaaawgtag tcttttttt tttttttttt ttgagacgga gtctcgctct    13800
tgtcgctcag gctggagtac agtggtgcga tctcggctca ctgcaacctc tgcctcccaa   13860
gttcaaacaa ttctcscgcc tcagcctctt gagtaactgg gattacaggt cgcccatcac   13920
cacgcccagc taattttgt attttagta gagatggggt tttgccatgt tggccaggct    13980
ggtcttgaac tcctgacctc agtgatccg cctgtctcag cctccctaaa tgtagtcttt    14040
cttaaagatg gggacataga ggtcccttc agacctccag gagtctgtga ttcaatgttg    14100
caggagatca ggaattggca tcagattgtt gggtagctgg gggtaacacg atgatgacta   14160
gcctgggtgt ggggcctcta tcacagaact tggaccagtg gaccatgcgc cagtcttcct   14220
tggagctgca gctcatgatc aagcagaccc ctaacaatgt gagtagtgcc tggaccctcc   14280
cttttcctgtg ctcacgttca gctccatgtg tcagggaggc ggtccaccac agaagaacct  14340
agatcctacc cttgggctct tgagctgaaa gataagaggg gatgggaaaa tggtgaacaa   14400
gtggagctga tgataaggga aatgggttga gagtgttgga gctctgagct gtggggaagc   14460
ttggtggtgg tggtggagcc tgtttctctg gccatagatg taaggaggta tgtaaaggag   14520
aagacagtga ggaattggag aaaatatggag gtactagagg gcatgattcc caacagagtt   14580
gcgttcctat ctccccatca atctccgcca gtgttgtcct tctccgtcat ctccgatctc   14640
```

```
tcctaccatc tgctttcctt cacccttagc tacctatttt agcacttctg tgcctttcat    14700
cctccccagg agatgaactc cctcttggag aacatcgcca aggccacaat cgaggttttc    14760
caacagtcag cagagacagg gtcatcttct ggaagtactg caagcaacat gcccagcagc    14820
agcaagacca agcctgtgct caggtcggat agaaacatgt taggacccat ccccttagga    14880
gtttatctgc tggtagcgtg agtgatatca gatgcgtgga gatgccagca tgtccatcag    14940
ggaaaggaga ggatagattg ttccagcctt gcctggctcc cctgtgaccc tgtgtcctct    15000
gtctgttctc cagctctcta gagcgctctg gtgtatggct ggtggccccc ctcattgcta    15060
aactgcccac ctcagtccag ggacatgtgt taaaggctgc tggggaagaa ttggagaagg    15120
gtcagcacct gggttcctct tcacgcaaag aacgtgatcg acaaaagcag aagaggtaaa    15180
ggggcttagg gagtggacca agattgaggg gtagaaagga aagaggcag gcccggggaa    15240 gaataaaatg ggccaaggag aagcatcata ggaaagtgga aaatcagagg ataagagtgg    15300
gcatggctga gcaagaggct agatcttaag agagtagtct ggagaatgag gttggaagtt    15360
gactcccaac ccacagtctc cctttctcc tctcctcttc tctcctcttc tcttctcttc    15420
tcttctcttc tcttctcttc tcttctcttc tcttctcttc tcttctcttc tttctcttgt    15480
ctctagcatg tccctattga gccagcagcc cttcttatcg ctggtgctaa catgtctgaa    15540
agggcaggat gaacaacgcg agggactcct tacctccctc tacagccagg tgcaccaggt    15600
acagatctct gggccatgga ggtgggcagg aggtcaggga aggatgcacc taaggggtta    15660
ctctgtactt ggaaacttca gtactttctg ataaacatat tggctgctgt gggatggaaa    15720
cacgaagatc cctgagctgc atattttatt tgtttctatt ctagattgtg ataattggc     15780 gagatgacca gtacttagat gattgcaaac caaagcagct tatgcatgag gcactcaaac    15840
tgcggctcaa cctggtgaga aggccagctg gggagaagaa ggaagagggt agggctggaa    15900
atgcggagtg caaaagcctc aggttgggga aatgggggt aaggatagag gccccaggtt    15960
attctgagtc ttgaagggtt ttttttttt ttggagtcag agtctcactc tgtcacccaa    16020
gctggagtgc agtggcgcca tctcagctca ctgcaacctc cacctcctgg gttcaagtga    16080
ttctcgtgcc tcaacctcct gagtagctgg gattacaggt gtgtaccacc acacctggct    16140
aatttttgta ttttttcatag agatggggtt tgaccatgct ggtcaggctg gtcttgaact    16200
ccttacctca aatgatccgt ctgtctcggc ctcccaaagt gctgggatta caggcatgag    16260
ccacccgtgc ccagcctgag tcttgaagta ttaaccttgt tctctgaaag tatgcaggga    16320
ctgaaagtgg ttaaggggc tggatcactg tggtcatggt ccaataggtt atgtaccctg    16380
gatccttgca gggcctctgc ctcagtatcc tagattctga ctgggccta gaagcactgg    16440 aaacccactg tggaatgttg aatggaatcc tggaaatcat tctgtccaat tcccatcact    16500
ttctaagtat ggaaacagag gcctagagac gtcaagaatt ccgtcattgt cttgagatca    16560
tgtagcaaat cataggctca actcaagcat ggccgggcgc ggtggctcac tcctgtaatc    16620
ccaacacttt ggaggccga ggtgggcgga tcacgaggtc aggagatcga gaccatcctg    16680
gttaacacga tgaaaccccg tctctactaa aaatacaaaa aaaattanct gggcgtggtg    16740
gcaggcgcct gtwrtcccag ctactcggga ggctgaggca ggagaatggc gtgaacccgg    16800
gaggcggagt ttgcagtaag ccgaggtcgc gccactgcac tctagcctgg gtgacagagc    16860
gagactccgt ctcaaaaaaa aaaaaaaaaa aaactcaagc atgaactcag gcgtcccaac    16920
tcagattgga actaagcttt cctgaaactc tggcctttgt ccctgagcca tctgactgac    16980
```

```
ttgttgtggc cctggcaggt gggggggcatg tttgacacgg tgcagcgcag cacccagcag   17040
accacggagt ggggccatgc tcctcctgga gatcatcatc agcggcactg tcgacatgca   17100
gtccaacaag taaagcatcc ccacccgctc cctgcagttt catacccaag aagctcccccc   17160 tactcccatg ccaggtgcac ccactgagat tggtgtggct gttactgtgg actccgtggc   17220
cctgggctcc ccatacagtt ttggtgccct tgggatgaca tattaagcac ctctccctgc   17280
ttgtgtcctc tgctgaggcc ttttctatc ttcacctctt tcttctttgg ttttctctct   17340
ggcttcctgt ctcagtgagc tcttcactac tgtgttggac atgctgaagc gtgctcatca   17400
atgggacatt ggctgcagac atgtctagca tctcgcaagg tagcatggag gaaaacaagc   17460
gtgcatacat gaacctggcg aagaagttgc aggtaagcag aggaagcggg ggcaaggttt   17520
gcggttactg gaatctgctg tccagcctca ggaacttgct tctggctgga gccctctacc   17580
tttccttctc acgtctgcct tttctttgtt actcatgccg tgagcattta ctgagtgggg   17640
gtcttctctg tgccaggttc tgtgctgtcc cctgagactt cccatccctg ttttctgtat   17700
ctctgaactc ttgtcccatc ttcctgtgcc tgcagaagga gttgggggag cgccagtcag   17760
acagtctgga aaaggttcgc cagctgctgc cactgcccaa gcagacccga gatgtcatca   17820
cgtgtgagcc acagggctcc cttatcgata ccaaggcaa caagattgct ggcttcgatt   17880
ccatcttcaa gaaggaggca tgttccattg tctgcccgtg tcccttgcct tttttcccct   17940
ttgggcaagg aactttgcct gcatcagctt tgtagctcca acagactcat caggattcag   18000
gagcccatca gtctctgccg gtgaacacca tctctggggt tttgagcaaa tcacttaact   18060
ttccttacat ttcatctcca tctttgaagt cccaccctct ttccttcacc ctgccctcac   18120
cttttaacat accacccatt tttcaatacc ctaccctcct ctttcctctg ctccacctgc   18180
cccatgtcct acccccacca tctatctggc cgacagcctg tatctctttt atttctgtgt   18240
ttccctacac ccacccatct ctgcacactt ttatcttttc cctctctgtc agttgcggta   18300
tttgttgagt aaccataatt attgtgtata gtttaaaacc caaagtctaa ctccttcata   18360
tatacattct cttcatctgt cttcctagtc catctgtctc ttttcctccg tctctgtctc   18420
tctccctgtc tgactcgttt gcctttcttt gtctctccac cttttgtct ctctcttcct   18480 gtatctttct ctctctgact cttttctcggc ctgcctaaag gcagagtctc tccctgcctt   18540
cctctctctc tttctctgcc ttcctttttc tgtcttcctc tgaatgtcaa tccstctccc   18600
tccccgctcc ctctctggct ttctccccaa ccccttttctc tcccgatctt ctctcccmac   18660
acgccccccg ccccgttagt tcatctcctc tcctggtctg ggctggcttc atcttgtgcc   18720
tccacacctc tccctgtgcc ccaccttca ctctctcccc gcataactct cttccgcatg   18780
tatatgtgta tccatgtctg tctgtctgct tcttaccatc tctcctgaat ctgcctatga   18840 ctttcttttct acccattcct acaaatgctt gcagtcttct gttttctaag tcccaacagc   18900
ttattgtttt tcatttctg gagcagggtc tacaggttc caccaaacag aagatctcgc   18960
cctgggatct ttttgagggg ttgaagccgt cagcaccact ctcttgggc tggtttggaa   19020 cagtccgagt ggaccggcga gtggctcgag gagaggagca gcagcggttg ctgctctacc   19080
acacacacct gaggccccgg ccccgcgcct attacctgga gccactgcca ctgccccag   19140 aagatgagga gccgcctgct cctaccctgc tagagcctga gaaaaggct ccagagcccc   19200 ccaaaactga caaaccgggg gctgctccac ccagtactga ggaacgcaag aagaagtcca   19260
ccaagggcaa gaaacgcagc cagccagcta ccaagacaga ggtgagcgcc tccccgtga   19320 cagttctccc acagcctctc acttcatgac gctccggttt ctggtttgtg ggaggggtgg   19380
```

```
gggcgcataa ggaagggtg ccattagaat cataataaaa attaaccata tacgaattca    19440
gctcctcttt acctcattct cccccagctc cccgacccca ttcagctaca acccactcac    19500
cctcttcctc tgccactcac acaggactat ggaatgggcc cgggtcggag cggcccttat    19560
ggtgtgacag tgcctccgga cctcctgcac cacccaaacc ctggttctat aacacacctt    19620
aactacaggc aaggctccat aggcctgtac acccagaacc agccactacc tgcaggtgag    19680
tgccagccac taggaatgct ggagggacct acctgtacac tccccctgcc caaggatga    19740 tgccattccc ctgaggagct atggatgtca aggacactga gcaagagaca gagggatgag    19800
gagcctagag gtcagcccac tctccttttc aggtggccct cgtgtggacc cataccgtcc    19860
tgtgcgctta ccaatgcaga agctgcccac ccgaccaact taccctggag tgctgcccac    19920
aaccatgact ggcgtcatgg gtttagaacc ctcctcttat aagacctctg tgtaccggca    19980
gcagcaacct cgcggtgcccc aaggacagcg ccttcgccaa cagctccagg caagatagt    20040 gagagggca gtagggaggg ctgtcaggga gaggggcttt tgagggtcac aggacggagg    20100
agacacttgg gatcttcaca aggacactca gggtgggaga cacaagagat gagatggcag    20160
caagcatttc ctgagtttga gttgttctct tttctcccctt tagcagagtc agggcatgtt    20220
gggacagtca tctgtccatc agatgactcc cagctcttcc tacggtttgc agacttccca    20280
ggtaagagcc tgggattgtg agactagggg gatgaggcaa gctgctctgc atactctcgg    20340
ccctgattcc ctctctcctt cttccctcca gggctatact ccttatgttt ctcatgtggg    20400
attgcagcaa cacacaggcc ctgcaggtac catggtgccc ccccagctac tccagccagc    20460
cttaccagag cacccaccct tctaccaatc ctactcttgt agatcctacc cgccacctgc    20520
aacagcggcc cagtggctat gtgcaccagc aggcccccac ctatggacat ggactgacct    20580
ccactcaaag gtacccaaag tagtggtgag ctaggaagag atgcagaggt ataagggagc    20640
atttgacttg ggaaagcctg tgcctgaaag tggtgggact ggtcagaact ttcggagaca    20700
tcaagaatac ttatctggcc acatagccca taaccacaga agtctcgagc tggaagggac    20760
cctggagacc aatagtttca tgactacttc cttaacagtt ctttgaggcc cagagagggg    20820
aaattgttta tctgactcaa ggaaaaatct gggctgggtg tggtagctca cactggtagt    20880
cccagcactt gggggcccaa ggtgggagaa tcagttgatt ccaggaattc gaggccagcc    20940
tgggcaacat agggagatcc catctctaca aaaaaaatac atatttttt gaaacagagt    21000 cgcactccat tgcccaggc tggagtgtcg tggcatgatc atggctcact gcagcctcga    21060
cctcygaggc tcaggtgatc ctcctacctc agcctcccaa gtagctagaa ctacaggcac    21120
acaccaccac gcccagctaa ttttttggat ttttagttga gatggggttt cgccatgttg    21180
cccaggctgg tcttgaactg agccaccaca cctggccaaa aaaaattt ttttaatta    21240 gacaggcgtg ttggtgcatg cctgtagtcc cagctactca ggaggctgag gtgggaagat    21300
tgcttgagct tgggagtttg aggctgcagt gagctgtaat ygcacaatga gccgagattg    21360
tgccacagca ctccagtggt gacagagtga gaccctgtyt caaaaaaaaa agaagaaaga    21420 aagaaaaag aaaaaaatat ctggagttca tagatgaact acatgataag gagtcgtaaa    21480
gccagtaccg gctttgaata ccaggttaaa taccaggatg gacaaatgaa tgaatcctcc    21540
caccatggtt aacgttagtc aagccttagt tgaggccttg taaccatgta tagagactct    21600
gaagcttagg attaagaaca ctggggagtg ggctaactgc ccattgtgtg gccagcacta    21660
taccaggact gggtgaggtg aagaaagata gcaaaaaaaa cccccacgat acatagttcc    21720
```

-continued

```
tcactacaaa gaatctttac tatagctggg gagatgagac ttatagaaga atattgagag   21780
aacactctga gcaaagatat aatcaggtat gcagttgtat gctatgaggt aaaatgtgga   21840
ttgagaaaaa gtacgtggta atatctgtgg gcctgactcm atcagagaat gtttcatgaa   21900
ggaggtcaga cttgagttgg cctctgaaga atagctgtga ttgggatttg tggagaagag   21960
gaaaagaaag ggcattccag gtagaggatg taacgtgaac aaagacatgg ggaccagaat   22020
gaggatggtg cctggggaga agggcctgga tggagtgtaa aatctgtgct ggggaagtca   22080
ctggggctag gctaggaggg ggcaggctga gagatggcct tgaatgctca gccgaagaat   22140
tgagacgcag tcccagaaag ggctcttttg atcagaagag tgataggagg agttgggtat   22200
gttgcaaggt tccttggaat gaatggatag gatgtgtact ggaaggtgca agaagaagac   22260
ttcaggccag gcacggtggc tcatgcctgt aatcccagta ctttgggagg cccaggcagg   22320
cagatcacct aagatcagga gttcgagacc agcctggtca acatggtgaa atcccgtctc   22380
tactaaaaat acaaaaatta tctgggtgtg gtggcatgtg cctgtaatcc cagctacttg   22440 ggggctgag gcaagagaat cacttgaacc tgagaggtgg aggttgcagt gagccgagat   22500
cgcatcattg cactccagcc tgggcaacag agtgagactc tgtctcaaaa aaaaaagaar   22560
acttgagacg gggagcctgg ccagtagact cttgaagtga tatacacatg tggtagaaca   22620
acttgaaatg ttatttggga acaacaacag caacagcaaa aaacctcaat gagtgtttat   22680
agaatgccta tcttgtgcta agactatttt tttctttct tttctttctt ttttttttt   22740 tttttgagan ggagtntcgc tctgtcatcc aggctggagt gcagtggtgc aattttggct   22800
cactgcaact tccacctccc aggttcaagc aattttcctg cctcagcctc ctgagtagct   22860
gggattacag gcatccacta ccacgctcag ctatttttt ttgtattttt gctagagatg   22920
gggtttcacc atgttgccag gctggtctag aactcctgac ctcaagtgat ccacccacct   22980
tagcctccca aagtgctggg attacaggtg tgagccaccg cacccagccc tattttcat   23040 ttttgtaaca gaaaaatagc taatgcagaa ttgaaaaatt cctaaccatt aaggttatga   23100
gacactaaaa tagagtatca tcttatgcaa cttattcccc agactggaag tctggttagt   23160
gacacgagga atgaatgaaa taacctgcta acgtttcttt caggtcaggg acccaaggtt   23220
tatactgacc ccctctcctc acctccctca tgccttgacc tctgaccctc ttatctttgg   23280
aggttttcac accagacact gcagcagaca cccatgataa gtaccatgac tccaatgagt   23340
gcccagggcg tccaggcagg cgtccgttca acagccatcc tacctgagca gcagcagcag   23400
cagcaacagc agcaacagca acagcagcag cagcagcaac agcaacagca gcagcagcag   23460
cagcagtacc acatccggca gcagcagcag cagcagatcc tgcgggtaag gcactgggat   23520
ttcatctggg acctgggagc ccagggagga agagaggcac aagttcttcc cacacagtta   23580
ccgagactaa acaaggcagt gtaccaaaac acctagcaga gcggctggcc tctagtggtg   23640
ctggagaagt tttctaccct ccccctttt gttttctggg gatcatagtg ggagagagtt   23700
ggacattgtc tgctgggtac cctagatttg gtttctttct gtgcagctgt ctaaaagggg   23760
aaggcagtag accccgagct cccaccctgc ttcctcatcc cctgccctca gcctttagt   23820 tctgaggctt agcttcctcc ctctgctcct tctgaagtat cttttgtgtt cttatagcag   23880
cagcagcaac agcaacagca gcagcagcag cagcagcaac agcaacagca gcagcaa     23940 cagcaacaac agcaacacca gcagcaacag cagcaacagg cggctcctcc ccaacccag   24000 ccccagtccc agcccaggt agctgctgga ctacagcccc aggctcaggg acagctgccc   24060
aggttgggca cgcagccagt gaactgggtt ggggacagta tggaataggg tagaggtggg   24120
```

```
aggcagggca tggcacccta aaaatggatt gggaggccag gcgcagtggc tcacgcctgt   24180
aatcccagca ctttgggagg ccaaggcagg tggatcactt gaggtcagga gttcaagacc   24240
agcctggcca agatggtgaa accccgtctc tactaaaaat acaaaaaata ataataataa   24300
ataagccggg catggtggca ggtgcctgtt atctcagcta ctcaagaggc tgaggcagag   24360
aattgcttga acttgggagg cagaggttgc agtgagccaa gatcatgcca ctgcactcca   24420
gcctggggga cagagcgaga ctccatctca aaaaaaaaaa cggattggga aaggaggttg   24480
aagaaggaga aaagttcgac ttcagtcttc cacttcctat ttccacccag ttccagcgcc   24540
aggggcttca gcagacccag cagcagcaac agacagcagc tttggtccgg caacttcaac   24600
aacagctctc tagtaagcct gcctgccttc ccaaggagaa ccccatggaa taaatttagg   24660
gggcggggtg ggccaaagta gctgaaacga tagcttcagg cccaggttat gagaggaggc   24720
attccattcc atccccttcc ctcgatacct gaacagcttt cctcgtgcat acccacaccc   24780
ctgcctggtc ttccatccct gataatctct ggttttttcac agatacccag ccacagccca   24840
gtaccaacat atttggacgc tactgagcca cctggaggaa ctgcttgtgc actgatgtg   24900 gccccaccct ttcctcttaa ttcccaatcc cattcctggg ctagcaccag tagtggttgg   24960
ggccctcccc tcaggctcca ttttttaataa gttttttagta tttttgttaa tgtgaggcat   25020
tgagctgttg ggttttgtat attatttata tagagacccc agagctgttg cacccaatac   25080
acagagcttc tttgcaaagg gagtgtgcga gttctgcatg tctgggaagg gtggtctctt   25140
gggagaatgc aggggggttgg accaacaagt cagagtcttc attctattct gatcatctcc   25200
cctgtttacc ttacactcta aaatttcttt ttttcttttt ttttgagacg gagtcttgct   25260
ctgtcgccca ggctggagtg cagtggcgcg atctcggctc actgcaacct ctgcctcccg   25320
ggttccagcg attctcctcc ctcagcctcc cgagcagctg ggattacagt tatgtgccat   25380
cacgcccggc taattttttgt gtttttttttg gtagagacag ggttccacca tgttggccag   25440
gcttgtctcg aactcctgac ctcatgatct acctgcctca gcctcccaaa gtgctgggac   25500
tacaagcgtg agccaccgcg cccggcctaa atttcttaat tctaattgga ttgctaccct   25560
ctcttcctct tcttcaacat ggcaacacat taaggtatag gcccttagtc tctttttatt   25620 tattttgag atggagtttt gctcttgtcg cccaggctag agttcagtgg cacagtctca   25680
gctcactgca acctccacct cctgggttca agtgattatc ctgcctcaga gcctctcgag   25740
tagctgggat tacaggcata tgccaccagg cctggctaat ttttgtattt ttagtagaga   25800
cggggtttca ccatgttggc caggctggtc tcgaactcct daccgcaggt gatctgcccg   25860
ccttggcctc ccaaagtgct gggattacag gcatgagcca ccacacccgt ccccttagtc   25920
ttttaagaag gggcaatgaa cattctcaac taaatgttgg agcttcttta cagctttcct   25980
ccatggggga taccgctg ggattgagga ggggccatta ggccagggga aacatcaata   26040
gaacctgatt cttcttccac aacaccccag atgttgggcc tcaaacaagc tggggagggt   26100
ggagatgaca gacactgcct acccttcttg tcatcttgtg tggtccccat catgcaccaa   26160
gtggcatacc tttcatagga cagagaactt ccctgagagt cacattcctg gatgaaaaat   26220
tgccctccat tggcatgtgc catcatagaa taggtcgtgg aaggaccgtt tggttctagg   26280
aggaagagag accagtaaaa ataagcaccc tttctctctc tgccctactg ccagaactgc   26340
ctgttctcac gtgaccccacc ttggcagtta cccaggatga cttgctcgct cccattttac   26400
agtagagaaa actcaaaact gttgccccag agtcacattt ggagctgcgg cagggccatt   26460
```

```
ctcgccctct tgctttccag tttgagttct agatccaagg ctgtccagga gagccaactg    26520
gtttactaca atggagtctt ggagtcttct gccctgccta gctagggctg aagaggatc    26580 agcctcagcc ttgtgagtgg gtggtacagg atgatttgac aacttaagga taacatgcaa    26640
gccatagttg caccctatta ctgggaagtg tctagtgtgc tggcaaaacc aggagcacca    26700
atcagtaccc aagttataaa aaataaaata gccctctttg aggcccacga agccctgctt    26760
atatgggact taccaagttt aagagttgcg tgcacaagga atggaactcc ccaacagtgt    26820
aaaggcaaac atgactgaag ctttcttctc acttattcta tcctgacata acattctga    26880 ggagccacag gagtacaggc ttggctggga tgagggacat tcagaggggc ttgggggttg    26940
ctaaacaaat ggcaggtgcg ccacatacaa aaacacaaga cacaaagaca ctgaacctgg    27000 agggagaga ctgaaatggt cagacaactg gcatgctgac agtctgacat gccccagcag    27060
aagcagcaga agggaacagc attgaccttt gggagagtga caggatgaga gcagagtggc    27120
cccactggtt gctgcttggg tagtgctggc gctgagaaat aagggatgct gattgaggtg    27180
gaggtgtgtt tttgtgtagt atgactgagg gttcctgcag gcagtgcctc agtttctccc    27240
tttgggacaa agtctcaagc tttgcgggta agtttgggc tagctgccct ggaagatcac    27300
ctgtctgata gcttgcaatc tgaggtgtgt gtgcgcgccc gcgtgagaga gagggagcgg    27360
aacgtgcctg agcatggggg gaattgggcc atgccccagg acttgagcca tctctggcac    27420
aaaaggagtt aatggcaggg accgcgcccc cccgtgtccg ggaacgcgca gcgcgccccc    27480
tcggtgcgcg ggcacagcag ccaggctgcc ggagagctga tctcggggat tcgggtgcgg    27540
agcccttggc ctggaggcga tatgggtggt ccgtggcccg gttcagtcgc ttgcagcagc    27600
ccggggaaca ggtgaggccg cctgccccgg tctctcatcc tctagctgcc cataccttgc    27660
ccccatccta acccctccca atcccaggct cctccactcc ccagccagtg gcccccatcc    27720
ctctcaaccc catgttctcc atcggtaccc ctgacccccg atcctccccc gcttctgttc    27780
tcccttctac ctcctcccta aatcccgcat ccctaacatc ctcccgccca tggtccctct    27840
atttccacag cccatcccgc atgctcatca aaataccct attgagggcc ccagccccca    27900
tcccgggatt gcacattgcc agtcccccct ccctgcagt gcagccccat cccccttcca    27960
tcatagcatc tcatagccag gctccctccc ccactatctg cagcccccc acccaatgga    28020 ggcctttatc ctatcctccc ccattccagt gcaactccat cccccaatcc attccaagcc    28080
ctcgtagccc ccaatactgc agttctcaat attggtccat tcctgcacaa tgccccgcgc    28140
ccagcaccgc tgcagcccca aaagtacccc gagatgccat tctcatcccc ggcattgctg    28200
cctccccttg tcttctccca aattgcaagt tggaccagga tggagatctt ggccttgggg    28260
attcacagtg ggtcctaggg tacagagggc gtttgggggt cggtccgatt gtctaggtgt    28320
tcacggggga ggggctgcag ggaattgact caaaggagaa tttggcattt ggcgccgaag    28380
ggttactgga gaggagggca tcccgaaagg gttaatgaa tttgtgggtt ggggggcagca    28440 cccaggggggt taatgtgggg gggttgctgg tggggaagct gtgtgaatga gcggtctgtg    28500
ccctggagtt gccatggana crgtgaatgg ggggattgtg tgaactcagc tgcggactat    28560
gcccccccca atacacaaca cccacccact ccctcctgcc ccacctccct actcctaccc    28620
cttccttccc cttcccctcc tccccacacc cgggtgcatt ctgggcagtg tctgggatct    28680
taccccccat actttgctcc ccatttcctc atttcctctg agcccccacc cctttagcca    28740 ctttaccgc cctccctcct cttcctttt cttctctctc tctctctctc tctctctctc    28800
tcacacacac acacacacag acacacacac acacacacac acacacacac acacacacac    28860
```

```
acacacacac acacacacat tctcattccc ctctcgtggt ggctgattgc cgggcgttcc   28920
caatctccct cccccacccc ttcagccagt tcttaaagga gcaggcctgc aatctgggaa   28980
ggcgggagaa atggaggaaa actaaatgtg catgtggcgt gggtgtgcgt gtgtgtgcgt   29040
gtgtgtgcgg gagcatgcgg gagtatctgt gtgtgcctgt gtctatgtgt tgactgtgta   29100
actgtgtcag aaggcctatg tgtctgagtg tgttgctatt tctgtttctg tctccaccta   29160
tgtgtcacca ttatgctgca tgtgtctgga tatttaccta tgcgggtatg tgtgattata   29220
tttcagtaag tctctatgtg tgtctctgaa tgtatcattc tgtgaggctc tggctgtgtg   29280
aggtgctctg tctcagaatg tgggactata tgagggatc  tctgtgggtt tggaatatat   29340
gtctctgtga gtgaatatcg cagtgtctgt gatcctggct tggtctctct cattccctct   29400
ttgagtcttt gtgagtttat ttctatgagt ctctgaatat gtgttcccca tgctccgttg   29460
tttatttat  aatacaccgg aagagcatcc acaatgccta gggtgctagg cagaactctt   29520
tctgcctcac ttctggaatt cggtgtgaat taagagagag ccaaccgaaa ggaccaaggc   29580
ttaaggattt gggagcagtg agggctgagg agaaatgtac aggaggggcg caggagggtc   29640
cgaggaggac tcccgtgaat ggctgtcccg ccctctgccc tgcctgaggg tgagggagtc   29700
tctctgtggg actctgccga tttgctgctt tctgttcttg tgtcttagtg tcccggagtg   29760
aggttgacaa tcccacccctg tcctgaagtg gaggtccctg tgtgggctta ccaggtccca   29820
agggctacac agctctgttc aagcagcatg cccaggacc  tgagctccat tttgtttct   29880
ccccacccccc tggctgtcac atgctattct ggctccagcc gaccctgatg aacccctttg   29940
gctgtagaat tgaagttggg caccgggaac ttgcagtggc aacaactgtc actgtcaaac   30000
cccttggatt ttccagccat ggccaggcac atagaatggt tctgattggc agtggatcat   30060
ctgtgggatc acagtccctg ggcccctggg catgtgaaac ctctcctaac tataagagaa   30120
tagcccaagc ccagcagggc ccccaaagac caactctgtt gccctcccag accatcttgg   30180
atgacgcata cttccctctt tccacaggcc tgtctggccc tgagggagtc ccctttctga   30240
agctgtggtg cttggacgac ctgctctcta cattgctggg cacctgtagg tgtccctcga   30300
gagctcagtt ttgaggttca agtcagtgtg gccatgaagg ggctgcctat tgggctgatg   30360
ctgtgaccct ggagtctgcc tctcctgcca gtcccctgc  ccggaacatg tggctgcggc   30420
ttggcccgcc ctcgctgtcc ctgagcccca agcccacggt tggcaggagc ctgtgcctca   30480
ccctgtggtt cctcagtttg gcgctgaggg ccagtaccca ggccccagca cccacagtca   30540
acactcactt tgggaagcta agggtgccc  gagtaccact gcccagtgag atcctggggc   30600
ctgtggacca atacctgggg gtgccctacg cagctccccc gatcggcgag aaacgtttcc   30660
tgccccctga accaccccca tcctggtcgg gcatccggaa cgccacacac tttcccccag   30720
tgtgccccca gaacatccac acagctgtgc ccgaagtcat gctgccggtc tggttcactg   30780
ccaacttgga tatcgtcgct acttacatcc aggagcccaa cgaagactgt ctctacctga   30840
acgtctatgt gccgacggag gatggtgagt gctgcggcca ggcactgtgc cctccctgcc   30900
tcccgcctgc cctgctgtgt ttgtggcttg catgtggttg tgtgccctgc agcatgcatc   30960
tgtctgtctg tgaaaatgct tctaaccatc actctgcttg gcctccacc  ccctccctg   31020
ttcttccctc tccagcatt  gtccgagctc ccatgtgtga gtgacactgt tgccaggagg   31080
ggcctggccc ggcctgagag ctctgacggg tctcggtcca gtgctggatg ggggtcccct   31140
gggggagtat gggtcacggc tggcagctac ccgcgggagg atgctggctc caccaggccc   31200
```

-continued

```
ccctgttgcc attccacctg cttcgaaagg tggtaggtgt gtgtggccaa gggcactggg    31260
tgtgtggggg gtggggcagc aagcctggtg ggtgatgctt aggtgcctcc tctttcacta    31320
gctgatgcct cctcccgcgg gggtcacact aaggtaagtg acagaaacaa ggagatggtg    31380
ggacaggctc tctgccatgt gccgcctgca gagcagctca gctcttgggg cctgggggt     31440
gggggtgca tgcccctggg cagaggcctc ctgttatttt ttagtttttt attcatttta     31500
cagtaaagcg gatttccaag gaatgcgccc gaaagcccaa caagaaaatt tgtaggaaag    31560
gaggtaggta gcgagccggc ggggaggggag agagagagag agggagggct gcctgcccac    31620
ctgcccttgc ccccaggacc cagccttcct ccaagtagcc caggctcagg gggcagtaag    31680
caggcataag cgccacctca tctgagggcc ctggctgcct tgcagggagg atttggtggc    31740
ctaaggcagg ctcagagcag aagcagcaac cctatttctt ccaatcttcc cagccccaaa    31800
ttccaccta aagtgtgtgc caaaggcaga gccagtggc ctctcggtga cacctcagga      31860
gaaactctag gaagccaaga tggagccaga ggctccaccc ttttcctagt gggtggagcc    31920
agaagaccat cccttctgtg ttctttctcc tggattgaaa gtctagactc aattttccca    31980
ccctgaagct tagaccaaac gtgtacacag gtttagtaac tcctgccata cacacctctg    32040
tctcccaccc cactacctct ggccagagtg tagctgatag acccaggctg ctctggtggc    32100
agaacttggg ggtctctggg aactatggac tttaaaggag gcaaaagatc ctgaatttta    32160
aatttaccct catgctgaga ggagtttctc ccctgtata ataattcttc ctgttggaat     32220
atcacttcat gttttctgta aagtgccttg gcatttacct tagagaatcc tccctgtatc    32280
tctggaagcg tctaaggcag gaatcagtat cccaattta cagatgagga aacaggccca     32340
ggggagtgac ttgctgctgc tcaaggcccc tgtcgctggt ctgtggcaga gctgggacca    32400
aaacctgggt ctcttgacct tcagggcgtg ttcctttcca ctgtagcaca cagaagcaac    32460
tcccatctgc tcattcccat ctccccaact caaaaaaat ggtgagatgt ggctgggctg     32520
gggagaattg gaacagtaac agcctaagga acaggtggaa aaatcacagc ttgatcccta    32580
caaccctctg gcaagctggg agtttgtttt cctttgatgt cctagggcag agtttctcag    32640
aatggggttg ccaggatttc tgggatgggg tgctccttac tgaataagaa tttctggggg    32700
cagagcctga aaatctatat gttgaacatg agccctgagc gcttctaatg cacacccgag    32760
catggaatga gacccgctgc tgtagggata gtatttcacc acagccccat accccaccca    32820
ggacctcaca caccataggc aattgatgtt ttttgtgtaa ttcagaagca tcatggtgct    32880
gcagaaagag tacaggtctg ggaagcacaa ggcctgagtc ccagctctgc tgccaactca    32940
cagtgagacc ttaggcaagt cttgtccttc aagaacctct gtttccacat ctgaggttgg    33000
tagggtacag ttctggcctt agcattccat tagcctgtaa atgaattcag gaggaaggtc    33060
tcttaaacct gcaggagagg ccgggcgtgg tggctcacgc ctgtaatccc agcactttgg    33120
gaggccgagg caggtggatc acctgaggtc ggaagttcga ccatcctg ctaatacgg       33180
caaaccccg tctctactaa aaatacaaa aaattagctg gcgtggtgg cggtgcctg        33240
tagttccggc tactcgggag gttgaggcag gagaatggca tgaacccagg aggcagagct    33300
tgcagtgagc cgagatcgtg ccactgcact ccagcctggg cgacagagcg agactccatc    33360
tcaaaaaaa aaaaaaaaa aagaaagaa agaaaagaa aaaacctga aggagagatg         33420
gcattcacat taaccatttc ttaggaagaa tgatcgccca gtaagagcct tgggctgtcc    33480
agtccagccc tgagagtgtg gccagagagc agactggaag ccccggctca acatgcaca    33540
tttaccaatc gtgattgttg actgtgggca aggccatgtg ctaggtgttg ttgggatgtg    33600
```

```
gagggatgtg aggtagagga aagatttaga aatgactaaa ggcctaatca ctgctctgaa   33660
gaagctctta gccttgtatt aaaactcagc tggtttggcc gggcgcggtg gcttatgcct   33720
ataattgcag cactttgaga ggccaagacg ggtgggtcac ttgagttcag gaattcgaga   33780
ccagcctggc caatatggtg aaaccccatc cctactaaaa atacaggtgc atggtggcac   33840
acacctgtag tcccagctac ttgggaggct ggggcaggag aatcgcttga acccaggagg   33900
tggaggttgc agtgagccga ggtggtgcca tcgcactcca gcctgggcaa caaggctgaa   33960
actccatcta aaaaagaaa aaaaaaaaac tcagctggtt tccctaagtc ccatgggcca   34020
atcaggaagt gggttccaga cagtgcaagg gaaggcattt ggtcatttca ctgttcaaat   34080
tagttcccta cccaggacct ggtggccatt tggaagagtg acaaatcccg cctcttgagg   34140
gagacccatc ctcggaggtc gttagggttg tggtgtgcag aggtctgggg accagcctgg   34200
ctgggatccc tcagcggcgc agggtctggg aatggtggtc ggcagtcagg ctggcctggg   34260
tgagaggcat ggcggctagg agctgctcag gaagtgccag gctgaaggag caaaggcatc   34320
tgtgtgaagg aggctgagac aatgcagcaa cccaggaaca cttttcagagg gattcacaag   34380 ggacttatct tctaagtcag ggatgatggg aaatgaaggg tttcctgggg aagacctgcc   34440
ccatctcccc aacaccccac cccatcaagt tggaaggaat tcgtgtctgg ggatgagcaa   34500
ttccttcccg tttggtaggc tgtccgcagt gtgagggatg atgcccatgt cccattaagg   34560
tttctgagga cagcactggc agtgttgag ctaatgtgtt aagacggtag gtgccaccgg   34620
aagttcaggg agccagaggc aatttctccc ctagagctgt gctcttgtcc tggttgaaaa   34680
gccattttgt aggatgaggg cagttcctgt tttgatgaat ggctgtaagg aaatctagtc   34740
atcagagtcc agaccggctg ggaaagaggg ctctttactc cctccaggct gagggtatct   34800
gatgtcatag atgcctgggt tggcagcaca gcccccctctg tttccacaca ctgaccagca   34860
tccagacagc cggtcctctc cctccacagc catcgccagg atgcacttct agcctcctta   34920
gaacaggaag gagaatctgt gccagcttag ccccagatcc taaatgtctc ccttctcacc   34980
tctagtctct tcttttttct cttcccctcc ttgcccttc tctcccccta catgcccac    35040 tgcttttctc atctatttct tcccttcctt ccccttccc ccaccccaga aagtggcat    35100 gatgcagtgg aaagaccatg ggctttggag tcaagcagac ctgggtgtga atcgcacctc   35160
tagcacttcc tagctgtgtg atcttgagca agtcacttta cccctctgaa cctcagtttc   35220
cccatcagtg aaacaataat aaggataggga cctatctcac tggggtgtaa ggatcaaaca   35280
atatggcaga agcagagtgt ctggcacatg gtgaatattc agtacatggt tggagctgtg   35340
accattattc ctatctcttt gtttctcttc tattttttt ctctctctct caccatccct   35400
ctctcctctt cccctttctt ctgtccctct ctccctctct ggctctctct acatctcaga   35460
gcaatgcttg ctgctctcaa cactggttcc tgtgggcagg aacccatttt gccattaacc   35520
agagcagggg ctccaacaag gaagaccaga gggaaagctt catctcccat tttctcctgt   35580
gggaatcagg gtcagctgag gcccagcttg agcctgccca ctgggcccca ggagctcagg   35640
cctggggtcc ctctacacgt ctctgccta agttacctcg tatccacaac ctccacactt    35700
gctggcagtg tcacccctca cccttggtac ctgaccctgc tctccagctc gacctgcctg   35760
tgttcacaca agcagcccct tccacccaga atgaatcctt cccctgagag ggtctctggc   35820
tctgtgccct ggcccacttg ctgctacctc cttcctcact ggaaaggtag ttggttgaga   35880
tgggctgttg gggacaagga ggcggggcaa ggcggtgcag aaaggccagc acagcagggg   35940
```

-continued

```
cctgcaacac catcatcctg atgaaggtct gggcctcagc ccaccccattc cctcagttct   36000
tgccatccct cctgcctgtc ctgggcccag gcccggagct ggcttgctgg gccacactgc   36060
agtcatgctg ttttttgaatt ctctctctgt tttgttctct gttctgtgct gttgtgtctc   36120
cccgtgtctg gtccccagga tccggcgcta agaaacaggg cgaggactta gcggataatg   36180
acggggatga agatgaaggt atttgggggc tgcagggcgc ggcggctggt gcatggcaca   36240
gagcccctcc ccttctcgat ggggagaagc cccgtctgtc tgtctgtctg tccgttggtg   36300
tgtttctgtt cctgtacaag gccgttgggc tgttcatctg tctttggccc tgttggccac   36360
tgggagttcc ggggtgatgg acatggctgg caggagcagg ggaccacaag cagagccatg   36420
gggaggacat cctccttgcc tgggtctccc gccccttccc catcttctgt ggttcagagg   36480
cacctgcccc tactgagcag cagggagagt ggagagaaag caggaccact gagggcgggg   36540
agaggacaaa gacaacggaa cggcaaggag attacctgtg tttcagtgaa gagacccctg   36600
tgtctcacag ggagcctggc ttctgggaga ggggcccccgc aggatggtga actgggaagt   36660
gaggcagtga caaccaaagg ggctggaaaa gcagcaccag aacctcccca gccttctaga   36720
aaagagagag atggtctcgg ggctaggggc tgcagtaggt acaagacaag gccagaaaga   36780
ctgggctaaa atgccaggct gaggccagga caccacagcc atcaatagat ggcataagat   36840
ccttgggcaa tgatcggacc agccttcctc cttggagaaa caagttctgt ttgctccgca   36900
gcagagagca ttcccttcct cctccatgcc ctggccctgc cctctgcccc cgaaggggcc   36960
aggcagctca gggggggccca gtggtgatgg gtagggctgt gctggcatgg cagagagtat   37020
tggtccagtt cacggactga caggctacag gcagaggtga tcaggcctgg agccttctct   37080
tgactgcccc agccctgatg ccgtgccgcc tgggctcggg agcagccgct tgatggtccc   37140
ttgttgaatg gcctctgggg aggctccatc ttcatcttgg tgctgactgg gagcaggctc   37200
tgtcattctt agttcttccc catccccaat gcttctggtt aagtctgccc agggagaatg   37260
gggaaatggg cacatggcta agaaaccatg tcaacaaggt tccccccacc ctatctctgc   37320
cattcactcc cctttcccac atccttcctt gttctctccc tgtgccaccc cttattccca   37380
cacctcttgt ctctgtctgc actgggggggc cagctgctgc caatggccgt ttttccatgt   37440
aactggtcta gtcttggggg tttcagggct cccccagctcc tgctctctaa agccatgtca   37500
ggtcccagga ctcctgggtg cccagggcag cgactcactt gatgtggcta aaggaccagc   37560
ccttcctctt tctgctgccc cccgccccca gggcccagcc atggcccact gaggcctggc   37620
tgtatcacat gcctggctgc cttcagctgg gaggcacttg aaaccagagc ctttaaaaat   37680
atcactgaag ccccactgtc tcgggctgat gcttgagctc caggttgagc aaccccatga   37740
gtcctgccct cagggatggc ggtggtgtcc tggcacctgg gatagctttg ctgcccgcac   37800
ccaccccctg ggctggcagg ggtgggggaa gcaagggcat cccacccagc ctgtgtctca   37860
ccccttctcc ttgcagacat ccgggacagt ggtgctaaac ccgtcatggt ctacatccac   37920
ggaggctctt acatggaagg gacaggcaac atgattgatg gcagcatcct cgccagttat   37980
ggcaatgtca tcgtcatcac cctcaactat cgggttggag tgctaggtat ggttccctgc   38040
ctggtgcctg gaaggaagac tggcttcgca agggggggagg aaagaatgct ggagaattta   38100
aaaacagata gccttgcttc tctagctggt gctaataacc acagtcaaaa tggtgttatc   38160
ctctggcccc tacccaaatg ctaggggctt cccatatcc ccaggccctt tcttggaagg   38220
tttagatgcc accagaaatt caattcaaac ttcacacctt ctctcaggtc ccaagccagg   38280
tctctgcttc cagactttga cttggctgag ttttgtagga tgcttcaatt ttccactgtc   38340
```

```
ctgtcttcac ctctacccac ccgccccaca tctctaaaca ccccacacat gcacagatat   38400
tccttccagt ccactccatg gccacacacc tatttaccct catgtgttta cacatccacc   38460
ccgccatgca cctgcaggaa gacggtgatt tctcactcac ccccataaag tacacacacc   38520
tagccccaca ttcacatctc caggcccctc acatgtaaac acattctcct agcactccag   38580
gtaactccat tcacatggtc tctccagaac acatatccac atacccacac ggtctgtgta   38640
ctccacgtct gcaccccgca gatggctctc accctccgca tgtacacaca cacatgctca   38700
tatacttctc cccatgtctc tgtagccaca tctaaaccga tacccacgat gcatacacac   38760
ccacactcac actttacccc catatttaca gcccacacaa aaacctacac cctgcacatc   38820
catgtccaca ccaaactcca cacatataca ccttaaatgt acataaatat tccttccacc   38880
caccccccac aaatacctac acacgcccgt atcccctgc acaccctact tccacatcca    38940
ctttacacat ccacctacca cacacacctg tccctcacta tctcctcaga aacacaaaca   39000
aatattcccc ttccctacac acatatactc ttacctgttt gtccacactg tcccacccca   39060
cacatacaca gatactacac acacaccata tccacatcta tatacatccc acacactgcc   39120
cttatgtcat tcccctacac atacattccc ccacacacac atccacatat gcatgcacgc   39180
gtatacatgc gcacactctt ccatatacag cctgtatatg tacacccagc acacacccat   39240
gcacttctcc cctcaccca ccccacaaat atatacacat ccgtgtacat ggggctgcat    39300
ctgtatccat acatgcacac acacctctac ccaggcccaa ccgcatccct caagtctccc   39360
cacacttcct taccccgtat atgcacacgt acacactctt tgtactctaa gcatgtcccc   39420
tgcacactcc cacccatcac acacatactc ccatgcatat gcactcattg ccgaaatgcc   39480
tcctcatatg cacccataca cctccccacc cccgcattct ctgctgtgca caagcttgtg   39540
tcagtcattt aggctgccct tgaacccgtg accttccttg gtgaccaccc atgcctatct   39600
atggccaagg tcttgaggta aacgagtgcc tcagagaggg tgactaagca cacagggccc   39660
tgctcatgct cccccaagcc ccgcatccct gtagtggcat gaagaagcca acttcttcct   39720
ggaggaagag tttcagcggg agtgtaggct cttggtcagg tctgtaggca tatgggtgct   39780
aaaccagcag ttaggcgtgg cttattccat ggctaactag gggacacgac catatttgat   39840 tttatttca tttaattttt gagacagggt ctcactcttg cccaggccag ttttgaactc   39900
ctgagctcaa gtgatcatcc tcccacctca agggccttat tttaatttgc ttatttattt   39960
atttatttat ttatttattt atttattatt tttattttgt ttttgaggca gagtctcact   40020
ctgtcgccca ggctggagtg caatggcacc atcttggctc actgcaacct ccgcctcccg   40080
ggttcaactg attctcctgc ctcagcctcc tgagtagctg ggattacagg cacctgctac   40140
catgccaggc taattttgt atttttagta gagacagggt ttcaccatgt tggccaggct   40200
ggtctcgaac tcctgacctt aggtgatctg cctgcctcag cctcccaaag tgctgggatt   40260
acaggcatga gccaccacgc ctggccctta attttctctt gactatattg ctttgtcagt   40320
tccaatctca gaggctccgg ggctgcattt cacttctggg tgcagttgta tgcccagaac   40380
ggcaatcttc tcttggttta caattaatac tatgtgagat aggaagatac tcttttgggg   40440
ttcaaactgc agaaatgatg ctcctttaaa aaagcaaagt cggtgtcccc ttcattggcg   40500
cccgggagac tgaatatgga gcatgcaggc cattcacgct ggcctcccca cggtctggta   40560
ggcttgggat gttgggatgt catggttctg ctcctgcccc tctgtctttc tgcatccacct   40620 cagacaccat ggtgaggctc ttgtaagctg ttctgtcctg ttgaatctca tggtaccatg   40680
```

```
aaggtggctg gaaacccaca cactagggct gcacactttc ttttttttaat taattaatta   40740
attaattaat taattttttga dacagagtct cactctgtca cccaggctgg agtgcagtgg   40800
tgcaatcatg gctcatcgca gcctcgacct cccaggctgg agtgatcctc ccacctcagc   40860
ctcccgagca gctgggatta tggattacag gtgtgcacca ccacacccag ctaattttttg   40920
tattttttagt agagacaagg tctcactatg ttggccaggc tggtctggaa ctcctgatct   40980
caagtgatcc acttgccttg gcctcccaaa gtgctgggat tacaggcgtg agccaccgcg   41040
cccggctggg ctgcacagtt tctagagagg aatgaacgcg caaatgtgat cacaaacaga   41100
tatgcagaca catgtacacg gtagttcaaa gccaaaagta attttgctac tttcttttct    41160
tagagtgaca gaaaacactc agctcagctg cttaaaaaaa tataaacaca atgctccatt   41220
ctataaggtt tattggaaaa tacaaagaat actaaaaata tgcttcagag cagctaggaa   41280
tgaagaaaga gagcatggaa aagagggaga gaaagaggag aaagcaagga agagaagaaa   41340
atgagaggat aatagagagt cagggagagg aagcagagag gagacagaag gagagactta   41400
ggatctgggg agagactcgg catttcacgt aggatgtgaa gtctccacag tgtcagttgg   41460
gaactgtggg ccgcacagaa ggctgtcgct ggtgagcatt ccgtatgata tcctgatttg   41520
ctgattactt cacaatccctt cggctgctct aatccttaag cttctacacc agaagttctt   41580
aacctttttgg ggcatcttgg acccttttga gattctgatg aaagctatgg actctcccct   41640
ggaacaatgc acacatgcgt gtgtgcacac acatgcatgt gcgcacacac acacttaatt   41700
ttacagggcc gggtgtggtg gctcacgcct gtaatcccag cactttggaa ggatgaggtg   41760
ggtggatcac ctgaggtcag gagttcaaga ccagcctggg caactaaaacc ctgtctctac   41820
taaaaataca aaagtgagct gggcatggtg gcatgcgccc gtagtcccag ctactcaaga   41880
ggctgaggca ggagaattgc ttgaacctgg gaggcggaag ttgcaatgag ccaagatcgt   41940
gccactgcac tctagcctgg gcaacagagt gagactccat ctcaaaaaaa aaagaaaagg   42000
aaaaagaaaa agaaaagaaa agaaagaaag aaaaaacaat tttacagatc ccccttaagt   42060
tcatccatga aagtcaggtt aagaactcgc acttgacagc cccgtcattt ggataaccag   42120
aacagcacat ctaggggggca ggaacattct tctttgggct taagcagttg atgatcaaat   42180
atcaccgaaa actcagaagg agtcctacac tgagatttgc tcagaagttc ctcaccactt   42240
cctgcacacc cttcagttcc tgttctggaa cacaaatata atcaataagc ccgtattgga   42300
tgccgggtac atataagatg tttgtttttg tctcttgaca ccagatgtag aacatggtt    42360
tgtccctgat gcttgggaat tttcttttct ttttttttttt taattgagac agagtcttgc   42420
tctgtcaccc aggctggagt gcagtggcac aatctcagct cactgccaac ctctgccgcc   42480
gggttcaagc gattctcgtg cctcagcctc tggagtatct gggattacag gcgcgcacca   42540
ccacgcccag ctattttttt ttttttttttt tttttaagd agaggcgggg gtttcgccat    42600
gttggccagg ctggtctcga actcctgatc tcaggtgatc cgccctcctc agccttccaa   42660
agtgctggga ttacaggtgt gagccactgc acccggcggg gaattttcct gtgtagtggg   42720
gcctttgttg ttttgttgcc caaagcatcc cagaacaggt ggtttgtttt ggaccccagt   42780
cacaggcatt cattcactct ccttcccatc agctttcctg agcactgaac ccatcagcgg   42840
ttcactctaa ggtgcttatc ttttttcttt ctttctttttt tttttttttttt ctttttgaga   42900
cagagtctcg ctctgtcgct caggctggag tgcaatggca tgatctcggc tcactacaac   42960
ctccgcctcc ccgttaaag caattctcct gcctcagcct cccaagtagc tgggattaca   43020
ggcgcctgcc accacacccg gcatattttt gtattttttag tagagacggg gtttcaccat   43080
```

```
gttggccagg ctggtcttga actcctgacc tcaggtgatc cacctgcctc ggcctcccaa   43140
agtgctggga ttacaggcat gagccatcac gcccagcctc taaggtgctt ttctagatat   43200
cttgggtgat tcatgaatgt tgagaatgtc acaggctaat ccatggatcc tctccaaggc   43260 agagggtag ctattatttg agaaggcccc actgggcttg aagccaacaa agaaagggac    43320
tccagcagga tataggatgt ggaaatccct gaggctgagg aagcaggcac ttgccaagtt   43380
ttactccagg ttccagaatt gaatcctaca tgcttgctca ggtaccctcc aggcaaaccg   43440
aaaacccagt aaacatcaag ccttgagtga cacaaatatc tggttttgtt acaatctgcc   43500
agattcccca tcttctgttg acgagcagtt taccatgaac tgcagtataa acttgggccc   43560
agggagactg gctccgattt attctgacag tttatggagt ttagtatttc agccttcatt   43620
ctcacatggt ttctgtggat ggttgagtta ctggggaact agcagtgagt gacctctccc   43680
agaatgccag atattgtgtg cttgtggttg gtcaggtttg ctgtcatctt cctgagcctg   43740
ttggagatag catttctttt ttcttttctt ttctttcttt tttttttttt tttgagatgg   43800
agtttcactc ttgttgccca ggctgcagtg caatggcgct atctcggctc accgcaacct   43860
ccgcctccca ggttcaagtg attctcctgc ctcagcctcc ctagtagctg ggattacagt   43920
cacatgccac caagcccggc taattttgta tttttagtag agatgggggtt tctccatgtt   43980 ggccaggctg gtctcgaact ccagacctca ggtgatctgc ccgccttggc ctcccaaagt   44040
gctgggatta caggcatgag ccaccacgcc tggcctggag atagcatttc aagcaggact   44100
cttcatggag tagggatcat tgacatggca tcatccacat gcttcagggc cccttaacca   44160
gagactcata ggatctgaga gagcagagag tgatggtcaa atcctccatc caatcacctg   44220
aggtcaggag ttcaagacca gcctggccaa catggcgaaa ccccatctct attaaaaata   44280
taaaaattag ccaggcatgg tggcaggcac ctgtaatccc agctactcgc aaggctgaga   44340
cagaagaatc acttgaacct gggaggcgga ggttgcagcg agccgagatc atgccattgc   44400
attccagcct gggcgacaag agtgaaactc cttctaaaaa aaaataaaata aataataaat   44460 aaatcctcca tccagccctt tcaggccttt gttcctaacc caggaaattg gtacattgga   44520
gaaatctgct ctactacatc caaatgcagg cttttgcctgc tgattaggcc aggcatgttt   44580
gacacatttc agtaaatgat gccttggcaa aggctgaagc caagaccact attgcctaaa   44640
tgaaagaaaa ggaaaagaga atacagggga aggagagagg agggaggact aaaagaagga   44700
cagtgatttc tgccagaggg tcccaaggct tgggcagctg ggttggatca tggtcaacag   44760
agttggggtt ttgagggatt ttttttttttt ggttgctttt ttanagatgg agtctcattc   44820
tgtcccccag gctggagtgc agtggggtaa taacagctca ctgcagcctt cacacctagg   44880
ctcaagtgat cctccagccc cagcctcctg agtggctggg accacaggca tgcaccacca   44940
caactggcta atttgttttg ttttaaaaac aaaaagggac agggtcttgc tacactggcc   45000
angttggtct caaacttctg acctcaagtg atcctcccac ctcagcctcc taaagtgctg   45060
ggattacagg tgtgagccac catgcctggc caagttttta agactcaaag gagcagcttc   45120
aatttctgaa tgggccacgc aaaggaaaag ctgatttcct tgtctggaag agcaagggtt   45180
ccttcttcat cctcatgcag gctttctcta attcattctc atttcctcct ctggaacctg   45240
gggctaaaga ggacttgtga ctagggcccg ggagaaataa ctaagtactt tacatactta   45300
attgtaccag aggtaaatta ataacacact tgaagaggat gagatgagct cttttgcaga   45360
agctaggtac agaaggactt gagaaagaca gtggtgaggt cttgtgactg tttgagtcta   45420
```

```
tttgaattca gcctctgcct atggactgca aggacgccag agaactcccc atgagctctg   45480
ggagtcttct ccaacatggc ctctcacaaa gttgattcca ggtgctgtga atgagctttt   45540
aactggggag taaaaaatac tgatccaagt gtgggtttcc aatgtgtagg agcttcacaa   45600
ttacccacct ccaaagactt cttccaaaag cctagggcag agaagacag agccttccaa    45660 gggacccaag gattcaggga agagagatga ataaggccg caggctcagt ctaaaatgga    45720
agcagagtag gggggaatat aggacatctc tgtgggatag ccagcaggtg ggcaggaagg   45780
tagtctccat ggcaacaagt ctccacagca gcaaatccca gcaggtgggt gggaaggtag   45840
tctccatggt gacatgtctc ctcagcagca aattccagtg gggggcggg aagacctgtt    45900 tctgtggtaa cgcactgcgc tacttcccca tttctccacc agatgaaaaa gatggtctga   45960
cccagtggtt tctcaacttt ggcaggtatc agcatcacct ggagagcttg ttaaaaacac   46020
agattgctgg gccccacccc agagtttctg attccttagg cctccaaggg agggaaatga   46080
ggacctgccc tgaaaatgag gggaaggggg ccatcaaggc cccggaagga agtggagagg   46140
gactgatttg aacaggaagg gcaaggagag cttagggatt gttgcctctt gggatcatct   46200
acacttcctt tggagagaga agaaagggga aagagaagta actatagagc tgcaatgtgc   46260
ccagcatgtt atagatgctt atgttcattt tatccttgtt acaaccctgt gaggtatttt   46320
tatccccatt ttacagaaga ggacactatg gcccagagat tttaaattaa gtgcccaagg   46380
ctacatgact aagatgtgat agagccagga ttcaaatcaa ggaccgtctg actccagggt   46440
ttccattcta tcttgccaga tgttagggta aggtccccaa tagtacatca gggcagagaa   46500
tgctgagttc tggacatttg cagtttctgc agtttgtctc ccacctggag gcatgcactt   46560
caaatggtct gcagacccct ccttccaagc tggataacag gtgggaggca gggagctgac   46620
ccctcctctg ttgacgatgc tggacattgc agaaggagc actgctttaa gttaactatg    46680
tgggaagaac tacactgcgt gctcattctc tattcccacc tcccctgttg accctgcctg   46740
ccgtcatcac ccaaatcctc catccctctg ccttcattgt cttcatgccc tttgttgaat   46800 ccaggttttcc tgagtactgg agatcaggct gccaagggca actatgggct ccttgaccag   46860
atccaggccc tccgctgggt gagcgagaat attgccttct cgggggaga ccccgccgg     46920 atcactgtct ttggctcggg cattggtgca tcctgcgtca gcctcctcac gttgtcacat   46980
cactcagagg gtgagtaact cgtggggcaa acatgaact agccaagtgc cggctgtccc    47040
agcatgcccc atccatgccc cagggcatcc aagggaatcg gccagctctc ttctaccagc   47100
ttggtatccc tttggcaaga agtggaagag aaatgtttct ctgggagaag tacttctccc   47160
aaagctggag agggaaggaa gagaatccca tttatgtcct gggaaagcaa gattctcctt   47220
ctgatgtggg agtcttattt tggggagtgg gaatagaaca attgtcccct cagaggacaa   47280
tagtttgaca gggggttgggg aggatctttc agtatgggaa ggacatgtta cttcacagta   47340
gagatatagg gtggaaattg gtttctaggt ctaagaaaca tccattctct gcctttctct   47400
ctgaagaaca agtctgtaca agaggggaaa catcctagag ggggaagtgg gtctgaaatg   47460
agagtcacta acccacgagg tgggcttctt ccataggacg atggtctatt atcagactcc   47520
agacctctcc ccgactgtgc aagctgccgg ggagattctc atttttggcc tctctccttg   47580
tggtgggtcc ctttgccagt gaccccttcca agagagcaga ataggtcctt tttgctcggc   47640
aggaaatgtt ttctccacct ctggactact gggaacattc tatctctgag aggcaaagct   47700
gagcttctca tgaagaaaag atcttcctga aataggtgcc ctttttctgaa gtaaggaaat   47760 ctgtgagcga ggatgctttt tttctttttt aattgaacac taacccctg agttagggac    47820
```

```
attctcacag gaagactttc catctcttga agaagttctg tctctctgag agagaagaac    47880
caccttcttt gacctagaaa ttctgtcttt gccctccag ggactaccct ggtgagggaa      47940
gacttaggtg ggatctgcct ctctaaagag agagactgtg ttcctaggtg accatagtgg    48000
gaacaggaat cttcccttt tccccaaagg agggcgaaat gacgggctgc aagggtgcct      48060
tggcctgaaa agacgttctg tgcctcctct gactggggac tcctccccta ggagaagaaa   48120
gcctttcctg gagtggtgct atgctttgtc tcatagggg cctgtgtctc tggaggtttg     48180
actttttttt tttctttgag acaagatctc gctctgttcc ccaggctctg tccccagtg    48240 cagtggtgtg atcacagctc actgcaacct gttcctccca ggctcaagtg atcctcctgc  48300
ctcagccccc agagtagctg ggactacag gtgcatgcta ccatgcccgg ctaattttgg    48360
ggataaattt tttttttgtag agacaggttt tcgccatgtt gcccaggctg gtctcaaact  48420
cctgagctca agcgatctgc ctacctcggc ctcccaaagt gctgggatta caggcgtgag  48480
ccactgtgcc tggccgagtt tgacttcttt aaagatctgt tctctctgtt tttctgtaat  48540
tgatgcatgg agaataatct ttgggaaaat gaggctgtct tttaagtagt aatctatcat  48600
ttctttccct ctcttccac tcatgcaaac tggctttctc ttaaaggaat ggaattatgt   48660
gcctgaggga caaattctcc cttgggaatg ttggggccag ggagagaatg atatcctttt  48720
tttttttcta gaggggaaaa ttatttcctt tttgagtttg ggggactggc tccctctctg   48780 ctagggaaa atctgaattt gaagtatcgg tagcttcaga taaaggaaa gtctctgcca   48840 ggcgcggtgg ctcacgcctg taaccccagt actttgggag gccaaggcgg gtggatcacc   48900
tgaagtcgga agttcaagac cagcctgacc aacatggtga aaccccgtct ctactaaaaa  48960
tacaaaatta gccgggcgtg gtggcgggtg cctgtaatcc cagctactcg ggaggctgag   49020
gcaagagaaa cgcttgaacc tgggaggcag aggttgcagt tagccgagat cccaccattg   49080
cactccagcc tgggcaacaa gagcaaaact ccatctccaa aaaaaaaaaa aaacaaagta   49140
tcagtggaga ccacagacgg ggagcacagg ttccctggag actttcagac ccgaaggcct  49200 ttgccccttgg gctccttccc caagccctca gaatgtgggg ctcttgcctg cctgcatttc  49260
tcatctctca tgaaaaagac tccttttgtgg tgcaagtgcc agctccctgg tggtgcgctg  49320
gcacggagct gggcccagct gggcaggaag caagagggga agacaaggag agataaagag   49380
aggcggcata agggggctga tgtctgggat tcaagggtt aattcttcct gacattgcct    49440 taaccctaa gttaccagcc atcgcaccag gacaggaag ggatggtgga agccatcaag      49500 gaagggttc agcaaccct cctttggccc tacatcatcc cctgccaaaa gagttgttcc     49560
cccttcctag cccatttaaa ccatgggca gcctcagtga caaaggaatg aagagattta    49620
tggctatgtg tgacacgaca gatctgacct ggtgctacct gtcttctgta ggacttttcc   49680
agagagccat catccaaagt ggctctgctc tgtccagctg ggctgtgaac taccaaccag   49740
tgaagtacac cagcctgctg gcagacaaag tgggctgtaa tgtgctggac accgtggata   49800
tggtggactg tcttcggcaa aagagtgcca aggagctggt agagcaggac atccagccag  49860
cccgctacca cgtggccttt ggccctgtga ttgatggtga tgtcattcct gatgaccctg   49920
agatcctcat ggagcaggc gagttcctca actatgacat catgctaggt gtcaaccagg   49980
gcgagggtct caagtttgtg gaaggggtgg tggaccctga ggatggtgtc tctggcactg   50040
actttgacta ttccgtctcc aattttgtgg acaatctgta tggctatcct gagggtaagg   50100
acaccctgcg agagaccatc aagttcatgt atacagactg ggcagaccgt gacaaccctg   50160
```

```
agacccgccg taaaacactg gtggcactct tcactgacca ccagtgggtg gagccctcag   50220
tggtgacagc cgatctgcat gcccgctacg gctcgcctac ctacttctac gccttctatc   50280
atcactgcca gagcctcatg aagcctgctt ggtcagatgc agctcatggg gatgaagtac   50340
cctatgtttt tggggttcct atggtaggcc ccactgacct tttcccctgc aacttctcca   50400
agaatgatgt tatgctcagt gctgtcgtca tgacctattg gaccaacttt gccaagactg   50460
ggtaaggaga aaatagggtt ttttttcctct ttgagacccc agcatgccct cccctctgct   50520
cctctagcta aacctcttcc atcatatccc ttcctaagat attcccaaaa tcttgcttgg   50580
tacccctcca ctcatcttcc tatctcccct tcctgagtct ttcatgccat ttttccttcc   50640
ttcaaaaatg ttgttgaggc ttagaactca gttagcatcg ggactaggaa ggaatgaggg   50700
ttactggaag aactatggga tttagccagg cccagtggct cacggctgta atcccagcac   50760
tttgggaggc aaaggcaggc agatcacttg agcccaggag ttcaagacca gccacggcaa   50820
catagaaaga ccctgtctct aaaagaaaaa gcattagcca ggcatggtag tgcatgcctg   50880
tagtcccagg tatttgggag gctgaggtgg gaggatcgct tgagcccgg agggtgaggc    50940
tacactgagc tgtgatcacg ccactgtact ctagcctggg tgacagagcg aaaccttatc   51000
ttaaacacac acacacacac acatatacac acacacacta tgggattcaa ggttagctgg   51060
tcacaggcta tgtgaaatag gaatgcagtg cttcagaaag agccttcagg gccaggcgcg   51120
gaggcttatg cctgtaatcc cagcactttg ggaggccaag gcaggtggat tgcctgagct   51180
caggagttcg aaaccagcct ggccaacatg gtgaaacacc gtctctacta ataacaaaa    51240
aatttgccag gcgtggtggc gggtgcctgt agtcccggct acctaggcag gagaattgct   51300
tgaacccagg aggcagaggt tgcagtgagc cgaggttgcc ccaccgcact ccagcctgtg   51360
cgacagagcg agactctgtc tcaaaaaaaa aaaagaaaa aaaaagagag aaagaaagag    51420
agagagagaa agaaaaaggg aagaaagaaa gaaagagaga gaaagaaaga aagagaaaaa   51480
aaaagaaag aaagaaagaa agaaagaaag aagaaagaa agaaagagaa agaaaagaaa    51540
gagaaagaaa gaaagaaaga aaagagact tcgggttcag caacttctgc ttgcttaata    51600
aaagaaagag gctttattag ggggctcctg gcaaaattgg gcagctgaaa agattgataa   51660
atgctcagta gcatgtgcaa agaaaaagca tctatagcct taatcttaaa ggatgagcgc   51720
cgggaaggag gatataggag ttcaagccct ggggaagaag caggtgtggg cagagcaggg   51780
gaccctgaaa aagatggaaa tggtgggaag ttctaaactg ggaaagaggt ttggctgtca   51840
gaggaaaaat gctgggcctt ttcctcatcc agatagagtg gtgacccag atttccatgt    51900
ggtatttcag ggatcccaac aagccggtcc cccaggacac caagttcatt cacaccaagg   51960
ccaaccgctt tgaggaagtg gcctggtcca aatacaatcc ccgagaccag ctctaccttc   52020
acatcgggct gaaaccaagg gtccgagatc attaccgggc cactaaggtg gccttttgga   52080
aacatctggt gccccaccta tacaacctgc atgacatgtt ccactatacg tccaccacca   52140
ccaaagtgcc gcctccggat accacccaca gctcccacat caccgcagg cccaatggca    52200
agacctggag caccaagcgg ccagccatct cacctgccta cagcaacgag aatgcccagg   52260
ggtcctggaa cggggaccag gatgcagggc cactcctggt ggagaaccct cgtgactact   52320
ccactgaatt aagtgtcacc atcgccgtgg gggcctccct cctgttcctt aacgttctgg   52380
ccttcgctgc cctctactac cgtaaggaca acggcgcca ggagccctg cggcagccta    52440
gccctcagcg gggagccggg gccccggagt tgggagctgc tccagaggag gagctggcag   52500
cattacaact gggcccacc caccacgagt gtgaggccgg tccccccat gacacgctgc     52560
```

```
gcctcactgc attgcccgac tacaccctga ccctgcggcg ctccccggat gacatcccac    52620
tcatgacccc caacaccatc actatgatcc ccaactccct ggtagggctg cagacattgc    52680 accectataa caccttttgcc gcagggttca acagtaccgg gctgcccac tcacactcca    52740 ctacccgggt atagctccaa ctcagagcac agccaatctc caggctccct ccctcccaga    52800
tccaggaaca catgcacaca cacacacaca cacacgcaga cacacacaca cacacacata    52860
tatgtatacg cacgcaccca caccctacag cagatccacc tgcacaaaca tagacagatg    52920
tggacatgca cccgcatgta caaaaacaca aatacgaag taaacctgaa caaacccttt    52980
aaatggggac gcagatgagt cctcggtaaa ccgaggaccc atgaaacagc agctgaagcc    53040
agctccctga atctgaccac agacactcct gggggggcctg aaagcaacag ctggacaccc    53100
ccttggtgct cgccttcggc ctctcttgga actgcaccac cgaccaactc cagacttggg    53160
agctttaaag agcaggatag ctcttcctcc ccaggacttg gtcttttttc tgggtcttgt    53220
tttgttgatt tttctttttt aattttggaa caaatgcttt tccaacccat gagtgctaag    53280
agcctctgga agggagggct tcaggcccga aggtctctct ggctctagga cccccagtgc    53340
tcacacaatc agaccaagga acaagacccc caggaaggaa acagatttaa gcaagaccat    53400
ggggtggaag gagaaagggg ctagcactgg atggagctgg agggtcgtag gggagagatc    53460
tccaactctc tctgtgtccg tgtggagggc tgcagagcct gcaggtgac ctgcttcccc    53520 aaaggccaac agcattggcc tggccagacc aggtgacctt agatttggtg aacaacgtac    53580
tatggaagcc acatcactat tgggccccca ggtctgatct gggttttgcc tctgcccttg    53640
gggaaatgct atcagaaatt cgccccattt tctttacagt cttttgtgtc tgtcatttct    53700
ctttcaaaaa ggcggtgttt tttgttgttg ttggttttttt tttttttta aagaaaagtt    53760 cttaaaacac taacggaaac ccatggagtt tgtcctttgt aaaaattta aacacagtgt    53820 cttgatataa aaataaaaaa tccagttagc actcccaacc tgcctccctt gcacaggcct    53880
tgccccaaca gacctccgaa cagggtgcct ctgcgggctg ggaatcaggc aatcaggcag    53940 cctcccctg cctcctgtat ctttaagctg agtctgggct gcactgtgcg gggttggggg    54000
ttgggggttg gggggggttgg gggttttggg ggcccctgc atgaaggcnt ctccaatctt    54060
aatcaggttg ctcttcccat cccctgccc ccagcgcgct gggttcctgc agctgaagcc    54120
tcctctcagc acttcaggcc tcctaatgaa atggcaaaa tacttccttc cttctctgca    54180
ccgctgcggc ctcctcctcc tcttacttct cctcctcctc ctctgntgca accaccctgc    54240
cctcaccttg gactggggc tgggaggagg tttgacctct aacgtgctga aattcttttct    54300 cctatctgaa tccagtgcag cgtcagacgt ggactccctg gccttgagtg actgacagag    54360
cagaggccct ctccttcccc agggatactt gtttgctgct ctgtgaatta gaactggaga    54420
agtccttggg gccctgggag cgattttct acaggattgt gatcagtgac tccctatcaa    54480
ccctggggca tggattcagt ggggcctcac agggttagca ttatgggatt tcatattatt    54540
ctcagtgact tgaaagactg aactgggagt gtgctcggca agtatgatag ttgggtgggg    54600
ttgctgatac ctcagaaagc aggaatagaa ttcttcaaat gaccctgata aaatgaggga    54660
gatgaaccat cacaaggagg accatgttca gagaggacga acacaggtag tgtgtacaaa    54720
gaccaaaacc tagaactaat acactaatat ggtacactgg agatgggcag tgattgactt    54780
gacacaagta tagttaaaaa gaagaagaac tggggagatg gtgtaagggt acatcacaag    54840
tgagtccatg gtgtaaaact ggttttttccc cctccttttcc tcacacccctt ctttcctttc    54900
```

-continued

```
ttttttccaa aactaatgtg gatcctgcat atagtaacaa aaacacagca tggaggatct    54960
gagaagtcat ccaagtgtga gttttagaac cagaagtcac ccgagagtca tctagtccaa    55020
cccatttatt ttatagttga ggaaatgggc ccagaaaagc ccgtcacagt tagtattaga    55080
aacagaccta gaatgccacc cagcactaca cgacccttgc catagtccca ctcaactcgt    55140
tccactctac ctgccattgg tcataccttt caaagcatga tgggtctacc cttggccaac    55200 acattttag caaaagtgga aagctagaga gggtctggag aagagcataa ataatgccac     55260
gggactaggt gctgtgtgtg tgtgcatgcg tgtgtgtg                            55298
```

<210> SEQ ID NO 2
<211> LENGTH: 6794
<212> TYPE: DNA
<213> ORGANISM: Homo sapiens

<400> SEQUENCE: 2

```
gaattcgcgg ccgcgtcgac ggcggccttc gggatcttga gctacgaaca ccggcccctg      60
aagcggccgc ggctgggggcc tcccgatgtt taccctcagg accccaaaca gaaggaggat     120
gaactgacgg ccttgaatgt aaaacaaggt ttcaataacc agcctgctgt ctctggggat     180
gagcatggca gtgccaagaa cgtcagcttc aatcctgcca agatcagttc caacttcagc     240
agcattattg cagagaaatt acgttgtaat accttcctg cactggtcg caggaagccc       300 caagtgaacc agaaggataa cttctggctg tgactgcac gatcccagag tgccattaac      360
acttggttca ctgacttggc tggcaccaag ccactcacgc aactagccaa aaaggtcccc     420
attttcagta agaaggaaga ggtgtttggg tacttagcca aatacacagt gcctgtgatg     480
cgggctgcct ggctcattaa gatgacctgt gcctactatg cagcaatctc tgagaccaag     540
gttaagaaga gacatgttga ccctttcatg gaatggactc agatcatcac caagtactta     600
tgggagcagt tacagaagat ggctgaatac taccggccag ggcctgcagg aagtgggggc     660
tgtggttcca cgatagggcc cttgccccat gatgtagagg tggcaatccg gcagtgggat     720
tacaccgaga agctggccat gttcatgttt caggatggaa tgctggacag acatgagttc     780
ctgacctggg tgcttgagtg ttttgagaag atccgccctg gagaggatga attgcttaaa     840
ctgctgctgc ctctgcttct ccgatactct ggggaatttg ttcagtctgc ataccctgtcc    900 cgccggcttg cctacttctg tacacggaga ctggccctgc agctggatgg tgtgagcagt     960
cactcatctc atgttatatc tgctcagtca acaagcacgc tacccaccac ccctgctcct    1020 cagccccaa ctagcagcac accctcgact cccttagtg acctgcttat gtgccctcag      1080
caccggcccc tggttttttgg cctcagctgt atcctacaga ccatcctcct gtgctgtcct    1140
agtgccttgg tttggcacta ctcactgact gatagcagaa ttaagaccgg ctcaccactt     1200
gaccacttgc ctattgcccc gtccaacctg cccatgccag agggtaacag tgccttcact     1260
cagcaggtcc gtgcaaagtt gcgggagatc gagcagcaga tcaaggagcg gggacaggca     1320
gttgaagttc gctggtcttt cgataaatgc caggaagcta ctgcaggctt caccattgga     1380
cgggtacttc atactttgga agtgctggac agccatagtt ttgaacgctc tgacttcagc     1440
aactctcttg actcccttttg taaccgaatc tttggattgg gacctagcaa ggatgggcat    1500
gagatctcct cagatgatga tgctgtggtg tcattgctat gtgaatgggc tgtcagctgc     1560
aagcgttctg gtcggcatcg tgctatggtg gtagccaagc tcctggagaa gagacaggcg     1620
gagattgagg ctgagcgttg tggagaatca gaagccgcag atgagaaggg ttccatcgcc     1680
tctggctccc tttctgctcc cagtgctccc attttccagg atgtcctcct gcagtttctg    1740
```

```
gatacacagg ctcccatgct gacggaccct cgaagtgaga gtgagcgggt ggaattcttt      1800
aacttagtac tgctgttctg tgaactgatt cgacatgatg tttctccca caacatgtat      1860 acttgcactc tcatctcccg agggaccttt gcctttggag cccctggtcc ccggcctccc      1920 tctcccttg atgatcctgc cgatgaccca gagcacaagg aggctgaagg cagcagcagc       1980
agcaagctgg aagatccagg gctctcagaa tctatggaca ttgaccctag ttccagtgtt      2040
ctctttgagg acatggagaa gcctgatttc tcattgttct cccctactat gccctgtgag      2100
gggaagggca gtccatcccc tgagaagcca gatgtcgaga aggaggtgaa gccccacccc      2160
aaggagaaga ttgaagggac ccttgggggtt ctttacgacc agccacgaca cgtgcagtac     2220
gccacccatt ttcccatccc ccaggaggag tcatgcagcc atgagtgcaa ccagcggttg      2280
gtcgtactgt ttgggtggg aaagcagcga gatgatgccc gccatgccat caagaaaatc       2340
accaaggata tcttgaaggt tctgaaccgc aaagggacag cagaaactga ccagcttgct      2400
cctattgtgc ctctgaatcc tggagacctg acattcttag gtggggagga tgggcagaag      2460
cggcgacgca accggcctga agccttcccc actgctgaag atatctttgc taagttccag      2520
cacctttcac attatgacca acaccaggtc acggctcagg tctcccggaa tgttctggag      2580
cagatcacga gctttgccct tggcatgtca taccacttgc ctctggtgca gcatgtgcag      2640
ttcatcttcg acctcatgga atattcactc agcatcagtg gcctcatcga ctttgccatt      2700
cagctgctga atgaactgag tgtagttgag gctgagctgc ttctcaaatc ctcggatctg      2760
gtgggcagct acactactag cctgtgcctg tgcatcgtgg ctgtcctgcg gcactatcat      2820
gcctgcctca tcctcaacca ggaccagatg gcacaggtct tgagggggct gtgtggcgtc      2880
gtgaagcatg ggatgaaccg gtccgatggc tcctctgcag agcgctgtat ccttgcttat      2940
ctctatgatc tgtacacctc ctgtagccat ttaaagaaca aatttgggga gctcttcagc      3000
gacttttgct caaaggtgaa gaacaccatc tactgcaacg tggagccatc ggaatcaaat      3060
atgcgctggg cacctgagtt catgatcgac actctagaga accctgcagc tcacaccttc      3120
acctacacgg ggctaggcaa gagtcttagt gagaaccctg ctaaccgcta cagctttgtc      3180
tgcaatgccc ttatgcacgt ctgtgtgggg caccatgatc ccgatagggt gaatgacatc      3240
gcaatcctgt gtgcagagct gaccggctat tgcaagtcac tgagtgcaga atggctagga      3300
gtgcttaagg ccttgtgctg ctcctctaac aatggcactt gtggtttcaa cgatctcctc      3360
tgcaatgttg atgtcagtga cctatctttt catgactcgc tggctacttt tgttgccatc      3420
ctcatcgctc ggcagtgttt gctcctggaa gatctgattc gctgtgctgc catcccttca      3480
ctccttaatg ctgcttgtag tgaacaggac tctgagccag gggcccggct tacctgccgc      3540
atcctccttc acctttcaa gacaccgcag ctcaatcctt gccagtctga tggaaacaag       3600
cctacagtag gaatccgctc ctcctgcgac cgccacctgc tggctgcctc ccagaaccgc      3660
atcgtggatg gagccgtgtt tgctgttctc aaggctgtgt tgtacttgg ggatgcggaa       3720 ctgaaaggtt caggcttcac tgtgacagga ggaacagaag aacttccaga ggaggaggga      3780
ggaggtggca gtggtggtcg gaggcagggt ggccgcaaca tctctgtgga gacagccagt      3840
ctggatgtct atgccaagta cgtgctgcgc agcatctgcc aacaggaatg ggtaggagaa      3900
cgttgcctta agtctctgtg tgaggacagc aatgacctgc aagacccagt gttgagtagt      3960
gcccaggcgc agcgcctcat gcagctcatt tgctatccac atcgactgct ggacaatgag      4020 gatgggggaaa accccagcg gcagcgcata aagcgcattc tccagaactt ggaccagtgg      4080
```

-continued

```
accatgcgcc agtcttcctt ggagctgcag ctcatgatca agcagacccc taacaatgag   4140
atgaactccc tcttggagaa catcgccaag gccacaatcg aggttttcca acagtcagca   4200
gagacagggt catcttctgg aagtactgca agcaacatgc ccagcagcag caagaccaag   4260
cctgtgctca gctctctaga gcgctctggt gtatggctgg tggcccccct cattgctaaa   4320
ctgcccacct cagtccaggg acatgtgtta aaggctgctg gggaagaatt ggagaagggt   4380
cagcacctgg gttcctcttc acgcaaagaa cgtgatcgac aaaagcagaa gagcatgtcc   4440
ctattgagcc agcagccctt cttatcgctg gtgctaacat gtctgaaagg caggatgaa    4500
caacgcgagg gactccttac ctccctctac agccaggtgc accagattgt gaataattgg   4560
cgagatgacc agtacttaga tgattgcaaa ccaaagcagc ttatgcatga ggcactcaaa   4620
ctgcggctca acctggtggg gggcatgttt gacacggtgc agcgcagcac ccagcagacc   4680
acggagtggg ccatgctcct cctggagatc atcatcagcg gcactgtcga catgcagtcc   4740
aacaatgagc tcttcactac tgtgttggac atgctgagcg tgctcatcaa tgggacattg   4800
gctgcagaca tgtctagcat ctcgcaaggt agcatggagg aaaacaagcg tgcatacatg   4860
aacctggcga agaagttgca gaaggagttg ggggagcgcc agtcagacag tctggaaaag   4920
gttcgccagc tgctgccact gcccaagcag acccgagatg tcatcacgtg tgagccacag   4980
ggctccctta tcgataccaa gggcaacaag attgctggct tcgattccat cttcaagaag   5040
gagggtctac agttttccac caaacagaag atctcgccct gggatctttt tgaggggttg   5100
aagccgtcag caccactctc ttggggctgg tttggaacag tccgagtgga ccggcgagtg   5160
gctcgaggag aggagcagca gcggttgctg ctctaccaca cacacctgag gccccggccc   5220
cgcgcctatt acctggagcc actgccactg cccccagaag atgaggagcc gcctgctcct   5280
accctgctag agcctgagaa aaaggctcca gagcccccca aaactgacaa accgggggct   5340
gctccaccca gtactgagga acgcaagaag aagtccacca agggcaagaa acgcagccag   5400
ccagctacca agacagagga ctatggaatg ggcccgggtc ggagcggccc ttatggtgtg   5460
acagtgcctc cggacctcct gcaccaccca aaccctggtt ctataacaca ccttaactac   5520
aggcaaggct ccataggcct gtacacccag aaccagccac tacctgcagg tggccctcgt   5580
gtggacccat accgtcctgt gcgcttacca atgcagaagc tgcccacccg accaacttac   5640
cctggagtgc tgcccacaac catgactggc gtcatgggtt tagaaccctc ctcttataag   5700
acctctgtgt accggcagca gcaacctgcg gtgcccaag acagcgcct tcgcaacag    5760
ctccagagtc agggcatgtt gggacagtca tctgtccatc agatgactcc cagctcttcc   5820
tacggtttgc agcttcccca gggctatact ccttatgttt ctcatgtggg attgcagcaa   5880
cacacaggcc ctgcaggtac catggtgccc cccagctact ccagccagcc ttaccagagc   5940
acccaccctt ctaccaatcc tactcttgta gatcctaccc gccacctgca acagcggccc   6000
agtggctatg tgcaccagca ggcccccacc tatggacatg gactgacctc cactcaaagg   6060
ttttcacacc agacactgca gcagacaccc atgataagta ccatgactcc aatgagtgcc   6120
cagggcgtcc aggcaggcgt ccgttcaaca gccatcctac ctgagcagca gcagcagcag   6180
caacagcagc aacagcaaca gcagcagcag cagcaacagc aacagcagca gcagcagcag   6240
cagtaccaca tccggcagca gcagcagcag cagatcctgc ggcagcagca gcaacagcaa   6300
cagcagcagc agcagcagca gcaacagcaa cagcagcagc agcaacagca acaacagcaa   6360
caccagcagc aacagcagca acaggcggct cctccccaac cccagcccca gtcccagccc   6420
cagttccagc gccaggggct tcagcagacc cagcagcagc aacagacagc agctttggtc   6480
```

```
cggcaacttc aacaacagct ctctaatacc cagccacagc ccagtaccaa catatttgga    6540
cgctactgag ccacctggag gaactgcttg tgcactggat gtggcccac cctttcctct    6600 taattcccaa tcccattcct gggctagcac cagtagtggt tggggccctc ccctcaggct    6660
ccatttttaa taagttttta gtattttgt taatgtgagg cattgagctg ttgggttttg     6720
tatattattt atatagagac cccagagctg ttgcacccaa tacacagagc ttctttgcaa    6780
aaaaaaaaaa aaaa                                                      6794
```

<210> SEQ ID NO 3
<211> LENGTH: 1764
<212> TYPE: DNA
<213> ORGANISM: Homo sapiens

<400> SEQUENCE: 3

```
gaattcccgg gtcgacccac gcgtccgtgt gaccctggag tctgcctctc ctgccagtcc      60
ccctgcccgg aacatgtggc tgcggcttgg cccgccctcg ctgtccctga gccccaagcc     120
cacggttggc aggagcctgt gcctcaccct gtggttcctc agtttggcgc tgagggccag     180
tacccaggcc ccagcaccca cagtcaacac tcactttggg aagctaaggg gtgcccgagt     240
accactgccc agtgagatcc tggggcctgt ggaccaatac ctgggggtgc cctacgcagc     300
tcccccgatc ggcgagaaac gtttcctgcc ccctgaacca cccccatcct ggtcgggcat     360
ccggaacgcc acacactttc ccccagtgtg ccccagaac atccacacag ctgtgcccga     420
agtcatgctg ccggtctggt tcactgccaa cttggatatc gtcgctactt acatccagga     480
gcccaacgaa gactgtctct acctgaacgt ctatgtgccg acggaggatg taaagcggat     540
ttccaaggaa tgcgcccgaa agcccaacaa gaaaatttgt aggaaaggaa gatccggcgc     600
taagaaacag ggcgaggact tagcggataa tgacggggat gaagatgaag acatccggga     660
cagtggtgct aaacccgtca tggtctacat ccacggaggc tcttacatgg aagggacagg     720
caacatgatt gatggcagca tcctcgccag ttatggcaat gtcatcgtca tcaccctcaa     780
ctatcgggtt ggagtgctag gtttcctgag tactggagat caggctgcca agggcaacta     840
tgggctcctt gaccagatcc aggccctccg ctgggtgagc gagaatattg ccttcttcgg     900
gggagacccc cgccggatca ctgtctttgg ctcgggcatt ggtgcatcct gcgtcagcct     960
cctcacgttg tcacatcact cagagggact tttccagaga gccatcatcc aaagtggctc    1020
tgctctgtcc agctgggctg tgaactacca accagtgaag tacaccagcc tgctggcaga    1080
caaagtgggc tgtaatgtgc tggacaccgt ggatatggtg gactgtcttc ggcaaaagag    1140
tgccaaggag ctggtagagc aggacatcca gccagcccgc taccacgtgg cctttggccc    1200
tgtgattgat ggtgatgtca ttcctgatga ccctgagatc ctcatggagc agggcgagtt    1260
cctcaactat gacatcatgc taggtgtcaa ccagggcgag ggtctcaagt ttgtggaagg    1320
ggtggtggac cctgaggatg gtgtctctgg cactgacttt gactattccg tctccaattt    1380
tgtggacaat ctgtatggct atcctgaggg taaggacacc ctgcgagaga ccatcaagtt    1440
catgtataca gactgggcag accgtgacaa ccctgagacc cgccgtaaaa cactggtggc    1500
actcttcact gaccaccagt gggtggagcc ctcagtggtg acagccgatc tgcatgcccg    1560
ctacggctcg cctacctact tctacgcctt ctatcatcac tgccagaacc tcatgaagcc    1620
tgcttggtca gatgcagctc atgggatga agtaccctat gttttgggg ttcctatggt     1680 aggccccact gaccttttcc cctgcaactt ctccaagaat gatgttatgc tcaaaaaaaa    1740
```
aaaaaaaggg cggccgctct aaag            1764

<210> SEQ ID NO 4
<211> LENGTH: 2818
<212> TYPE: DNA
<213> ORGANISM: Homo sapiens

<400> SEQUENCE: 4

| | | | | | |
|---|---|---|---|---|---|
| ctcgggcatt | ggtgcatcct | gcgtcagcct | cctcacgttg | tcacatcact | cagagggact | 60 |
| tttccagaga | gccatcatcc | aaagtggctc | tgctctgtcc | agctgggctg | tgaactacca | 120 |
| accagtgaag | tacaccagcc | tgctggcaga | caaagtgggc | tgtaatgtgc | tggacaccgt | 180 |
| ggatatggtg | gactgtcttc | ggcaaaagag | tgccaaggag | ctggtagagc | aggacatcca | 240 |
| gccagcccgc | taccacgtgg | cctttggccc | tgtgattgat | ggtgatgtca | ttcctgatga | 300 |
| ccctgagatc | ctcatggagc | agggcgagtt | cctcaactat | gacatcatgc | taggtgtcaa | 360 |
| ccagggcgag | ggtctcaagt | tgtggaagg | ggtggtggac | cctgaggatg | gtgtctctgg | 420 |
| cactgacttt | gactattccg | tctccaattt | tgtggacaat | ctgtatggct | atcctgaggg | 480 |
| taaggacacc | ctgcgagaga | ccatcaagtt | catgtataca | gactgggcag | accgtgacaa | 540 |
| ccctgagacc | cgccgtaaaa | cactggtggc | actcttcact | gaccaccagt | gggtggagcc | 600 |
| ctcagtggtg | acagccgatc | tgcatgcccg | ctacggctcg | cctacctact | tctacgcctt | 660 |
| ctatcatcac | tgccagagcc | tcatgaagcc | tgcttggtca | gatgcagctc | atggggatga | 720 |
| agtaccctat | gttttttggg | ttcctatggt | aggccccact | gaccttttcc | cctgcaactt | 780 |
| ctccaagaat | gatgttatgc | tcagtgctgt | cgtcatgacc | tattggacca | actttgccaa | 840 |
| gactggggat | cccaacaagc | cggtccccca | ggacaccaag | ttcattcaca | ccaaggccaa | 900 |
| ccgctttgag | gaagtggcct | ggtccaaata | caatccccga | ccagctctac | cttcacat | 960 |
| cgggctgaaa | ccaagggtcc | gagatcatta | ccgggccact | aagtggggct | tttggaaaca | 1020 |
| tctggtgccc | cacctataca | acctgcatga | catgttccac | tatcgtccca | ccaccaa | 1080 |
| agtgccgcct | ccggatacca | cccacagctc | ccacatcacc | cgcaggccca | atggcaagac | 1140 |
| ctggagcacc | aagcggccag | ccatctcacc | tgcctacagc | aacgagaatg | cccaggggtc | 1200 |
| ctggaacggg | gaccaggatg | cagggccact | cctggtggag | aaccctcgtg | actactccac | 1260 |
| tgaattaagt | gtcaccatcg | ccgtgggggc | ctccctcctg | ttccttaacg | ttctggcctt | 1320 |
| cgctgccctc | tactaccgta | aggacaaacg | gcgccaggag | ccctgcggc | agcctagccc | 1380 |
| tcagcgggga | gccggggccc | cggagttggg | agctgctcca | gaggaggagc | tggcagcatt | 1440 |
| acaactgggc | cccaccccac | acgagtgtga | ggccggtccc | cccatgaca | cgctgcgcct | 1500 |
| cactgcattg | cccgactaca | ccctgaccct | gcggcgctcc | ccggatgaca | tcccactcat | 1560 |
| gaccccaac | accatcacta | tgatccccaa | ctccctggta | gggctgcaga | cattgcaccc | 1620 |
| ctataacacc | tttgccgcag | ggttcaacag | taccgggctg | ccccactcac | actccactac | 1680 |
| ccgggtatag | ctccaactca | gagcacagcc | aatctccagg | ctccctcccct | cccagatcca | 1740 |
| ggaacacatg | cacacacaca | cacacacaca | cgcagacaca | cacacacaca | cacatatatg | 1800 |
| tatacgcacg | cacccacacc | ctacagcaga | tccacctgca | caaacataga | cagatgtgga | 1860 |
| catgcacccg | catgtacaaa | aacacaaata | cggaagtaaa | cctgaacaaa | ccctttaaat | 1920 |
| ggggacgcag | atgagtcctc | ggtaaaccga | ggacccatga | acagcagct | gaagccagct | 1980 |
| ccctgaatct | gaccacagac | actcctgggg | ggcctgaaag | caacagctgg | acacccctt | 2040 |
| ggtgctcgcc | ttcggcctct | cttggaactg | caccaccgac | caactccaga | cttgggagct | 2100 |

```
ttaaagagca ggatagctct tcctccccag gacttggtct tttttctggg tcttgttttg   2160 ttgattttc ttttttaatt ttggaacaaa tgcttttcca acccatgagt gctaagagcc    2220
tctggaaggg agggcttcag gcccgaaggt ctctctggct ctaggacccc cagtgctcac   2280
acaatcagac caaggaacaa gaccccccagg aaggaaacag atttaagcaa gaccatgggg  2340
tggaaggaga aagggggctag cactggatgg agctggaggg tcgtagggga gagatctcca  2400
actctctctg tgtccgtgtg gagggctgca gagcctgcag ggtgacctgc ttccccaaag   2460
gccaacagca ttggcctggc cagaccaggt gaccttagat ttggtgaaca acgtactatg   2520
gaagccacat cactattggg cccccaggtc tgatctgggt tttgcctctg cccttgggga   2580
aatgctatca gaaattcgcc ccattttctt tacagtcttt tgtgtctgtc atttctcttt   2640
caaaaaggcg gtgttttttg ttgttgttgg tttttttttt tttttaaaga aaagttctta   2700
aaacactaac ggaaacccat ggagtttgtc ctttgtaaaa attttaaaca cagtgtcttg   2760
atataaaaat aaaaaatcca gttagcactc ccaaaaaaaa aaaaaaaaa aaaaaaa      2818

<210> SEQ ID NO 5
<211> LENGTH: 4233
<212> TYPE: DNA
<213> ORGANISM: Homo sapiens
<220> FEATURE:
<221> NAME/KEY: misc_feature
<222> LOCATION: (3)..(3)
<223> OTHER INFORMATION: n is not determined
<221> NAME/KEY: misc_feature
<222> LOCATION: (4171)..(4171)
<223> OTHER INFORMATION: n is not determined
<221> NAME/KEY: misc_feature
<222> LOCATION: (4179)..(4179)
<223> OTHER INFORMATION: n is not determined
<221> NAME/KEY: misc_feature
<222> LOCATION: (4181)..(4181)
<223> OTHER INFORMATION: n is not determined
<221> NAME/KEY: misc_feature
<222> LOCATION: (4197)..(4197)
<223> OTHER INFORMATION: n is not determined
<221> NAME/KEY: misc_feature
<222> LOCATION: (4228)..(4228)
<223> OTHER INFORMATION: n is not determined

<400> SEQUENCE: 5
tcngcacgcg gaaagaagca catggctgaa tatcgacggt ttccatatgg ggattggtgg    60
cgacgactcc tggagcccgt cagtatcggc ggaattcgcg gccgcgtcga cctgatctcg   120
gggattcggg tgcggagccc ttggcctgga ggcgatatgg gtggtccgtg gcccggttca   180
gtcgcttgca gcagcccggg gaacaggcct gtctggccct gagggagtcc cctttctgaa   240
gctgtggtgc ttggacgacc tgctctctac attgctgggc acctgtaggt gtccctcgag   300
agctcagttt tgaggttcaa gtcagtgtgg ccatgaaggg gctgcctatt gggctgatgc   360
tgtgaccctg gagtctgcct ctcctgccag tcccctgcc cggaacatgt ggctgcggct   420
tggcccgccc tcgctgtccc tgagccccaa gccacggtt ggcaggagcc tgtgcctcac    480
cctgtggttc ctcagtttgg cgctgagggc cagtacccag gccccagcac ccacagtcaa   540
cactcacttt gggaagctaa ggggtgcccg agtaccactg cccagtgaga tcctggggcc   600
tgtggaccaa tacctggggg tgccctacgc agctcccccg atcggcgaga aacgtttcct   660 gcccctgaa ccaccccat cctggtcggg catccggaac gccacacact ttccccagt     720 gtgcccccag aacatccaca cagctgtgcc cgaagtcatg ctgccggtct ggttcactgc   780
caacttggat atcgtcgcta cttacatcca ggagcccaac gaagactgtc tctacctgaa   840
```

-continued

```
cgtctatgtg ccgacggagg atggatccgg cgctaagaaa cagggcgagg acttagcgga    900
taatgacggg gatgaagatg aagacatccg ggacagtggt gctaaacccg tcatggtcta    960
catccacgga ggctcttaca tggaagggac aggcaacatg attgatggca gcatcttcgc   1020
cagttatggc aatgtcatag tcatcaccct caactatcgg gttggagtga taggtttcct   1080
gagtactgga gatcaggctg ccaagggcaa ctatgggctc cttgaccaga tccaggccct   1140
ccgctgggtg agcgagaata ttgccttctt cggggagac ccccgccgga tcactgtctt    1200
tggctcgggc attggtgcat cctgcgtcag cctcctcacg ttgtcacatc actcagaggg   1260
actttttccag agagccatca tccaaagtgg ctctgctctg tccagctggg ctgtgaacta   1320
ccaaccagtg aagtacacca gcctgctggc agacaaagtg ggctgtaatg tgctggacac   1380
cgtggatatg gtggactgtc ttcggcaaaa gagtgccaag gagctggtag agcaggacat   1440
ccagccagcc cgctaccacg tggcctttgg ccctgtgatt gatggtgatg tcattcctga   1500
tgaccctgag atcctcatgg agcagggcga gttcctcaac tatgacatca tgctaggtgt   1560
caaccagggc gagggtctca gtttgtgga aggggtggtg gaccctgagg atggtgtctc    1620
tggcactgac tttgactatt ccgtctccaa ttttgtggac aatctgtatg ctatcctga    1680
gggtaaggac accctgcgag agaccatcaa gttcatgtat acagactggg cagaccgtga   1740
caaccctgag acccgccgta aaacactggt ggcactcttc actgaccacc agtgggtgga   1800
gccctcagtg gtgacagccg atctgcatgc ccgctacggc tcgcctacct acttctacgc   1860
cttctatcat cactgccaga gcctcatgaa gcctgcttgg tcagatgcag ctcatgggga   1920
tgaagtaccc tatgttttg gggttcctat ggtaggcccc actgacccttt tcccctgcaa    1980
cttctccaag aatgatgtta tgctcagtgc tgtcgtcatg acctattgga ccaactttgc   2040
caagactggg gatcccaaca agccggtccc ccaggacacc aagttcattc acaccaaggc   2100
caaccgcttt gaggaagtgg cctggtccaa atacaatccc cgagaccagc tctaccttca   2160
catcgggctg aaaccaaggg tccgagatca ttaccgggcc actaaggtgg ccttttggaa   2220
acatctggtg ccccacctat acaacctgca tgacatgttc cactatacgt ccaccaccac   2280
caaagtgccg cctccggata ccacccacag ctcccacatc acccgcaggc caatggcaa    2340
gacctggagc accaagcggc cagccatctc acctgcctac agcaacgaga atgcccaggg   2400
gtcctggaac ggggaccagg atgccagggc cactcctggt ggagaaccct cgtgactact   2460
ccactgaatt aagtgtcacc atcgccgtgg gggcctccct cctgttcctt aacgttctgg   2520
ccttcgctgc cctctactac cgtaaggaca acggcgcca ggagccctg cggcagccta    2580
gccctcagcg gggagccggg gccccggagt tgggagctgc tccagaggag gagctggcag   2640
cattacaact gggccccacc caccacgagt gtgaggccgg tcccccccat gacacgctgc   2700
gcctcactgc attgcccgac tacaccctga ccctgcggcg ctcccggat gacatcccac    2760
tcatgacccc caacaccatc actatgatcc ccaactccct ggtagggctg cagacattgc   2820
accccctataa caccttttgcc gcagggttca acagtaccgg gctgccccac tcacactcca   2880
ctacccgggt atagctccaa ctcagagcac agccaatctc caggctccct ccctcccaga   2940
tccaggaaca catgcacaca cacacacaca cacgcagaca cacacacaca cacacata    3000
tatgtatacg cacgcaccca cccctacag cagatccacc tgcacaaaca tagacagatg    3060
tggacatgca cccgcatgta caaaaacaca aatacgaag taaacctgaa caaacccttt    3120
aaatggggac gcagatgagt cctcggtaaa ccgaggaccc atgaaacagc agctgaagcc   3180
```

-continued

| | |
|---|---|
| agctccctga atctgaccac agacactcct ggggggcctg aaagcaacag ctggacaccc | 3240 |
| ccttggtgct cgccttcggc ctctcttgga actgcaccac cgaccaactc cagacttggg | 3300 |
| agctttaaag agcaggatag ctcttcctcc ccaggacttg gtcttttttc tgggtcttgt | 3360 |
| tttgttgatt tttctttttt aattttggaa caaatgcttt tccaacccat gagtgctaag | 3420 |
| agcctctgga agggagggct tcaggcccga aggtctctct ggctctagga cccccagtgc | 3480 |
| tcacacaatc agaccaagga acaagacccc caggaaggaa acagatttaa gcaagaccat | 3540 |
| ggggtggaag gagaaagggg ctagcactgg atggagctgg agggtcgtag gggagagatc | 3600 |
| tccaactctc tctgtgtccg tgtggagggc tgcagagcct gcaggtgac ctgcttcccc | 3660 |
| aaaggccaac agcattggcc tggccagacc aggtgacctt agatttggtg aacaacgtac | 3720 |
| tatggaagcc acatcactat tgggccccca gtctgatct gggttttgcc tctgcccttg | 3780 |
| gggaaatgct atcagaaatt cgcccccattt tctttacagt cttttgtgtc tgtcatttct | 3840 |
| cttcaaaaaa ggcggtgttt tttgttgttg ttggtttttt ttttttttta aagaaaagtt | 3900 |
| cttaaaacac taacgaaaaa aaaagtcga cgcggccgcg aattccagct gagcgccggt | 3960 |
| cgctaccatt accagttggt ctggtgtcaa aaataataat aaccgggcag gccatgtctg | 4020 |
| cccgtatttc gcgtaaggaa atccattgta ctgccggacc accgactgtg agccactccg | 4080 |
| gccatggcgt acgcactgac ctgcttactg atttgtaaaa ccggtccggc catcacgctc | 4140 |
| acataacgtc cacgcaggct ctcatagtga nacgtatcnt nccccggtca tcactgngct | 4200 |
| gctcttttc gacgcggcga accccccngg cag | 4233 |

<210> SEQ ID NO 6
<211> LENGTH: 4436
<212> TYPE: DNA
<213> ORGANISM: Homo sapiens
<220> FEATURE:
<221> NAME/KEY: misc_feature
<222> LOCATION: (2)..(3)
<223> OTHER INFORMATION: n is not determined

<400> SEQUENCE: 6

| | |
|---|---|
| gnnrwtacgc tagcttgggt ggtcatatgg ccatggaggc cccggggatc cgaattcgcg | 60 |
| gccgcgtcga cggaacatgt ggctgcggct tggcccgccc tcgctgtccc tgagccccaa | 120 |
| gcccacggtt ggcaggagcc tgtgcctcac cctgtggttc ctcagtttgg cgctgagggc | 180 |
| cagtacccag gccccagcac ccacagtcaa cactcacttt gggaagctaa ggggtgcccg | 240 |
| agtaccactg cccagtgaga tcctggggcc tgtggaccaa tacctggggg tgccctacgc | 300 |
| agctccccccg atcggcgaga aacgtttcct gcccccctgaa ccaccccat cctggtcggg | 360 |
| catccggaac gccacacact ttcccccagt gtgcccccag aacatccaca cagctgtgcc | 420 |
| ccaagtcatg ctgccggtct ggttcactgc caacttggat atcgtcgcta cttacatcca | 480 |
| ggagcccaac gaagactgtc tctacctgaa cgtctatgtg ccgacggagg atggtgagtg | 540 |
| ctgcggccag gcactgtgcc ctccctgcct ccgcctgcc ctgctgtgtt tgtggccttgc | 600 |
| atgtggttgt gtgccctgca gcatgcatct gtctgtctgt gaaaatgctt ctaaccatca | 660 |
| ctctgcttgg cctcccaccc cctccctgt tcttccctct cccagcattg tccgagctcc | 720 |
| catgtgtgag tgacactgtt gccaggaggg gcctggcccg gctgagagc tctgacgggt | 780 |
| ctcggtccag tgctggatgg gggtcccctg ggggagtatg ggtcacggct ggcagctacc | 840 |
| cgcgggagga tgctggctcc accaggcccc cctgttgcca ttccacctgc ttcgaaaggt | 900 |
| ggtaggtgtg tgtggccaag ggcactgggt gtgtgggggg tggggcagca agcctggtgg | 960 |

-continued

```
gtgatgctta ggtgcctcct ctttcactag ctgatgcctc ctcccgcggg ggtcacacta    1020
aggtaagtga cagaaacaag gagatggtgg gacaggctct ctgccatgtg ccgcctgcag    1080
agcagctcag ctcttggggc ctgggggggtg ggggggtgcat gccctgggc agaggcctcc   1140 tgttattttt tagtttttta ttcattttac agtaaagcgg atttccaagg aatgcgcccg    1200
aaagcccaac aagaaaattt gtaggaaagg aggatccggc gctaagaaac agggcgagga    1260
cttagcggat aatgacgggg atgaagatga agacatccgg acagtggtg ctaaacccgt     1320 catggtctac atccacggag gctcttacat ggaagggaca ggcaacatga ttgatggcag    1380
catcctcgcc agttatggca atgtcatcgt catcaccctc aactatcggg ttggagtgct    1440
aggtttcctg agtactggag atcaggctgc caagggcaac tatgggctcc ttgaccagat    1500
ccaggccctc cgctgggtga gcgagaatat tgccttcttc gggggagacc cccgccggat    1560
cactgtcttt ggctcgggca ttggtgcatc ctgcgtcagc ctcctcacgt tgtcacatca    1620
ctcagaggga cttttccaga gagccatcat ccaaagtggc tctgctctgt ccagctgggc    1680
tgtgaactac caaccagtga agtacaccag cctgctggca gacaaagtgg gctgtaatgt    1740
gctggacacc gtggatatgg tggactgtct tcggcaaaag agtgccaagg agctggtaga    1800
gcaggacatc cagccagccc gctaccacgt ggcctttggc cctgtgattg atggtgatgt    1860
cattcctgat gaccctgaga tcctcatgga gcagggcgag ttcctcaact atgacatcat    1920
gctaggtgtc aaccagggcg agggtctcaa gtttgtggaa ggggtggtgg accctgagga    1980
tggtgtctct ggcactgact ttgactattc cgtctccaat tttgtggaca atctgtatgg    2040
ctatcctgag ggtaaggaca ccctgcgaga gaccatcaag ttcatgtata cagactgggc    2100
agaccgtgac aaccctgaga cccgccgtaa aacactggtg gcactcttca ctgaccacca    2160
gtgggtggag ccctcagtgg tgacagccga tctgcatgcc cgctacggct cgcctaccta    2220
cttctacgcc ttctatcatc actgccagag cctcatgaag cctgcttggt cagatgcagc    2280
tcatggggat gaagtaccct atgtttttgg ggttcctatg gtaggcccca ctgaccttt     2340 cccctgcaac ttctccaaga atgatgttat gctcagtgct gtcgtcatga cctattggac    2400
caactttgcc aagactgggg atcccaacaa gccggtcccc caggacacca agttcattca    2460
caccaaggcc aaccgctttg aggaagtggc ctggtccaaa tacaatcccc gagaccagct    2520
ctaccttcac atcgggctga accaagggt ccgagatcat taccgggcca ctaaggtggc    2580
cttttggaaa catctggtgc cccacctata caacctgcat gacatgttcc actatacgtc    2640
caccaccacc aaagtgccgc ctccggatac cacccacagc tcccacatca cccgcaggcc    2700
caatggcaag acctggagca ccaagcggcc agccatctca cctgcctaca gcaacgagaa    2760
tgcccagggg tcctggaacg gggaccagga tgcagggcca ctcctggtgg agaaccctcg    2820
tgactactcc actgaattaa gtgtcaccat cgccgtgggg gcctccctcc tgttccttaa    2880
cgttctggcc ttcgctgccc tctactaccg taaggacaaa cggcgccagg agcccctgcg    2940
gcagcctagc cctcagcggg gagccggggc cccggagttg ggagctgctc cagaggagga    3000
gctggcagca ttacaactgg gccccaccca ccacgagtgt gaggccggtc cccccatga    3060 cacgctgcgc ctcactgcat tgcccgacta caccctgacc ctgcggcgct ccccggatga    3120
catcccactc atgacccca acaccatcac tatgatcccc aactccctgg tagggctgca    3180
gacattgcac ccctataaca cctttgccgc agggttcaac agtaccgggc tgccccactc    3240
acactccact acccgggtat agctccaact cagagcacag ccaatctcca ggctccctcc    3300
```

-continued

| | |
|---|---|
| ctcccagatc caggaacaca tgcacacaca cacacacaca cacgcagaca cacacacaca | 3360 |
| cacacatata tgtatacgca cgcacccaca ccctacagca gatccacctg cacaaacata | 3420 |
| gacagatgtg gacatgcacc cgcatgtaca aaaacacaaa tacggaagta aacctgaaca | 3480 |
| aaccctttaa atggggacgc agatgagtcc tcggtaaacc gaggacccat gaaacagcag | 3540 |
| ctgaagccag ctccctgaat ctgaccacag acactcctgg ggggcctgaa agcaacagct | 3600 |
| ggacaccccc ttggtgctcg ccttcggcct ctcttggaac tgcaccaccg accaactcca | 3660 |
| gacttgggag ctttaaagag caggatagct cttcctcccc aggacttggt cttttttctg | 3720 |
| ggtcttgttt tgttgatttt tctttttttaa ttttggaaca aatgcttttc caacccatga | 3780 |
| gtgctaagag cctctggaag ggagggcttc aggcccgaag gtctctctgg ctctaggacc | 3840 |
| cccagtgctc acacaatcag accaaggaac aagaccccca ggaaggaaac agatttaagc | 3900 |
| aagaccatgg ggtggaagga gaaggggct agcactggat ggagctggag ggtcgtaggg | 3960 |
| gagagatctc caactctctc tgtgtccgtg tggagggctg cagagcctgc agggtgacct | 4020 |
| gcttccccaa aggccaacag cattggcctg ccagaccag gtgaccttag atttggtgaa | 4080 |
| caacgtacta tggaagccac atcactattg ggcccccagg tctgatctgg gttttgcctc | 4140 |
| tgcccttggg gaaatgctat cagaaattcg ccccatttc tttacagtct tttgtgtctg | 4200 |
| tcatttctct ttcaaaaagg cggtgttttt tgttgttgtt ggttttttt tttttttta | 4260 |
| aagaaaagtt cttaaaacac taacggaaac ccatggagtt tgtcctttgt aaaaatttta | 4320 |
| aacacagtgt cttgatataa aaataaaaaa tccagttagc cctcccaaaa aaaaaaaaaa | 4380 |
| aaaaaaaaaa rctcgagaga tctatgaatc gtagatactg aaaaaccccg caaccc | 4436 |

<210> SEQ ID NO 7
<211> LENGTH: 6558
<212> TYPE: DNA
<213> ORGANISM: Mus musculus

<400> SEQUENCE: 7

| | |
|---|---|
| gcacatggct gaatatcgac ggtttccata tggggattgg tggcgacgac tcctggagcc | 60 |
| cgtcagtatc ggcggaattc gcggccgcgt cgacaggagg atgaactgac ggctttgaat | 120 |
| gtaaaacaag gtttcaataa ccagcctgct gtctctgggg acgaacatgg cagtgccaag | 180 |
| aacgtcaact tcaatcctgc caagatcagt tccaacttca gcagcatcat cgcagagaag | 240 |
| ttaaggtgta atactctctc tgacactggt cgcaggaagt ccctaatgaa ccagaaggac | 300 |
| aacttctggc tggtgactgc aagatctcag agtgctatta cacctggtt cactgacctg | 360 |
| gctggcacca aaccactcac acacctagcc aaaaaggtcc ccattttcag taaaaaggaa | 420 |
| gaagtatttg ggtatttggc caaatacacg gtgcctgtga tgcgggctgc ctggctcatt | 480 |
| aagatgactt gtgcctacta tgcagcaatg tctgagacta aggttaagaa gaaaaatact | 540 |
| gctgacccct tcactgaatg gactcaaatc atcacaaagt acttgtggga gcagctacag | 600 |
| aagatggctg agtactatcg gccagggcct gcaggaagtg gaggctgtgg ttctactata | 660 |
| gggcctttgc cccatgatgt agagatggcc atcaggcagt gggattacaa tgagaagctc | 720 |
| gccttgttca tgtttcagga tggaatgctg acagacatg agttcctgac ttgggtgctt | 780 |
| gagtgttttg agaaaatacg ccctggagaa gatgaattgc ttaaattgct gcttccccta | 840 |
| ctgctgcgat actcagggga gtttgttcag tctgcctatc tgtcccgccg ccttgcctac | 900 |
| ttctgtaccc ggagattggc tctccagctg gatggtgtga gcagccactc atctcatgtc | 960 |
| atagctgctc agtcaacaag ttctctgccc actaccccag cacctcagcc cccaactagc | 1020 |

```
agtacaccct cgactccctt tagtgacctg cttatgtgcc ctcagcatcg tccctggtt    1080 tttggcctca gctgtatcct tcagaccatc cttctgtgtt gccctagtgc cctagtttgg    1140
cactactcat tgactgatag ccgaattaag accggctcac cacttgacca cctgcctatt    1200
gctccttcca acttgcccat gccagagggt aacagtgcct ttactcagca ggtccgtgca    1260
aaattacgag agatcgaaca acagatcaag gagcgtggac aagcagttga ggttcgctgg    1320
tcttttgata agtgccagga agctactgca ggtttcacca ttggacgggt gctccatact    1380
ttagaagtgc tggatagcca tagtttcgag cgctctgact ttagtaactc tcttgactcc    1440
ctttgtaatc gaatctttgg attggggcct agtaaggatg gtcatgagat ttcctctgat    1500
gatgatgctg tggtatcatt attgtgtgaa tgggctgtaa gctgcaaacg ctcaggtcgg    1560
catcgtgcta tggtagtagc caaactccta gagaagagac aagcagaaat tgaggctgag    1620
cgctgcggag aatctgaagc agctgatgag aagggctccg tcgcctctgg ttccctttcc    1680
gctcctagtg cacccatttt ccaggatgtc ctcctgcagt ttctggatac acaggctccc    1740
atgctgactg atccccgaag tgaaagtgag cgagtagaat tctttaactt ggtactgctc    1800
ttctgtgaac tgatccgaca tgatgtcttc tcccataata tgtacacctg cactctcatc    1860
tctcgggggg atcttgcatt tggagcccct ggtcctcggc ctccctctcc ctttgatgat    1920
cctacagatg atccagagcg caaggaggct gaaggcagca gcagcagcaa gctagaggac    1980
ccagggctct ctgaatctat ggacatcgac cctagttcca ctgtgctttt tgaggacatg    2040
gaaaagcctg atttctcatt gttctcccct actatgcctt gtgaggggaa gggaagccca    2100
tcccctgaga aaccagatgt cgaaaaggaa gtaaaacccc cagccaaaga gaagatcgag    2160
gggacacttg ggattctgta tgaccagcca cgacatgtgc agtatgccac acactttcca    2220
atcccacagg aggagtcatg cagccatgag tgcaaccagc ggttggtcgt actgtttggg    2280
gtggggaagc agcgagatga tgcccgccat gccatcaaga agattaccaa ggatatcctg    2340
aaggttctga atcgcaaggg gacagcagaa actgaccagc ttgctcctat tgtgcctctg    2400
aatcctggag acctgacatt cttaggtggg aagatgggc agaagcgacg acgcaaccgg    2460
cccgaagcct tccccactgc tgaagatatt tttgctaagt tccagcacct ttcccattat    2520
gaccaacacc aggtcacggc tcaggtctcc cggaacgttc tggagcagat cacgagcttc    2580
gcccttggca tgtcgtacca cttgcctctg gtgcagcatg tgcagttcat cttcgacctc    2640
atggaatatt cactgagcat cagtggcctc atcgactttg ccatccagtt actgaatgag    2700
ctgagtgtgg ttgaggcgga gctccttctc aaatcgtcgg atctggtggg cagctacact    2760
accagcctgt gcttatgtat cgtggctgtc cttcgacact atcatgcctg cctcatcctc    2820
aatcaggacc agatggcgca agtgtttgag gggctctgtg gcgtggtgaa acatggaatg    2880
aaccgttcag atggctcctc tgcagagcgc tgtatccttg cttatctcta tgatctgtat    2940
acctcctgta gccatttaaa gagcaaattt ggggagctct tcagtgactt ttgctcaaaa    3000
gtgaagaaca ccatctactg taacgtggag ccatcggaat ccaatatgcg ctgggcaccg    3060
gagttcatga ttgacactct ggagaaccct gccgctcaca ctttcaccta cacggggctc    3120
ggcaagagtc ttagtgagaa ccctgctaac cgctatagct ttgtgtgcaa tgctcttatg    3180
cacgtctgcg tgggccacca tgatcctgat agggtaaatg acatcgccat cctttgtgca    3240
gagctgaccg gctattgcaa gtccttgagt gctgagtggc taggagtact taaggccttg    3300
tgctgctcct cgaacaatgg cacttgtggt ttcaatgatc tcctgtgcaa cgtagacgtc    3360
```

-continued

```
agtgatttgt cttttcatga ttccttggct acttttgttg ctatcctcat cgcccgtcaa   3420
tgtttgctcc tagaagacct gattcgctgt gcagccatcc cttcactcct caatgctgct   3480
tgtagtgagc aggattctga gccaggagcc aggcttactt gccgaatcct cctccacctg   3540
ttcaagacgc cacaactcaa tccttgccag tctgatggaa acaaacctac tgttggaatc   3600
cggtcctcct gtgaccgcca cctgctggct gcctcccaga accgcatcgt ggatgggct   3660 gtgtttgctg ttctcaaggc tgtgtttgta ctcggagatg cggagctaaa aggttcaggc   3720
tttactgtgc cgggaggaac agaagaactt ccagaagagg agggaggagg tggtagtagc   3780
ggtcggagac agggtggccg caacatctct gtggagacag caagtctgga tgtctatgcc   3840
aagtacgtgc tgcgaagcat ctgccaacag gaatgggtag agaacgttg ccttaagtca   3900 ctgtgtgagg atagcaatga tctacaagac ccagtgttga gtagtgccca ggcccagcgc   3960
ctcatgcaac ttatctgcta cccacatcga ctgctggaca atgaggatgg agaaaacccc   4020
cagcggcagc gcattaaacg tattctcaag aatttagacc aatggaccat gcgccagtcc   4080
tctttggagc tacagttgat gatcaagcag accccccaaca ctgagatgaa ctctctcttg   4140
gagaacattg ccaaggccac aatcgaggtt ttccaacagt cagcagagac gggtcatct   4200 tctggaagta cagcaagcaa catgcccagc agcagcaaga ccaaacctgt gctcagctct   4260
ctagagcgat ctggtgtatg gttggtggct cctctcattg ccaaactgcc cacttcagtc   4320
cagggccatg tattaaaagc tgctggggag gaactggaaa aggtcagca cctgggctct   4380 tcttcccgta agaacgaga tcgacagaaa cagaagagca tgtccctgtt gagccaacag   4440
cctttcttat cactggtgct aacatgtctg aaaggacagg atgagcagcg cgagggactc   4500
ctggcctccc tccacagcca ggtgcaccag attgtgatta ttggcgaga aaaccagtac   4560 ttagatgatt gcaaaccaaa gcagctaatg catgaggcac tcaaactgcg gctcaacctg   4620
gtggggggca tgtttgacac tgtgcagcgt agtacccagc agactacaga gtgggcccag   4680
cttctccttg agatcatcat cagcggcact gtggacatgc agtctaacaa tgagctcttc   4740
actactgtgt tggacatgct gagcgtgctt atcaacggaa cgttggctgc agacatgtcc   4800
agtatctcgc aaggcagcat ggaggaaaac aagcgtgcat atatgaacct ggtgaagaag   4860
cttcagaagg acttggggga cgccaatca gacagtctgg agaaggttca ccaactgttg   4920
ccactaccca gcagaaccg agatgtcata acctgtgagc cacagggctc ccttattgac   4980
accaagggca caagattgc tggcttcgat tccatcttca agaaggaggg tctacaagtt   5040
tctaccaaac aaaagatctc tccctgggag ctttttgagg gcctgaagcc atcaacagca   5100
ccactgtcat gggcctggtt tggcacagtc cgagtggacc gcagagtggc acgaggggag   5160
gagcagcagc ggctgttgct ctatcatacc cacctgaggc ctcgacccag agcctattac   5220
ctggaaccac tacctctgcc cccagaagat gaggagccac cagcccctgc cctactagag   5280
cctgagaaaa aggctcctga gcccccaag actgacaaac caggggctgc tcctccgagc   5340
actgaggagc gcaaaaagaa gtctaccaag ggcaaaaaac gcagccagcc agccaccaag   5400
aacgaggact atggcatggg gccaggtcgg agtggcccct atggtgtgac agtgcctcca   5460
gaccttctac accatgcaaa tcctggttct atatcccacc ttagctacag gcaaagctcc   5520
atgggcctgt atacccaaaa ccagccacta cctgctggtg gccctcgtgt ggatccatac   5580
cgccccgtgc gattaccaat gcaaaagctg ccaactcgac caacttatcc cggtgtgctg   5640
cctacaacta tgtctactgt catgggccta gaaccctctt cttataagac atctgtatac   5700
cggcagcagc aacccacagt gccccaggga cagcgccttc gccaacagct ccagcagagt   5760
```

-continued

```
cagggatgt tgggacagtc atctgtccat cagatgaccc ctagttcttc ctatggtttg    5820
cagacttccc agctctcttc tccttctctc cagggctata catcctatgt ttctcatgtg    5880
ggattgcagc aacacacagg ccctgcagat cctacccgcc acctgcaaca gcggcccagt    5940
ggctatgtgc atcagcaggc cccaacctat gggcatggac tgacttccac tcaaaggttt    6000
tcacaccaga cactgcagca gacacccatg atgggtacca tgactccgtt gagtgcccag    6060
ggtgtccagg caggcgtccg ttcaacttcc atcctgcctg agcagcagca acaacaacag    6120
cagcaacaac aacagcagca gcagcaacag cagcagcagc aacaacaaca gcagcagcag    6180
cagcagcaac aacaacagca gtaccatatc cgacagcaac agcagcagca gcagatgcta    6240
cggcaacagc agcaacaaca gcaacagcag cagcagcagc aacagcagca gcagcaacaa    6300
caacagcaac agcagcagca gcagccacac cagcagcagc agcaggcagc tcctcccaa    6360 ccccagcccc agtcccagcc ccagttccag cgccagggcc tgcagcagac ccagcagcag    6420
caacagacag cagctttggt ccggcaaatt caacaacagc tctctaatac ccagccacag    6480
cccagcacca acatatttgg acgctactga gtcacctgga ggaactgctt gtccactgga    6540
tgtggcccag caggcmtc                                                  6558
```

<210> SEQ ID NO 8
<211> LENGTH: 2023
<212> TYPE: PRT
<213> ORGANISM: Homo sapiens

<400> SEQUENCE: 8

```
Met Arg Ala Ala Trp Leu Ile Lys Met Thr Cys Ala Tyr Tyr Ala Ala
1               5                   10                  15

Ile Ser Glu Thr Lys Val Lys Lys Arg His Val Asp Pro Phe Met Glu
                20                  25                  30

Trp Thr Gln Ile Ile Thr Lys Tyr Leu Trp Glu Gln Leu Gln Lys Met
            35                  40                  45

Ala Glu Tyr Tyr Arg Pro Gly Pro Ala Gly Ser Gly Gly Cys Gly Ser
        50                  55                  60

Thr Ile Gly Pro Leu Pro His Asp Val Glu Val Ala Ile Arg Gln Trp
65                  70                  75                  80

Asp Tyr Thr Glu Lys Leu Ala Met Phe Met Phe Gln Asp Gly Met Leu
                85                  90                  95

Asp Arg His Glu Phe Leu Thr Trp Val Leu Glu Cys Phe Glu Lys Ile
                100                 105                 110

Arg Pro Gly Glu Asp Glu Leu Leu Lys Leu Leu Leu Pro Leu Leu Leu
            115                 120                 125

Arg Tyr Ser Gly Glu Phe Val Gln Ser Ala Tyr Leu Ser Arg Arg Leu
        130                 135                 140

Ala Tyr Phe Cys Thr Arg Arg Leu Ala Leu Gln Leu Asp Gly Val Ser
145                 150                 155                 160

Ser His Ser Ser His Val Ile Ser Ala Gln Ser Thr Ser Thr Leu Pro
                165                 170                 175

Thr Thr Pro Ala Pro Gln Pro Pro Thr Ser Ser Thr Pro Ser Thr Pro
                180                 185                 190

Phe Ser Asp Leu Leu Met Cys Pro Gln His Arg Pro Leu Val Phe Gly
            195                 200                 205

Leu Ser Cys Ile Leu Gln Thr Ile Leu Leu Cys Cys Pro Ser Ala Leu
        210                 215                 220
```

-continued

| | | | | | | | | | | | |
|---|---|---|---|---|---|---|---|---|---|---|---|
|Val|Trp|His|Tyr|Ser|Leu|Thr|Asp|Ser|Arg|Ile|Lys|Thr|Gly|Ser|Pro|
|225| | | | |230| | | | |235| | | | |240|

Val Trp His Tyr Ser Leu Thr Asp Ser Arg Ile Lys Thr Gly Ser Pro
225                 230                 235                 240

Leu Asp His Leu Pro Ile Ala Pro Ser Asn Leu Pro Met Pro Glu Gly
                245                 250                 255

Asn Ser Ala Phe Thr Gln Gln Val Arg Ala Lys Leu Arg Glu Ile Glu
                260                 265                 270

Gln Gln Ile Lys Glu Arg Gly Gln Ala Val Glu Val Arg Trp Ser Phe
            275                 280                 285

Asp Lys Cys Gln Glu Ala Thr Ala Gly Phe Thr Ile Gly Arg Val Leu
290                 295                 300

His Thr Leu Glu Val Leu Asp Ser His Ser Phe Glu Arg Ser Asp Phe
305                 310                 315                 320

Ser Asn Ser Leu Asp Ser Leu Cys Asn Arg Ile Phe Gly Leu Gly Pro
                325                 330                 335

Ser Lys Asp Gly His Glu Ile Ser Ser Asp Asp Ala Val Val Ser
                340                 345                 350

Leu Leu Cys Glu Trp Ala Val Ser Cys Lys Arg Ser Gly Arg His Arg
            355                 360                 365

Ala Met Val Val Ala Lys Leu Leu Glu Lys Arg Gln Ala Glu Ile Glu
370                 375                 380

Ala Glu Arg Cys Gly Glu Ser Glu Ala Ala Asp Glu Lys Gly Ser Ile
385                 390                 395                 400

Ala Ser Gly Ser Leu Ser Ala Pro Ser Ala Pro Ile Phe Gln Asp Val
                405                 410                 415

Leu Leu Gln Phe Leu Asp Thr Gln Ala Pro Met Leu Thr Asp Pro Arg
            420                 425                 430

Ser Glu Ser Glu Arg Val Glu Phe Phe Asn Leu Val Leu Leu Phe Cys
                435                 440                 445

Glu Leu Ile Arg His Asp Val Phe Ser His Asn Met Tyr Thr Cys Thr
        450                 455                 460

Leu Ile Ser Arg Gly Asp Leu Ala Phe Gly Ala Pro Gly Pro Arg Pro
465                 470                 475                 480

Pro Ser Pro Phe Asp Asp Pro Ala Asp Pro Glu His Lys Glu Ala
                485                 490                 495

Glu Gly Ser Ser Ser Lys Leu Glu Asp Pro Gly Leu Ser Glu Ser
            500                 505                 510

Met Asp Ile Asp Pro Ser Ser Val Leu Phe Glu Asp Met Glu Lys
        515                 520                 525

Pro Asp Phe Ser Leu Phe Ser Pro Thr Met Pro Cys Glu Gly Lys Gly
530                 535                 540

Ser Pro Ser Pro Glu Lys Pro Asp Val Glu Lys Val Lys Pro Pro
545                 550                 555                 560

Pro Lys Glu Lys Ile Glu Gly Thr Leu Gly Val Leu Tyr Asp Gln Pro
                565                 570                 575

Arg His Val Gln Tyr Ala Thr His Phe Pro Ile Pro Gln Glu Glu Ser
            580                 585                 590

Cys Ser His Glu Cys Asn Gln Arg Leu Val Val Leu Phe Gly Val Gly
            595                 600                 605

Lys Gln Arg Asp Asp Ala Arg His Ala Ile Lys Lys Ile Thr Lys Asp
        610                 615                 620

Ile Leu Lys Val Leu Asn Arg Lys Gly Thr Ala Glu Thr Asp Gln Leu
625                 630                 635                 640

Ala Pro Ile Val Pro Leu Asn Pro Gly Asp Leu Thr Phe Leu Gly Gly

-continued

```
                645                 650                 655
Glu Asp Gly Gln Lys Arg Arg Asn Arg Pro Glu Ala Phe Pro Thr
            660                 665                 670

Ala Glu Asp Ile Phe Ala Lys Phe Gln His Leu Ser His Tyr Asp Gln
            675                 680                 685

His Gln Val Thr Ala Gln Val Ser Arg Asn Val Leu Glu Gln Ile Thr
            690                 695                 700

Ser Phe Ala Leu Gly Met Ser Tyr His Leu Pro Leu Val Gln His Val
705                 710                 715                 720

Gln Phe Ile Phe Asp Leu Met Glu Tyr Ser Leu Ser Ile Ser Gly Leu
                725                 730                 735

Ile Asp Phe Ala Ile Gln Leu Leu Asn Glu Leu Ser Val Val Glu Ala
            740                 745                 750

Glu Leu Leu Leu Lys Ser Ser Asp Leu Val Gly Ser Tyr Thr Thr Ser
            755                 760                 765

Leu Cys Leu Cys Ile Val Ala Val Leu Arg His Tyr His Ala Cys Leu
770                 775                 780

Ile Leu Asn Gln Asp Gln Met Ala Gln Val Phe Glu Gly Leu Cys Gly
785                 790                 795                 800

Val Val Lys His Gly Met Asn Arg Ser Asp Gly Ser Ser Ala Glu Arg
                805                 810                 815

Cys Ile Leu Ala Tyr Leu Tyr Asp Leu Tyr Thr Ser Cys Ser His Leu
                820                 825                 830

Lys Asn Lys Phe Gly Glu Leu Phe Ser Asp Phe Cys Ser Lys Val Lys
            835                 840                 845

Asn Thr Ile Tyr Cys Asn Val Glu Pro Ser Glu Ser Asn Met Arg Trp
850                 855                 860

Ala Pro Glu Phe Met Ile Asp Thr Leu Glu Asn Pro Ala Ala His Thr
865                 870                 875                 880

Phe Thr Tyr Thr Gly Leu Gly Lys Ser Leu Ser Glu Asn Pro Ala Asn
                885                 890                 895

Arg Tyr Ser Phe Val Cys Asn Ala Leu Met His Val Cys Val Gly His
                900                 905                 910

His Asp Pro Asp Arg Val Asn Asp Ile Ala Ile Leu Cys Ala Glu Leu
            915                 920                 925

Thr Gly Tyr Cys Lys Ser Leu Ser Ala Glu Trp Leu Gly Val Leu Lys
930                 935                 940

Ala Leu Cys Cys Ser Ser Asn Asn Gly Thr Cys Gly Phe Asn Asp Leu
945                 950                 955                 960

Leu Cys Asn Val Asp Val Ser Asp Leu Ser Phe His Asp Ser Leu Ala
                965                 970                 975

Thr Phe Val Ala Ile Leu Ile Ala Arg Gln Cys Leu Leu Leu Glu Asp
            980                 985                 990

Leu Ile Arg Cys Ala Ala Ile Pro  Ser Leu Leu Asn Ala  Ala Cys Ser
            995                 1000                1005

Glu Gln  Asp Ser Glu Pro Gly  Ala Arg Leu Thr Cys  Arg Ile Leu
    1010                1015                1020

Leu His  Leu Phe Lys Thr Pro  Gln Leu Asn Pro Cys  Gln Ser Asp
    1025                1030                1035

Gly Asn  Lys Pro Thr Val Gly  Ile Arg Ser Ser Cys  Asp Arg His
    1040                1045                1050

Leu Leu  Ala Ala Ser Gln Asn  Arg Ile Val Asp Gly  Ala Val Phe
    1055                1060                1065
```

-continued

```
Ala Val Leu Lys Ala Val Phe Val Leu Gly Asp Ala Glu Leu Lys
    1070            1075                1080

Gly Ser Gly Phe Thr Val Thr Gly Gly Thr Glu Glu Leu Pro Glu
    1085            1090                1095

Glu Glu Gly Gly Gly Ser Gly Gly Arg Arg Gln Gly Gly Arg
    1100            1105                1110

Asn Ile Ser Val Glu Thr Ala Ser Leu Asp Val Tyr Ala Lys Tyr
    1115            1120                1125

Val Leu Arg Ser Ile Cys Gln Gln Glu Trp Val Gly Glu Arg Cys
    1130            1135                1140

Leu Lys Ser Leu Cys Glu Asp Ser Asn Asp Leu Gln Asp Pro Val
    1145            1150                1155

Leu Ser Ser Ala Gln Ala Gln Arg Leu Met Gln Leu Ile Cys Tyr
    1160            1165                1170

Pro His Arg Leu Leu Asp Asn Glu Asp Gly Glu Asn Pro Gln Arg
    1175            1180                1185

Gln Arg Ile Lys Arg Ile Leu Gln Asn Leu Asp Gln Trp Thr Met
    1190            1195                1200

Arg Gln Ser Ser Leu Glu Leu Gln Leu Met Ile Lys Gln Thr Pro
    1205            1210                1215

Asn Asn Glu Met Asn Ser Leu Leu Glu Asn Ile Ala Lys Ala Thr
    1220            1225                1230

Ile Glu Val Phe Gln Gln Ser Ala Glu Thr Gly Ser Ser Ser Gly
    1235            1240                1245

Ser Thr Ala Ser Asn Met Pro Ser Ser Ser Lys Thr Lys Pro Val
    1250            1255                1260

Leu Ser Ser Leu Glu Arg Ser Gly Val Trp Leu Val Ala Pro Leu
    1265            1270                1275

Ile Ala Lys Leu Pro Thr Ser Val Gln Gly His Val Leu Lys Ala
    1280            1285                1290

Ala Gly Glu Glu Leu Glu Lys Gly Gln His Leu Gly Ser Ser Ser
    1295            1300                1305

Arg Lys Glu Arg Asp Arg Gln Lys Gln Lys Ser Met Ser Leu Leu
    1310            1315                1320

Ser Gln Gln Pro Phe Leu Ser Leu Val Leu Thr Cys Leu Lys Gly
    1325            1330                1335

Gln Asp Glu Gln Arg Glu Gly Leu Leu Thr Ser Leu Tyr Ser Gln
    1340            1345                1350

Val His Gln Ile Val Asn Asn Trp Arg Asp Asp Gln Tyr Leu Asp
    1355            1360                1365

Asp Cys Lys Pro Lys Gln Leu Met His Glu Ala Leu Lys Leu Arg
    1370            1375                1380

Leu Asn Leu Val Gly Gly Met Phe Asp Thr Val Gln Arg Ser Thr
    1385            1390                1395

Gln Gln Thr Thr Glu Trp Ala Met Leu Leu Leu Glu Ile Ile Ile
    1400            1405                1410

Ser Gly Thr Val Asp Met Gln Ser Asn Asn Glu Leu Phe Thr Thr
    1415            1420                1425

Val Leu Asp Met Leu Ser Val Leu Ile Asn Gly Thr Leu Ala Ala
    1430            1435                1440

Asp Met Ser Ser Ile Ser Gln Gly Ser Met Glu Glu Asn Lys Arg
    1445            1450                1455
```

-continued

```
Ala Tyr Met Asn Leu Ala Lys Lys Leu Gln Lys Glu Leu Gly Glu
            1460                1465            1470

Arg Gln Ser Asp Ser Leu Glu Lys Val Arg Gln Leu Leu Pro Leu
    1475            1480                1485

Pro Lys Gln Thr Arg Asp Val Ile Thr Cys Glu Pro Gln Gly Ser
    1490            1495                1500

Leu Ile Asp Thr Lys Gly Asn Lys Ile Ala Gly Phe Asp Ser Ile
    1505            1510                1515

Phe Lys Lys Glu Gly Leu Gln Val Ser Thr Lys Gln Lys Ile Ser
    1520            1525                1530

Pro Trp Asp Leu Phe Glu Gly Leu Lys Pro Ser Ala Pro Leu Ser
    1535            1540                1545

Trp Gly Trp Phe Gly Thr Val Arg Val Asp Arg Arg Val Ala Arg
    1550            1555                1560

Gly Glu Glu Gln Gln Arg Leu Leu Leu Tyr His Thr His Leu Arg
    1565            1570                1575

Pro Arg Pro Arg Ala Tyr Tyr Leu Glu Pro Leu Pro Leu Pro Pro
    1580            1585                1590

Glu Asp Glu Glu Pro Pro Ala Pro Thr Leu Leu Glu Pro Glu Lys
    1595            1600                1605

Lys Ala Pro Glu Pro Lys Thr Asp Lys Pro Gly Ala Ala Pro
    1610            1615                1620

Pro Ser Thr Glu Glu Arg Lys Lys Lys Ser Thr Lys Gly Lys Lys
    1625            1630                1635

Arg Ser Gln Pro Ala Thr Lys Thr Glu Asp Tyr Gly Met Gly Pro
    1640            1645                1650

Gly Arg Ser Gly Pro Tyr Gly Val Thr Val Pro Pro Asp Leu Leu
    1655            1660                1665

His His Pro Asn Pro Gly Ser Ile Thr His Leu Asn Tyr Arg Gln
    1670            1675                1680

Gly Ser Ile Gly Leu Tyr Thr Gln Asn Gln Pro Leu Pro Ala Gly
    1685            1690                1695

Gly Pro Arg Val Asp Pro Tyr Arg Pro Val Arg Leu Pro Met Gln
    1700            1705                1710

Lys Leu Pro Thr Arg Pro Thr Tyr Pro Gly Val Leu Pro Thr Thr
    1715            1720                1725

Met Thr Gly Val Met Gly Leu Glu Pro Ser Ser Tyr Lys Thr Ser
    1730            1735                1740

Val Tyr Arg Gln Gln Gln Pro Ala Val Pro Gln Gly Gln Arg Leu
    1745            1750                1755

Arg Gln Gln Leu Gln Gln Ser Gln Gly Met Leu Gly Gln Ser Ser
    1760            1765                1770

Val His Gln Met Thr Pro Ser Ser Ser Tyr Gly Leu Gln Thr Ser
    1775            1780                1785

Gln Gly Tyr Thr Pro Tyr Val Ser His Val Gly Leu Gln Gln His
    1790            1795                1800

Thr Gly Pro Ala Gly Thr Met Val Pro Pro Ser Tyr Ser Ser Gln
    1805            1810                1815

Pro Tyr Gln Ser Thr His Pro Ser Thr Asn Pro Thr Leu Val Asp
    1820            1825                1830

Pro Thr Arg His Leu Gln Gln Arg Pro Ser Gly Tyr Val His Gln
    1835            1840                1845

Gln Ala Pro Thr Tyr Gly His Gly Leu Thr Ser Thr Gln Arg Phe
```

-continued

```
                 1850                1855                1860

Ser His  Gln Thr Leu Gln Gln  Thr Pro Met Ile Ser  Thr Met Thr
    1865                1870                1875

Pro Met  Ser Ala Gln Gly Val  Gln Ala Gly Val Arg  Ser Thr Ala
    1880                1885                1890

Ile Leu  Pro Glu Gln Gln Gln  Gln Gln Gln Gln Gln  Gln Gln Gln
    1895                1900                1905

Gln Gln  Gln Gln Gln Gln Gln  Gln Gln Gln Gln Gln  Gln Gln Gln
    1910                1915                1920

Tyr His  Ile Arg Gln Gln Gln  Gln Gln Gln Ile Leu  Arg Gln Gln
    1925                1930                1935

Gln Gln  Gln Gln Gln Gln Gln  Gln Gln Gln Gln Gln  Gln Gln Gln
    1940                1945                1950

Gln Gln  Gln Gln Gln Gln Gln  Gln Gln His Gln Gln  Gln Gln Gln
    1955                1960                1965

Gln Gln  Ala Ala Pro Pro Gln  Pro Gln Pro Gln Ser  Gln Pro Gln
    1970                1975                1980

Phe Gln  Arg Gln Gly Leu Gln  Gln Thr Gln Gln Gln  Gln Gln Thr
    1985                1990                1995

Ala Ala  Leu Val Arg Gln Leu  Gln Gln Gln Leu Ser  Asn Thr Gln
    2000                2005                2010

Pro Gln  Pro Ser Thr Asn Ile  Phe Gly Arg
    2015                2020

<210> SEQ ID NO 9
<211> LENGTH: 2074
<212> TYPE: PRT
<213> ORGANISM: Mus musculus

<400> SEQUENCE: 9

Met Asn Gln Lys Asp Asn Phe Trp Leu Val Thr Ala Arg Ser Gln Ser
1               5                   10                  15

Ala Ile Asn Thr Trp Phe Thr Asp Leu Ala Gly Thr Lys Pro Leu Thr
            20                  25                  30

His Leu Ala Lys Lys Val Pro Ile Phe Ser Lys Lys Glu Glu Val Phe
        35                  40                  45

Gly Tyr Leu Ala Lys Tyr Thr Val Pro Val Met Arg Ala Ala Trp Leu
    50                  55                  60

Ile Lys Met Thr Cys Ala Tyr Tyr Ala Ala Met Ser Glu Thr Lys Val
65                  70                  75                  80

Lys Lys Lys Asn Thr Ala Asp Pro Phe Thr Glu Trp Thr Gln Ile Ile
                85                  90                  95

Thr Lys Tyr Leu Trp Glu Gln Leu Gln Lys Met Ala Glu Tyr Tyr Arg
            100                 105                 110

Pro Gly Pro Ala Gly Ser Gly Gly Cys Gly Ser Thr Ile Gly Pro Leu
        115                 120                 125

Pro His Asp Val Glu Met Ala Ile Arg Gln Trp Asp Tyr Asn Glu Lys
    130                 135                 140

Leu Ala Leu Phe Met Phe Gln Asp Gly Met Leu Asp Arg His Glu Phe
145                 150                 155                 160

Leu Thr Trp Val Leu Glu Cys Phe Glu Lys Ile Arg Pro Gly Glu Asp
                165                 170                 175

Glu Leu Leu Lys Leu Leu Pro Leu Leu Leu Arg Tyr Ser Gly Glu
            180                 185                 190
```

-continued

```
Phe Val Gln Ser Ala Tyr Leu Ser Arg Arg Leu Ala Tyr Phe Cys Thr
            195                 200                 205
Arg Arg Leu Ala Leu Gln Leu Asp Gly Val Ser Ser His Ser Ser His
        210                 215                 220
Val Ile Ala Ala Gln Ser Thr Ser Ser Leu Pro Thr Thr Pro Ala Pro
225                 230                 235                 240
Gln Pro Pro Thr Ser Ser Thr Pro Ser Thr Pro Phe Ser Asp Leu Leu
                245                 250                 255
Met Cys Pro Gln His Arg Pro Leu Val Phe Gly Leu Ser Cys Ile Leu
            260                 265                 270
Gln Thr Ile Leu Leu Cys Cys Pro Ser Ala Leu Val Trp His Tyr Ser
        275                 280                 285
Leu Thr Asp Ser Arg Ile Lys Thr Gly Ser Pro Leu Asp His Leu Pro
    290                 295                 300
Ile Ala Pro Ser Asn Leu Pro Met Pro Glu Gly Asn Ser Ala Phe Thr
305                 310                 315                 320
Gln Gln Val Arg Ala Lys Leu Arg Glu Ile Glu Gln Gln Ile Lys Glu
                325                 330                 335
Arg Gly Gln Ala Val Glu Val Arg Trp Ser Phe Asp Lys Cys Gln Glu
            340                 345                 350
Ala Thr Ala Gly Phe Thr Ile Gly Arg Val Leu His Thr Leu Glu Val
        355                 360                 365
Leu Asp Ser His Ser Phe Glu Arg Ser Asp Phe Ser Asn Ser Leu Asp
    370                 375                 380
Ser Leu Cys Asn Arg Ile Phe Gly Leu Gly Pro Ser Lys Asp Gly His
385                 390                 395                 400
Glu Ile Ser Ser Asp Asp Ala Val Val Ser Leu Leu Cys Glu Trp
                405                 410                 415
Ala Val Ser Cys Lys Arg Ser Gly Arg His Arg Ala Met Val Val Ala
            420                 425                 430
Lys Leu Leu Glu Lys Arg Gln Ala Glu Ile Glu Ala Glu Arg Cys Gly
        435                 440                 445
Glu Ser Glu Ala Ala Asp Glu Lys Gly Ser Val Ala Ser Gly Ser Leu
    450                 455                 460
Ser Ala Pro Ser Ala Pro Ile Phe Gln Asp Val Leu Leu Gln Phe Leu
465                 470                 475                 480
Asp Thr Gln Ala Pro Met Leu Thr Asp Pro Arg Ser Glu Ser Glu Arg
                485                 490                 495
Val Glu Phe Phe Asn Leu Val Leu Leu Phe Cys Glu Leu Ile Arg His
            500                 505                 510
Asp Val Phe Ser His Asn Met Tyr Thr Cys Thr Leu Ile Ser Arg Gly
        515                 520                 525
Asp Leu Ala Phe Gly Ala Pro Gly Pro Arg Pro Ser Pro Phe Asp
    530                 535                 540
Asp Pro Thr Asp Pro Glu Arg Lys Glu Ala Glu Gly Ser Ser Ser
545                 550                 555                 560
Ser Lys Leu Glu Asp Pro Gly Leu Ser Glu Ser Met Asp Ile Asp Pro
                565                 570                 575
Ser Ser Thr Val Leu Phe Glu Asp Met Glu Lys Pro Asp Phe Ser Leu
            580                 585                 590
Phe Ser Pro Thr Met Pro Cys Glu Gly Lys Gly Ser Pro Ser Pro Glu
        595                 600                 605
Lys Pro Asp Val Glu Lys Glu Val Lys Pro Pro Ala Lys Glu Lys Ile
```

-continued

```
            610                 615                 620
Glu Gly Thr Leu Gly Ile Leu Tyr Asp Gln Pro Arg His Val Gln Tyr
625                 630                 635                 640
Ala Thr His Phe Pro Ile Pro Gln Glu Glu Ser Cys Ser His Glu Cys
                    645                 650                 655
Asn Gln Arg Leu Val Val Leu Phe Gly Val Gly Lys Gln Arg Asp Asp
            660                 665                 670
Ala Arg His Ala Ile Lys Lys Ile Thr Lys Asp Ile Leu Lys Val Leu
            675                 680                 685
Asn Arg Lys Gly Thr Ala Glu Thr Asp Gln Leu Ala Pro Ile Val Pro
690                 695                 700
Leu Asn Pro Gly Asp Leu Thr Phe Leu Gly Gly Glu Asp Gly Gln Lys
705                 710                 715                 720
Arg Arg Arg Asn Arg Pro Glu Ala Phe Pro Thr Ala Glu Asp Ile Phe
                    725                 730                 735
Ala Lys Phe Gln His Leu Ser His Tyr Asp Gln His Gln Val Thr Ala
                    740                 745                 750
Gln Val Ser Arg Asn Val Leu Glu Gln Ile Thr Ser Phe Ala Leu Gly
            755                 760                 765
Met Ser Tyr His Leu Pro Leu Val Gln His Val Gln Phe Ile Phe Asp
770                 775                 780
Leu Met Glu Tyr Ser Leu Ser Ile Ser Gly Leu Ile Asp Phe Ala Ile
785                 790                 795                 800
Gln Leu Leu Asn Glu Leu Ser Val Val Glu Ala Glu Leu Leu Leu Lys
                    805                 810                 815
Ser Ser Asp Leu Val Gly Ser Tyr Thr Thr Ser Leu Cys Leu Cys Ile
            820                 825                 830
Val Ala Val Leu Arg His Tyr His Ala Cys Leu Ile Leu Asn Gln Asp
            835                 840                 845
Gln Met Ala Gln Val Phe Glu Gly Leu Cys Gly Val Val Lys His Gly
850                 855                 860
Met Asn Arg Ser Asp Gly Ser Ser Ala Glu Arg Cys Ile Leu Ala Tyr
865                 870                 875                 880
Leu Tyr Asp Leu Tyr Thr Ser Cys Ser His Leu Lys Ser Lys Phe Gly
                    885                 890                 895
Glu Leu Phe Ser Asp Phe Cys Ser Lys Val Lys Asn Thr Ile Tyr Cys
                    900                 905                 910
Asn Val Glu Pro Ser Glu Ser Asn Met Arg Trp Ala Pro Glu Phe Met
            915                 920                 925
Ile Asp Thr Leu Glu Asn Pro Ala Ala His Thr Phe Thr Tyr Thr Gly
930                 935                 940
Leu Gly Lys Ser Leu Ser Glu Asn Pro Ala Asn Arg Tyr Ser Phe Val
945                 950                 955                 960
Cys Asn Ala Leu Met His Val Cys Val Gly His His Asp Pro Asp Arg
                    965                 970                 975
Val Asn Asp Ile Ala Ile Leu Cys Ala Glu Leu Thr Gly Tyr Cys Lys
                    980                 985                 990
Ser Leu Ser Ala Glu Trp Leu Gly Val Leu Lys Ala Leu Cys Cys Ser
                    995                 1000                1005
Ser Asn Asn Gly Thr Cys Gly Phe Asn Asp Leu Leu Cys Asn Val
        1010            1015               1020
Asp Val Ser Asp Leu Ser Phe His Asp Ser Leu Ala Thr Phe Val
        1025            1030               1035
```

-continued

```
Ala Ile Leu Ile Ala Arg Gln Cys Leu Leu Glu Asp Leu Ile
1040            1045            1050

Arg Cys Ala Ala Ile Pro Ser Leu Leu Asn Ala Ala Cys Ser Glu
1055            1060            1065

Gln Asp Ser Glu Pro Gly Ala Arg Leu Thr Cys Arg Ile Leu Leu
1070            1075            1080

His Leu Phe Lys Thr Pro Gln Leu Asn Pro Cys Gln Ser Asp Gly
1085            1090            1095

Asn Lys Pro Thr Val Gly Ile Arg Ser Ser Cys Asp Arg His Leu
1100            1105            1110

Leu Ala Ala Ser Gln Asn Arg Ile Val Asp Gly Ala Val Phe Ala
1115            1120            1125

Val Leu Lys Ala Val Phe Val Leu Gly Asp Ala Glu Leu Lys Gly
1130            1135            1140

Ser Gly Phe Thr Val Pro Gly Gly Thr Glu Glu Leu Pro Glu Glu
1145            1150            1155

Glu Gly Gly Gly Gly Ser Ser Gly Arg Arg Gln Gly Gly Arg Asn
1160            1165            1170

Ile Ser Val Glu Thr Ala Ser Leu Asp Val Tyr Ala Lys Tyr Val
1175            1180            1185

Leu Arg Ser Ile Cys Gln Gln Glu Trp Val Gly Glu Arg Cys Leu
1190            1195            1200

Lys Ser Leu Cys Glu Asp Ser Asn Asp Leu Gln Asp Pro Val Leu
1205            1210            1215

Ser Ser Ala Gln Ala Gln Arg Leu Met Gln Leu Ile Cys Tyr Pro
1220            1225            1230

His Arg Leu Leu Asp Asn Glu Asp Gly Glu Asn Pro Gln Arg Gln
1235            1240            1245

Arg Ile Lys Arg Ile Leu Lys Asn Leu Asp Gln Trp Thr Met Arg
1250            1255            1260

Gln Ser Ser Leu Glu Leu Gln Leu Met Ile Lys Gln Thr Pro Asn
1265            1270            1275

Thr Glu Met Asn Ser Leu Leu Glu Asn Ile Ala Lys Ala Thr Ile
1280            1285            1290

Glu Val Phe Gln Gln Ser Ala Glu Thr Gly Ser Ser Ser Gly Ser
1295            1300            1305

Thr Ala Ser Asn Met Pro Ser Ser Ser Lys Thr Lys Pro Val Leu
1310            1315            1320

Ser Ser Leu Glu Arg Ser Gly Val Trp Leu Val Ala Pro Leu Ile
1325            1330            1335

Ala Lys Leu Pro Thr Ser Val Gln Gly His Val Leu Lys Ala Ala
1340            1345            1350

Gly Glu Glu Leu Glu Lys Gly Gln His Leu Gly Ser Ser Ser Arg
1355            1360            1365

Lys Glu Arg Asp Arg Gln Lys Gln Lys Ser Met Ser Leu Leu Ser
1370            1375            1380

Gln Gln Pro Phe Leu Ser Leu Val Leu Thr Cys Leu Lys Gly Gln
1385            1390            1395

Asp Glu Gln Arg Glu Gly Leu Leu Ala Ser Leu His Ser Gln Val
1400            1405            1410

His Gln Ile Val Ile Asn Trp Arg Glu Asn Gln Tyr Leu Asp Asp
1415            1420            1425
```

-continued

```
Cys Lys Pro Lys Gln Leu Met His Glu Ala Leu Lys Leu Arg Leu
    1430                1435                1440
Asn Leu Val Gly Gly Met Phe Asp Thr Val Gln Arg Ser Thr Gln
    1445                1450                1455
Gln Thr Thr Glu Trp Ala Gln Leu Leu Leu Glu Ile Ile Ile Ser
    1460                1465                1470
Gly Thr Val Asp Met Gln Ser Asn Asn Glu Leu Phe Thr Thr Val
    1475                1480                1485
Leu Asp Met Leu Ser Val Leu Ile Asn Gly Thr Leu Ala Ala Asp
    1490                1495                1500
Met Ser Ser Ile Ser Gln Gly Ser Met Glu Glu Asn Lys Arg Ala
    1505                1510                1515
Tyr Met Asn Leu Val Lys Lys Leu Gln Lys Asp Leu Gly Glu Arg
    1520                1525                1530
Gln Ser Asp Ser Leu Glu Lys Val His Gln Leu Leu Pro Leu Pro
    1535                1540                1545
Lys Gln Asn Arg Asp Val Ile Thr Cys Glu Pro Gln Gly Ser Leu
    1550                1555                1560
Ile Asp Thr Lys Gly Asn Lys Ile Ala Gly Phe Asp Ser Ile Phe
    1565                1570                1575
Lys Lys Glu Gly Leu Gln Val Ser Thr Lys Gln Lys Ile Ser Pro
    1580                1585                1590
Trp Glu Leu Phe Glu Gly Leu Lys Pro Ser Thr Ala Pro Leu Ser
    1595                1600                1605
Trp Ala Trp Phe Gly Thr Val Arg Val Asp Arg Arg Val Ala Arg
    1610                1615                1620
Gly Glu Glu Gln Gln Arg Leu Leu Leu Tyr His Thr His Leu Arg
    1625                1630                1635
Pro Arg Pro Arg Ala Tyr Tyr Leu Glu Pro Leu Pro Leu Pro Pro
    1640                1645                1650
Glu Asp Glu Glu Pro Pro Ala Pro Ala Leu Leu Glu Pro Glu Lys
    1655                1660                1665
Lys Ala Pro Glu Pro Pro Lys Thr Asp Lys Pro Gly Ala Ala Pro
    1670                1675                1680
Pro Ser Thr Glu Glu Arg Lys Lys Lys Ser Thr Lys Gly Lys Lys
    1685                1690                1695
Arg Ser Gln Pro Ala Thr Lys Asn Glu Asp Tyr Gly Met Gly Pro
    1700                1705                1710
Gly Arg Ser Gly Pro Tyr Gly Val Thr Val Pro Pro Asp Leu Leu
    1715                1720                1725
His His Ala Asn Pro Gly Ser Ile Ser His Leu Ser Tyr Arg Gln
    1730                1735                1740
Ser Ser Met Gly Leu Tyr Thr Gln Asn Gln Pro Leu Pro Ala Gly
    1745                1750                1755
Gly Pro Arg Val Asp Pro Tyr Arg Pro Val Arg Leu Pro Met Gln
    1760                1765                1770
Lys Leu Pro Thr Arg Pro Thr Tyr Pro Gly Val Leu Pro Thr Thr
    1775                1780                1785
Met Ser Thr Val Met Gly Leu Glu Pro Ser Ser Tyr Lys Thr Ser
    1790                1795                1800
Val Tyr Arg Gln Gln Gln Pro Thr Val Pro Gln Gly Gln Arg Leu
    1805                1810                1815
Arg Gln Gln Leu Gln Gln Ser Gln Gly Met Leu Gly Gln Ser Ser
```

-continued

| | 1820 | | | | 1825 | | | | 1830 | | |

Val His Gln Met Thr Pro Ser Ser Tyr Gly Leu Gln Thr Ser
    1835                1840                1845

Gln Leu Ser Ser Pro Ser Leu Gln Gly Tyr Thr Ser Tyr Val Ser
    1850                1855                1860

His Val Gly Leu Gln Gln His Thr Gly Pro Ala Asp Pro Thr Arg
    1865                1870                1875

His Leu Gln Gln Arg Pro Ser Gly Tyr Val His Gln Gln Ala Pro
    1880                1885                1890

Thr Tyr Gly His Gly Leu Thr Ser Thr Gln Arg Phe Ser His Gln
    1895                1900                1905

Thr Leu Gln Gln Thr Pro Met Met Gly Thr Met Thr Pro Leu Ser
    1910                1915                1920

Ala Gln Gly Val Gln Ala Gly Val Arg Ser Thr Ser Ile Leu Pro
    1925                1930                1935

Glu Gln Gln Gln Gln Gln Gln Gln Gln Gln Gln Gln Gln
    1940                1945                1950

Gln Gln Gln Gln Gln Gln Gln Gln Gln Gln Gln Gln Gln
    1955                1960                1965

Gln Gln Gln Gln Tyr His Ile Arg Gln Gln Gln Gln Gln Gln
    1970                1975                1980

Met Leu Arg Gln Gln Gln Gln Gln Gln Gln Gln Gln Gln Gln
    1985                1990                1995

Gln Gln Gln Gln Gln Gln Gln Gln Gln Gln Gln Gln Gln
    2000                2005                2010

Pro His Gln Gln Gln Gln Ala Ala Pro Pro Gln Pro Gln Pro
    2015                2020                2025

Gln Ser Gln Pro Gln Phe Gln Arg Gln Gly Leu Gln Gln Thr Gln
    2030                2035                2040

Gln Gln Gln Gln Thr Ala Ala Leu Val Arg Gln Ile Gln Gln Gln
    2045                2050                2055

Leu Ser Asn Thr Gln Pro Gln Pro Ser Thr Asn Ile Phe Gly Arg
    2060                2065                2070

Tyr

<210> SEQ ID NO 10
<211> LENGTH: 12
<212> TYPE: DNA
<213> ORGANISM: Homo sapiens

<400> SEQUENCE: 10
cagcaacacc ag                                                        12

<210> SEQ ID NO 11
<211> LENGTH: 24
<212> TYPE: DNA
<213> ORGANISM: Homo sapiens

<400> SEQUENCE: 11
ctgcttcctc atcccctgcc ctca                                           24

<210> SEQ ID NO 12
<211> LENGTH: 25
<212> TYPE: DNA
<213> ORGANISM: Homo sapiens

<400> SEQUENCE: 12

```
gggctgtagt ccaaacagct acctg                                           25
```

<210> SEQ ID NO 13
<211> LENGTH: 253
<212> TYPE: DNA
<213> ORGANISM: Homo sapiens

<400> SEQUENCE: 13

```
ctgcttcctc atcccctgcc ctcagccctt tagttctgag gcttagcttc ctccctctgc     60
tccttctgaa gtatcttttg tgttcttata gcagcagcag caacagcaac agcagcagca    120
gcagcagcag caacagcaac agcagcagca gcaacagcaa caacagcaac accagcagca    180
acagcagcaa caggcggctc ctccccaacc ccagccccag tccagccccc aggtagctgc    240
tggactacag ccc                                                       253
```

<210> SEQ ID NO 14
<211> LENGTH: 265
<212> TYPE: DNA
<213> ORGANISM: Homo sapiens

<400> SEQUENCE: 14

```
ctgcttcctc atcccctgcc ctcagccctt tagttctgag gcttagcttc ctccctctgc     60
tccttctgaa gtatcttttg tgttcttata gcagcagcag caacagcaac agcagcagca    120
gcagcagcag caacagcaac agcagcagca gcaacagcaa caacagcaac accagcagca    180
acaccagcag caacagcagc aacaggcggc tcctccccaa ccccagcccc agtcccagcc    240
ccaggtagct gctggactac agccc                                          265
```

<210> SEQ ID NO 15
<211> LENGTH: 238
<212> TYPE: DNA
<213> ORGANISM: Homo sapiens

<400> SEQUENCE: 15

```
ctgcttcctc atcccctgcc ctcagccctt tagttctgag gcttagcttc ctccctctgc     60
tccttctgaa gtatcttttg tgttcttata gcagcagcag caacagcaac agcagcagca    120
gcagcagcag caacagcaac agcaacaaca gcaacaccag cagcaacagc agcaacaggc    180
ggctcctccc caaccccagc ccagtccca gccccaggta gctgctggac tacagccc       238
```

<210> SEQ ID NO 16
<211> LENGTH: 265
<212> TYPE: DNA
<213> ORGANISM: Homo sapiens

<400> SEQUENCE: 16

```
ctgcttcctc atcccctgcc ctcagccctt tagttctgag gcttagcttc ctccctctgc     60
tccttctgaa gtatcttttg tgttcttata gcagcagcag caacagcaac agcagcagca    120
gcagcagcag caacagcaac agcagcagca gcaacagcaa caacagcaac accagcagca    180
acaccagcag caacagcagc aacaggcggc tcctccccaa ccccagcccc agtcccagcc    240
ccaggtagct gctggactac agccc                                          265
```

<210> SEQ ID NO 17
<211> LENGTH: 265
<212> TYPE: DNA
<213> ORGANISM: Homo sapiens

```
<400> SEQUENCE: 17
ctgcttcctc atccctgcc ctcagccctt tagttctgag gcttagcttc ctccctctgc    60
tccttctgaa gtatcttttg tgttcttata gcagcagcag caacagcaac agcagcagca   120
gcagcagcag caacagcaac agcagcagca gcaacagcaa caacagcaac accagcagca   180
acaccagcag caacagcagc aacaggcggc tcctccccaa ccccagcccc agtcccagcc   240
ccaggtagct gctggactac agccc                                        265

<210> SEQ ID NO 18
<211> LENGTH: 265
<212> TYPE: DNA
<213> ORGANISM: Homo sapiens

<400> SEQUENCE: 18
ctgcttcctc atccctgcc ctcagccctt tagttctgag gcttagcttc ctccctctgc    60
tccttctgaa gtatcttttg tgttcttata gcagcagcag caacagcaac agcagcagca   120
gcagcagcag caacagcaac agcagcagca gcaacagcaa caacagcaac accagcagca   180
acaccagcag caacagcagc aacaggcggc tcctccccaa ccccagcccc agtcccagcc   240
ccaggtagct gctggactac agccc                                        265

<210> SEQ ID NO 19
<211> LENGTH: 15
<212> TYPE: DNA
<213> ORGANISM: Homo sapiens

<400> SEQUENCE: 19
cagcagcagc aacag                                                    15

<210> SEQ ID NO 20
<211> LENGTH: 843
<212> TYPE: PRT
<213> ORGANISM: Rattus norvegicus

<400> SEQUENCE: 20
```

Met Ala Leu Pro Arg Cys Met Trp Pro Asn Tyr Val Trp Arg Ala Met
1               5                   10                  15

Met Ala Cys Val Val His Arg Gly Ser Gly Ala Pro Leu Thr Leu Cys
                20                  25                  30

Leu Leu Gly Cys Leu Leu Gln Thr Phe His Val Leu Ser Gln Lys Leu
            35                  40                  45

Asp Asp Val Asp Pro Leu Val Thr Thr Asn Phe Gly Lys Ile Arg Gly
        50                  55                  60

Ile Lys Lys Glu Leu Asn Asn Glu Ile Leu Gly Pro Val Ile Gln Phe
65                  70                  75                  80

Leu Gly Val Pro Tyr Ala Ala Pro Pro Thr Gly Glu His Arg Phe Gln
                85                  90                  95

Pro Pro Glu Pro Pro Ser Pro Trp Ser Asp Ile Arg Asn Ala Thr Gln
            100                 105                 110

Phe Ala Pro Val Cys Pro Gln Asn Ile Ile Asp Gly Arg Leu Pro Glu
        115                 120                 125

Val Met Leu Pro Val Trp Phe Thr Asn Asn Leu Asp Val Val Ser Ser
    130                 135                 140

Tyr Val Gln Asp Gln Ser Glu Asp Cys Leu Tyr Leu Asn Ile Tyr Val
145                 150                 155                 160

Pro Thr Glu Asp Val Lys Arg Ile Ser Lys Glu Cys Ala Arg Lys Pro

-continued

```
                165                 170                 175
Gly Lys Lys Ile Cys Arg Lys Gly Asp Ile Arg Asp Ser Gly Gly Pro
                180                 185                 190

Lys Pro Val Met Val Tyr Ile His Gly Gly Ser Tyr Met Glu Gly Thr
                195                 200                 205

Gly Asn Leu Tyr Asp Gly Ser Val Leu Ala Ser Tyr Gly Asn Val Ile
                210                 215                 220

Val Ile Thr Val Asn Tyr Arg Leu Gly Val Leu Gly Phe Leu Ser Thr
225                 230                 235                 240

Gly Asp Gln Ala Ala Lys Gly Asn Tyr Gly Leu Leu Asp Leu Ile Gln
                245                 250                 255

Ala Leu Arg Trp Thr Ser Glu Asn Ile Gly Phe Phe Gly Gly Asp Pro
                260                 265                 270

Leu Arg Ile Thr Val Phe Gly Ser Gly Ala Gly Gly Ser Cys Val Asn
                275                 280                 285

Leu Leu Thr Leu Ser His Tyr Ser Glu Gly Asn Arg Trp Ser Asn Ser
                290                 295                 300

Thr Lys Gly Leu Phe Gln Arg Ala Ile Ala Gln Ser Gly Thr Ala Leu
305                 310                 315                 320

Ser Ser Trp Ala Val Ser Phe Gln Pro Ala Lys Tyr Ala Arg Ile Leu
                325                 330                 335

Ala Thr Lys Val Gly Cys Asn Val Ser Asp Thr Val Glu Leu Val Glu
                340                 345                 350

Cys Leu Gln Lys Lys Pro Tyr Lys Glu Leu Val Asp Gln Asp Val Gln
                355                 360                 365

Pro Ala Arg Tyr His Ile Ala Phe Gly Pro Val Ile Asp Gly Asp Val
                370                 375                 380

Ile Pro Asp Asp Pro Gln Ile Leu Met Glu Gln Gly Glu Phe Leu Asn
385                 390                 395                 400

Tyr Asp Ile Met Leu Gly Val Asn Gln Gly Glu Gly Leu Lys Phe Val
                405                 410                 415

Glu Asn Ile Val Asp Ser Asp Asp Gly Val Ser Ala Ser Asp Phe Asp
                420                 425                 430

Phe Ala Val Ser Asn Phe Val Asp Asn Leu Tyr Gly Tyr Pro Glu Gly
                435                 440                 445

Lys Asp Val Leu Arg Glu Thr Ile Lys Phe Met Tyr Thr Asp Trp Ala
450                 455                 460

Asp Arg His Asn Pro Glu Thr Arg Arg Lys Thr Leu Leu Ala Leu Phe
465                 470                 475                 480

Thr Asp His Gln Trp Val Ala Pro Ala Val Ala Thr Ala Asp Leu His
                485                 490                 495

Ser Asn Phe Gly Ser Pro Thr Tyr Phe Tyr Ala Phe Tyr His His Cys
                500                 505                 510

Gln Thr Asp Gln Val Pro Ala Trp Ala Asp Ala Ala His Gly Asp Glu
                515                 520                 525

Val Pro Tyr Val Leu Gly Ile Pro Met Ile Gly Pro Thr Glu Leu Phe
                530                 535                 540

Pro Cys Asn Phe Ser Lys Asn Asp Val Met Leu Ser Ala Val Val Met
545                 550                 555                 560

Thr Tyr Trp Thr Asn Phe Ala Lys Thr Gly Asp Pro Asn Gln Pro Val
                565                 570                 575

Pro Gln Asp Thr Lys Phe Ile His Thr Lys Pro Asn Arg Phe Glu Glu
                580                 585                 590
```

```
Val Ala Trp Thr Arg Tyr Ser Gln Lys Asp Gln Leu Tyr Leu His Ile
            595                 600                 605

Gly Leu Lys Pro Arg Val Lys Glu His Tyr Arg Ala Asn Lys Val Asn
            610                 615                 620

Leu Trp Leu Glu Leu Val Pro His Leu His Asn Leu Asn Asp Ile Ser
625                 630                 635                 640

Gln Tyr Thr Ser Thr Thr Thr Lys Val Pro Ser Thr Asp Ile Thr Leu
            645                 650                 655

Arg Pro Thr Arg Lys Asn Ser Thr Pro Val Thr Ser Ala Phe Pro Thr
            660                 665                 670

Ala Lys Gln Asp Asp Pro Lys Gln Gln Pro Ser Pro Phe Ser Val Asp
            675                 680                 685

Gln Arg Asp Tyr Ser Thr Glu Leu Ser Val Thr Ile Ala Val Gly Ala
            690                 695                 700

Ser Leu Leu Phe Leu Asn Ile Leu Ala Phe Ala Leu Tyr Tyr Lys
705                 710                 715                 720

Lys Asp Lys Arg Arg His Asp Val His Arg Arg Cys Ser Pro Gln Arg
            725                 730                 735

Thr Thr Thr Asn Asp Leu Thr His Ala Pro Glu Glu Ile Met Ser
            740                 745                 750

Leu Gln Met Lys His Thr Asp Leu Asp His Glu Cys Glu Ser Ile His
            755                 760                 765

Pro His Glu Val Val Leu Arg Thr Ala Cys Pro Pro Asp Tyr Thr Leu
            770                 775                 780

Ala Met Arg Arg Ser Pro Asp Asp Val Pro Leu Met Thr Pro Asn Thr
785                 790                 795                 800

Ile Thr Met Ile Pro Asn Thr Ile Pro Gly Ile Gln Pro Leu His Thr
            805                 810                 815

Phe Asn Thr Phe Thr Gly Gly Gln Asn Asn Thr Leu Pro His Pro His
            820                 825                 830

Pro His Pro His Ser His Ser Thr Thr Arg Val
            835                 840

<210> SEQ ID NO 21
<211> LENGTH: 836
<212> TYPE: PRT
<213> ORGANISM: Rattus norvegicus

<400> SEQUENCE: 21

Met Trp Leu Leu Ala Leu Cys Leu Val Gly Leu Ala Gly Ala Gln Arg
1               5                   10                  15

Gly Gly Gly Gly Pro Gly Gly Gly Ala Pro Gly Gly Pro Gly Leu Gly
                20                  25                  30

Leu Gly Ser Leu Gly Glu Glu Arg Phe Pro Val Val Asn Thr Ala Tyr
            35                  40                  45

Gly Arg Val Arg Gly Val Arg Arg Glu Leu Asn Asn Glu Ile Leu Gly
        50                  55                  60

Pro Val Val Gln Phe Leu Gly Val Pro Tyr Ala Thr Pro Pro Leu Gly
65                  70                  75                  80

Ala Arg Arg Phe Gln Pro Pro Glu Ala Pro Ala Ser Trp Pro Gly Val
                85                  90                  95

Arg Asn Ala Thr Thr Leu Pro Pro Ala Cys Pro Gln Asn Leu His Gly
                100                 105                 110

Ala Leu Pro Ala Ile Met Leu Pro Val Trp Phe Thr Asp Asn Leu Glu
```

```
              115                 120                 125
Ala Ala Ala Thr Tyr Val Gln Asn Gln Ser Glu Asp Cys Leu Tyr Leu
            130                 135                 140
Asn Leu Tyr Val Pro Thr Glu Asp Gly Pro Leu Thr Lys Lys Arg Asp
145                 150                 155                 160
Glu Ala Thr Leu Asn Pro Pro Asp Thr Asp Ile Arg Asp Ser Gly Lys
                165                 170                 175
Lys Pro Val Met Leu Phe Leu His Gly Gly Ser Tyr Met Glu Gly Thr
                180                 185                 190
Gly Asn Met Phe Asp Gly Ser Val Leu Ala Ala Tyr Gly Asn Val Ile
                195                 200                 205
Val Ala Thr Leu Asn Tyr Arg Leu Gly Val Leu Gly Phe Leu Ser Thr
            210                 215                 220
Gly Asp Gln Ala Ala Lys Gly Asn Tyr Gly Leu Leu Asp Gln Ile Gln
225                 230                 235                 240
Ala Leu Arg Trp Leu Ser Glu Asn Ile Ala His Phe Gly Gly Asp Pro
                245                 250                 255
Glu Arg Ile Thr Ile Phe Gly Ser Gly Ala Gly Ala Ser Cys Val Asn
                260                 265                 270
Leu Leu Ile Leu Ser His His Ser Glu Gly Leu Phe Gln Lys Ala Ile
                275                 280                 285
Ala Gln Ser Gly Thr Ala Ile Ser Ser Trp Ser Val Asn Tyr Gln Pro
            290                 295                 300
Leu Lys Tyr Thr Arg Leu Leu Ala Ala Lys Val Gly Cys Asp Arg Glu
305                 310                 315                 320
Asp Ser Thr Glu Ala Val Glu Cys Leu Arg Arg Lys Ser Ser Arg Glu
                325                 330                 335
Leu Val Asp Gln Asp Val Gln Pro Ala Arg Tyr His Ile Ala Phe Gly
                340                 345                 350
Pro Val Val Asp Gly Asp Val Val Pro Asp Asp Pro Glu Ile Leu Met
                355                 360                 365
Gln Gln Gly Glu Phe Leu Asn Tyr Asp Met Leu Ile Gly Val Asn Gln
            370                 375                 380
Gly Glu Gly Leu Lys Phe Val Glu Asp Ser Ala Glu Ser Glu Asp Gly
385                 390                 395                 400
Val Ser Ala Ser Ala Phe Asp Phe Thr Val Ser Asn Phe Val Asp Asn
                405                 410                 415
Leu Tyr Gly Tyr Pro Glu Gly Lys Asp Val Leu Arg Glu Thr Ile Lys
                420                 425                 430
Phe Met Tyr Thr Asp Trp Ala Asp Arg Asp Asn Gly Glu Met Arg Arg
                435                 440                 445
Lys Thr Leu Leu Ala Leu Phe Thr Asp His Gln Trp Val Ala Pro Ala
450                 455                 460
Val Ala Thr Ala Lys Leu His Ala Asp Tyr Gln Ser Pro Val Tyr Phe
465                 470                 475                 480
Tyr Thr Phe Tyr His His Cys Gln Ala Glu Gly Arg Pro Glu Trp Ala
                485                 490                 495
Asp Ala Ala His Gly Asp Glu Leu Pro Tyr Val Phe Gly Val Pro Met
                500                 505                 510
Val Gly Ala Thr Asp Leu Phe Pro Cys Asn Phe Ser Lys Asn Asp Val
            515                 520                 525
Met Leu Ser Ala Val Val Met Thr Tyr Trp Thr Asn Phe Ala Lys Thr
            530                 535                 540
```

```
Gly Asp Pro Asn Gln Pro Val Pro Gln Asp Thr Lys Phe Ile His Thr
545                 550                 555                 560

Lys Pro Asn Arg Phe Glu Glu Val Val Trp Ser Lys Phe Asn Ser Lys
            565                 570                 575

Glu Lys Gln Tyr Leu His Ile Gly Leu Lys Pro Arg Val Arg Asp Asn
        580                 585                 590

Tyr Arg Ala Asn Lys Val Ala Phe Trp Leu Glu Leu Val Pro His Leu
    595                 600                 605

His Asn Leu His Thr Glu Leu Phe Thr Thr Thr Arg Leu Pro Pro
610                 615                 620

Tyr Ala Thr Arg Trp Pro Pro Arg Thr Pro Gly Pro Gly Thr Ser Gly
625                 630                 635                 640

Thr Arg Arg Pro Pro Pro Ala Thr Leu Pro Pro Glu Ser Asp Ile
                645                 650                 655

Asp Leu Gly Pro Arg Ala Tyr Asp Arg Phe Pro Gly Asp Ser Arg Asp
            660                 665                 670

Tyr Ser Thr Glu Leu Ser Val Thr Val Ala Val Gly Ala Ser Leu Leu
        675                 680                 685

Phe Leu Asn Ile Leu Ala Phe Ala Ala Leu Tyr Tyr Lys Arg Asp Arg
690                 695                 700

Arg Gln Glu Leu Arg Cys Arg Arg Leu Ser Pro Pro Gly Gly Ser Gly
705                 710                 715                 720

Ser Gly Val Pro Gly Gly Pro Leu Leu Pro Thr Ala Gly Arg Glu
                725                 730                 735

Leu Pro Pro Glu Glu Glu Leu Val Ser Leu Gln Leu Lys Arg Gly Gly
            740                 745                 750

Gly Val Gly Ala Asp Pro Ala Glu Ala Leu Arg Pro Ala Cys Pro Pro
        755                 760                 765

Asp Tyr Thr Leu Ala Leu Arg Arg Ala Pro Asp Asp Val Pro Leu Leu
770                 775                 780

Ala Pro Gly Ala Leu Thr Leu Leu Pro Ser Gly Leu Gly Pro Pro
785                 790                 795                 800

Pro Pro Pro Pro Pro Ser Leu His Pro Phe Gly Pro Phe Pro Pro Pro
                805                 810                 815

Pro Pro Thr Ala Thr Ser His Asn Asn Thr Leu Pro His Pro His Ser
            820                 825                 830

Thr Thr Arg Val
            835

<210> SEQ ID NO 22
<211> LENGTH: 848
<212> TYPE: PRT
<213> ORGANISM: Rattus norvegicus

<400> SEQUENCE: 22

Met Trp Leu Gln Leu Gly Leu Pro Ser Leu Ser Leu Ser Pro Thr Pro
1               5                   10                  15

Thr Val Gly Arg Ser Leu Cys Leu Ile Leu Trp Phe Leu Ser Leu Val
            20                  25                  30

Leu Arg Ala Ser Thr Gln Ala Pro Ala Pro Thr Val Asn Thr His Phe
        35                  40                  45

Gly Lys Leu Arg Gly Ala Arg Val Pro Leu Pro Ser Glu Ile Leu Gly
    50                  55                  60

Pro Val Asp Gln Tyr Leu Gly Val Pro Tyr Ala Ala Pro Pro Ile Gly
```

-continued

```
                65                  70                  75                  80
        Glu Lys Arg Phe Leu Pro Pro Glu Pro Pro Ser Trp Ser Gly Ile
                            85                  90                  95
        Arg Asn Ala Thr His Phe Pro Val Cys Pro Gln Asn Ile His Thr
                           100                 105                 110
        Ala Val Pro Glu Val Met Leu Pro Val Trp Phe Thr Ala Asn Leu Asp
                           115                 120                 125
        Ile Val Ala Thr Tyr Ile Gln Glu Pro Asn Glu Asp Cys Leu Tyr Leu
                           130                 135                 140
        Asn Val Tyr Val Pro Thr Glu Asp Val Lys Arg Ile Ser Lys Glu Cys
        145                     150                 155                 160
        Ala Arg Lys Pro Asn Lys Lys Ile Cys Arg Lys Gly Ser Gly Ala
                           165                 170                 175
        Lys Lys Gln Gly Glu Asp Leu Ala Asp Asn Asp Gly Asp Glu Asp Glu
                           180                 185                 190
        Asp Ile Arg Asp Ser Gly Ala Lys Pro Val Met Val Tyr Ile His Gly
                           195                 200                 205
        Gly Ser Tyr Met Glu Gly Thr Gly Asn Met Ile Asp Gly Ser Val Leu
                           210                 215                 220
        Ala Ser Tyr Gly Asn Val Ile Val Ile Thr Leu Asn Tyr Arg Val Gly
        225                     230                 235                 240
        Val Leu Gly Phe Leu Ser Thr Gly Asp Gln Ala Ala Lys Gly Asn Tyr
                           245                 250                 255
        Gly Leu Leu Asp Gln Ile Gln Ala Leu Arg Trp Val Ser Glu Asn Ile
                           260                 265                 270
        Ala Phe Phe Gly Gly Asp Pro Arg Arg Ile Thr Val Phe Gly Ser Gly
                           275                 280                 285
        Ile Gly Ala Ser Cys Val Ser Leu Leu Thr Leu Ser His His Ser Glu
                           290                 295                 300
        Gly Leu Phe Gln Arg Ala Ile Ile Gln Ser Gly Ser Ala Leu Ser Ser
        305                     310                 315                 320
        Trp Ala Val Asn Tyr Gln Pro Val Lys Tyr Thr Ser Leu Leu Ala Asp
                           325                 330                 335
        Lys Val Gly Cys Asn Val Leu Asp Thr Val Asp Met Val Asp Cys Leu
                           340                 345                 350
        Arg Gln Lys Ser Ala Lys Glu Leu Val Glu Gln Asp Ile Gln Pro Ala
                           355                 360                 365
        Arg Tyr His Val Ala Phe Gly Pro Val Ile Asp Gly Asp Val Ile Pro
                           370                 375                 380
        Asp Asp Pro Glu Ile Leu Met Glu Gln Gly Glu Phe Leu Asn Tyr Asp
        385                     390                 395                 400
        Ile Met Leu Gly Val Asn Gln Gly Glu Gly Leu Lys Phe Val Glu Gly
                           405                 410                 415
        Val Val Asp Pro Glu Asp Gly Val Ser Gly Thr Asp Phe Asp Tyr Ser
                           420                 425                 430
        Val Ser Asn Phe Val Asp Asn Leu Tyr Gly Tyr Pro Glu Gly Lys Asp
                           435                 440                 445
        Thr Leu Arg Glu Thr Ile Lys Phe Met Tyr Thr Asp Trp Ala Asp Arg
                           450                 455                 460
        Asp Asn Pro Glu Thr Arg Arg Lys Thr Leu Val Ala Leu Phe Thr Asp
        465                     470                 475                 480
        His Gln Trp Val Glu Pro Ser Val Val Thr Ala Asp Leu His Ala Arg
                           485                 490                 495
```

-continued

```
Tyr Gly Ser Pro Thr Tyr Phe Tyr Ala Phe Tyr His His Cys Gln Ser
            500                 505                 510

Leu Met Lys Pro Ala Trp Ser Asp Ala Ala His Gly Asp Glu Val Pro
            515                 520                 525

Tyr Val Phe Gly Val Pro Met Val Gly Pro Thr Asp Leu Phe Pro Cys
            530                 535                 540

Asn Phe Ser Lys Asn Asp Val Met Leu Ser Ala Val Val Met Thr Tyr
545                 550                 555                 560

Trp Thr Asn Phe Ala Lys Thr Gly Asp Pro Asn Lys Pro Val Pro Gln
                565                 570                 575

Asp Thr Lys Phe Ile His Thr Lys Ala Asn Arg Phe Glu Glu Val Ala
                580                 585                 590

Trp Ser Lys Tyr Asn Pro Arg Asp Gln Leu Tyr Leu His Ile Gly Leu
            595                 600                 605

Lys Pro Arg Val Arg Asp His Tyr Arg Ala Thr Lys Val Ala Phe Trp
            610                 615                 620

Lys His Leu Val Pro His Leu Tyr Asn Leu His Asp Met Phe His Tyr
625                 630                 635                 640

Thr Ser Thr Thr Thr Lys Val Pro Pro Pro Asp Thr Thr His Ser Ser
                645                 650                 655

His Ile Thr Arg Arg Pro Asn Gly Lys Thr Trp Ser Thr Lys Arg Pro
                660                 665                 670

Ala Ile Ser Pro Ala Tyr Ser Asn Glu Asn Ala Pro Gly Ser Trp Asn
            675                 680                 685

Gly Asp Gln Asp Ala Gly Pro Leu Leu Val Glu Asn Pro Arg Asp Tyr
690                 695                 700

Ser Thr Glu Leu Ser Val Thr Ile Ala Val Gly Ala Ser Leu Leu Phe
705                 710                 715                 720

Leu Asn Val Leu Ala Phe Ala Leu Tyr Tyr Arg Lys Asp Lys Arg
                725                 730                 735

Arg Gln Glu Pro Leu Arg Gln Pro Ser Pro Gln Arg Gly Thr Gly Ala
            740                 745                 750

Pro Glu Leu Gly Thr Ala Pro Glu Glu Glu Leu Ala Ala Leu Gln Leu
            755                 760                 765

Gly Pro Thr His His Glu Cys Glu Ala Gly Pro Pro His Asp Thr Leu
            770                 775                 780

Arg Leu Thr Ala Leu Pro Asp Tyr Thr Leu Thr Leu Arg Arg Ser Pro
785                 790                 795                 800

Asp Asp Ile Pro Leu Met Thr Pro Asn Thr Ile Thr Met Ile Pro Asn
                805                 810                 815

Ser Leu Val Gly Leu Gln Thr Leu His Pro Tyr Asn Thr Phe Ala Ala
                820                 825                 830

Gly Phe Asn Ser Thr Gly Leu Pro Asn Ser His Ser Thr Thr Arg Val
                835                 840                 845

<210> SEQ ID NO 23
<211> LENGTH: 823
<212> TYPE: PRT
<213> ORGANISM: Homo sapiens

<400> SEQUENCE: 23

Met Trp Leu Arg Leu Gly Pro Pro Ser Leu Ser Leu Ser Pro Lys Pro
1               5                   10                  15

Thr Val Gly Arg Ser Leu Cys Leu Thr Leu Trp Phe Leu Ser Leu Ala
```

-continued

```
              20                  25                  30
Leu Arg Ala Ser Thr Gln Ala Pro Ala Pro Thr Val Asn Thr His Phe
             35                  40                  45
Gly Lys Leu Arg Gly Ala Arg Val Pro Leu Pro Ser Glu Ile Leu Gly
 50                  55                  60
Pro Val Asp Gln Tyr Leu Gly Val Pro Tyr Ala Ala Pro Pro Ile Gly
 65                  70                  75                  80
Glu Lys Arg Phe Leu Pro Pro Glu Pro Pro Ser Trp Ser Gly Ile
                 85                  90                  95
Arg Asn Ala Thr His Phe Pro Pro Val Cys Pro Gln Asn Ile His Thr
                100                 105                 110
Ala Val Pro Glu Val Met Leu Pro Val Trp Phe Thr Ala Asn Leu Asp
                115                 120                 125
Ile Val Ala Thr Tyr Ile Gln Glu Pro Asn Glu Asp Cys Leu Tyr Leu
                130                 135                 140
Asn Val Tyr Val Pro Thr Glu Asp Gly Ser Gly Ala Lys Lys Gln Gly
145                 150                 155                 160
Glu Asp Leu Ala Asp Asn Asp Gly Asp Glu Asp Glu Asp Ile Arg Asp
                165                 170                 175
Ser Gly Ala Lys Pro Val Met Val Tyr Ile His Gly Gly Ser Tyr Met
                180                 185                 190
Glu Gly Thr Gly Asn Met Ile Asp Gly Ser Ile Phe Ala Ser Tyr Gly
                195                 200                 205
Asn Val Ile Val Ile Thr Leu Asn Tyr Arg Val Gly Val Ile Gly Phe
    210                 215                 220
Leu Ser Thr Gly Asp Gln Ala Ala Lys Gly Asn Tyr Gly Leu Leu Asp
225                 230                 235                 240
Gln Ile Gln Ala Leu Arg Trp Val Ser Glu Asn Ile Ala Phe Phe Gly
                245                 250                 255
Gly Asp Pro Arg Arg Ile Thr Val Phe Gly Ser Gly Ile Gly Ala Ser
                260                 265                 270
Cys Val Ser Leu Leu Thr Leu Ser His His Ser Glu Gly Leu Phe Gln
                275                 280                 285
Arg Ala Ile Ile Gln Ser Gly Ser Ala Leu Ser Ser Trp Ala Val Asn
    290                 295                 300
Tyr Gln Pro Val Lys Tyr Thr Ser Leu Leu Ala Asp Lys Val Gly Cys
305                 310                 315                 320
Asn Val Leu Asp Thr Val Asp Met Val Asp Cys Leu Arg Gln Lys Ser
                325                 330                 335
Ala Lys Glu Leu Val Glu Gln Asp Ile Gln Pro Ala Arg Tyr His Val
                340                 345                 350
Ala Phe Gly Pro Val Ile Asp Gly Asp Val Ile Pro Asp Asp Pro Glu
                355                 360                 365
Ile Leu Met Glu Gln Gly Glu Phe Leu Asn Tyr Asp Ile Met Leu Gly
    370                 375                 380
Val Asn Gln Gly Glu Gly Leu Lys Phe Val Glu Gly Val Val Asp Pro
385                 390                 395                 400
Glu Asp Gly Val Ser Gly Thr Asp Phe Asp Tyr Ser Val Ser Asn Phe
                405                 410                 415
Val Asp Asn Leu Tyr Gly Tyr Pro Glu Gly Lys Asp Thr Leu Arg Glu
                420                 425                 430
Thr Ile Lys Phe Met Tyr Thr Asp Trp Ala Asp Arg Asp Asn Pro Glu
    435                 440                 445
```

-continued

```
Thr Arg Arg Lys Thr Leu Val Ala Leu Phe Thr Asp His Gln Trp Val
    450                 455                 460
Glu Pro Ser Val Val Thr Ala Asp Leu His Ala Arg Tyr Gly Ser Pro
465                 470                 475                 480
Thr Tyr Phe Tyr Ala Phe Tyr His His Cys Gln Ser Leu Met Lys Pro
            485                 490                 495
Ala Trp Ser Asp Ala Ala His Gly Asp Glu Val Pro Tyr Val Phe Gly
            500                 505                 510
Val Pro Met Val Gly Pro Thr Asp Leu Phe Pro Cys Asn Phe Ser Lys
        515                 520                 525
Asn Asp Val Met Leu Ser Ala Val Val Met Thr Tyr Trp Thr Asn Phe
    530                 535                 540
Ala Lys Thr Gly Asp Pro Asn Lys Pro Val Pro Gln Asp Thr Lys Phe
545                 550                 555                 560
Ile His Thr Lys Ala Asn Arg Phe Glu Glu Val Ala Trp Ser Lys Tyr
            565                 570                 575
Asn Pro Arg Asp Gln Leu Tyr Leu His Ile Gly Leu Lys Pro Arg Val
            580                 585                 590
Arg Asp His Tyr Arg Ala Thr Lys Val Ala Phe Trp Lys His Leu Val
        595                 600                 605
Pro His Leu Tyr Asn Leu His Asp Met Phe His Tyr Thr Ser Thr Thr
    610                 615                 620
Thr Lys Val Pro Pro Asp Thr Thr His Ser Ser His Ile Thr Arg
625                 630                 635                 640
Arg Pro Asn Gly Lys Thr Trp Ser Thr Lys Arg Pro Ala Ile Ser Pro
            645                 650                 655
Ala Tyr Ser Asn Glu Asn Ala Gln Gly Ser Trp Asn Gly Asp Gln Asp
            660                 665                 670
Ala Gly Pro Leu Leu Val Glu Asn Pro Arg Asp Tyr Ser Thr Glu Leu
        675                 680                 685
Ser Val Thr Ile Ala Val Gly Ala Ser Leu Leu Phe Leu Asn Val Leu
    690                 695                 700
Ala Phe Ala Ala Leu Tyr Tyr Arg Lys Asp Lys Arg Arg Gln Glu Pro
705                 710                 715                 720
Leu Arg Gln Pro Ser Pro Gln Arg Gly Ala Gly Ala Pro Glu Leu Gly
            725                 730                 735
Ala Ala Pro Glu Glu Glu Leu Ala Leu Gln Leu Gly Pro Thr His
            740                 745                 750
His Glu Cys Glu Ala Gly Pro Pro His Asp Thr Leu Arg Leu Thr Ala
        755                 760                 765
Leu Pro Asp Tyr Thr Leu Thr Leu Arg Arg Ser Pro Asp Asp Ile Pro
    770                 775                 780
Leu Met Thr Pro Asn Thr Ile Thr Met Ile Pro Asn Ser Leu Val Gly
785                 790                 795                 800
Leu Gln Thr Leu His Pro Tyr Asn Thr Phe Ala Ala Gly Phe Asn Ser
            805                 810                 815
Thr Gly Leu Pro His Ser His
            820

<210> SEQ ID NO 24
<211> LENGTH: 553
<212> TYPE: PRT
<213> ORGANISM: Homo sapiens
```

-continued

```
<400> SEQUENCE: 24

Met Trp Leu Arg Leu Gly Pro Pro Ser Leu Ser Leu Ser Pro Lys Pro
1               5                   10                  15

Thr Val Gly Arg Ser Leu Cys Leu Thr Leu Trp Phe Leu Ser Leu Ala
            20                  25                  30

Leu Arg Ala Ser Thr Gln Ala Pro Ala Pro Thr Val Asn Thr His Phe
        35                  40                  45

Gly Lys Leu Arg Gly Ala Arg Val Pro Leu Pro Ser Glu Ile Leu Gly
    50                  55                  60

Pro Val Asp Gln Tyr Leu Gly Val Pro Tyr Ala Ala Pro Pro Ile Gly
65                  70                  75                  80

Glu Lys Arg Phe Leu Pro Pro Glu Pro Pro Ser Trp Ser Gly Ile
                85                  90                  95

Arg Asn Ala Thr His Phe Pro Val Cys Pro Gln Asn Ile His Thr
                100                 105                 110

Ala Val Pro Glu Val Met Leu Pro Val Trp Phe Thr Ala Asn Leu Asp
            115                 120                 125

Ile Val Ala Thr Tyr Ile Gln Glu Pro Asn Glu Asp Cys Leu Tyr Leu
        130                 135                 140

Asn Val Tyr Val Pro Thr Glu Asp Val Lys Arg Ile Ser Lys Glu Cys
145                 150                 155                 160

Ala Arg Lys Pro Asn Lys Lys Ile Cys Arg Lys Gly Ser Gly Ala
                165                 170                 175

Lys Lys Gln Gly Glu Asp Leu Ala Asp Asn Asp Gly Asp Glu Asp Glu
            180                 185                 190

Asp Ile Arg Asp Ser Gly Ala Lys Pro Val Met Val Tyr Ile His Gly
        195                 200                 205

Gly Ser Tyr Met Glu Gly Thr Gly Asn Met Ile Asp Gly Ser Ile Leu
    210                 215                 220

Ala Ser Tyr Gly Asn Val Ile Val Ile Thr Leu Asn Tyr Arg Val Gly
225                 230                 235                 240

Val Leu Gly Phe Leu Ser Thr Gly Asp Gln Ala Ala Lys Gly Asn Tyr
                245                 250                 255

Gly Leu Leu Asp Gln Ile Gln Ala Leu Arg Trp Val Ser Glu Asn Ile
                260                 265                 270

Ala Phe Phe Gly Gly Asp Pro Arg Arg Ile Thr Val Phe Gly Ser Gly
            275                 280                 285

Ile Gly Ala Ser Cys Val Ser Leu Leu Thr Leu Ser His His Ser Glu
        290                 295                 300

Gly Leu Phe Gln Arg Ala Ile Ile Gln Ser Gly Ser Ala Leu Ser Ser
305                 310                 315                 320

Trp Ala Val Asn Tyr Gln Pro Val Lys Tyr Thr Ser Leu Leu Ala Asp
                325                 330                 335

Lys Val Gly Cys Asn Val Leu Asp Thr Val Asp Met Val Asp Cys Leu
            340                 345                 350

Arg Gln Lys Ser Ala Lys Glu Leu Val Glu Gln Asp Ile Gln Pro Ala
        355                 360                 365

Arg Tyr His Val Ala Phe Gly Pro Val Ile Asp Gly Asp Val Ile Pro
    370                 375                 380

Asp Asp Pro Glu Ile Leu Met Glu Gln Gly Glu Phe Leu Asn Tyr Asp
385                 390                 395                 400

Ile Met Leu Gly Val Asn Gln Gly Glu Gly Leu Lys Phe Val Glu Gly
                405                 410                 415
```

```
Val Val Asp Pro Glu Asp Gly Val Ser Gly Thr Asp Phe Asp Tyr Ser
            420             425             430

Val Ser Asn Phe Val Asp Asn Leu Tyr Gly Tyr Pro Glu Gly Lys Asp
            435             440             445

Thr Leu Arg Glu Thr Ile Lys Phe Met Tyr Thr Asp Trp Ala Asp Arg
        450             455             460

Asp Asn Pro Glu Thr Arg Arg Lys Thr Leu Val Ala Leu Phe Thr Asp
465             470             475             480

His Gln Trp Val Glu Pro Ser Val Val Thr Ala Asp Leu His Ala Arg
            485             490             495

Tyr Gly Ser Pro Thr Tyr Phe Tyr Ala Phe Tyr His His Cys Gln Asn
            500             505             510

Leu Met Lys Pro Ala Trp Ser Asp Ala Ala His Gly Asp Glu Val Pro
        515             520             525

Tyr Val Phe Gly Val Pro Met Val Gly Pro Thr Asp Leu Phe Pro Cys
        530             535             540

Asn Phe Ser Lys Asn Asp Val Met Leu
545             550
```